(12) United States Patent
Marineau et al.

(10) Patent No.: US 11,124,527 B2
(45) Date of Patent: Sep. 21, 2021

(54) COMPOUNDS FOR THE MODULATION OF MYC ACTIVITY

(71) Applicants: Syros Pharmaceuticals, Inc., Cambridge, MA (US); Christopher Roberts, Belmont, MA (US); Yi Zhang, Belmont, MA (US); Francis Beaumier, Mont-Saint-Hilaire (CA); Luce Lépissier, Montreal (CA)

(72) Inventors: Jason J. Marineau, Franklin, MA (US); Peter B. Rahl, Natick, MA (US); Kevin Sprott, Needham, MA (US); Stephane Ciblat, Montreal (CA); Boubacar Sow, Saint-Laurent (CA); Robin Larouche-Gauthier, Montreal (CA); Lauren Berstler, Somerville, MA (US); Christopher Roberts, Belmont, MA (US); Yi Zhang, Belmont, MA (US); Francis Beaumier, Mont-Saint-Hilaire (CA); Luce Lépissier, Montreal (CA)

(73) Assignee: Syros Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 15/579,830

(22) PCT Filed: Jun. 3, 2016

(86) PCT No.: PCT/US2016/035690
§ 371 (c)(1),
(2) Date: Dec. 5, 2017

(87) PCT Pub. No.: WO2016/196910
PCT Pub. Date: Dec. 8, 2016

(65) Prior Publication Data
US 2018/0354972 A1    Dec. 13, 2018

Related U.S. Application Data

(60) Provisional application No. 62/171,766, filed on Jun. 5, 2015.

(51) Int. Cl.
C07D 513/04    (2006.01)
A61P 35/00     (2006.01)
C07D 495/04    (2006.01)

(52) U.S. Cl.
CPC .......... *C07D 513/04* (2013.01); *A61P 35/00* (2018.01); *C07D 495/04* (2013.01)

(58) Field of Classification Search
CPC ............................... C07D 513/04; A61P 35/00
See application file for complete search history.

(56) References Cited

U.S. PATENT DOCUMENTS

2011/0053915 A1    3/2011  Ivaschenko et al.

FOREIGN PATENT DOCUMENTS

WO    WO-2008020438 A2      2/2008
WO    WO-2012148889 A1 *   11/2012  ........... C07D 495/04

OTHER PUBLICATIONS

Dang. "MYC on the path to cancer," Cell, 2012, 149, pp. 22-35.
Hermeking. "The MYC oncogene as a cancer drug target," Current Cancer Drug Targets, 2003, 3, pp. 163-175.
Nesbit et al. "MYC oncogenes and human neoplastic disease," Oncogene, 1999, 18, pp. 3004-3016.
Tansey. "Mammaliam MYC proteins and cancer," New Journal of Science, 2014, pp. 1-27.

* cited by examiner

*Primary Examiner* — Golam M Shameem
(74) *Attorney, Agent, or Firm* — Goodwin Procter LLP

(57) ABSTRACT

The present invention provides novel compounds of Formulas (I) and (II) and pharmaceutically acceptable salts, solvates, hydrates, tautomers, stereoisomers, isotopically labeled derivatives, and compositions thereof. Also provided are methods and kits involving the compounds or compositions for treating or preventing proliferative diseases, e.g., cancers (e.g., breast cancer, prostate cancer, lymphoma, lung cancer, pancreatic cancer, ovarian cancer, neuroblastoma, or colorectal cancer), benign neoplasms, angio genesis, inflammatory diseases, fibrosis (e.g., polycystic kidney disease), autoinflammatory diseases, and autoimmune diseases in a subject.

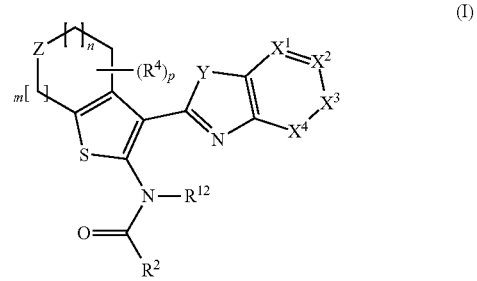

30 Claims, No Drawings

COMPOUNDS FOR THE MODULATION OF MYC ACTIVITY

CROSS REFERENCE TO RELATED APPLICATIONS

The present application is a U.S. National Phase Application under 35 U.S.C. § 371 of International Application PCT/US2016/035690, filed Jun. 3, 2016, which claims priority under 35 U.S.C. § 119(e) to U.S. Provisional Application No. 62/171,766, filed on Jun. 5, 2015. The entire disclosures of each of the foregoing applications are incorporated herein by reference.

BACKGROUND OF THE INVENTION

The transcription factor c-Myc plays an important role in the regulation of cell proliferation, cell growth, apoptosis, the cell cycle, and oncogenesis. c-Myc, a basic helix-loop-helix (bHLH) leucine zipper protein, is the most frequently occurring oncoprotein in a wide range of cancers, including breast, lung, and prostate cancers, where its deregulation provides growth factor-independent growth (Tansey, W. P. *New J Sci* (2014) 2014: 1-27; Dang, C. V. *Cell* (2012) 149:22-35). Myc proteins arise from three distinct gene families, c-myc, N-myc, and L-myc, each of which functions in an analogous manner but exhibits differences in expression levels and potency (Nesbit, C. E. et al, *Oncogene* (1999) 13:3004-3016; Tansey, W. P. *New J Sci* (2014) 2014:1-27; Dang, C. V. *Cell* (2012) 149:22-35). c-Myc requires heterodimerization with the small bHLH leucine zipper protein Max to bind DNA and activate gene transcription. Interaction of c-Myc with Max occurs at all c-Myc-bound genes in the genome and is essential for its oncogencity (Tansey, W. P. *New J Sci* (2014) 2014: 1-27). Further, Max is capable of dimerization with additional bHLH proteins that may influence the c-Myc-Max interaction, such as Mad and Mxl1 (Tansey, W. P. *New J Sci* (2014) 2014: 1-27; C. Grandori et al, *Ann Rev Cell Dev Biol* (2000) 16:653-699)

The myc gene is deregulated in cancer through multiple mechanisms including gene amplification, chromosomal translocation, deregulated upstream signaling, and protein stabilization, where the end result is increased levels of the resulting Myc protein (Nesbit, C. E. et al, *Oncogene* (1999) 13:3004-3016). Transgenic mouse models studies have demonstrated that genetic inactivation of myc leads to tumor regression in a range of cancer types (Jain, M. *Science* (2002) 297:102-104; Felsher, D. et al, *Mol Cell* (1999) 4:199-207; Choi, P. S. et al, *Proc Natl Acad Sci USA* (2011) 108:17432-17437; Murphy, D. et al. *Cancer Cell* (2008) 14:447-457; He, T. C. et al, *Science* (1998) 281:1509-1512). In some models, even brief inactivation of Myc significantly improves survival rates (Murphy, D. et al. *Cancer Cell* (2008) 14:447-457; Chesi, M. et al. *Cancer Cell* (2008) 13:167-180; Pelengaris, S. et al, *Mol Cell* (1999) 3:565-577). Additional studies have confirmed these findings in a number of other aggressive tumor models, where the prediction is that Myc inhibitors would have broad utility across multiple cancer types (Hermeking, H. *Curr Cancer Drug Targets* (2003) 3:163-175; Soucek, L. *Nature* (2008) 455: 679-683; Konstantinopoulos, P. et al, *JAMA* (2011) 305: 2349-2350; Soucek, L. et al, *Nature* (2008) 455:679-683). As such, there is a need to identify compounds that are capable of modulating Myc activity for use as therapeutic agents.

SUMMARY OF THE INVENTION

The present invention provides Myc inhibitors, for example c-Myc inhibitors, and in particular selective c-Myc inhibitors of Formula (I), and pharmaceutically acceptable salts, solvates, hydrates, tautomers, stereoisomers, isotopically labeled derivatives, and compositions thereof. The present invention further provides methods of using the compounds of the invention, and pharmaceutically acceptable salts, solvates, hydrates, tautomers, stereoisomers, isotopically labeled derivatives, and compositions thereof, to study the inhibition of c-Myc or other Myc family members (e.g., N-Myc or L-Myc), as well as the interaction of c-Myc with DNA or Max. The present invention still further provides methods of using the compounds of the invention, and pharmaceutically acceptable salts, solvates, hydrates, tautomers, stereoisomers, isotopically labeled derivatives, and compositions thereof, as therapeutics for the prevention and/or treatment of diseases associated with overexpression and/or aberrant activity of c-Myc or other Myc family members (e.g., N-Myc or L-Myc). In certain embodiments, the inventive compounds are used for the prevention and/or treatment of proliferative diseases (e.g., cancers (e.g., breast cancer, prostate cancer, lymphoma, lung cancer, pancreatic cancer, ovarian cancer, neuroblastoma, or colorectal cancer), benign neoplasms, angiogenesis, inflammatory diseases, fibrosis (e.g., polycystic kidney disease), autoinflammatory diseases, and autoimmune diseases) in a subject.

In one aspect, the present invention provides compounds of Formula (I):

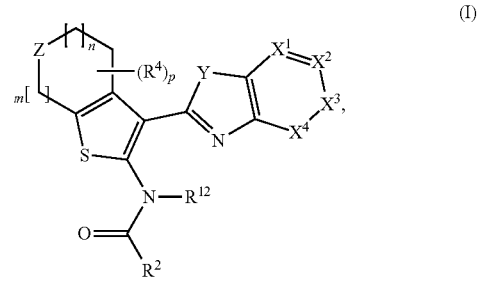

and pharmaceutically acceptable salts, solvates, hydrates, tautomers, stereoisomers, and isotopically labeled derivatives thereof, wherein $X^1$, $X^2$, $X^3$, $X^4$, Y, Z, $R^2$, $R^4$, $R^{12}$, m, n, p, and subvariables thereof are as defined herein.

In another aspect, the present invention provides pharmaceutical compositions comprising a compound of Formula (I), or a pharmaceutically acceptable salt, solvate, hydrate, tautomer, stereoisomer, or isotopically labeled derivative thereof, and optionally a pharmaceutically acceptable excipient. In certain embodiments, the pharmaceutical compositions described herein include a therapeutically effective amount of a compound of Formula (I), or a pharmaceutically acceptable salt, solvate, hydrate, tautomer, stereoisomer, or isotopically labeled derivative thereof. The pharmaceutical composition may be useful for treating and/or preventing a proliferative or infectious disease.

In another aspect, the present invention provides methods of down-regulating the expression of c-Myc or other Myc family members (e.g., N-Myc or L-Myc) in a cell. In some embodiments, the method comprises contacting the cell with a compound of Formula (I) or a pharmaceutically acceptable salt, solvate, hydrate, tautomer, stereoisomer, or isotopically labeled derivative thereof, and optionally a pharmaceutically acceptable excipient, or compositions thereof.

In another aspect, the present invention provides methods of inhibiting the activity of c-Myc or other Myc family members (e.g., N-Myc or L-Myc) in a cell. In some embodiments, the method comprises contacting the cell with a compound of Formula (I) or a pharmaceutically acceptable salt, solvate, hydrate, tautomer, stereoisomer, or isotopically labeled derivative thereof, and optionally a pharmaceutically acceptable excipient, or compositions thereof.

In another aspect, the present invention provides methods of reducing Myc-regulated transcription of a gene in a cell (e.g. reducing transcription regulated by c-Myc, N-Myc, or L-Myc). In some embodiments, the method comprises contacting the cell with a compound of Formula (I) or a pharmaceutically acceptable salt, solvate, hydrate, tautomer, stereoisomer, or isotopically labeled derivative thereof, and optionally a pharmaceutically acceptable excipient, or compositions thereof.

In another aspect, the present invention provides methods for treating and/or preventing proliferative diseases. Exemplary proliferative diseases include cancers (e.g., breast cancer, prostate cancer, lymphoma, lung cancer, pancreatic cancer, ovarian cancer, neuroblastoma, or colorectal cancer), benign neoplasms, angiogenesis, inflammatory diseases, fibrosis (e.g., polycystic kidney disease), autoinflammatory diseases, and autoimmune diseases. In other embodiments, the present invention provides methods for treating and/or preventing an infectious disease (e.g., a viral infection).

In another aspect, the present invention provides methods for treating a proliferative disease (e.g., cancers (e.g., breast cancer, prostate cancer, lymphoma, lung cancer, pancreatic cancer, ovarian cancer, neuroblastoma, or colorectal cancer), benign neoplasms, angiogenesis, inflammatory diseases, fibrosis (e.g., polycystic kidney disease), autoinflammatory diseases, and autoimmune diseases) characterized by deregulated activity of c-Myc or other Myc family members (e.g., N-Myc or L-Myc). In some embodiments, the deregulated activity of c-Myc or other Myc family members (e.g., N-Myc or L-Myc) comprises deregulation of upstream signaling, gene amplification, or chromosomal translocation by c-Myc or other Myc family members (e.g., N-Myc or L-Myc). In some embodiments, the proliferative disease is characterized by overexpression of c-Myc or other Myc family members (e.g., N-Myc or L-Myc). In some embodiments, the method comprises administering to a subject a compound of Formula (I) or a pharmaceutically acceptable salt, solvate, hydrate, tautomer, stereoisomer, or isotopically labeled derivative thereof, and optionally a pharmaceutically acceptable excipient, or compositions thereof.

In another aspect, the present invention provides methods for treating a proliferative disease (e.g., cancer (e.g., breast cancer, prostate cancer, lymphoma, or colorectal cancer), benign neoplasm, angiogenesis, inflammatory diseases, autoinflammatory diseases, and autoimmune diseases) characterized by deregulation of other bHLH transcription factors, e.g., MITF, TWIST1, Max, E2A/TCF3, and HES1. In some embodiments, the proliferative disease is characterized by deregulation of the interaction between c-Myc and other bHLH transcription factors, e.g., Max. In some embodiments, the method comprises administering to a subject a compound of Formula (I) or a pharmaceutically acceptable salt, solvate, hydrate, tautomer, stereoisomer, or isotopically labeled derivative thereof, and optionally a pharmaceutically acceptable excipient, or compositions thereof.

In another aspect, the present invention provides methods for treating a subject determined to exhibit deregulated activity of c-Myc or other Myc family members (e.g., N-Myc or L-Myc). In some embodiments, the deregulated Myc activity comprises overexpression of c-Myc or other Myc family members (e.g., N-Myc or L-Myc). In some embodiments, the method comprises administering to a subject a compound of Formula (I) or a pharmaceutically acceptable salt, solvate, hydrate, tautomer, stereoisomer, or isotopically labeled derivative thereof, and optionally a pharmaceutically acceptable excipient, or compositions thereof.

In another aspect, the present invention provides methods of reducing transcription of a gene upregulated in a proliferative disease (e.g., cancers (e.g., breast cancer, prostate cancer, lymphoma, lung cancer, pancreatic cancer, ovarian cancer, neuroblastoma, or colorectal cancer), benign neoplasms, angiogenesis, inflammatory diseases, fibrosis (e.g., polycystic kidney disease), autoinflammatory diseases, and autoimmune diseases). In some embodiments, the method comprises administering to a subject a compound of Formula (I) or a pharmaceutically acceptable salt, solvate, hydrate, tautomer, stereoisomer, or isotopically labeled derivative thereof, and optionally a pharmaceutically acceptable excipient, or compositions thereof.

In another aspect, the present invention provides methods of treating a proliferative disease characterized by Myc addiction (e.g., addiction to c-Myc or other Myc family members, e.g., N-Myc or L-Myc). In some embodiments, the method comprises administering to a subject a compound of Formula (I) or a pharmaceutically acceptable salt, solvate, hydrate, tautomer, stereoisomer, or isotopically labeled derivative thereof, and optionally a pharmaceutically acceptable excipient, or compositions thereof.

In another aspect, the present invention provides methods of inducing apoptosis of a cell in a biological sample or a subject. In some embodiments, the apoptosis is triggered by c-Myc or other Myc family members (e.g., N-Myc or L-Myc). In some embodiments, the method comprises administering to a subject a compound of Formula (I) or a pharmaceutically acceptable salt, solvate, hydrate, tautomer, stereoisomer, or isotopically labeled derivative thereof, and optionally a pharmaceutically acceptable excipient, or compositions thereof.

In another aspect, the present invention provides methods of inducing terminal differentiation of a cell in a biological sample or subject. In some embodiments, the terminal differentiation is triggered by c-Myc or other Myc family members (e.g., N-Myc or L-Myc). In some embodiments, the method comprises administering to a subject a compound of Formula (I) or a pharmaceutically acceptable salt, solvate, hydrate, tautomer, stereoisomer, or isotopically labeled derivative thereof, and optionally a pharmaceutically acceptable excipient, or compositions thereof.

In another aspect, the present invention provides methods of inducing senescence of a cell in a biological sample or subject. In some embodiments, the senescence is triggered by c-Myc or other Myc family members (e.g., N-Myc or L-Myc). In some embodiments, the method comprises administering to a subject a compound of Formula (I) or a pharmaceutically acceptable salt, solvate, hydrate, tautomer, stereoisomer, or isotopically labeled derivative thereof, and optionally a pharmaceutically acceptable excipient, or compositions thereof.

In another aspect, the present invention provides methods of disrupting the interaction of one or more bHLH transcription factors, e.g., Myc (e.g., c-Myc or other Myc family members (e.g., N-Myc or L-Myc)), MITF, TWIST1, Max, E2A/TCF3, or HES1, with DNA in a cell. In some embodiments, a compound Formula (I) or a pharmaceutically acceptable salt, solvate, hydrate, tautomer, stereoisomer, or isotopically labeled derivative thereof may disrupt the interaction of one or more bHLH transcription factors, e.g., Myc (e.g., c-Myc or other Myc family members (e.g., N-Myc or L-Myc)), MITF, TWIST1, Max, E2A/TCF3, or HES1, with DNA in a cell.

In another aspect, the present invention provides methods of disrupting the activity of a complex of bHLH transcription factors, e.g., Myc (e.g., c-Myc or other Myc family members (e.g., N-Myc or L-Myc)), MITF, TWIST1, Max, E2A/TCF3, or HES1, in a cell. In some embodiments, a compound Formula (I) or a pharmaceutically acceptable salt, solvate, hydrate, tautomer, stereoisomer, or isotopically labeled derivative thereof may disrupt the activity of a complex of bHLH transcription factors, e.g., Myc (e.g., c-Myc or other Myc family members (e.g., N-Myc or L-Myc)), MITF, TWIST1, Max, E2A/TCF3, or HES1, in a cell.

In yet another aspect, the present invention provides compounds of Formula (I), and pharmaceutically acceptable salts, solvates, hydrates, tautomers, stereoisomers, isotopically labeled derivatives, and compositions thereof, for use in the treatment or prevention of an infectious disease in a subject. In certain embodiments, the infectious disease is a viral infection.

Another aspect of the present invention relates to kits comprising a container with a compound of Formula (I), or a pharmaceutically acceptable salt, solvate, hydrate, tautomer, stereoisomer, or isotopically labeled derivative thereof, or a pharmaceutical composition thereof. In certain embodiments, the kits described herein further include instructions for administering the compound of Formula (I), or the pharmaceutically acceptable salt, solvate, hydrate, tautomer, stereoisomer, or isotopically labeled derivative thereof, or the pharmaceutical composition thereof.

The details of one or more embodiments of the invention are set forth herein. Other features, objects, and advantages of the invention will be apparent from the Detailed Description, the Figures, the Examples, and the Claims.

DEFINITIONS

Definitions of specific functional groups and chemical terms are described in more detail below. The chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

It is to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups and a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The term "tautomers" refer to compounds that are interchangeable forms of a particular compound structure, and that vary in the displacement of hydrogen atoms and electrons. Thus, two structures may be in equilibrium through the movement of π electrons and an atom (usually H). For example, enols and ketones are tautomers because they are rapidly interconverted by treatment with either acid or base. Another example of tautomerism is the aci- and nitro-forms of phenylnitromethane that are likewise formed by treatment with acid or base.

Tautomeric forms may be relevant to the attainment of the optimal chemical reactivity and biological activity of a compound of interest.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}$C- or $^{14}$C-enriched carbon are within the scope of this invention. Such compounds are useful, for example, as analytical tools, as probes in biological assays, or as therapeutic agents in accordance with the present invention.

Where a particular enantiomer is preferred, it may, in some embodiments be provided substantially free of the corresponding enantiomer, and may also be referred to as "optically enriched." "Optically-enriched," as used herein, means that the compound is made up of a significantly greater proportion of one enantiomer. In certain embodiments the compound is made up of at least about 90% by weight of a preferred enantiomer. In other embodiments the compound is made up of at least about 95%, 98%, or 99% by weight of a preferred enantiomer. Preferred enantiomers may be isolated from racemic mixtures by any method known to those skilled in the art, including chiral high pressure liquid chromatography (HPLC) and the formation and crystallization of chiral salts or prepared by asymmetric syntheses. See, for example, Jacques et al., *Enantiomers, Racemates and Resolutions* (Wiley Interscience, New York, 1981); Wilen, et al., *Tetrahedron* 33:2725 (1977); Eliel, E. L. *Stereochemistry of Carbon Compounds* (McGraw-Hill, N Y, 1962); Wilen, S. H. *Tables of Resolving Agents and Optical Resolutions* p. 268 (E. L. Eliel, Ed., Univ. of Notre Dame Press, Notre Dame, Ind. 1972).

The term "aliphatic" or "aliphatic group", as used herein, denotes a hydrocarbon moiety that may be straight-chain (i.e., unbranched), branched, or cyclic (including fused, bridging, and spiro-fused polycyclic) and may be completely saturated or may contain one or more units of unsaturation, but which is not aromatic. Unless otherwise specified, aliphatic groups contain 1-6 carbon atoms. In some embodiments, aliphatic groups contain 1-4 carbon atoms, and in yet other embodiments aliphatic groups contain 1-3 carbon atoms. Suitable aliphatic groups include, but are not limited to, linear or branched, alkyl, alkenyl, and alkynyl groups, and hybrids thereof such as (carbocyclyl)alkyl, (carbocyclyl)alkyl or (carbocyclyl)alkenyl.

The term "alkyl," as used herein, refers to a monovalent saturated, straight- or branched-chain hydrocarbon such as a straight or branched group of 1-12, 1-10, or 1-6 carbon atoms, referred to herein as $C_1$-$C_{12}$ alkyl, $C_1$-$C_{10}$ alkyl, and $C_1$-$C_6$ alkyl, respectively. Examples of alkyl groups include, but are not limited to, methyl, ethyl, n-propyl, isopropyl, n-butyl, iso-butyl, sec-butyl, sec-pentyl, iso-pentyl, tert-butyl, n-pentyl, neopentyl, n-hexyl, sec-hexyl, and the like.

The terms "alkenyl" and "alkynyl" are art-recognized and refer to unsaturated aliphatic groups analogous in length and possible substitution to the alkyls described above, but that contain at least one double or triple bond, respectively. Exemplary alkenyl groups include, but are not limited to, —CH=$CH_2$ and —$CH_2$CH=$CH_2$.

The term "alkylene" refers to the diradical of an alkyl group.

The terms "alkenylene" and "alkynylene" refer to the diradicals of an alkenyl and an alkynyl group, respectively.

The terms "halo" or "halogen" refer to fluorine (fluoro, —F), chlorine (chloro, —Cl), bromine (bromo, —Br), or iodine (iodo, —I).

The term "haloalkyl" refers to a monovalent saturated straight or branched alkyl chain wherein at least one carbon atom in the chain is substituted with a halogen, e.g., F, Cl, Br, or I. In some embodiments, a haloalkyl group may comprise, e.g., 1-12, 1-10, or 1-6 carbon atoms, referred to herein as $C_1$-$C_{12}$ haloalkyl, $C_1$-$C_{10}$ haloalkyl, and $C_1$-$C_6$ haloalkyl. In certain instances, a haloalkyl group comprises 1, 2, 3, or 4 independently selected halogens substituted on 1, 2, 3, or 4 individual carbon atoms in the alkyl chain. In some embodiments, more than one halogen may be substituted on a single carbon atom. Representative haloalkyl groups include —$CH_2$F, —$CF_3$, $CH_2$CH(Cl)$CH_3$, and the like.

The term "haloalkylene" refers to the diradical of a haloalkyl group.

The term "heteroalkyl" refers to a monovalent saturated straight or branched alkyl chain wherein at least one carbon atom in the chain is replaced with a heteroatom, such as O, S, or N. In some embodiments, a heteroalkyl group may comprise, e.g., 1-12, 1-10, or 1-6 carbon atoms, referred to herein as $C_1$-$C_{12}$ heteroalkyl, $C_1$-$C_{10}$ heteroalkyl, and $C_1$-$C_6$ heteroalkyl. In certain instances, a heteroalkyl group comprises 1, 2, 3, or 4 independently selected heteroatoms in place of 1, 2, 3, or 4 individual carbon atoms in the alkyl chain. Representative heteroalkyl groups include —$CH_2CH_2OCH_3$, —$CH_2CH_2NHCH_3$, —$CH_2CH_2N(CH_3)$$CH_3$, and the like.

The term "heteroalkylene" refers to the diradical of a heteralkyl group.

The term "methylene unit" refers to a divalent —$CH_2$— group present in an alkyl, alkenyl, alkynyl, alkylene, alkenylene, or alkynylene moiety.

The term "carbocyclic ring system", as used herein, means a monocyclic, or fused, spiro-fused, and/or bridged bicyclic or polycyclic hydrocarbon ring system, wherein each ring is either completely saturated or contains one or more units of unsaturation, but where no ring is aromatic.

The term "carbocyclyl" refers to a radical of a carbocyclic ring system. Representative carbocyclyl groups include cycloalkyl groups (e.g., cyclopentyl, cyclobutyl, cyclopentyl, cyclohexyl and the like), and cycloalkenyl groups (e.g., cyclopentenyl, cyclohexenyl, cyclopentadienyl, and the like).

The term "aromatic ring system" is art-recognized and refers to a monocyclic, bicyclic or polycyclic hydrocarbon ring system, wherein at least one ring is aromatic.

The term "aryl" refers to a radical of an aromatic ring system. Representative aryl groups include fully aromatic ring systems, such as phenyl, naphthyl, and anthracenyl, and ring systems where an aromatic carbon ring is fused to one or more non-aromatic carbon rings, such as indanyl, phthalimidyl, naphthimidyl, or tetrahydronaphthyl, and the like.

The term "heteroaromatic ring system" is art-recognized and refers to monocyclic, bicyclic or polycyclic ring system wherein at least one ring is both aromatic and comprises a heteroatom; and wherein no other rings are heterocyclyl (as defined below). In certain instances, a ring which is aromatic and comprises a heteroatom contains 1, 2, 3, or 4 independently selected ring heteroatoms in such ring.

The term "heteroaryl" refers to a radical of a heteroaromatic ring system. Representative heteroaryl groups include ring systems where (I) each ring comprises a heteroatom and is aromatic, e.g., imidazolyl, oxazolyl, thiazolyl, triazolyl, pyrrolyl, furanyl, thiophenyl pyrazolyl, pyridinyl, pyrazinyl, pyridazinyl, pyrimidinyl, indolizinyl, purinyl, naphthyridinyl, and pteridinyl; (ii) each ring is aromatic or carbocyclyl, at least one aromatic ring comprises a heteroatom and at least one other ring is a hydrocarbon ring or e.g., indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, carbazolyl, acridinyl, phenazinyl, phenothiazinyl, phenoxazinyl, pyrido[2,3-b]-1,4-oxazin-3(4H)-one, thiazolo-[4,5-c]-pyridinyl, 4,5,6,7-tetrahydrothieno[2,3-c]pyridinyl, 5,6-dihydro-4H-thieno[2,3-c]pyrrolyl, 4,5,6,7,8-tetrahydroquinolinyl and 5,6,7,8-tetrahydroisoquinolinyl; and (iii) each ring is aromatic or carbocyclyl, and at least one aromatic ring shares a bridgehead heteroatom with another aromatic ring, e.g., 4H-quinolizinyl. In certain embodiments, the heteroaryl is a monocyclic or bicyclic ring, wherein each of said rings contains 5 or 6 ring atoms where 1, 2, 3, or 4 of said ring atoms are a heteroatom independently selected from N, O, and S.

The term "heterocyclic ring system" refers to monocyclic, or fused, spiro-fused, and/or bridged bicyclic and polycyclic ring systems where at least one ring is saturated or partially unsaturated (but not aromatic) and comprises a heteroatom. A heterocyclic ring system can be attached to its pendant group at any heteroatom or carbon atom that results in a stable structure and any of the ring atoms can be optionally substituted.

The term "heterocyclyl" refers to a radical of a heterocyclic ring system. Representative heterocyclyls include ring systems in which (i) every ring is non-aromatic and at least one ring comprises a heteroatom, e.g., tetrahydrofuranyl, tetrahydrothienyl, pyrrolidinyl, pyrrolidonyl, piperidinyl, pyrrolinyl, decahydroquinolinyl, oxazolidinyl, piperazinyl, dioxanyl, dioxolanyl, diazepinyl, oxazepinyl, thiazepinyl, morpholinyl, and quinuclidinyl; (ii) at least one ring is non-aromatic and comprises a heteroatom and at least one other ring is an aromatic carbon ring, e.g., 1,2,3,4-tetrahydroquinolinyl; and (iii) at least one ring is non-aromatic and comprises a heteroatom and at least one other ring is aromatic and comprises a heteroatom, e.g., 3,4-dihydro-1H-pyrano[4,3-c]pyridinyl, and 1,2,3,4-tetrahydro-2,6-naphthyridinyl. In certain embodiments, the heterocyclyl is a monocyclic or bicyclic ring, wherein each of said rings contains 3-7 ring atoms where 1, 2, 3, or 4 of said ring atoms are a heteroatom independently selected from N, O, and S.

The term "saturated heterocyclyl" refers to a radical of heterocyclic ring system wherein every ring is saturated, e.g., tetrahydrofuran, tetrahydro-2H-pyran, pyrrolidine, piperidine and piperazine.

"Partially unsaturated" refers to a group that includes at least one double or triple bond. A "partially unsaturated" ring system is further intended to encompass rings having multiple sites of unsaturation, but is not intended to include aromatic groups (e.g., aryl or heteroaryl groups) as herein defined. Likewise, "saturated" refers to a group that does not contain a double or triple bond, i.e., contains all single bonds.

As described herein, compounds of the invention may contain "optionally substituted" moieties. In general, the term "substituted", whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at each position. Combinations of substituents envisioned under this invention are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

Suitable substituents for an optionally substituted alkyl, alkylene, haloalkyl, haloalkylene, heteroalkyl, heteroalkylene, carbocyclyl, heterocyclyl, aryl group and heteroaryl group include halogen, =O, —CN, —OR$^c$, —NR$^d$R$^e$, —S(O)$_k$R$^c$, —NR$^c$S(O)$_2$R$^c$, —S(O)$_2$NR$^d$R$^e$, —C(=O)OR$^c$, —OC(=O)OR$^c$, —OC(=O)R$^c$, —OC(=S)OR$^c$, —C(=S)OR$^c$, —O(C=S)R$^c$, —C(=O)NR$^d$R$^e$, —NR$^c$C(=O)R$^c$, —C(=S)NR$^d$R$^e$, —NR$^c$C(=S)R$^c$, —NR$^c$(C=O)OR$^c$, —O(C=O)NR$^d$R$^e$, —NR$^c$(C=S)OR$^c$, —O(C=S)NR$^d$R$^e$, —NR$^c$(C=O)NR$^d$R$^e$, —NR$^c$(C=S)NR$^d$R$^e$, —C(=S)R$^c$, —C(=O)R$^c$, C$_1$-C$_6$ alkyl, C$_1$-C$_6$ haloalkyl, C$_1$-C$_6$ heteroalkyl, carbocyclyl, (C$_1$-C$_6$-alkylene)-carbocyclyl, (C$_1$-C$_6$-heteroalkylene)-carbocyclyl, heterocyclyl, (C$_1$-C$_6$-alkylene)-heterocyclyl, (C$_1$-C$_6$-heteroalkylene)-heterocyclyl, aryl, (C$_1$-C$_6$-alkylene)-aryl, (C$_1$-C$_6$-heteroalkylene)-aryl, heteroaryl, (C$_1$-C$_6$-alkylene)-heteroaryl, or (C$_1$-C$_6$-heteroalkylene)-heteroaryl, wherein each of said alkyl, alkylene, heteroalkyl, heteroalkylene, carbocyclyl, heterocyclyl, aryl and heteroaryl are optionally substituted with one or more of halogen, OR$^c$, —NO$_2$, —CN, —NR$^c$C(=O)R$^c$, —NR$^d$R$^e$, —S(O)$_k$R$^c$, —C(=O)OR$^c$, —C(=O)NR$^d$R$^e$, —C(=O)R$^c$, C$_1$-C$_6$ alkyl, C$_1$-C$_6$ haloalkyl, or C$_1$-C$_6$ heteroalkyl, and wherein R$^c$ is hydrogen, hydroxy, C$_1$-C$_6$ alkyl, C$_1$-C$_6$ heteroalkyl, carbocyclyl, (C$_1$-C$_6$-alkylene)-carbocyclyl, (C$_1$-C$_6$-heteroalkylene)-carbocyclyl, heterocyclyl, (C$_1$-C$_6$-alkylene)-heterocyclyl, (C$_1$-C$_6$-heteroalkylene)-heterocyclyl, aryl, (C$_1$-C$_6$-alkylene)-aryl, (C$_1$-C$_6$-heteroalkylene)-aryl, heteroaryl, (C$_1$-C$_6$-alkylene)-heteroaryl, or (C$_1$-C$_6$-heteroalkylene)-heteroaryl, each of which is optionally substituted with one or more of halogen, hydroxy, C$_1$-C$_6$ alkyl, C$_1$-C$_6$ haloalkyl, C$_1$-C$_6$ heteroalkyl, carbocyclyl, heterocyclyl, aryl, or heteroaryl; R$^d$ and R$^e$ are each independently selected from hydrogen, C$_1$-C$_6$ alkyl, or C$_1$-C$_6$ heteroalkyl; and k is 0, 1 or 2.

These and other exemplary substituents are described in more detail in the Detailed Description, Figures, Examples, and Claims. The invention is not intended to be limited in any manner by the above exemplary listing of substituents.

Other Definitions

The following definitions are more general terms used throughout the present application:

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid, and perchloric acid or with organic acids such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and N$^+$(C$_{1-4}$ alkyl)$_4^-$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

The term "solvate" refers to forms of the compound that are associated with a solvent, usually by a solvolysis reaction. This physical association may include hydrogen bonding. Conventional solvents include water, methanol, ethanol, acetic acid, DMSO, THF, diethyl ether, and the like. The compounds of Formula (I) may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolable solvates. Representative solvates include hydrates, ethanolates, and methanolates.

The term "hydrate" refers to a compound which is associated with water. Typically, the number of the water molecules contained in a hydrate of a compound is in a definite ratio to the number of the compound molecules in the hydrate. Therefore, a hydrate of a compound may be represented, for example, by the general formula R.x $H_2O$, wherein R is the compound and wherein x is a number greater than 0. A given compound may form more than one type of hydrates, including, e.g., monohydrates (x is 1), lower hydrates (x is a number greater than 0 and smaller than 1, e.g., hemihydrates (R.0.5 $H_2O$)), and polyhydrates (x is a number greater than 1, e.g., dihydrates (R.2 $H_2O$) and hexahydrates (R.6 $H_2O$)).

A "subject" to which administration is contemplated includes, but is not limited to, humans (i.e., a male or female of any age group, e.g., a pediatric subject (e.g., infant, child, adolescent) or adult subject (e.g., young adult, middle-aged adult, or senior adult)) and/or other non-human animals, for example, mammals (e.g., primates (e.g., cynomolgus monkeys, rhesus monkeys); commercially relevant mammals such as cattle, pigs, horses, sheep, goats, cats, and/or dogs) and birds (e.g., commercially relevant birds such as chickens, ducks, geese, and/or turkeys). In certain embodiments, the animal is a mammal. The animal may be a male or female and at any stage of development. A non-human animal may be a transgenic animal.

The terms "administer," "administering," or "administration," as used herein refers to implanting, absorbing, ingesting, injecting, inhaling, or otherwise introducing an inventive compound, or a pharmaceutical composition thereof.

As used herein, the terms "treatment," "treat," and "treating" refer to reversing, alleviating, delaying the onset of, or inhibiting the progress of a "pathological condition" (e.g., a disease, disorder, or condition, or one or more signs or symptoms thereof) described herein. In some embodiments, "treatment," "treat," and "treating" require that signs or symptoms of the disease disorder or condition have developed or have been observed. In other embodiments, treatment may be administered in the absence of signs or symptoms of the disease or condition. For example, treatment may be administered to a susceptible individual prior to the onset of symptoms (e.g., in light of a history of symptoms and/or in light of genetic or other susceptibility factors). Treatment may also be continued after symptoms have resolved, for example, to delay or prevent recurrence.

As used herein, the terms "condition," "disease," and "disorder" are used interchangeably.

An "effective amount" of a compound of Formula (I) refers to an amount sufficient to elicit the desired biological response, i.e., treating the condition. As will be appreciated by those of ordinary skill in this art, the effective amount of a compound of Formula (I) may vary depending on such factors as the desired biological endpoint, the pharmacokinetics of the compound, the condition being treated, the mode of administration, and the age and health of the subject. An effective amount encompasses therapeutic and prophylactic treatment. For example, in treating cancer, an effective amount of an inventive compound may reduce the tumor burden or stop the growth or spread of a tumor.

A "therapeutically effective amount" of a compound of Formula (I) is an amount sufficient to provide a therapeutic benefit in the treatment of a condition or to delay or minimize one or more symptoms associated with the condition. In some embodiments, a therapeutically effective amount is an amount sufficient to provide a therapeutic benefit in the treatment of a condition or to minimize one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces or avoids symptoms or causes of the condition, or enhances the therapeutic efficacy of another therapeutic agent.

A "prophylactically effective amount" of a compound of Formula (I) is an amount sufficient to prevent a condition, or one or more symptoms associated with the condition or prevent its recurrence. A prophylactically effective amount of a compound means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent.

A "proliferative disease" refers to a disease that occurs due to abnormal growth or extension by the multiplication of cells (Walker, *Cambridge Dictionary of Biology*; Cambridge University Press: Cambridge, UK, 1990). A proliferative disease may be associated with: 1) the pathological proliferation of normally quiescent cells; 2) the pathological migration of cells from their normal location (e.g., metastasis of neoplastic cells); 3) the pathological expression of proteolytic enzymes such as the matrix metalloproteinases (e.g., collagenases, gelatinases, and elastases); or 4) the pathological angiogenesis as in proliferative retinopathy and tumor metastasis. Exemplary proliferative diseases include cancers (i.e., "malignant neoplasms"), benign neoplasms, angiogenesis, inflammatory diseases, autoinflammatory diseases, and autoimmune diseases.

The terms "neoplasm" and "tumor" are used herein interchangeably and refer to an abnormal mass of tissue wherein the growth of the mass surpasses and is not coordinated with the growth of a normal tissue. A neoplasm or tumor may be "benign" or "malignant," depending on the following characteristics: degree of cellular differentiation (including morphology and functionality), rate of growth, local invasion, and metastasis. A "benign neoplasm" is generally well differentiated, has characteristically slower growth than a malignant neoplasm, and remains localized to the site of origin. In addition, a benign neoplasm does not have the capacity to infiltrate, invade, or metastasize to distant sites. Exemplary benign neoplasms include, but are not limited to, lipoma, chondroma, adenomas, acrochordon, senile angiomas, seborrheic keratoses, lentigos, and sebaceous hyperplasias. In some cases, certain "benign" tumors may later give rise to malignant neoplasms, which may result from additional genetic changes in a subpopulation of the tumor's neoplastic cells, and these tumors are referred to as "pre-malignant neoplasms." An exemplary pre-malignant neoplasm is a teratoma. In contrast, a "malignant neoplasm" is generally poorly differentiated (anaplasia) and has characteristically rapid growth accompanied by progressive infiltration, invasion, and destruction of the surrounding tissue. Furthermore, a malignant neoplasm generally has the capacity to metastasize to distant sites.

As used herein, the term "cancer" refers to a malignant neoplasm (*Stedman's Medical Dictionary*, 25th ed.; Hensyl ed.; Williams & Wilkins: Philadelphia, 1990). Exemplary cancers include, but are not limited to, acoustic neuroma; adenocarcinoma; adrenal gland cancer; anal cancer; angiosarcoma (e.g., lymphangiosarcoma, lymphangioendotheliosarcoma, hemangiosarcoma); appendix cancer; benign monoclonal gammopathy; biliary cancer (e.g., cholangiocarcinoma); bladder cancer; breast cancer (e.g., adenocarcinoma of the breast, papillary carcinoma of the breast, mammary cancer, medullary carcinoma of the breast); brain cancer (e.g., meningioma, glioblastomas, glioma (e.g., astrocytoma, oligodendroglioma), medulloblastoma); bronchus cancer; carcinoid tumor; cervical cancer (e.g., cervical adenocarcinoma); choriocarcinoma; chordoma; craniopharyngioma; colorectal cancer (e.g., colon cancer, rectal cancer, colorectal adenocarcinoma); connective tissue cancer; epithelial carcinoma; ependymoma; endotheliosarcoma (e.g., Kaposi's sarcoma, multiple idiopathic hemorrhagic sarcoma); endometrial cancer (e.g., uterine cancer, uterine sarcoma); esophageal cancer (e.g., adenocarcinoma of the esophagus, Barrett's adenocarcinoma); Ewing's sarcoma; eye cancer (e.g., intraocular melanoma, retinoblastoma); familiar hypereosinophilia; gall bladder cancer; gastric cancer (e.g., stomach adenocarcinoma); gastrointestinal stromal tumor (GIST); germ cell cancer; head and neck cancer (e.g., head and neck squamous cell carcinoma, oral cancer (e.g., oral squamous cell carcinoma), throat cancer (e.g., laryngeal cancer, pharyngeal cancer, nasopharyngeal cancer, oropharyngeal cancer)); hematopoietic cancers (e.g., leukemia such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL)); lymphoma such as Hodgkin lymphoma (HL) (e.g., B-cell HL, T-cell HL) and non-Hodgkin lymphoma (NHL) (e.g., B-cell NHL such as diffuse large cell lymphoma (DLCL) (e.g., diffuse large B-cell lymphoma), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., Waldenstrim's macroglobulinemia), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphomalleukemia, peripheral T-cell lymphoma (PTCL) (e.g., cutaneous T-cell lymphoma (CTCL) (e.g., mycosis fungoides, Sezary syndrome), angioimmunoblastic T-cell lymphoma, extranodal natural killer T-cell lymphoma, enteropathy type T-cell lymphoma, subcutaneous panniculitis-like T-cell lymphoma, and anaplastic large cell lymphoma); a mixture of one or more leukemial-lymphoma as described above; and multiple myeloma (MM)), heavy chain disease (e.g., alpha chain disease, gamma chain disease, mu chain disease); hemangioblastoma; hypopharynx cancer; inflammatory myofibroblastic tumors; immunocytic amyloidosis; kidney cancer (e.g., nephroblastoma a.k.a. Wilms' tumor, renal cell carcinoma); liver cancer (e.g., hepatocellular cancer (HCC), malignant hepatoma); lung cancer (e.g., bronchogenic carcinoma, small cell lung cancer (SCLC), non-small cell lung cancer (NSCLC), adenocarcinoma of the lung); leiomyosarcoma (LMS); mastocytosis (e.g., systemic mastocytosis); muscle cancer; myelodysplastic syndrome (MDS); mesothelioma; myeloproliferative disorder (MPD) (e.g., polycythemia vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)); neuroblastoma; neurofibroma (e.g., neurofibromatosis (NF) type 1 or type 2, schwannomatosis); neuroendocrine cancer (e.g., gastroenteropancreatic neuroendocrine tumor (GEP-NET), carcinoid tumor); osteosarcoma (e.g., bone cancer); ovarian cancer (e.g., cystadenocarcinoma, ovarian embryonal carcinoma, ovarian adenocarcinoma); papillary adenocarcinoma; pancreatic cancer (e.g., pancreatic adenocarcinoma, intraductal papillary mucinous neoplasm (IPMN), Islet cell tumors); penile cancer (e.g., Paget's disease of the penis and scrotum); pinealoma; primitive neuroectodermal tumor (PNT); plasma cell neoplasia; paraneoplastic syndromes; intraepithelial neoplasms; prostate cancer (e.g., prostate adenocarcinoma); rectal cancer; rhabdomyosarcoma; salivary gland cancer; skin cancer (e.g., squamous cell carcinoma (SCC), keratoacanthoma (KA), melanoma, basal cell carcinoma (BCC)); small bowel cancer (e.g., appendix cancer); soft tissue sarcoma (e.g., malignant fibrous histiocytoma (MFH), liposarcoma, malignant peripheral nerve sheath tumor (MPNST), chondrosarcoma, fibrosarcoma, myxosarcoma); sebaceous gland carcinoma; small intestine cancer; sweat gland carcinoma; synovioma; testicular cancer (e.g., seminoma, testicular embryonal carcinoma); thyroid cancer (e.g., papillary carcinoma of the thyroid, papillary thyroid carcinoma (PTC), medullary thyroid cancer); urethral cancer; vaginal cancer; and vulvar cancer (e.g., Paget's disease of the vulva).

The term "angiogenesis" refers to the formation and the growth of new blood vessels. Normal angiogenesis occurs in the healthy body of a subject for healing wounds and for restoring blood flow to tissues after injury. The healthy body controls angiogenesis through a number of means, e.g., angiogenesis-stimulating growth factors and angiogenesis inhibitors. Many disease states, such as cancer, diabetic blindness, age-related macular degeneration, rheumatoid arthritis, and psoriasis, are characterized by abnormal (i.e., increased or excessive) angiogenesis. Abnormal angiogenesis refers to angiogenesis greater than that in a normal body, especially angiogenesis in an adult not related to normal angiogenesis (e.g., menstruation or wound healing). Abnormal angiogenesis can provide new blood vessels that feed diseased tissues and/or destroy normal tissues, and in the case of cancer, the new vessels can allow tumor cells to escape into the circulation and lodge in other organs (tumor metastases).

As used herein, an "inflammatory disease" refers to a disease caused by, resulting from, or resulting in inflammation. The term "inflammatory disease" may also refer to a dysregulated inflammatory reaction that causes an exaggerated response by macrophages, granulocytes, and/or T-lymphocytes leading to abnormal tissue damage and/or cell death. An inflammatory disease can be either an acute or chronic inflammatory condition and can result from infections or non-infectious causes. Inflammatory diseases include, without limitation, atherosclerosis, arteriosclerosis, autoimmune disorders, multiple sclerosis, systemic lupus erythematosus, polymyalgia rheumatica (PMR), gouty arthritis, degenerative arthritis, tendonitis, bursitis, psoriasis, cystic fibrosis, arthrosteitis, rheumatoid arthritis, inflammatory arthritis, Sjogren's syndrome, giant cell arteritis, progressive systemic sclerosis (scleroderma), ankylosing spondylitis, polymyositis, dermatomyositis, pemphigus, pemphigoid, diabetes (e.g., Type I), myasthenia gravis, Hashimoto's thyroiditis, Graves' disease, Goodpasture's disease, mixed connective tissue disease, sclerosing cholangitis, inflammatory bowel disease, Crohn's disease, ulcerative colitis, pernicious anemia, inflammatory dermatoses, usual interstitial pneumonitis (UIP), asbestosis, silicosis, bronchiectasis, berylliosis, talcosis, pneumoconiosis, sarcoidosis, desquamative interstitial pneumonia, lymphoid interstitial pneumonia, giant cell interstitial pneumonia, cellular interstitial pneumonia, extrinsic allergic alveolitis, Wegener's granulomatosis and related forms of angiitis (temporal arteritis and polyarteritis nodosa), inflammatory dermatoses, hepatitis, delayed-type hypersensitivity reactions (e.g., poison ivy dermatitis), pneumonia, respiratory tract inflammation, Adult Respiratory Distress Syndrome (ARDS), encephalitis, immediate hypersensitivity reactions, asthma, hayfever, allergies, acute anaphylaxis, rheumatic fever, glomerulonephritis, pyelonephritis, cellulitis, cystitis, chronic cholecystitis, ischemia (ischemic injury), reperfusion injury, allograft rejection, host-versus-graft rejection, appendicitis, arteritis, blepharitis, bronchiolitis, bronchitis, cervicitis, cholangitis, chorioamnionitis, conjunctivitis, dacryoadenitis, dermatomyositis, endocarditis, endometritis, enteritis, enterocolitis, epicondylitis, epididymitis, fasciitis, fibrositis, gastritis, gastroenteritis, gingivitis, ileitis, iritis, laryngitis, myelitis, myocarditis, nephritis, omphalitis, oophoritis, orchitis, osteitis, otitis, pancreatitis, parotitis, pericarditis, pharyngitis, pleuritis, phlebitis, pneumonitis, proctitis, prostatitis, rhinitis, salpingitis, sinusitis, stomatitis, synovitis, testitis, tonsillitis, urethritis, urocystitis, uveitis, vaginitis, vasculitis, vulvitis, vulvovaginitis, angitis, chronic bronchitis, osteomyelitis, optic neuritis, temporal arteritis, transverse myelitis, necrotizing fasciitis, and necrotizing enterocolitis.

As used herein, an "autoimmune disease" refers to a disease arising from an inappropriate immune response of the body of a subject against substances and tissues normally present in the body. In other words, the immune system mistakes some part of the body as a pathogen and attacks its own cells. This may be restricted to certain organs (e.g., in autoimmune thyroiditis) or involve a particular tissue in different places (e.g., Goodpasture's disease which may affect the basement membrane in both the lung and kidney). The treatment of autoimmune diseases is typically with immunosuppression, e.g., medications which decrease the immune response. Exemplary autoimmune diseases include, but are not limited to, glomerulonephritis, Goodpasture's syndrome, necrotizing vasculitis, lymphadenitis, peri-arteritis nodosa, systemic lupus erythematosis, rheumatoid, arthritis, psoriatic arthritis, systemic lupus erythematosis, psoriasis, ulcerative colitis, systemic sclerosis, dermatomyositis/polymyositis, anti-phospholipid antibody syndrome, scleroderma, pemphigus vulgaris, ANCA-associated vasculitis (e.g., Wegener's granulomatosis, microscopic polyangiitis), uveitis, Sjogren's syndrome, Crohn's disease, Reiter's syndrome, ankylosing spondylitis, Lyme arthritis, Guillain-Barré syndrome, Hashimoto's thyroiditis, and cardiomyopathy.

The term "autoinflammatory disease" refers to a category of diseases that are similar but different from autoimmune diseases. Autoinflammatory and autoimmune diseases share common characteristics in that both groups of disorders result from the immune system attacking a subject's own tissues and result in increased inflammation. In autoinflammatory diseases, a subject's innate immune system causes inflammation for unknown reasons. The innate immune system reacts even though it has never encountered autoantibodies or antigens in the subject. Autoinflammatory disorders are characterized by intense episodes of inflammation that result in such symptoms as fever, rash, or joint swelling. These diseases also carry the risk of amyloidosis, a potentially fatal buildup of a blood protein in vital organs. Autoinflammatory diseases include, but are not limited to, familial Mediterranean fever (FMF), neonatal onset multisystem inflammatory disease (NOMID), tumor necrosis factor (TNF) receptor-associated periodic syndrome (TRAPS), deficiency of the interleukin-1 receptor antagonist (DIRA), and Behcet's disease.

The term "biological sample" refers to any sample including tissue samples (such as tissue sections and needle biopsies of a tissue); cell samples (e.g., cytological smears (such as Pap or blood smears) or samples of cells obtained by microdissection); samples of whole organisms (such as samples of yeasts or bacteria); or cell fractions, fragments or organelles (such as obtained by lysing cells and separating the components thereof by centrifugation or otherwise). Other examples of biological samples include blood, serum, urine, semen, fecal matter, cerebrospinal fluid, interstitial fluid, mucus, tears, sweat, pus, biopsied tissue (e.g., obtained by a surgical biopsy or needle biopsy), nipple aspirates, milk, vaginal fluid, saliva, swabs (such as buccal swabs), or any material containing biomolecules that is derived from a first biological sample. Biological samples also include those biological samples that are transgenic, such as transgenic oocyte, sperm cell, blastocyst, embryo, fetus, donor cell, or cell nucleus.

DETAILED DESCRIPTION OF CERTAIN EMBODIMENTS OF THE INVENTION

Compounds

In one embodiment of the present invention, provided are compounds of Formula (I):

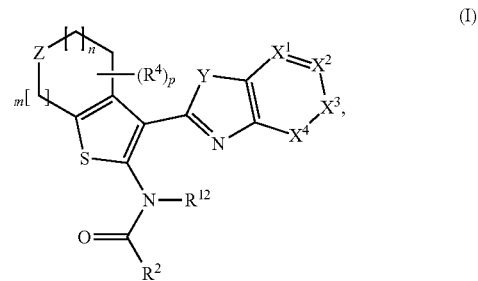

or a pharmaceutically acceptable salt solvate, hydrate, tautomer, or stereoisomer thereof, wherein:

each of $X^1$, $X^2$, $X^3$ and $X^4$ is independently selected from C(R), N and N(O), wherein one or two of $X^1$, $X^2$, $X^3$ and $X^4$ is N or one of $X^1$, $X^2$, $X^3$ and $X^4$ is N(O);

each R is independently selected from hydrogen, halogen, —CN, $C_1$-$C_8$ alkyl, $C_1$-$C_8$ heteroalkyl, $N(R^{3a})(R^{3b})$, C(O)($C_1$-$C_6$ alkyl), $C(O)O(C_1$-$C_6$ alkyl), ($C_0$-$C_6$ alkylene)-carbocyclyl, ($C_1$-$C_6$ heteroalkylene)-carbocyclyl, ($C_0$-$C_6$ alkylene)-heterocyclyl, ($C_1$-$C_6$ heteroalkylene)-heterocyclyl, ($C_0$-$C_6$ alkylene)-aryl, ($C_1$-$C_6$ heteroalkylene)-aryl, and ($C_0$-$C_6$ alkylene)-heteroaryl, wherein any alkyl, alkylene, heteroalkyl, heteroalkylene, carbocyclyl, heterocyclyl, aryl or heteroaryl portion of R is optionally and independently substituted;

Y is selected from O, S and $N(R^{3a})$;

Z is selected from $C(R^{4a})(N(R^5)(R^6))$ and $N(R^1)$;

$R^1$ is selected from hydrogen, $C_1$-$C_6$ alkyl, $C_1$-$C_6$ heteroalkyl, ($C_0$-$C_6$ alkylene)-carbocyclyl, ($C_1$-$C_6$ heteroalkylene)-carbocyclyl, ($C_0$-$C_6$ alkylene)-heterocyclyl, ($C_1$-$C_6$ heteroalkylene)-heterocyclyl, ($C_0$-$C_6$ alkylene)-aryl, ($C_1$-$C_6$ heteroalkylene)-aryl, ($C_0$-$C_6$ alkylene)-heteroaryl, ($C_1$-$C_6$ heteroalkylene)-heteroaryl, $CH_2C(O)OR^7$, $CH_2C(O)N(R^{10})(R^{11})$, and $CH_2CH_2N(R^{10})(R^{11})$, wherein:

$R^{10}$ is hydrogen or $C_1$-$C_4$ alkyl;

$R^{11}$ is selected from hydrogen, $C_1$-$C_4$ alkyl, $C_1$-$C_4$ heteroalkyl, ($C_0$-$C_4$ alkylene)-carbocyclyl, ($C_0$-$C_4$ alkylene)-heterocyclyl, ($C_0$-$C_4$ alkylene)-aryl, ($C_0$-$C_4$ alkylene)-heteroaryl, ($C_1$-$C_4$ alkyl)-O—($C_1$-$C_4$ alkyl), ($C_1$-$C_4$ alkyl)-N—($C_1$-$C_4$ alkyl)$_2$, ($C_1$-$C_4$ alkyl)-NH—($C_1$-$C_4$ alkyl), C(O)—($C_1$-$C_4$ alkyl), and C(O)—O—($C_1$-$C_4$ alkyl), or $R^{10}$ and $R^{11}$ are taken together with the nitrogen atom to which they are commonly bound to form a 4-11 membered heterocyclyl or heteroaryl; and any alkyl, alkylene, heteroalkyl, heteroalkylene, heterocyclyl, heteroaryl, aryl or carbocyclyl portion of $R^1$ is optionally substituted;

$R^2$ is selected from $C(R^{2a})(R^{2b})(R^{2c})$, carbocyclyl, aryl, heterocyclyl and heteroaryl, wherein any carbocyclyl, aryl, heterocyclyl and heteroaryl is optionally substituted;

$R^{2a}$ is selected from hydrogen, halogen, —CN, $C_1$-$C_4$ alkyl, $C_1$-$C_4$ heteroalkyl and $C_1$-$C_4$ haloalkyl, wherein any alkyl, heteroalkyl or haloalkyl is optionally substituted;

each of $R^{2b}$ and $R^{2c}$ is independently selected from hydrogen, halogen, —CN, $C_1$-$C_6$ alkyl, $C_1$-$C_6$ heteroalkyl, C(O)($C_1$-$C_6$ alkyl), C(O)($C_1$-$C_6$ heteroalkyl), C(O)O($C_1$-$C_6$ alkyl), C(O)O($C_1$-$C_6$ heteroalkyl), $C(O)N(R^{3a})(R^{3b})$, ($C_0$-$C_6$ alkylene)-carbocyclyl, ($C_1$-$C_6$ heteroalkylene)-carbocyclyl, ($C_0$-$C_6$ alkylene)-heterocyclyl, ($C_1$-$C_6$ heteroalkylene)-heterocyclyl, ($C_0$-$C_6$ alkylene)-aryl, ($C_1$-$C_6$ heteroalkylene)-aryl, ($C_0$-$C_6$ alkylene)-heteroaryl and ($C_1$-$C_6$ heteroalkylene)-heteroaryl, wherein any alkyl, alkylene, heteroalkyl, heteroalkylene, carbocyclyl, heterocyclyl, aryl or heteroaryl portion of $R^{2b}$ and $R^{2c}$ is optionally and independently substituted;

each of $R^{3a}$ and $R^{3b}$ is independently selected from hydrogen, $C_1$-$C_6$ alkyl, or $C_1$-$C_6$ heteroalkyl, each of which is optionally substituted;

each $R^4$ is independently selected from halogen, —CN, $C_1$-$C_8$ alkyl, $C_1$-$C_8$ heteroalkyl, $N(R^{3a})(R^{3b})$, C(O)($C_1$-$C_6$ alkyl), C(O)($C_1$-$C_6$ heteroalkyl), C(O)O($C_1$-$C_6$ alkyl), $C(O)N(R^{3a})(R^{3b})$, ($C_0$-$C_6$ alkylene)-carbocyclyl, ($C_1$-$C_6$ heteroalkylene)-carbocyclyl, ($C_0$-$C_6$ alkylene)-heterocyclyl, ($C_1$-$C_6$ heteroalkylene)-heterocyclyl, ($C_0$-$C_6$ alkylene)-aryl, ($C_1$-$C_6$ heteroalkylene)-aryl, ($C_0$-$C_6$ alkylene)-heteroaryl, and ($C_1$-$C_6$ heteroalkylene)-heteroaryl, wherein any alkyl, alkylene, heteroalkyl, heteroalkylene, carbocyclyl, heterocyclyl, aryl or heteroaryl portion of $R^4$ is optionally and independently substituted;

$R^{4a}$ is selected from hydrogen and $C_1$-$C_6$ alkyl;

each of $R^5$ and $R^6$ is independently selected from hydrogen, $C_1$-$C_6$ alkyl, $C_1$-$C_6$ heteroalkyl, C(O)($C_1$-$C_6$ alkyl), C(O)O($C_1$-$C_6$ alkyl), ($C_0$-$C_6$ alkylene)-carbocyclyl, ($C_1$-$C_6$ heteroalkylene)-carbocyclyl, ($C_0$-$C_6$ alkylene)-heterocyclyl, ($C_1$-$C_6$ heteroalkylene)-heterocyclyl, ($C_0$-$C_6$ alkylene)-aryl, ($C_1$-$C_6$ heteroalkylene)-aryl, ($C_0$-$C_6$ alkylene)-heteroaryl, and ($C_1$-$C_6$ heteroalkylene)-heteroaryl, wherein any alkyl, alkylene, heteroalkyl, heteroalkylene, carbocyclyl, heterocyclyl, aryl or heteroaryl portion of each of $R^5$ and $R^6$ is optionally and independently substituted; or $R^5$ and $R^6$ are taken together with the nitrogen atom to which they are commonly bound to form an optionally substituted heterocyclyl;

$R^{12}$ is hydrogen, $C_1$-$C_6$ alkyl, $C_1$-$C_6$ heteroalkyl, ($C_0$-$C_3$ alkylene)-carbocyclyl, ($C_0$-$C_3$ alkylene)-heterocyclyl;

n is 0, 1 or 2;

m is 0, 1 or 2;

n+m=1, 2 or 3; and p is 0, 1, 2, 3, 4, 5 or 6.

In certain embodiments, one or two of $X^1$, $X^2$, $X^3$, and $X^4$ is each independently N and the others of $X^1$, $X^2$, $X^3$, and $X^4$ are each independently C(R). In certain embodiments, one of $X^1$, $X^2$, $X^3$, and $X^4$ is each independently N or N(O) and the others of $X^1$, $X^2$, $X^3$, and $X^4$ are independently C(R). In certain embodiments, one of $X^1$, $X^2$, $X^3$, and $X^4$ is each independently N and the others of $X^1$, $X^2$, $X^3$, and $X^4$ are independently C(R).

In certain embodiments, $X^1$ is N or N(O), and each of $X^2$, $X^3$, and $X^4$ is independently C(R). In certain embodiments, $X^2$ is N or N(O), and each of X, $X^3$, and $X^4$ is independently C(R). In certain embodiments, $X^3$ is N or N(O), and each of $X^1$, $X^2$, and $X^4$ is independently C(R). In certain embodiments, $X^4$ is N or N(O), and each of $X^1$, $X^2$, and $X^3$ is independently C(R). In certain embodiments, $X^3$ is N, and each of $X^1$, $X^2$, and $X^4$ is independently C(R).

In certain embodiments, R is independently selected from hydrogen, halogen, $C_1$-$C_8$ alkyl, $C_1$-$C_8$ heteroalkyl, $N(R^{3a})(R^{3b})$, C(O)($C_1$-$C_6$ alkyl), and C(O)O($C_1$-$C_6$ alkyl), wherein any alkyl or heteroalkyl is optionally substituted. In certain embodiments, R is independently selected from hydrogen, halogen, $C_1$-$C_4$ alkyl, $C_1$-$C_4$ heteroalkyl, $N(R^{3a})(R^{3b})$, C(O)($C_1$-$C_4$ alkyl), and C(O)O($C_1$-$C_4$ alkyl), wherein any alkyl or heteroalkyl is optionally substituted. In certain embodiments, R is independently selected from hydrogen, halogen, optionally substituted $C_1$-$C_4$ alkyl, and C(O)O($C_1$-$C_4$ alkyl). In certain embodiments, R is independently selected from hydrogen, halogen, optionally substituted methyl, and C(O)O($C_1$-$C_2$ alkyl). In certain embodiments, R is independently selected from hydrogen, fluoro, chloro, bromo, $C(O)OCH_3$, and methyl optionally substituted with halogen. In certain embodiments, R is independently selected from hydrogen, fluoro, chloro, bromo, methyl, $CHF_2$, and $C(O)OCH_3$.

In certain embodiments, each R is independently selected from hydrogen, halogen and optionally substituted methyl. In certain embodiments, R is independently selected from hydrogen, chloro, —$CH_3$ and —$CHF_2$. In certain embodiments, R is hydrogen.

In certain embodiments, Y is selected from O and S. In certain embodiments, Y is O. In certain embodiments, Y is S.

In certain embodiments, Y is $N(R^{3a})$, and $R^{3a}$ is hydrogen.

In certain embodiments, Z is $N(R^1)$. In certain embodiments, Z is $N(R^1)$, and $R^1$ is selected from hydrogen, $C_1$-$C_6$ alkyl, $C_1$-$C_6$ heteroalkyl, ($C_0$-$C_6$ alkylene)-heterocyclyl, ($C_1$-$C_6$ heteroalkylene)-heterocyclyl, $CH_2C(O)OR^7$, $CH_2C(O)N(R^{10})(R^{11})$, and $CH_2CH_2N(R^{10})(R^{11})$, wherein $R^{10}$ is hydrogen or methyl and $R^{11}$ is selected from hydrogen, $C_1$-$C_4$ alkyl, ($C_0$-$C_2$ alkylene)-carbocyclyl, ($C_0$-$C_2$ alkylene)-heterocyclyl, ($C_1$-$C_3$ alkyl)-O—($C_1$-$C_4$ alkyl), and C(O)—O—($C_1$-$C_4$ alkyl), or $R^{10}$ and $R^{11}$ are taken together with the nitrogen to which they are commonly bound to form a 4-11 membered heterocyclyl, and any alkyl, alkylene, heteroalkyl, heteroalkylene, carbocyclyl or heterocyclyl portion of $R^1$ is optionally substituted.

In certain embodiments, $R^1$ is selected from hydrogen, $C_1$-$C_6$ alkyl, $C_1$-$C_6$ heteroalkyl, ($C_0$-$C_6$ alkylene)-heterocyclyl, ($C_1$-$C_6$ heteroalkylene)-heterocyclyl, $CH_2C(O)OR^7$, $CH_2C(O)N(R^1)(R^{11})$, and $CH_2CH_2N(R^1)(R^{11})$, wherein $R^{10}$ is hydrogen or methyl and $R^{11}$ is selected from hydrogen, $C_1$-$C_4$ alkyl, ($C_0$-$C_2$ alkylene)-carbocyclyl, ($C_0$-$C_2$ alkylene)-heterocyclyl, ($C_1$-$C_3$ alkyl)-O—($C_1$-$C_4$ alkyl), and C(O)—O—($C_1$-$C_4$ alkyl), or $R^{10}$ and $R^{11}$ are taken together with the nitrogen to which they are commonly bound to form a 4-11 membered heterocyclyl, and any alkyl, alkylene, heteroalkyl, carbocyclyl or heterocyclyl portion of $R^1$ is optionally substituted with up to three substituents independently selected from halogen, hydroxy, methyl, —$NH_2$, —$NH(CH_3)$—, —$N(CH_3)_2$, —$CH_2NH_2$, —$CH_2CH_2NH_2$, and heteroaryl.

In certain embodiments, $R^1$ is selected from hydrogen, methyl, ethyl, isopropyl, oxetan-3-yl, morpholin-4-ylpropan-2-yl, 1-methylpiperazin-4-ylcarbonylmethyl, 2-(pyridin-3-yl)ethylaminocarbonylmethyl, 1-(1H-imidazol-4-yl)methylaminocarbonylmethyl, 3,4-dihydroisoquinolin-2(1H)-ylcarbonylmethyl, 4-(1H-tetrazol-5-yl)phenylaminocarbonylmethyl, 4-(dimethylamino)phenylaminocarbonylmethyl, 1-(4,6-dimethyl-2-oxo-(pyridine-3-yl))methylaminocarbonylmethyl, 2-aminoethyl, 2-(1-methoxy)ethylaminocarbonylmethyl, 2-(morpholin-4-yl)ethyl, and 2-(tert-butoxycarbonylamino)ethyl.

In certain embodiments, $R^1$ is selected from hydrogen, $C_1$-$C_6$ alkyl, and ($C_0$-$C_6$ alkylene)-heterocyclyl, and any alkyl, alkylene, or heterocyclyl portion of $R^1$ is optionally substituted.

In certain embodiments, $R^1$ is selected from hydrogen, methyl, ethyl, isopropyl, ($C_0$-$C_6$ alkylene)-morpholin-4-yl, and $CH_2CH_2N(R^{10})(R^{11})$, wherein each of $R^{10}$ and $R^{11}$ is independently hydrogen or methyl.

In certain embodiments, $R^1$ is selected from hydrogen, methyl, ethyl, isopropyl, —$(CH_2)_2NH_2$,

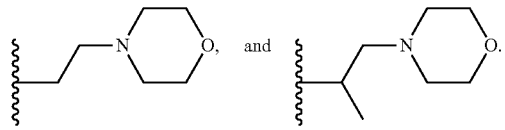

In some embodiments, $R^1$ is selected from hydrogen, isopropyl and ethyl. In some embodiments, $R^1$ is hydrogen. In some embodiments, $R^1$ is isopropyl. In some embodiments, $R^1$ is ethyl.

In certain embodiments, Z is $C(R^{4a})(N(R^5)(R^6))$. In certain embodiments, Z is $C(R^{4a})(N(R^5)(R^6))$, $R^{4a}$ is selected from hydrogen and $C_1$-$C_6$ alkyl, $R^5$ is selected from hydrogen and optionally substituted $C_1$-$C_6$ alkyl, and $R^6$ is selected from hydrogen, $C_1$-$C_6$ alkyl, C(O)($C_1$-$C_6$ alkyl), C(O)O($C_1$-$C_6$ alkyl), ($C_0$-$C_6$ alkylene)-heterocyclyl, ($C_0$-$C_6$ alkylene)-heteroaryl, wherein any alkyl, heterocyclyl, or heteroaryl portion of $R^{4a}$, $R^5$ or $R^6$ is optionally and independently substituted. In some embodiments, Z is $C(R^{4a})(N(R^5)(R^6))$, $R^{4a}$ is selected from hydrogen and $C_1$-$C_6$ alkyl, and $R^5$ and $R^6$ are taken together with the nitrogen atom to which they are commonly bound to form an optionally substituted heterocyclyl.

In certain embodiments, Z is $C(R^{4a})(N(R^5)(R^6))$, $R^{4a}$ is hydrogen, $R^5$ is selected from hydrogen and $C_1$-$C_6$ alkyl, and $R^6$ is selected from hydrogen, $C_1$-$C_6$ alkyl, C(O)($C_1$-$C_6$ alkyl), C(O)O($C_1$-$C_6$ alkyl), ($C_0$-$C_6$ alkylene)-heterocyclyl, and ($C_0$-$C_6$ alkylene)-heteroaryl, wherein any alkyl, heterocyclyl, or heteroaryl portion of $R^5$ or $R^6$ is optionally and independently substituted.

In certain embodiments, Z is $C(R^{4a})(N(R^5)(R^6))$, $R^{4a}$ is hydrogen, $R^5$ is hydrogen or methyl, and $R^6$ is selected from hydrogen, $C_1$-$C_6$ alkyl, C(O)($C_1$-$C_6$ alkyl), ($C_0$-$C_6$ alkylene)-heterocyclyl, and ($C_0$-$C_6$ alkylene)-heteroaryl, wherein any alkyl, heterocyclyl, or heteroaryl portion of $R^5$ or $R^6$ is optionally and independently substituted.

In certain embodiments, Z is $C(R^{4a})(N(R^5)(R^6))$, $R^{4a}$ is hydrogen, $R^5$ is hydrogen or methyl, and $R^6$ is selected from hydrogen, methyl, C(O)$CH_3$, piperidin-4-yl, piperidin-4-ylmethyl, pyridin-4-yl, pyridin-4-ylmethyl, 1-tert-butoxycarbonylpiperidin-4-yl, and tetrahydropyran-4-yl, each of which is optionally and independently substituted.

In certain embodiments, Z is $C(R^{4a})(N(R^5)(R^6))$, $R^{4a}$ is hydrogen, and each of $R^5$ and $R^6$ is independently selected from hydrogen or $C_1$-$C_6$ alkyl, wherein any alkyl portion of $R^5$ or $R^6$ is optionally and independently substituted.

In certain embodiments, Z is $C(R^{4a})(N(R^5)(R^6))$, $R^{4a}$ is hydrogen, and each of $R^5$ and $R^6$ is independently hydrogen or methyl.

In certain embodiments, Z is $C(R^{4a})(N(R^5)(R^6))$, $R^{4a}$ is hydrogen, and each of $R^5$ and $R^6$ is independently hydrogen.

In certain embodiments, $R^2$ is selected from $C(R^{2a})(R^{2b})(R^{2c})$, carbocyclyl, heterocyclyl, and heteroaryl, each of which is optionally substituted. In certain embodiments, $R^2$ is selected from $C(R^{2a})(R^{2b})(R^{2c})$ and heteroaryl, each of which is optionally substituted.

In certain embodiments, $R^2$ is $C(R^{2a})(R^{2b})(R^{2c})$. In certain embodiments, $R^2$ is $C(R^{2a})(R^{2b})(R^{2c})$, $R^{2a}$ is selected from hydrogen, halogen, $C_1$-$C_6$ alkyl, and $C_1$-$C_6$ heteroalkyl, and each of $R^{2b}$ and $R^{2c}$ is independently selected from hydrogen, $C_1$-$C_6$ alkyl, $C_1$-$C_6$ heteroalkyl, C(O)($C_1$-$C_6$ alkyl), C(O)($C_1$-$C_6$ heteroalkyl), C(O)O($C_1$-$C_6$ alkyl), C(O)N($R^{3a}$)($R^{3b}$), ($C_0$-$C_6$ alkylene)-carbocyclyl, ($C_1$-$C_6$ heteroalkylene)-carbocyclyl, ($C_0$-$C_6$ alkylene)-heterocyclyl, ($C_1$-$C_6$ heteroalkylene)-heterocyclyl, ($C_0$-$C_6$ alkylene)-aryl, ($C_1$-$C_6$ heteroalkylene)-aryl, ($C_0$-$C_6$ alkylene)-heteroaryl, and ($C_1$-$C_6$ heteroalkylene)-heteroaryl, wherein any alkyl, alkylene, heteroalkyl, heteroalkylene, carbocyclyl, heterocyclyl, aryl, or heteroaryl portion of $R^{2a}$, $R^{2b}$ and $R^{2c}$ is optionally substituted.

In certain embodiments, $R^2$ is $C(R^{2a})(R^{2b})(R^{2c})$, $R^{2a}$ is hydrogen, and each of $R^{2b}$ and $R^{2c}$ is independently selected from hydrogen, $C_1$-$C_6$ alkyl, $C_1$-$C_6$ heteroalkyl, C(O)($C_1$-$C_6$ alkyl), C(O)($C_1$-$C_6$ heteroalkyl), C(O)O($C_1$-$C_6$ alkyl), C(O)N($R^{3a}$)($R^{3b}$), ($C_1$-$C_6$ alkylene)-carbocyclyl, ($C_1$-$C_6$ heteroalkylene)-carbocyclyl, ($C_0$-$C_6$ alkylene)-heterocyclyl, ($C_1$-$C_6$ heteroalkylene)-heterocyclyl, ($C_0$-$C_6$ alkylene)-aryl, ($C_1$-$C_6$ heteroalkylene)-aryl, ($C_0$-$C_6$ alkylene)-heteroaryl, and ($C_1$-$C_6$ heteroalkylene)-heteroaryl, wherein any alkyl, alkylene, heteroalkyl, heteroalkylene, carbocyclyl, heterocyclyl, aryl, or heteroaryl portion of $R^{2b}$ and $R^{2c}$ is optionally and independently substituted.

In certain embodiments, $R^2$ is $C(R^{2a})(R^{2b})(R^{2c})$, $R^{2a}$ is hydrogen, and each of $R^{2b}$ and $R^{2c}$ is independently selected from hydrogen, $C_1$-$C_6$ alkyl, $C_1$-$C_6$ heteroalkyl, C(O)($C_1$-$C_6$ alkyl), C(O)N($R^{3a}$)($R^{3b}$), ($C_0$-$C_6$ alkylene)-carbocyclyl, ($C_1$-$C_6$ heteroalkylene)-carbocyclyl, ($C_0$-$C_6$ alkylene)-heterocyclyl, ($C_1$-$C_6$ heteroalkylene)-heterocyclyl, ($C_0$-$C_6$ alkylene)-aryl, ($C_1$-$C_6$ heteroalkylene)-aryl, ($C_0$-$C_6$ alkylene)-heteroaryl, and ($C_1$-$C_6$ heteroalkylene)-heteroaryl, wherein any alkyl, alkylene, heteroalkyl, heteroalkylene, carbocyclyl, heterocyclyl, aryl, or heteroaryl portion of $R^{2b}$ and $R^{2c}$ is optionally and independently substituted with halogen, hydroxy, $C_1$-$C_6$ alkyl, $C_1$-$C_6$ heteroalkyl, =O, O—($C_1$-$C_6$ alkyl), heterocyclyl, or heteroaryl, each of which is optionally substituted.

In certain embodiments, $R^2$ is $C(R^{2a})(R^{2b})(R^{2c})$, $R^{2a}$ is hydrogen, $R^{2b}$ is hydrogen or $C_1$-$C_6$ alkyl, and $R^{2c}$ is selected from hydrogen, $C_1$-$C_6$ alkyl, $C_1$-$C_6$ heteroalkyl, C(O)($C_1$-$C_6$ alkyl), C(O)N($R^{3a}$)($R^{3b}$), ($C_0$-$C_6$ alkylene)-carbocyclyl, ($C_1$-$C_6$ heteroalkylene)-carbocyclyl, ($C_0$-$C_6$ alkylene)-heterocyclyl, ($C_1$-$C_6$ heteroalkylene)-heterocyclyl, ($C_0$-$C_6$ alkylene)-aryl, ($C_1$-$C_6$ heteroalkylene)-aryl, ($C_0$-$C_6$ alkylene)-heteroaryl, and ($C_1$-$C_6$ heteroalkylene)-heteroaryl, wherein any alkyl, alkylene, heteroalkyl, heteroalkylene, carbocyclyl, heterocyclyl, aryl, or heteroaryl portion of $R^{2b}$ and $R^{2c}$ is optionally and independently substituted.

In certain embodiments, $R^2$ is $C(R^{2a})(R^{2b})(R^{2c})$, $R^{2a}$ is hydrogen, $R^{2b}$ is hydrogen or $C_1$-$C_6$ alkyl, and $R^{2c}$ is selected from hydrogen, $C_1$-$C_6$ alkyl, $C_1$-$C_6$ heteroalkyl, $C(O)(C_1$-$C_6$ alkyl), or $C(O)N(R^{3a})(R^{3b})$, wherein any alkyl or heteroalkyl portion of $R^{2c}$ is optionally substituted.

In certain embodiments, $R^2$ is $C(R^{2a})(R^{2b})(R^{2c})$, $R^{2a}$ is hydrogen, $R^{2b}$ is hydrogen, and $R^{2c}$ is selected from hydrogen, $C_1$-$C_6$ alkyl, $C_1$-$C_6$ heteroalkyl, $C(O)(C_1$-$C_6$ alkyl), or $C(O)N(R^{3a})(R^{3b})$, wherein any alkyl or heteroalkyl portion of $R^{2b}$ and $R^{2c}$ is optionally and independently substituted with $C_1$-$C_6$ alkyl.

In certain embodiments, $R^2$ is $C(R^{2a})(R^{2b})(R^{2c})$, and $R^{2a}$ is hydrogen, $R^{2b}$ is hydrogen, and $R^{2c}$ is selected from $C_1$-$C_6$ alkyl, $C_1$-$C_6$ heteroalkyl, ($C_1$-$C_6$ heteroalkylene)-carbocyclyl, ($C_1$-$C_6$ heteroalkylene)-heterocyclyl, ($C_1$-$C_6$ heteroalkylene)-aryl, and ($C_1$-$C_6$ heteroalkylene)-heteroaryl, any alkyl, alkylene, cycloalkyl, aryl, heterocyclyl, or heteroaryl portion of $R^{2c}$ is optionally substituted. In a more specific aspect of these embodiments, $R^{2c}$ is selected from $C_1$-$C_6$ alkyl, —$(CH_2)$—$N(R^{13})$—$C_1$-$C_4$ alkyl, —$(CH_2)$—$N(R^{13})$—$C_1$-$C_4$ alkylene-O-alkyl, —$(CH_2)$—$N(R^{13})$—$C_1$-$C_4$ alkylene-C(O)—O-alkyl, —$(CH_2)$—$N(R^{13})$—$C_1$-$C_4$ alkylene-cycloalkyl, —$(CH_2)$—$N(R^{13})$-cycloalkyl, —$(CH_2)_2$—N-linked heterocyclyl, —$(CH_2)$—$N(R^{13})$-heterocyclyl, —$(CH_2)$—$N(R^{13})$—$C_1$-$C_4$ alkylene-heterocyclyl, —$CH_2$—N-linked heterocyclyl, —$(CH_2)$—$N(R^{13})$—$C_1$-$C_4$ alkylene-heteroaryl, and —$(CH_2)$—$N(R^{13})$—$C_1$-$C_4$ alkylene-aryl, wherein $R^{13}$ is hydrogen, $C_1$-$C_4$ alkyl; and any alkyl, alkylene, cycloalkyl, aryl, heterocyclyl, or heteroaryl portion of $R^{2c}$ is optionally substituted. In certain embodiments, $R^{2c}$ is $(CH_2)$—N-linked heterocyclyl (e.g., $(CH_2)$—N-linked fused bicyclic heterocyclyl, $(CH_2)$—N-linked spiro bicyclic heterocyclyl, or $(CH_2)$—N-linked bridged bicyclic heterocyclyl, each of which is optionally substituted). In certain embodiments, $R^{2c}$ is —$(CH_2)$—$N(R^{13})$—$C_1$-$C_4$ alkylene-cycloalkyl, wherein the cycloalkyl is selected from cyclopropyl, cyclobutyl, cyclopentyl, and cyclohexyl, each of which is optionally substituted. In certain embodiments, $R^{2c}$ is —$(CH_2)$—$N(R^{13})$—$C_1$-$C_4$ alkylene-heterocyclyl, wherein the heterocyclyl is selected from pyrrolidinyl, piperidinyl, piperazinyl, tetrahydrofuranyl, azetidinyl, azepanyl, tetrahydropyranyl, and oxazepanyl, each of which is optionally substituted. In certain embodiments, $R^{2c}$ is —$(CH_2)$—$N(R^{13})$—$C_1$-$C_4$ alkylene-heteroaryl, wherein each heteroaryl is selected from pyrrolyl, pyrazolyl, imidazolyl, oxazolyl, isoxazolyl, thiazolyl, thiophenyl, oxadiazolyl, and pyridyl, each of which is optionally substituted.

In certain embodiments, any alkyl, alkylene, cycloalkyl, aryl, heterocyclyl, or heteroaryl portion of $R^{2c}$ is optionally substituted with one or more substituents independently selected from halo, hydroxy, oxo, —CN, —$NH_2$, —$NH(C_1$-$C_4$ alkyl), —$N(C_1$-$C_4$ alkyl)$_2$, —$C_1$-$C_4$ alkyl, —$C_1$-$C_4$ hydroxyalkyl, —$C(O)NH_2$, —$C(O)OH$, —$C(O)O$—$C_1$-$C_4$ alkyl, —$C_1$-$C_4$ alkyl-O—$C_1$-$C_4$ alkyl, —O—$C_1$-$C_4$ alkyl, —O—$C_3$-$C_6$ cycloalkyl, phenyl, and halo-substituted phenyl.

In certain embodiments, $R^2$ is $C(R^{2a})(R^{2b})(R^{2c})$, and $R^{2a}$ is hydrogen, $R^{2b}$ is hydrogen or $CH_3$, and $R^{2c}$ is selected from hydrogen, $CH_2NHCH(CH_3)CH_2CH_3$, $CH_2N(CH_3)CH(CH_3)CH_2CH_3$, $CH_2NHCH_3$, $CH_2NHCH_2CH_2OCH_3$, $CH_2N(CH_3)_2$, $CH_2NH(CH_2)_3(OCH_2CH_2)_3CH_2NH_2$, $CH_2NHCH_2CH_2N(CH_2CH_3)_2$, $CH_2NHC(CH_3)_3$, $CH_2NHCH(CH_3)_2$, $CH_2N(CH(CH_3)CH_2CH_3)C(O)OC(CH_3)_3$, $C(O)NHCH(CF_3)_2$, $CH_2SCH(CH_3)CH_2CH_3$, $CH_2S(O)CH(CH_3)CH_2CH_3$, $CH_2S(O)_2CH(CH_3)CH_2CH_3$, $C(O)N(CH_2CH_2OCH_3)_2$, $CH_2CH_2NHCH(CH_3)CH_2CH_3$, $CH_2OCH(CH_3)CH_2CH_3$, $CH_2CH(OH)CH(CH_3)CH_2CH_3$, $CH_2C(O)CH(CH_3)CH_2CH_3$, $C(O)NHCH(CF_3)CH_2CH_3$, $C(O)NHCH(CH_3)CH_2CH_3$, $C(CH_3)_2NHCH(CH_3)CH_2CH_3$, $CH(CH_3)NHCH(CH_3)CH_2CH_3$, $CH_2NHC(O)CH_2CH_3$, and $CH_2NHCH_2C(O)OCH_2CH_3$.

In certain embodiments, $R^2$ is $C(R^{2a})(R^{2b})(R^{2c})$, and $R^{2a}$ is hydrogen, $R^{2b}$ is hydrogen or $CH_3$, and $R^{2c}$ is selected from hydrogen, $CH_2NHCH(CH_3)CH_2CH_3$, $CH_2N(CH_3)CH(CH_3)CH_2CH_3$, $CH_2NHCH_3$, $CH_2NHCH_2CH_2OCH_3$, $CH_2N(CH_3)_2$, $CH_2NH(CH_2)_3(OCH_2CH_2)_3CH_2NH_2$, $CH_2NHCH_2CH_2N(CH_2CH_3)_2$, $CH_2NHC(CH_3)_3$, $CH_2NHCH(CH_3)_2$, $CH_2CH_2NHCH(CH_3)CH_2CH_3$, and $CH_2OCH(CH_3)CH_2CH_3$.

In certain embodiments, $R^2$ is $C(R^{2a})(R^{2b})(R^{2c})$, $R^{2a}$ is hydrogen, $R^{2b}$ is hydrogen, and $R^{2c}$ is selected from hydrogen, $C_1$-$C_6$ alkyl, and $C_1$-$C_6$ heteroalkyl, wherein any alkyl or heteroalkyl portion of $R^{2b}$ and $R^{2c}$ is optionally and independently substituted with $C_1$-$C_6$ alkyl.

In certain embodiments, $R^2$ is $C(R^{2a})(R^{2b})(R^{2c})$, $R^{2a}$ is hydrogen, $R^{2b}$ is hydrogen, and $R^{2c}$ is selected from hydrogen and $CH_2NHCH(CH_3)CH_2CH_3$. In certain embodiments, $R^2$ is $C(R^{2a})(R^{2b})(R^{2c})$, and each of $R^{2a}$, $R^{2b}$, and $R^{2c}$ is independently hydrogen.

In certain embodiments, $R^2$ is $C(R^{2a})(R^{2b})(R^{2c})$, $R^{2a}$ is hydrogen, $R^{2b}$ is hydrogen or $C_1$-$C_6$ alkyl, and $R^{2c}$ is selected from hydrogen, ($C_1$-$C_6$ heteroalkylene)-carbocyclyl, ($C_1$-$C_6$ heteroalkylene)-heterocyclyl, ($C_1$-$C_6$ heteroalkylene)-aryl, and ($C_1$-$C_6$ heteroalkylene)-heteroaryl, wherein any alkyl, heteroalkylene, carbocyclyl, heterocyclyl, aryl, or heteroaryl portion of $R^{2b}$ and $R^{2c}$ is optionally and independently substituted.

In certain embodiments, $R^2$ is $C(R^{2a})(R^{2b})(R^{2c})$, $R^{2a}$ is hydrogen, $R^{2b}$ is hydrogen or $C_1$-$C_6$ alkyl, and $R^{2c}$ is selected from hydrogen, ($C_1$-$C_6$ heteroalkylene)-carbocyclyl, ($C_1$-$C_6$ heteroalkylene)-heterocyclyl, ($C_1$-$C_6$ heteroalkylene)-aryl, and ($C_1$-$C_6$ heteroalkylene)-heteroaryl, wherein any alkyl, heteroalkylene, carbocyclyl, heterocyclyl, aryl, or heteroaryl portion of $R^{2b}$ and $R^{2c}$ is optionally and independently substituted with halogen, hydroxy, $C_1$-$C_6$ alkyl, $C_1$-$C_6$ heteroalkyl, O—($C_1$-$C_6$ alkyl), heterocyclyl, or heteroaryl, each of which is optionally substituted.

In certain embodiments, $R^2$ is $C(R^{2a})(R^{2b})(R^{2c})$, $R^{2a}$ is hydrogen, $R^{2b}$ is hydrogen or $CH_3$, and $R^{2c}$ is selected from hydrogen, 1-(pyridine-4-yl)ethyl-1-aminomethyl, 2,2-(pyridin-3-yl)ethylaminomethyl, 2-(1-(1-methyl-1H-pyrazol-4-yl)methyl)aminomethyl, 1,2,3,4-tetrahydroisoquinolin-2-methyl, pyridin-3-ylaminomethyl, 4-methylpiperazin-1-ylmethyl, morpholin-4-ylmethyl, 2-(2-chlorophenyl)ethylaminomethyl, 1-methylaniline, 4-(1H-tetrazol-5-yl)methylaniline, 2-(3-hydroxyphenyl)aminomethyl, 2-(3-methoxyphenyl)aminomethyl, 2-(3-fluorophenyl)aminomethyl, 1-phenylmethylaminomethyl, 4,6-dimethyl-3-(pyridine-2(1H)-onyl)methylaminomethyl, 1H-pyrrol-2,5-dionyl-aminomethyl, 2-(pyridine-3-yl)ethylaminomethyl, 1-(sec-butyl)piperidin-4-ylmethyl, 1-(sec-butyl)piperidin-3-ylmethyl, 1-(sec-butyl)pyrrolidin-3-ylmethyl, cyclohexylaminomethyl, tetrahydro-2H-pyran-4ylaminomethyl, tetrahydro-2H-thiopyran-4ylaminomethyl, and 4-tetrahydro-2H-thiopyran-1,1-dioxoaminomethyl.

In certain embodiments, $R^2$ is $C(R^{2a})(R^{2b})(R^{2c})$, $R^{2a}$ is hydrogen, $R^{2b}$ is hydrogen, and $R^{2c}$ is selected from hydrogen, ($C_1$-$C_6$ heteroalkylene)-carbocyclyl, ($C_1$-$C_6$ heteroalkylene)-heterocyclyl, ($C_1$-$C_6$ heteroalkylene)-aryl, and ($C_1$-$C_6$ heteroalkylene)-heteroaryl, wherein any alkyl, heteroalkylene, carbocyclyl, heterocyclyl, aryl, or heteroaryl portion of $R^{2b}$ and $R^{2c}$ is optionally and independently substituted with halogen, hydroxy, $C_1$-$C_6$ alkyl, $C_1$-$C_6$ heteroalkyl, O—($C_1$-$C_6$ alkyl), heterocyclyl, or heteroaryl, each of which is optionally substituted.

In certain embodiments, each $R^4$ is independently selected from halogen, $C_1$-$C_8$ alkyl, $C_1$-$C_8$ heteroalkyl, $N(R^{3a})(R^{3b})$, $C(O)(C_1$-$C_6$ alkyl), $C(O)O(C_1$-$C_6$ alkyl), $C(O)N(R^{3a})(R^{3b})$, ($C_0$-$C_6$ alkylene)-carbocyclyl, ($C_1$-$C_6$ heteroalkylene)-carbocyclyl, ($C_0$-$C_6$ alkylene)-heterocyclyl, ($C_1$-$C_6$ heteroalkylene)-heterocyclyl, ($C_0$-$C_6$ alkylene)-aryl, and ($C_0$-$C_6$ alkylene)-heteroaryl, wherein any alkyl, alkylene, heteroalkyl, heteroalkylene, carbocyclyl, heterocyclyl, aryl or heteroaryl portion of each $R^4$ is optionally and independently substituted.

In certain embodiments, each $R^4$ is independently selected from hydrogen, halogen, $C_1$-$C_8$ alkyl, $C_1$-$C_8$ heteroalkyl, $N(R^{3a})(R^{3b})$, ($C_0$-$C_6$ alkylene)-heterocyclyl, and ($C_0$-$C_6$ alkylene)-heteroaryl, wherein any alkyl, alkylene, heteroalkyl, heterocyclyl or heteroaryl portion of each $R^4$ is optionally and independently substituted.

In certain embodiments, each $R^4$ is independently selected from halogen, $C_1$-$C_4$ alkyl, $C_1$-$C_4$ heteroalkyl, $N(R^{3a})(R^{3b})$, and ($C_0$-$C_4$ alkylene)-heteroaryl, wherein each of $R^{3a}$ and $R^{3b}$ is independently selected from hydrogen and $C_1$-$C_4$ alkyl, and any alkyl, alkylene, heteroalkyl, heterocyclyl or heteroaryl portion of each $R^4$ is optionally and independently substituted.

In certain embodiments, each $R^4$ is independently selected from halogen, $N(R^{3a})(R^{3b})$, $C_1$-$C_8$ alkyl and $C_1$-$C_8$ heteroalkyl, wherein any alkyl or heteroalkyl portion of $R^4$ is optionally substituted. In certain embodiments, each $R^4$ is independently selected from hydrogen, halogen, $C_1$-$C_4$ alkyl, $NH(C_1$-$C_4$ alkyl), and $N(C_1$-$C_4$ alkyl)$_2$.

In certain embodiments, each $R^4$ is independently selected from optionally substituted $C_1$-$C_4$ alkyl. In certain embodiments, each $R^4$ is independently selected from methyl, ethyl, isopropyl, $CHF_2$, and $CF_3$. In certain embodiments, each $R^4$ is methyl.

In certain embodiments, at least one $R^4$ is $N(R^{3a})(R^{3b})$ and each of $R^{3a}$ and $R^{3b}$ is independently hydrogen or methyl. In some embodiments, at least one $R^4$ is $NH_2$, $NH(CH_3)$, or $N(CH_3)_2$.

In certain embodiments, at least one $R^4$ is halogen. In certain embodiments, at least one $R^4$ is fluoro, chloro, bromo, or iodo.

In certain embodiments, $R^{4a}$ is hydrogen.

In certain embodiments, $R^{12}$ is selected from hydrogen or $C_1$-$C_6$ alkyl. In certain embodiments, $R^{12}$ is hydrogen or methyl. In certain embodiments, $R^{12}$ is hydrogen.

In certain embodiments, p is 0, 1, 2, or 3. In certain embodiments, p is 0, 1, or 2. In certain embodiments, p is 0. In certain embodiments, p is 1. In certain embodiments, p is 2.

In certain embodiments, when p is 1 or 2, each $R^4$ is independently selected from halogen, $C_1$-$C_8$ alkyl, $C_1$-$C_8$ heteroalkyl, or $N(R^{3a})(R^{3b})$, wherein each of $R^{3a}$ and $R^{3b}$ is independently hydrogen or $C_1$-$C_4$ alkyl and any alkyl or heteroalkyl portion of $R^4$ is optionally substituted. In certain embodiments, when p is 1 or 2, each $R^4$ is independently halogen or optionally substituted $C_1$-$C_8$ alkyl. In certain embodiments, when p is 1 or 2, each $R^4$ is independently halogen or optionally substituted $C_1$-$C_4$ alkyl. In certain embodiments, when p is 1 or 2, each $R^4$ is independently fluoro, methyl, ethyl, or $CF_3$. In certain embodiments, when p is 1 or 2, each $R^4$ is independently fluoro, methyl, or $CF_3$. In certain embodiments, when p is 1 or 2, each $R^4$ is methyl.

In certain embodiments, when p is 1 or 2, each $R^4$ is independently $N(R^{3a})(R^{3b})$ and each of $R^{3a}$ and $R^{3b}$ is independently hydrogen or $C_1$-$C_4$ alkyl.

In certain embodiments, when p is 1 or 2, each $R^4$ is independently fluoro, chloro, bromo, or iodo.

In certain embodiments, n is 0 or 1. In certain embodiments, n is 0. In certain embodiments, n is 1. In certain embodiments, n is 2.

In certain embodiments, m is 0. In certain embodiments, m is 1.

In certain embodiments, m is 1 and n is 0, 1, or 2. In certain embodiments, m is 1 and n is 0 or 1. In certain embodiments, m is 1 and n is 1 or 2. In certain embodiments, m is 1 and n is 1. In certain embodiments, m is 1 and n is 0. In certain embodiments, m is 1 and n is 1. In certain embodiments, m is 1 and n is 2.

In certain embodiments, a compound of Formula (I) is isotopically labelled. In certain embodiments, a hydrogen, carbon, nitrogen, or oxygen atom of a compound of Formula (I) is isotopically labeled. In certain embodiments, a nitrogen atom of a compound of Formula (I) is $^{15}N$.

In certain embodiments, a compound of Formula (I) has the structure of Formula (Ia):

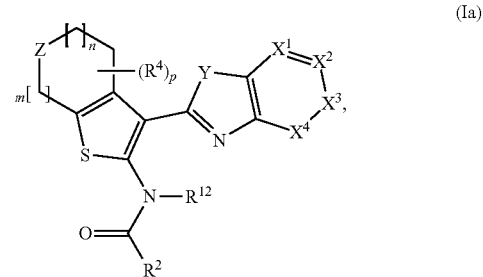

(Ia)

or a pharmaceutically acceptable salt, solvate, hydrate, tautomer, or stereoisomer thereof, wherein:

each of $X^1$, $X^2$, $X^3$ and $X^4$ is independently selected from C(R), N and N(O), wherein one of $X^1$, $X^2$, $X^3$ and $X^4$ is N or N(O);

each R is independently selected from hydrogen, halogen, $C_1$-$C_8$ alkyl, $N(R^{3a})(R^{3b})$, $C(O)(C_1$-$C_6$ alkyl), and $C(O)O(C_1$-$C_6$ alkyl), wherein each alkyl portion of R is independently and optionally substituted;

Y is selected from O and S;

Z is selected from $C(R^{4a})(N(R^5)(R^6))$ and $N(R^1)$;

$R^1$ is selected from hydrogen, $C_1$-$C_6$ alkyl and ($C_0$-$C_6$ alkylene)-heterocyclyl, wherein each alkyl or alkylene portion of $R^1$ is optionally substituted;

$R^2$ is selected from $C(R^{2a})(R^{2b})(R^{2c})$, wherein:

$R^{2a}$ is hydrogen;

each of $R^{2b}$ and $R^{2c}$ is independently selected from hydrogen, halogen, $C_1$-$C_6$ alkyl, $C_1$-$C_6$ heteroalkyl, ($C_0$-$C_6$ alkylene)-heterocyclyl, ($C_1$-$C_6$ heteroalkylene)-heterocyclyl, ($C_0$-$C_6$ alkylene)-aryl, ($C_1$-$C_6$ heteroalkylene)-aryl, ($C_0$-$C_6$ alkylene)-heteroaryl, and ($C_1$-$C_6$ heteroalkylene)-heteroaryl, wherein any alkyl, alkylene, heteroalkyl, heteroalkylene, heterocyclyl, aryl or heteroaryl portion of $R^{2b}$ and $R^{2c}$ is optionally and independently substituted;

each of $R^{3a}$ and $R^{3b}$ is independently selected from hydrogen and optionally substituted $C_1$-$C_4$ alkyl;

each $R^4$ is independently selected from hydrogen, halogen, $C_1$-$C_8$ alkyl, $C_1$-$C_8$ heteroalkyl, $N(R^{3a})(R^{3b})$, wherein any alkyl or heteroalkyl portion of $R^4$ is optionally and independently substituted;

$R^{4a}$ is selected from hydrogen and $C_1$-$C_6$ alkyl;

each of $R^5$ and $R^6$ is independently selected from hydrogen, $C_1$-$C_6$ alkyl, $C(O)(C_1$-$C_6$ alkyl), $(C_0$-$C_6$ alkylene)-heterocyclyl and $(C_0$-$C_6$ alkylene)-heteroaryl, wherein any alkyl or alkylene of each of $R^5$ and $R^6$ is optionally and independently substituted;

$R^{12}$ is hydrogen or $C_1$-$C_6$ alkyl;

n is 0, 1, or 2;

m is 0 or 1;

n+m=1, 2 or 3; and p is 0, 1, 2, or 3.

In certain embodiments, a compound of Formula (Ia) has the structure of Formula (Ib):

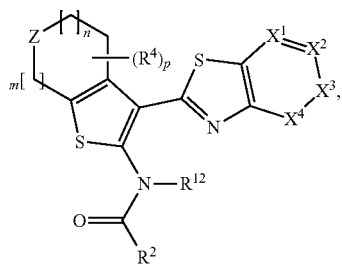

(Ib)

or a pharmaceutically acceptable salt, solvate, hydrate, tautomer, or stereoisomer thereof, wherein each of $X^1$, $X^2$, $X^3$, $X^4$, R, Z, $R^1$, $R^2$, $R^{2a}$, $R^{2b}$, $R^{2c}$, $R^{3a}$, $R^{3b}$, $R^4$, $R^{4a}$, $R^5$, $R^6$, $R^{12}$, n, m, and p are defined as for Formula (Ia).

In certain embodiments, a compound of Formula (Ib) has the structure of Formula (Ic):

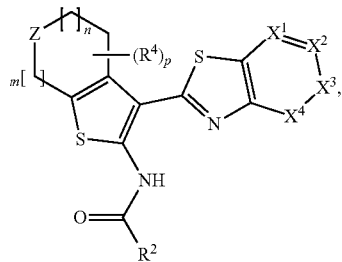

(Ic)

or a pharmaceutically acceptable salt, solvate, hydrate, tautomer, or stereoisomer thereof, wherein each of $X^1$, $X^2$, $X^3$, $X^4$, R, Z, $R^1$, $R^2$, $R^{2a}$, $R^{2b}$, $R^{2c}$, $R^{3a}$, $R^{3b}$, $R^4$, $R^{4a}$, $R^5$, $R^6$, n, m, and p are defined as for Formula (Ib).

In certain embodiments, a compound of Formula (Ic) has the structure of Formula (Id):

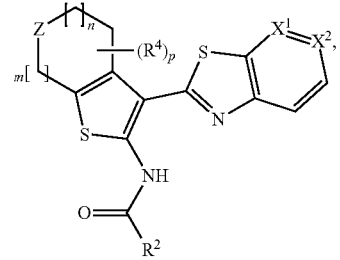

(Id)

or a pharmaceutically acceptable salt, solvate, hydrate, tautomer, or stereoisomer thereof, wherein each of $X^1$, $X^2$, R, Z, $R^1$, $R^2$, $R^{2a}$, $R^{2b}$, $R^{2c}$, $R^{3a}$, $R^{3b}$, $R^4$, $R^{4a}$, $R^5$, $R^6$, n, m, and p are defined as for Formula (Ic).

In certain embodiments, a compound of Formula (Id) has the structure of Formula (Ie):

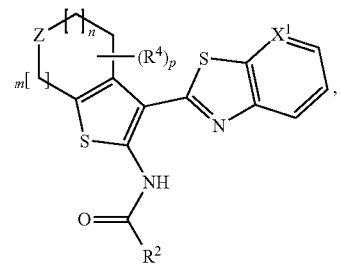

(Ie)

or a pharmaceutically acceptable salt, solvate, hydrate, tautomer, or stereoisomer thereof, wherein each of $X^1$, R, Z, $R^1$, $R^2$, $R^{2a}$, $R^{2b}$, $R^{2c}$, $R^{3a}$, $R^{3b}$, $R^4$, $R^{4a}$, $R^5$, $R^6$, n, m, and p are defined as for Formula (Id).

In certain embodiments, a compound of Formula (Ie) has the structure of Formula (Ie-1):

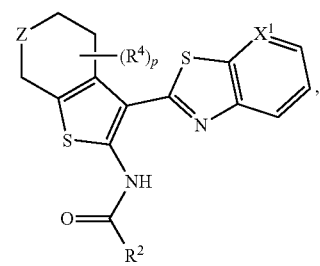

(Ie-1)

or a pharmaceutically acceptable salt, solvate, hydrate, tautomer, or stereoisomer thereof, wherein each of $X^1$, R, Z, $R^1$, $R^2$, $R^{2a}$, $R^{2b}$, $R^{2c}$, $R^{3a}$, $R^{3b}$, $R^4$, $R^{4a}$, $R^5$, $R^6$, and p are defined as for Formula (Ie).

In certain embodiments, a compound of Formula (Ie-1) has the structure of Formula (Ie-2):

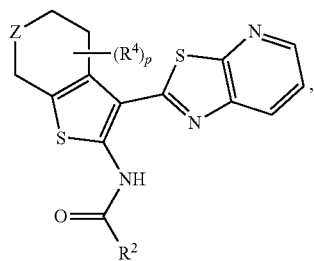

(Ie-2)

or a pharmaceutically acceptable salt, solvate, hydrate, tautomer, or stereoisomer thereof, wherein each of R, Z, $R^1$, $R^2$, $R^{2a}$, $R^{2b}$, $R^{2c}$, $R^{3a}$, $R^{3b}$, $R^4$, $R^{4a}$, $R^5$, $R^6$, and p are defined as for Formula (Ie-1).

In certain embodiments, the compound of Formula (Ie-2) is the compound:

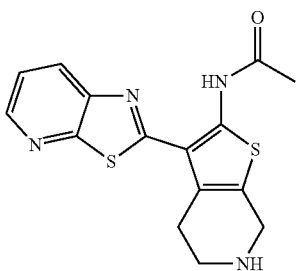

In certain embodiments, a compound of Formula (Ie) has the structure of Formula (If):

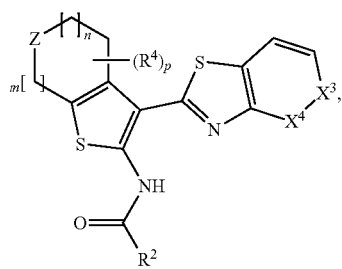

(If)

or a pharmaceutically acceptable salt, solvate, hydrate, tautomer, or stereoisomer thereof, wherein each of $X^3$, $X^4$, R, Z, $R^1$, $R^2$, $R^{2a}$, $R^{2b}$, $R^{2c}$, $R^{3a}$, $R^{3b}$, $R^4$, $R^{4a}$, $R^5$, $R^6$, n, m, and p are defined as for Formula (Ie).

In certain embodiments, a compound of Formula (If) has the structure of Formula (Ig):

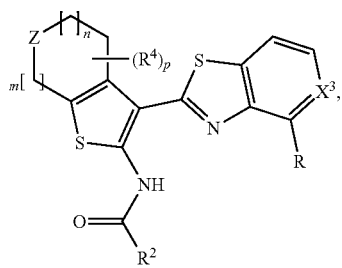

(Ig)

or a pharmaceutically acceptable salt, solvate, hydrate, tautomer, or stereoisomer thereof, wherein each of $X^3$, R, Z, $R^1$, $R^2$, $R^{2a}$, $R^{2b}$, $R^{2c}$, $R^{3a}$, $R^{3b}$, $R^4$, $R^{4a}$, $R^5$, $R^6$, n, m, and p are defined as for Formula (If).

In certain embodiments, a compound of Formula (Ig) has the structure of Formula (Ig-1):

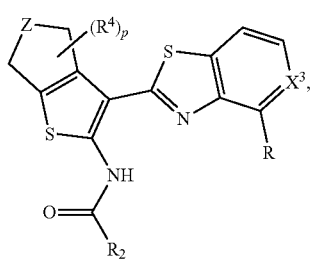

(Ig-1)

or a pharmaceutically acceptable salt, solvate, hydrate, tautomer, or stereoisomer thereof, wherein each of $X^3$, R, Z, $R^1$, $R^2$, $R^{2a}$, $R^{2b}$, $R^{2c}$, $R^{3a}$, $R^{3b}$, $R^4$, $R^{4a}$, $R^5$, $R^6$, and p are defined as for Formula (Ig).

In certain embodiments, a compound of Formula (Ig-1) has the structure of Formula (Ig-2):

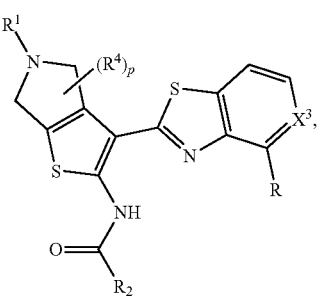

(Ig-2)

or a pharmaceutically acceptable salt, solvate, hydrate, tautomer, or stereoisomer thereof, wherein each of $X^3$, R, $R^1$, $R^2$, $R^{2a}$, $R^{2b}$, $R^{2c}$, $R^{3a}$, $R^{3b}$, $R^4$, n, m, and p are defined as for Formula (Ig-1).

In certain embodiments, a compound of Formula (Ig-2) has the structure of Formula (Ig-3):

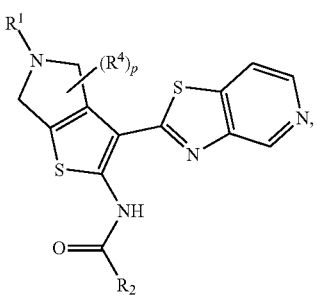

(Ig-3)

or a pharmaceutically acceptable salt, solvate, hydrate, tautomer, or stereoisomer thereof, wherein each of $R^1$, $R^2$, $R^{2a}$, $R^{2b}$, $R^{2c}$, $R^{3a}$, $R^{3b}$, $R^4$, n, m, and p are defined as for Formula (Ig-2).

In certain embodiments, the compound of Formula (Ig-3) is the compound:

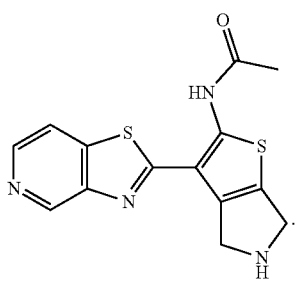 [SMILES: CC(=O)Nc1sc2c(c1-c1nc3cnccc3s1)CNC2]

In certain embodiments, a compound of Formula (Ig) has the structure of Formula (Ih):

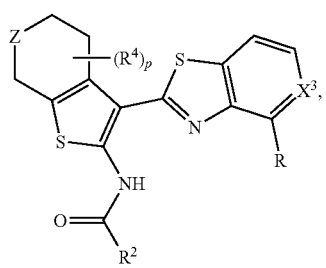
(Ih)

or a pharmaceutically acceptable salt, solvate, hydrate, tautomer, or stereoisomer thereof, wherein each of $X^3$, R, Z, $R^1$, $R^2$, $R^{2a}$, $R^{2b}$, $R^{2c}$, $R^{3a}$, $R^{3b}$, $R^4$, $R^{4a}$, $R^5$, $R^6$, and p are defined as for Formula (Ig).

In certain embodiments, a compound of Formula (Ih) has the structure of Formula (Ih-1):

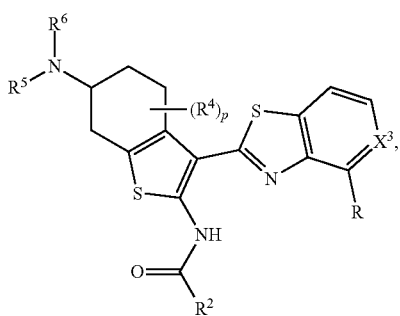
(Ih-1)

or a pharmaceutically acceptable salt, solvate, hydrate, tautomer, or stereoisomer thereof, wherein each of $X^3$, $R^1$, $R^2$, $R^{2a}$, $R^{2b}$, $R^{2c}$, $R^{3a}$, $R^{3b}$, $R^4$, $R^5$, $R^6$, and p are defined as for Formula (Ih).

In certain embodiments, a compound of Formula (Ih-1) has the structure of Formula (Ih-2):

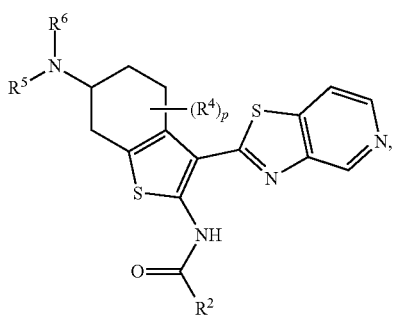
(Ih-2)

or a pharmaceutically acceptable salt, solvate, hydrate, tautomer, or stereoisomer thereof, wherein each of $R^2$, $R^{2a}$, $R^{2b}$, $R^{2c}$, $R^{3a}$, $R^{3b}$, $R^4$, $R^5$, $R^6$, and p are defined as for Formula (Ih-1).

In certain embodiments, the compound of Formula (Ih-2) is the compound:

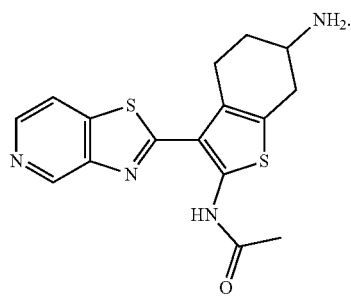 [SMILES: CC(=O)Nc1sc2c(c1-c1nc3cnccc3s1)CCC(N)C2]

In certain embodiments, a compound of Formula (Ih) has the structure of Formula (Ii):

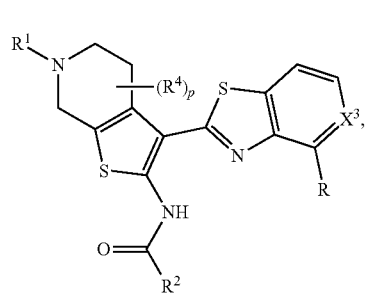
(Ii)

or a pharmaceutically acceptable salt, solvate, hydrate, tautomer, or stereoisomer thereof, wherein each of $X^3$, R, $R^1$, $R^2$, $R^{2a}$, $R^{2b}$, $R^{2c}$, $R^{3a}$, $R^{3b}$, $R^4$, and p are defined as for Formula (Ih).

In certain embodiments, a compound of Formula (Ii) has the structure of Formula (Ii-1):

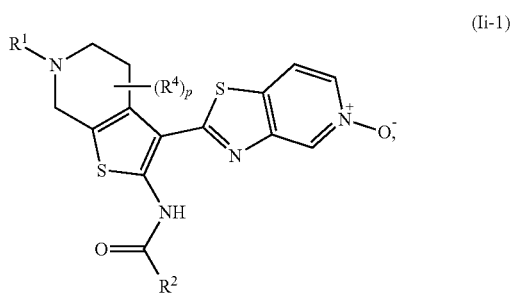
(Ii-1)

or a pharmaceutically acceptable salt, solvate, hydrate, tautomer, or stereoisomer thereof, wherein each of $R^1$, $R^2$, $R^{2a}$, $R^{2b}$, $R^{2c}$, $R^{3a}$, $R^{3b}$, $R^4$, and p are defined as for Formula (Ii).

In certain embodiments, the compound of Formula (Ii-1) is the compound:

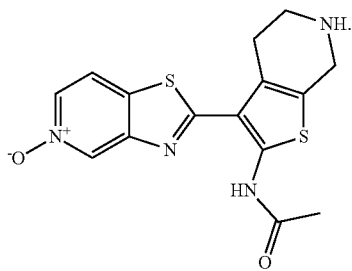

In certain embodiments, a compound of Formula (Ii) has the structure of Formula (Ij):

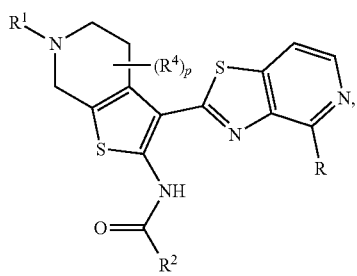

(Ij)

or a pharmaceutically acceptable salt, solvate, hydrate, tautomer, or stereoisomer thereof, wherein each of R, $R^1$, $R^2$, $R^{2a}$, $R^{2b}$, $R^{2c}$, $R^{3a}$, $R^{3b}$, $R^4$, and p are defined as for Formula (Ii).

In certain embodiments, the compound of Formula (I) has the structure of Formula (II):

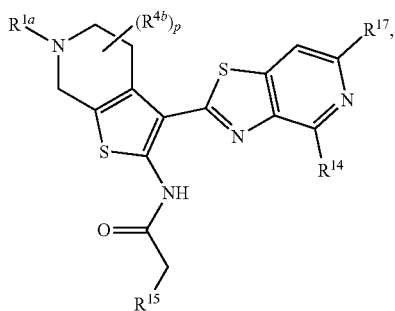

(II)

or a pharmaceutically acceptable salt thereof, wherein:
$R^{1a}$ is selected from hydrogen and $C_1$-$C_3$ alkyl;
each $R^{4b}$, if present, is $C_1$-$C_3$ alkyl;
$R^{13a}$ is selected from hydrogen and $C_1$-$C_3$ alkyl;
$R^{17}$ and $R^{14}$ are independently selected from hydrogen, halo, $C_1$-$C_3$ alkyl and $C_1$-$C_3$ haloalkyl;
$R^{15}$ is selected from hydrogen, $C_1$-$C_3$ alkyl, and —$CH_2$—$N(R^{13a})(R^{16})$;

$R^{16}$ is selected from $C_1$-$C_6$ alkyl, $C_1$-$C_6$ heteroalkyl, —($C_0$-$C_2$ alkylene)-heterocyclyl, —($C_0$-$C_2$ alkylene)-$C_3$-$C_6$ cycloalkyl, or ($C_1$-$C_2$ alkylene)-heteroaryl, wherein any heteroalkyl, alkylene, cycloalkyl, heterocyclyl or heteroaryl portion of $R^{11a}$ is optionally substituted; or $R^{13a}$ and $R^{16}$ are taken together to form an optionally substituted heterocyclyl; and p is 0, 1 or 2.

In some embodiments of Formula II, $R^{1a}$ is selected from hydrogen, ethyl and isopropyl.

In some embodiments, of Formula II, each $R^{4b}$, if present, is —$CH_3$.

In some embodiments, of Formula II, $R^{13a}$ is selected from hydrogen and —$CH_3$.

In some embodiments, of Formula II, $R^{17}$ is selected from hydrogen, chloro, and —$CH_3$.

In some embodiments, of Formula II, $R^{14}$ is selected from hydrogen, —$CH_3$ and —$CHF_2$.

In some embodiments, of Formula II, $R^{15}$ is selected from hydrogen, $NHR^{16}$, and $N(CH_3)R^{16}$.

In some embodiments, of Formula II, $R^{16}$ is selected from -heterocyclyl, —$CH_2$— heterocyclyl, —$(CH_2)_2$-heterocyclyl, —$CH_2$-heteroaryl, —$CH(CH_3)$-heteroaryl, —$(CH_2)_2$-heteroaryl, —$CH(CH_3)$—$CH_2$-heteroaryl, —$CH_3$, —$CH_2CH_3$, —$CH(CH_3)CH_2CH_3$, —$CH_2CH_2$—O—$CH_3$, —$(CH_2)_3$—$C(O)OCH_3$, —$CH(CH_2OH)CH_2CH(CH_3)_2$, —$CH(CH(CH_3)_2)CH_2OCH_3$, —($C_3$-$C_5$ cycloalkyl), —$CH_2$-($C_3$-$C_5$ cycloalkyl), and —$CH(CH_3)$—($C_3$-$C_5$ cycloalkyl), or wherein $R^{16}$ is taken together with $R^{13a}$ and the nitrogen atom to which they are bound to form a N-linked heterocyclyl, wherein each heterocyclyl, heteroaryl and cycloalkyl portion of $R^{16}$ or the N-linked heterocyclyl formed when $R^{16}$ is taken together with $R^{13a}$ is optionally substituted with one or more substituents independently selected from oxo, hydroxy, —$CH_3$, —$CH_2OCH_3$, —$OCH_3$, —$NH_2$, —$N(CH_3)_2$, —$C(O)OH$, and —O-cycloalkyl.

Although, as indicated above, various embodiments and aspects thereof for a variable in Formula (I), e.g., Formulas (Ia), (Ib), (Ic), (Id), (Ie), (Ie-1), (Ie-2), (If), (Ig), (Ig-1), (Ig-2), (Ig-3), (Ih), (Ih-1), (Ih-2), (Ii), (Ii-1), (Ij), or (II) may be selected from a group of chemical moieties, the invention also encompasses as further embodiments and aspects thereof situations where such variable is: a) selected from any subset of chemical moieties in such a group; and b) any single member of such a group.

Although various embodiments and aspects thereof are set forth (or implied, as discussed in the preceding paragraph) individually for each variable in Formula (I) above, e.g., Formulas (Ia), (Ib), (Ic), (Id), (Ie), (Ie-1), (Ie-2), (If), (Ig), (Ig-1), (Ig-2), (Ig-3), (Ih), (Ih-1), (Ih-2), (Ii), (Ii-1), (Ij), or (II) the invention encompasses all possible combinations of the different embodiments and aspects for each of the variables in Formula (I), e.g., Formulas (Ia), (Ib), (Ic), (Id), (Ie), (Ie-1), (Ie-2), (If), (Ig), (Ig-1), (Ig-2), (Ig-3), (Ih), (Ih-1), (Ih-2), (Ii), (Ii-1), (Ij) or (II).

In certain embodiments, the compound of Formula (I) is selected from the group consisting of any one of the compounds in Table 1 and pharmaceutically acceptable salts, solvates, hydrates, tautomers, stereoisomers, and isotopically labeled derivatives thereof.

TABLE 1

Exemplary Compounds and NMR/LCMS Data

| Compound | Structure | NMR/LCMS |
|---|---|---|
| 100 | 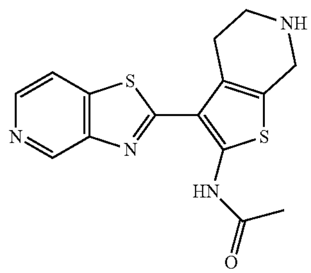 [SMILES: CC(=O)Nc1sc2c(c1-c1nc3cnccc3s1)CCNC2] | $^{1}$H NMR (DMSO-d6, 400 MHz): δ 12.18 (s, 1 H), 9.54-9.64 (m, 1 H), 8.66 (d, J = 5.93 Hz, 1 H), 8.49 (d, J = 5.51 Hz, 1 H), 4.34 (br. s, 2 H), 3.45-3.53 (m, 2 H), 3.14-3.21 (m, 2 H), 2.37 (s, 3 H), 1.91 (s, 1 H); LCMS: 331 |
| 101 | 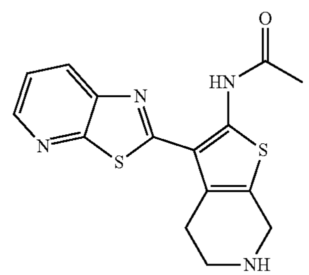 [SMILES: CC(=O)Nc1sc2c(c1-c1nc3cccnc3s1)CCNC2] | $^{1}$H NMR (DMSO-d6, 400 MHz): δ 12.33 (br. s, 1 H), 8.65 (dd, J = 1.63, 4.42 Hz, 1 H), 8.56 (dd, J = 1.63, 8.14 Hz, 1 H), 7.67 (dd, J = 4.65, 8.37 Hz, 1 H), 4.35 (s, 2 H), 3.50 (t, J = 6.05 Hz, 2 H), 3.15 (t, J = 5.82 Hz, 2 H), 2.55 (t, J = 1.86 Hz, 1 H), 2.34 (s, 3 H); LCMS: 331.3 |
| 102 | 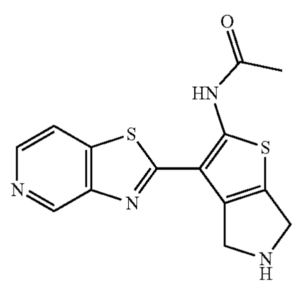 [SMILES: CC(=O)Nc1sc2c(c1-c1nc3cnccc3s1)CNC2] | $^{1}$H NMR (DMSO-d6, 400 MHz): δ 11.81 (br. s, 1H), 10.59 (br. s, 1H), 9.67 (s, 1H), 8.70 (d, J = 5.29 Hz, 1H), 8.61 (d, J = 4.85 Hz, 1H), 4.67 (br. s, 2H), 4.53 (br. s, 2H), 2.39 (s, 3H); LCMS: 316.95 |
| 103 | 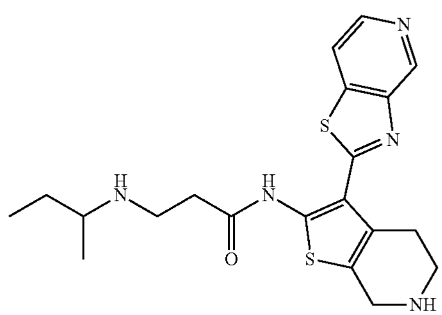 [SMILES: CCC(C)NCCC(=O)Nc1sc2c(c1-c1nc3cnccc3s1)CCNC2] | $^{1}$H NMR (400 MHz, DMSO-d6) δ 12.25 (s, 1H), 9.64 (bs, 1H), 9.54 (s, 1H), 8.97-8.89 (m, 1H), 8.63 (d, J = 5.6 Hz, 1H), 8.41 (d, J = 5.6 Hz, 1H), 4.35 (s, 2H), 3.75-3.62 (m, 2H), 3.48 (dt, J = 9.5, 4.5 Hz, 3H), 3.28 (d, J = 8.0 Hz, 2H), 3.16 (q, J = 7.3, 6.7 Hz, 4H), 1.81 (m, 1H), 1.51 (dt, J = 14.4, 7.6 Hz, 1H), 1.25 (d, J = 6.5 Hz, 3H), 0.92 (t, J = 7.5 Hz, 3H).; LCMS: 416.1 |
| 104 | 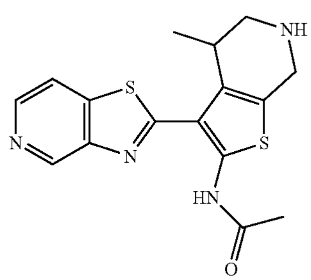 [SMILES: CC(=O)Nc1sc2c(c1-c1nc3cnccc3s1)C(C)CNC2] | $^{1}$H NMR (400 MHz, CD3OD) δ 9.61 (s, 1H), 8.66 (d, J = 6.0 Hz, 1H), 8.58 (dd, J = 5.9, 0.8 Hz, 1H), 4.50-4.36 (m, 2H), 3.84 (dt, J = 7.6, 4.0 Hz, 1H), 3.78-3.52 (m, 2H), 2.38 (s, 3H), 1.42 (d, J = 7.0 Hz, 3H).; LCMS: 344.93 |

TABLE 1-continued

Exemplary Compounds and NMR/LCMS Data

| Compound | Structure | NMR/LCMS |
|---|---|---|
| 105 | 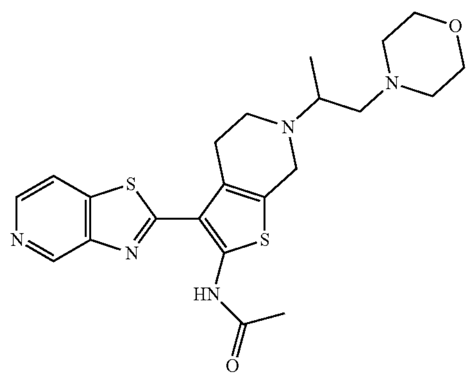 [SMILES: CC(=O)Nc1sc2c(c1-c1nc3cnccc3s1)CCN(C(C)CN1CCOCC1)C2] | $^1$H NMR (400 MHz, DMSO-d6) δ 12.32 (s, 1H). 9.41 (d. J = 1.0 Hz, 1H), 8.52 (d, J = 5.4 Hz, 1H), 8.22 (dd, J = 5.3, 1.0 Hz, 1H), 4.03 (s, 2H), 3.69 (d, J = 15.0 Hz, 1H), 3.63-3.51 (m, 4H), 3.29 (s, 2H), 2.95-2.79 (m, 5H), 2.68-2.59 (m, 2H), 2.47-2.27 (m, 4H), 0.99 (d, J = 6.5 Hz, 3H).; LCMS: 458.1 |
| 106 | 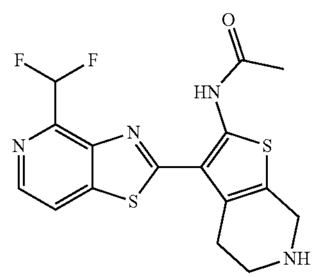 [SMILES: CC(=O)Nc1sc2c(c1-c1nc3c(C(F)F)nccc3s1)CCNC2] | $^1$H NMR (400 MHz, Methanol-d4) δ 8.55 (d, J = 4.00 Hz, 1H), 8.27 (d, J = 7.99 Hz, 1H), 7.18 (t, J = 51.98 Hz, 1H), 4.28 (s, 2 H), 3.52 (t, J = 4.00 Hz, 2 H), 3.24 (t, J = 4.00 Hz, 2H), 2.37 (s, 3H). ; LCMS: 381.12 |
| 107 | 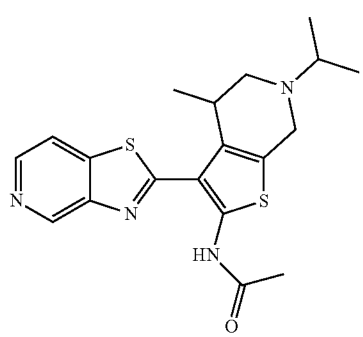 [SMILES: CC(=O)Nc1sc2c(c1-c1nc3cnccc3s1)C(C)CN(C(C)C)C2] | $^1$H NMR (400 MHz, DMSO-d6) δ 11.75 (s, 1H), 9.88 (s, 1H), 9.44 (d, J = 7.6 Hz, 1H), 9.19 (s, 1H), 8.60 (t, J = 4.9 Hz, 1H), 8.32 (t, J = 5.0 Hz, 1H), 4.57-4.37 (m, 2H), 3.79-3.56 (m, 4H), 2.26 (s, 3H), 1.36 (dd, J = 12.7, 6.6 Hz, 6H), 1.25 (d, J = 7.1 Hz, 3H). ; LCMS: 387.05 |
| 108 | 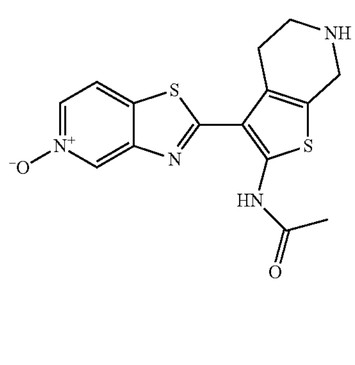 | $^1$H NMR (400 MHz, DMSO-d6) δ 9.32 (s, 1H), 8.38-8.22 (m, 2H), 4.32 (s, 2H), 3.51-3.46 (m, 2H), 3.14 (q, J = 6.3, 5.1 Hz, 2H), 2.34 (s, 3H).; LCMS: 346.93 |

… TABLE 1-continued

Exemplary Compounds and NMR/LCMS Data

| Compound | Structure | NMR/LCMS |
|---|---|---|
| 109 | 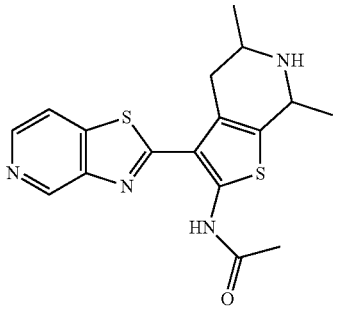 [SMILES: CC(=O)Nc1sc2c(c1-c1nc3cnccc3s1)CC(C)NC2C] | $^1$H NMR (400 MHz, DMSO-d6) δ 12.17 (d, J = 3.5 Hz, 1H), 9.92 (s, 1H), 9.68 (d, J = 10.5 Hz, 2H), 8.68 (d, J = 5.7 Hz, 1H), 8.54 (d, J = 5.7 Hz, 1H), 4.86-4.76 (m, 1H), 4.69 (s, 1H), 4.42 (s, 1H), 3.86 (p, J = 6.8 Hz, 1H), 3.75-3.54 (m, 4H), 3.49 (hept, J = 5.5, 4.5 Hz, 1H), 3.43-3.27 (m, 2H), 2.87 (dd, J = 16.3, 7.8 Hz, 1H), 2.61 (s, 1H), 2.58-2.52 (m, 2H), 2.45 (d, J = 2.8 Hz, 1H), 2.36 (s, 3H), 2.04-1.88 (m, 1H), 1.83-1.71 (m, 1H), 1.72-1.37 (m, 8H), 1.30-1.16 (m, 4H), 1.16-0.97 (m, 1H), 0.86 (t, J = 7.5 Hz, 1H) (mixture of diastereomers).; LCMS: 358.95 |
| 110 | 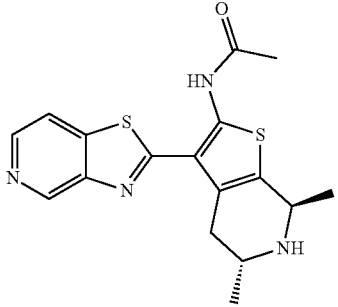 [SMILES: CC(=O)Nc1sc2c(c1-c1nc3cnccc3s1)C[C@@H](C)N[C@@H]2C] | $^1$H NMR (400 MHz, DMSO-d6) δ 12.16 (s, 1H), 10.06 (d, J = 10.3 Hz, 1H), 9.81 (d, J = 10.9 Hz, 1H), 9.71 (s, 1H), 8.70 (d, J = 5.9 Hz, 1H), 8.60 (d, J = 5.9 Hz, 1H), 4.83-4.76 (m, 1H), 3.86 (dt, J = 13.7, 7.6 Hz, 1H), 3.41-3.27 (m, 1H), 2.89 (dd, J = 16.1, 8.3 Hz, 1H), 2.37 (s, 3H), 1.65 (d, J = 6.7 Hz, 3H), 1.50 (dd, J = 22.1, 6.4 Hz, 3H).; LCMS: 358.9 |
| 111 | 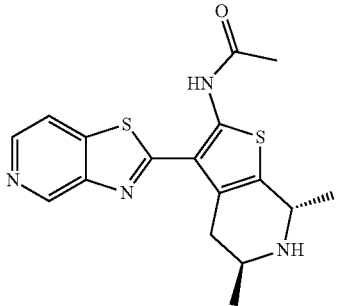 [SMILES: CC(=O)Nc1sc2c(c1-c1nc3cnccc3s1)C[C@H](C)N[C@H]2C] | $^1$H NMR (400 MHz, DMSO-d6) δ 12.17 (s, 1H), 10.03-10.01 (m, 1H), 9.78-9.75 (m, 1H), 9.69 (s, 1H), 8.69 (d, J = 5.8 Hz, 1H), 8.57 (d, J = 5.8 Hz, 1H), 4.80 (s, 1H), 3.87 (d, J = 8.7 Hz, 1H), 3.41-3.27 (m, 1H), 2.90 (td, J = 16.3, 15.2, 9.5 Hz, 1H), 2.37 (s, 3H), 1.64 (d, J = 6.7 Hz, 3H), 1.49 (dd, J = 21.5, 6.4 Hz, 3H).; LCMS: 358.9 |
| 112 | 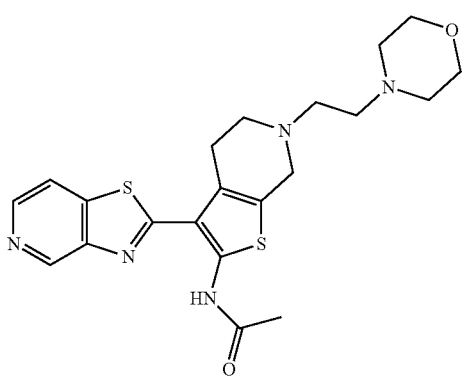 [SMILES: CC(=O)Nc1sc2c(c1-c1nc3cnccc3s1)CCN(CCN1CCOCC1)C2] | $^1$H NMR (DMSO-d6, 400 MHz): δ 12.32 (s, 1H), 9.41 (s, 1H), 8.53 (d, J = 5.38 Hz, 1H), 8.23 (d, J = 5.38 Hz, 1H), 3.64 (m, 2H), 3.55-3.60 (m, 4H), 2.85-2.96 (m, 4H), 2.67 (d, J = 1.96 Hz, 3H), 2.38-2.46 (m, 4H), 2.34 (s, 3H), 2.32-2.29 (m, 1H); LCMS: 444.05 |

TABLE 1-continued

Exemplary Compounds and NMR/LCMS Data

| Compound | Structure | NMR/LCMS |
|---|---|---|
| 113 | 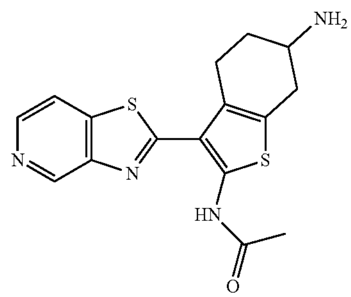 [SMILES: CC(=O)Nc1sc2c(c1-c1nc3cnccc3s1)CCC(N)C2] | ¹H NMR (DMSO-d6, 400 MHz): δ 12.24 (s, 1H), 9.62 (s, 1H), 8.65 (d, J = 5.73 Hz, 1H), 8.50 (d, J = 5.29 Hz, 1H), 8.29 (br. s, 2H), 3.58-3.60 (m, 1H), 3.10 (d, J = 16.32 Hz, 2H), 2.96 (d, J = 8.82 Hz, 1H), 2.81-2.83 (m, 1H), 2.35 (s, 3H), 2.21-2.24 (m, 1H), 1.97 (d, J = 15.44 Hz, 1H).; LCMS: 344.95 |
| 114 | 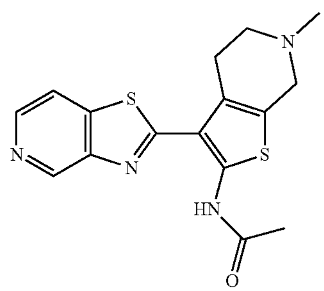 [SMILES: CC(=O)Nc1sc2c(c1-c1nc3cnccc3s1)CCN(C)C2] | ¹H NMR (DMSO-d6, 400 MHz): δ 12.32 (s, 1H), 9.41 (s, 1H), 8.53 (d, J = 5.29 Hz, 1H), 8.22 (d, J = 5.73 Hz, 1H), 3.51 (s, 2H), 2.93-2.97 (m, 2H), 2.73-2.78 (m, 2H), 2.39 (s, 3H), 2.34 (s, 3H).; LCMS: 344.95 |
| 115 | 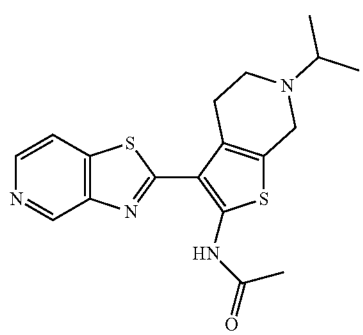 [SMILES: CC(=O)Nc1sc2c(c1-c1nc3cnccc3s1)CCN(C(C)C)C2] | ¹H NMR (DMSO-d6, 400 MHz): δ 12.32 (s, 1H), 9.39 (s, 1H), 8.52 (d, J = 5.32 Hz, 1H), 8.21 (d, J = 5.32 Hz, 1H), 3.63 (s, 2H), 2.78-2.97 (m, 5H), 2.34 (s, 3H), 1.07 (d, J = 6.65 Hz, 6H); LCMS: 372.91 |
| 116 | 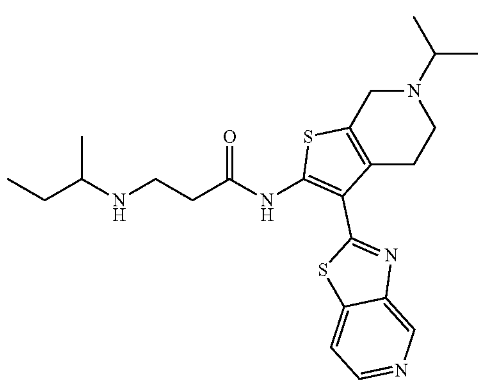 [SMILES: CCC(C)NCCC(=O)Nc1sc2c(c1-c1nc3cnccc3s1)CCN(C(C)C)C2] | ¹H NMR (DMSO-d6, 400 MHz): δ 12.26 (s, 1H), 10.85 (s, 1H), 9.53 (s, 1H), 8.94 (s, 1H), 8.86 (s, 1H), 8.62 (d, J = 5.6 Hz, 1H), 8.40 (d, J = 5.5 Hz, 1H), 4.57-4.48 (m, 1H), 4.40 (dd, J = 15.3, 8.6 Hz, 1H), 3.87-3.77 (m, 1H), 3.72-3.63 (m, 2H), 3.44-3.26 (m, 5H), 3.16 (t, J = 7.2 Hz, 3H), 1.89-1.74 (m, 1H), 1.59-1.33 (m, 6H), 1.25 (d, J = 6.5 Hz, 6H); LCMS: 458.2 |

TABLE 1-continued

Exemplary Compounds and NMR/LCMS Data

| Compound | Structure | NMR/LCMS |
|---|---|---|
| 117 | 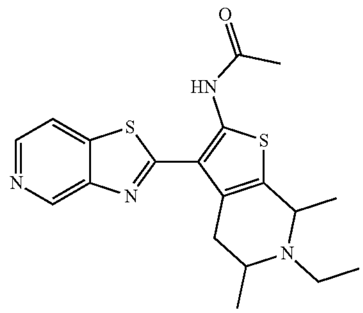 [SMILES: CCN1C(C)Cc2c(sc(NC(C)=O)c2-c2nc3cnccc3s2)C1C] | ¹H NMR (400 MHz, DMSO-d6) δ 12.36 (s, 1H), 9.40 (s, 1H), 8.52 (d, J = 5.4 Hz, 1H), 8.22 (d, J = 5.3 Hz, 1H), 3.98 (q, J = 6.8 Hz, 1H), 3.36 (t, J = 6.6 Hz, 1H), 2.80 (dd, J = 15.9, 4.3 Hz, 1H), 2.60 (tt, J = 16.0, 8.0 Hz, 2H), 2.36-2.21 (m, 4H), 1.38 (d, J = 6.8 Hz, 3H), 1.19 (d, J = 6.6 Hz, 3H), 1.04 (t, J = 7.0 Hz, 3H).; LCMS: 387 |
| 118 | 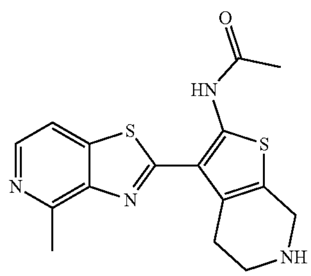 [SMILES: CC(=O)Nc1sc2c(c1-c1nc3c(C)nccc3s1)CCNC2] | ¹H NMR (400 MHz, DMSO-d6) δ 12.32 (br. s, 1H), 9.47 (br. s, 1H), 8.47-8.50 (m, 1H), 8.23-8.26 (m, 1H), 4.35 (br. s, 2H), 3.46-3.51 (m, 2H), 3.16-3.20 (m, 2H), 3.01 (br. s, 3H), 2.34 (br. s, 3H); LCMS: 345.1 |
| 119 | 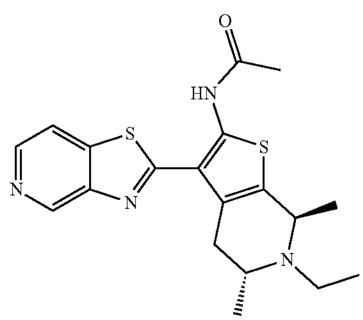 [SMILES: CCN1[C@H](C)Cc2c(sc(NC(C)=O)c2-c2nc3cnccc3s2)[C@H]1C] | ¹H NMR (400 MHz, DMSO-d6) δ 12.36 (s, 1H), 9.41 (s, 1H), 8.52 (d, J = 5.38 Hz, 1H), 8.23 (d, J = 5.38 Hz, 1H), 3.99 (d, J = 6.36 Hz, 1H), 2.80 (dd, J = 4.40, 15.65 Hz, 1H), 2.53-2.70 (m, 3H), 2.34 (s, 3H), 2.28 (dd, J = 6.60, 12.96 Hz, 1H), 1.38 (d, J = 6.36 Hz, 3H), 1.19 (d, J = 6.36 Hz, 3H), 1.04 (t, J = 6.85 Hz, 3H); LCMS: 387.05 |
| 120 | 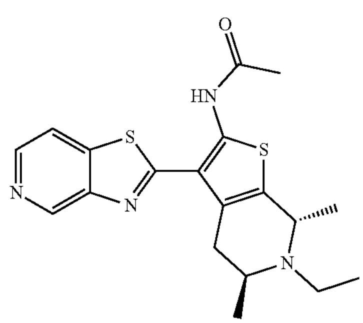 [SMILES: CCN1[C@@H](C)Cc2c(sc(NC(C)=O)c2-c2nc3cnccc3s2)[C@@H]1C] | ¹H NMR (400 MHz, DMSO-d6) δ 12.35 (br. s, 1H), 9.40 (s, 1H), 8.52 (d, J = 5.38 Hz, 1H), 8.22 (d, J = 4.89 Hz, 1H), 3.99 (d, J = 6.36 Hz, 1H), 2.80 (d, J = 12.23 Hz, 1H), 2.54-2.70 (m, 3H), 2.34 (s, 3H), 2.21-2.31 (m, 1H), 1.38 (d, J = 6.85 Hz, 3H), 1.19 (d, J = 6.36 Hz, 3H), 1.04 (t, J = 6.85 Hz, 3H); LCMS: 387.05 |
| 121 | 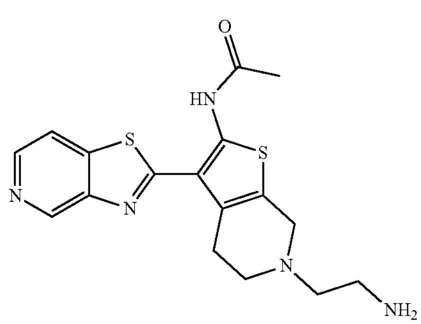 [SMILES: CC(=O)Nc1sc2c(c1-c1nc3cnccc3s1)CCN(CCN)C2] | ¹H NMR (400 MHz, DMSO-d6/D2O): δ 9.63 (s, 1H), 8.67 (d, J = 5.7 Hz, 1H), 8.52 (d, J = 5.7 Hz, 1H), 4.66 (s, 2H), 3.51 (s, 3H), 3.43-3.30 (m, 4H), 2.38 (s, 3H) (1 aliphatic proton merged in NMR solvent signal).; LCMS: 374 |

TABLE 1-continued

Exemplary Compounds and NMR/LCMS Data

| Compound | Structure | NMR/LCMS |
|---|---|---|
| 122 | 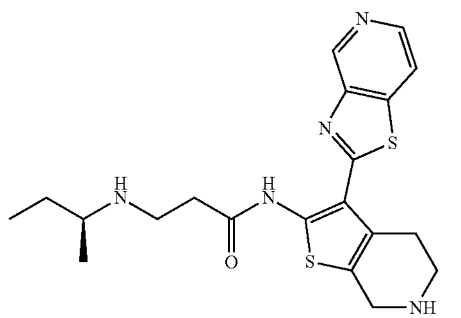 [SMILES: CC[C@H](C)NCCC(=O)Nc1sc2c(c1-c1nc3cnccc3s1)CCNC2] | $^1$H NMR (400 MHz, DMSO-d6/D2O) δ 9.55 (s, 1H), 8.63 (d, J = 5.7 Hz, 1H), 8.45 (d, J = 5.8 Hz, 1H), 4.34 (s, 2H), 3.48 (t, J = 6.0 Hz, 2H), 3.29-3.28 (m, 2H), 3.18-3.07 (m, 5H), 1.76 (dt, J = 12.3, 5.4 Hz, 1H), 1.49 (dt, J = 14.9, 7.9 Hz, 1H), 1.23 (d, J = 6.5 Hz, 3H), 0.91 (t, J = 7.4 Hz, 3H).; LCMS: 416 |
| 123 | 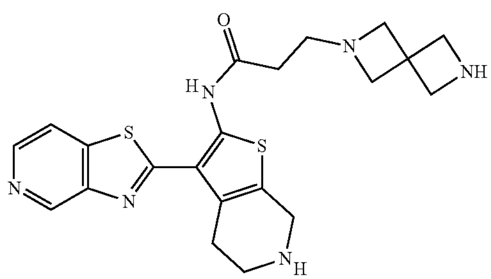 | $^1$H NMR (400 MHz, MeOD) d 9.477 (br, s, 1H), 8.590-8.576 (d, J = 6.4 Hz, 1H), 8.372-8.358 (d, J = 6.4 Hz, 1H), 4.497-4.442 (m, 6H), 4.327-4.301 (m, 4H), 3.660-3.646 (d, J = 5.6 Hz, 4H), 3.354-3.302 (m, 2H), 3.151 (s, 1H); LCMS: 441.2 |
| 124 | 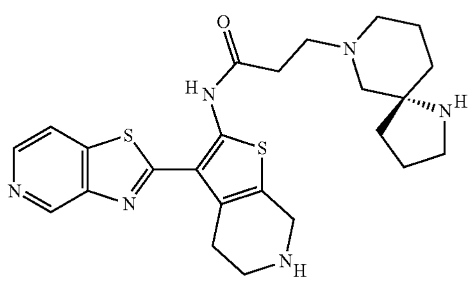 | $^1$H NMR (400 MHz, MeOD) d ppm 9.546 (s, 1 H), 8.618-8.603 (d, J = 6.00 Hz, 1 H), 8.455-8.440 (d, J = 6.00 Hz, 1 H), 4.442 (br. s., 2 H), 3.679-3.651 (t, J = 5.60 Hz, 2 H), 3.443-3.361 (m, 7 H), 3.202-3.188 (m, 2 H), 3.027-2.906 (m, 2 H), 2.129-1.881 (m, 9 H); LCMS: 483.3 |
| 125 | 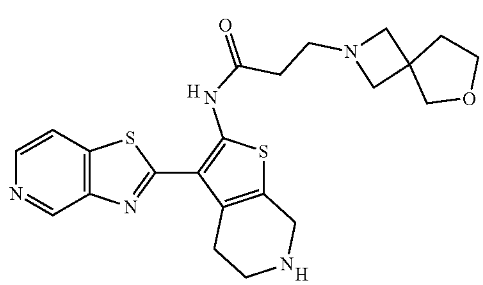 | $^1$H NMR (400 MHz, MeOD) d 9.446 (s, 1H), 8.566 (s, 1H), 8.333-8.319 (d, J = 5.6 Hz, 1H), 4.446 (s, 2H), 4.289 (br. s., 4H), 3.917 (s, 2H), 3.831-3.797 (t, J = 6.8 Hz, 2H), 3.689-3.647 (m, 2H), 3.355 (m, 2H), 3.167-3.135 (t, J = 6.4 Hz, 2H), 2.285 (br. s., 2H); LCMS: 456.2 |
| 126 | 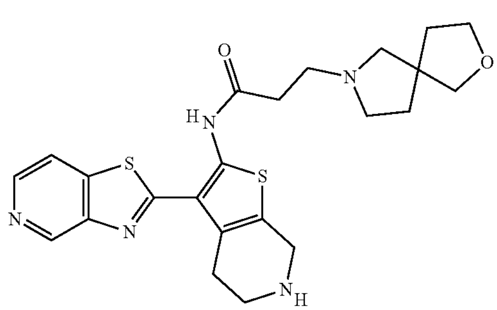 | $^1$H NMR (400 MHz, MeOD) d 9.496 (s, 1H), 8.587-5-8.599 (d, J = 4.80 Hz, 1H), 8.374-8.388 (d, J = 5.60 Hz, 1H), 4.447 (s, 2H), 3.877-3.895 (t, J = 3.6 Hz, 2H), 3.649-3.730 (m, 7H), 3.298-3.359 (m, 7H), 2.085-2.120 (t, J = 7.00 Hz, 4H); LCMS: 470.2 |

TABLE 1-continued

Exemplary Compounds and NMR/LCMS Data

| Compound | Structure | NMR/LCMS |
|---|---|---|
| 127 | 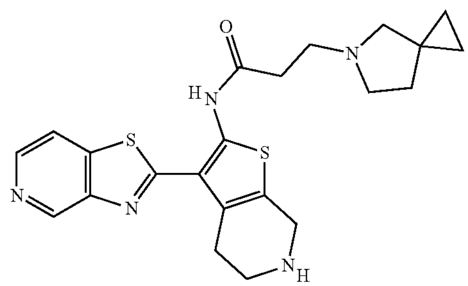 | ¹H NMR (400 MHz, MeOD) d 0.790 (br. s., 1H), 8.585-8.572 (d, J = 5.2 Hz, 1H), 8.353-8.339 (d, J = 5.6 Hz, 1H), 4.446 (br. s., 2H), 3.7.3-3.648 (m, 5H), 3.372-3.261 (m, 7H), 2.172-2.043 (m, 2H), 0.808-0.751 (m, 4H); LCMS: 440.2 |
| 128 | 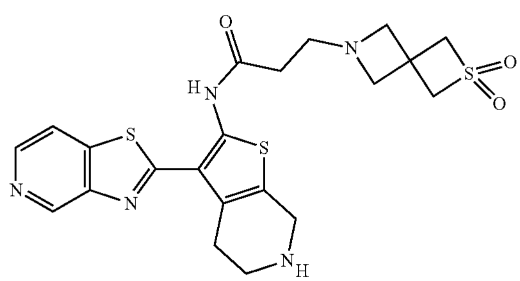 | ¹H NMR (400 MHz, MeOD) d 9.443 (br. s, 1H), 8.580-8.566 (d, J = 5.6 Hz, 1H), 8.329-8.315 (d, J = 5.6 Hz, 1H), 4.548 (br. S, 4H), 4469-4.445 (d, J = 9.6 Hz 6H), 3.725-3.645 (m, 4H), 3.363-3.340 (m, 2H), 3.182-3.151 (m, 2H); LCMS: 490.2 |
| 129 | 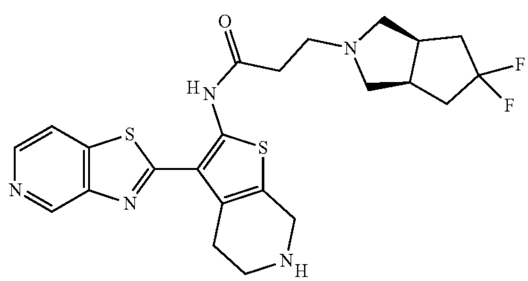 | ¹H NMR (400 MHz, MeOD) d 9.542 (br, s, 1H), 8.620-8.607 (d, J = 5.2 Hz, 1H), 8.459-8.445 (d, J = 5.6 Hz, 1H), 4.447 (s, 2H), 3.697-3.651 (m, 6H), 3.373-3.358 (m, 4H), 3.321-3.140 (m, 4H), 2.429-2.378 (m, 2H), 2.193-2.097 (m, 2H); LCMS: 490.1 |
| 130 | 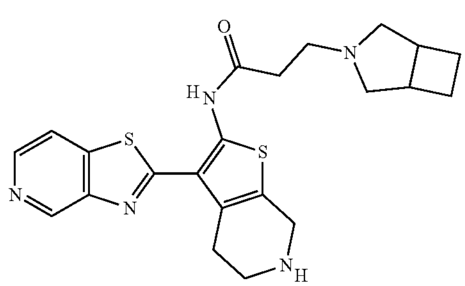 | ¹H NMR (400 MHz, MeOD) d 9.480 (br, s, 1H), 8.542 (s, 1H), 8.383-8.369 (d, J = 5.6 Hz, 1H), 4.371 (s, 2H), 3.705-3.576 (m, 6H), 3.287-3.274 (m, 4H), 3.182-3.171 (m, 4H), 2.299 (br, m, 2H), 1.080 (br, m, 2H); LCMS: 440.1 |
| 131 | 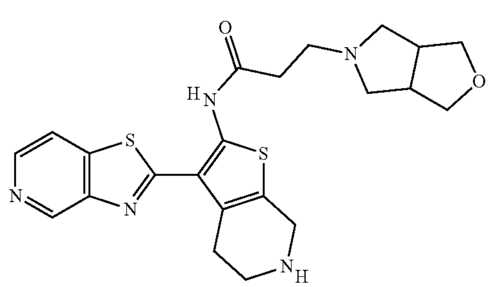 | ¹H NMR (400 MHz, MeOD) d 9.509 (br, s, 1H), 8.605-8.591 (d, J = 5.6 Hz, 1H), 8.415-8.401 (d, J = 5.6 Hz, 1H), 4.446 (s, 2H), 3.894-3.870 (d, J = 9.6, 2H), 3.679-3.629 (m, 6H), 3.373-3.358 (m, 4H), 3.341-3.283 (m, 4H), 3.267-3.180 (m, 2H); LCMS: 456.1 |

TABLE 1-continued

Exemplary Compounds and NMR/LCMS Data

| Compound | Structure | NMR/LCMS |
|---|---|---|
| 132 | 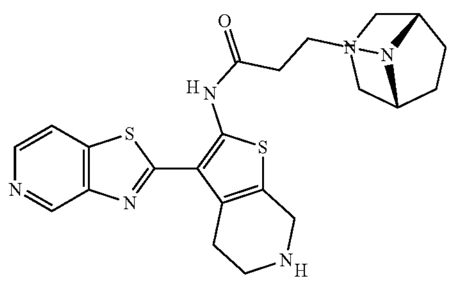 | ¹H NMR (400 MHz, MeOD) d 9.557 (br, s, 1H), 8.631-8.617 (d, J = 5.6 Hz, 1H), 8.476 (br, s, 1H), 4.446 (s, 2H), 3.952 (s, 1H), 3.686-3.655 (t, J = 6.2 2H), 3.383-3.340 (m, 2H), 3.025-2.904 (m, 6H), 2.644-2.614 (m, 2H), 1.936-1.835 (m, 4H); LCMS: 455.1 |
| 133 | 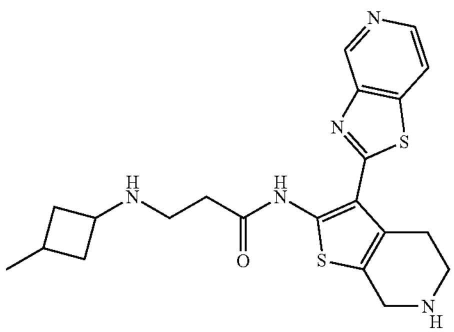 | ¹H NMR (400 MHz, MeOD) d 9.491 (s, 1H), 8.588 (s, 1H), 8.409-8.395 (d, J = 5.6 Hz, 1H), 4.449 (s, 2H), 3.681-3.651 (m, 2H), 3.354-3.302 (m, 4H), 3.202-3.161 (m, 2H), 2.538-2.392 (m, 2H), 2.088-2.067 (m, 1H), 1.805-1.800 (m, 1H), 1.220-1.137 (dd, J1 = 26.4 Hz, J2 = 6.8 Hz, 3H); LCMS: 428.1 |
| 134 | 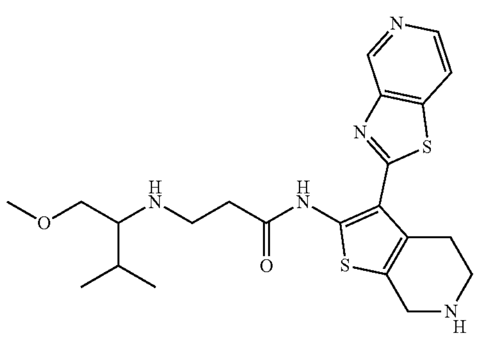 | ¹H NMR (400 MHz, MeOD) d 9.498 (s, 1H), 8.602-8.588 (d, J = 5.6 Hz, 1H), 8.397-8.384 (d, J = 5.6 Hz, 1H), 4.450 (s, 2H), 3.726-3.652 (m, 7H), 3.568-3.552 (m, 3H), 3.430-3.354 (m, 2H), 3.430-3.240 (m, 2H), 3.223-2.172 (d, J = 6.8 Hz, 2H), 1.144-1.128 (d, J = 6.4 Hz, 3H), 1.072-1.056 (d, J = 6.4 Hz, 1H); LCMS: 460.1 |
| 135 | 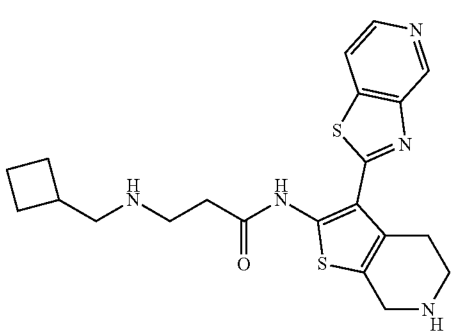 | ¹H NMR (400 MHz, MeOD) d 9.500 (s, 1H), 8.592 (s, 1H), 8.402-8.392 (d, J = 4, 1H), 4.446 (s, 1H), 3.679-3.649 (t, J = 6, 2H), 3.444-3.346 (t, J = 6, 2H), 3.302-3.215 (m, 2H), 3.199-3.166 (m, 4H), 3.147-2.725 (m, 1H), 2.212-2.191 (m, 2H), 2.004-1.920 (m, 2H), 1.913-1.850 (m, 4H); LCMS: 428.1 |

TABLE 1-continued
Exemplary Compounds and NMR/LCMS Data
| Compound | Structure | NMR/LCMS |
|---|---|---|
| 136 | 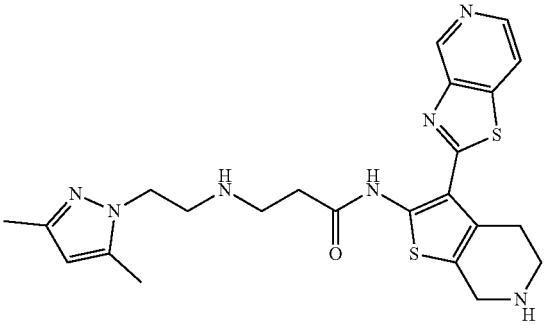 | $^1$H NMR (400 MHz, MeOD) d 9.546 (s, 1H), 8.600-8.585 (d, J = 6, 1H), 8.521-8.505 (d, J = 6.4, 1H), 5.834 (s, 1H), 4.407 (s, 2H), 4.293-4.265 (t, J = 5.6, 2H), 3.637-3.623 (t, J = 5.6 Hz, 2H), 3.527-3.455 (m, 4H), 3.249-3.223 (m, 4H), 2.220 (s, 3H), 2.153 (s, 3H); LCMS: 482.1 |
| 137 | 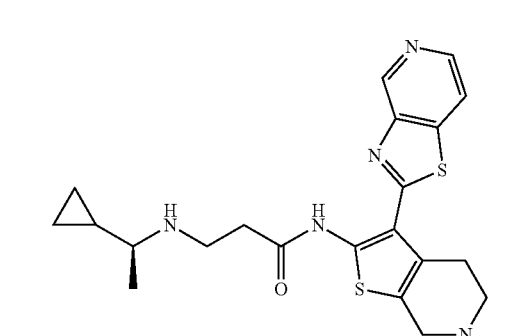 | $^1$H NMR (400 MHz, MeOD) d 9.467 (s, 1H), 8.548-8.534 (d, J = 5.6 Hz, 1H), 8.384-8.370 (d, J = 5.6 Hz, 1H), 4.424 (s, 2H), 3.643-3.517 (m, 4H), 3.308-3.179 (m, 4H), 2.696-2.656 (m, 1H), 1.443-1.430 (d, J = 5.2 Hz, 3H), 1.037-1.015 (m, 1H), 0.753-0.696 (m, 2H), 0.591-0.579 (m, 1H), 0.349-0.337 (m, 1H); LCMS: 428.1 |
| 138 | 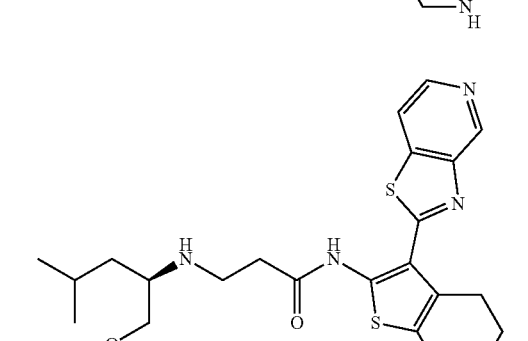 | $^1$H NMR (400 MHz, MeOD) d 9.525 (s, 1H), 8.578-8.563 (d, J = 6 Hz, 1H), 8.522-8.507 (d, J = 6 Hz, 1H), 4.375 (s, 2H), 3.848-3.825 (m, 1H), 3.612-3.582 (m, 3H), 3.486-3.454 (m, 2H), 3.284-3.272 (m, 3H), 3.224-3.175 (m, 2H), 1.683-1.588 (m, 2H), 1.509-1.476 (m, 1H), 0.938-0.899 (m, 6H); LCMS: 460.1 |
| 139 | 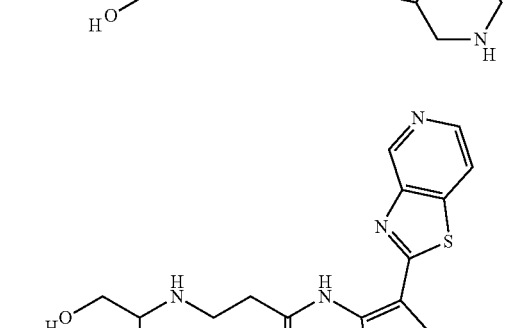 | $^1$H NMR (400 MHz, MeOD) d 9.594 (s, 1H), 8.667-8.652 (d, J = 6 Hz, 1H), 8.617-8.601 (d, J = 6.4 Hz, 1H), 4.495-4.447 (m, 3H), 3.991-3.969 (m, 2H), 3.684-3.669 (m, 2H), 3.351-3.345 (M, 1H), 3.304-3.297 (m, 3H), 3.234-3.218 (m, 2H); LCMS: 498.1 |

TABLE 1-continued

Exemplary Compounds and NMR/LCMS Data

| Compound | Structure | NMR/LCMS |
|---|---|---|
| 140 | 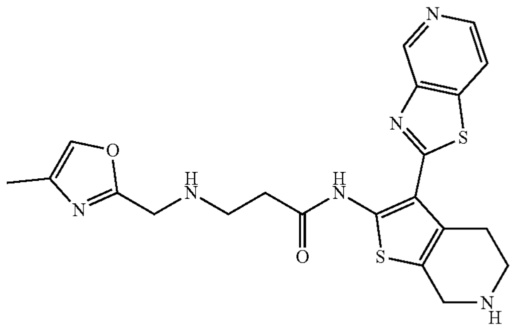 | ¹H NMR (400 MHz, MeOD) d 9.497 (s, 1H), 8.597-8.582 (d, J = 6 Hz, 1H), 8.420-8.407 (d, J = 5.2, 1H), 7.710 (s, 1H), 4.490-4.448 (d, J = 16.8 Hz, 4H), 3.680-3.602 (m, 4H), 3.364-3.351 (t, J = 5.2, 2H), 3.282-3.266 (t, J = 6.4 Hz, 2H), 2.164 (s, 3H); LCMS: 455.1 |
| 141 | 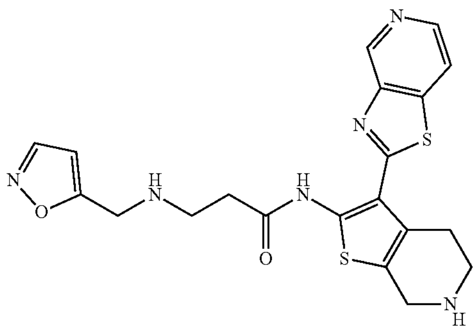 | ¹H NMR (400 MHz, MeOD) d 9.526 (s, 1H), 8.609-8.597 (d, J = 4.8 Hz, 1H), 8.495-8.457 (m, 2H), 6.704-6.701 (s, 1H), 4.616 (s, 2H), 4.447 (s, 2H), 3.682-3.651 (m, 2H), 3.576-3.545 (m, 2H), 3.359-3.346 (m, 2H), 3.275-3.243 (m, 2H); LCMS: 441.1 |
| 142 | 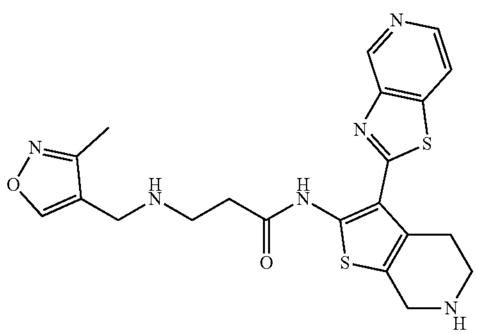 | ¹H NMR (400 MHz, MeOD) d 9.504 (s, 1H), 8.819 (s, 1H), 8.600-8.586 (d, J = 5.6 Hz, 1H), 8.431-8.417 (d, J = 5.6 Hz, 1H), 4.447 (s, 2H), 4.245 (s, 2H), 3.679-3.648 (t, J = 6.2 Hz, 2H), 3.529-3.514 (t, J = 6 Hz, 2H), 3.364-3.335 (t, J = 5.8 Hz, 2H), 3.270-3.255 (t, J = 2 Hz, 2H), 2.393 (s, 3H); LCMS: 455.1 |
| 143 | 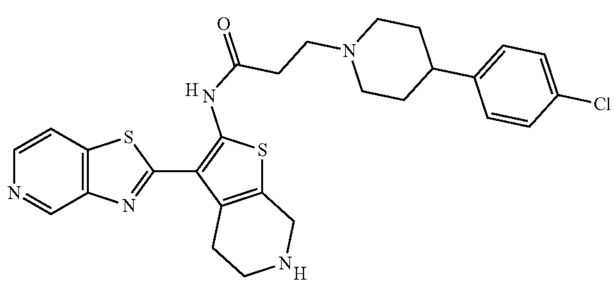 | ¹H NMR (400 MHz, MeOD) d 9.628 (s, 1H), 8.650-8.634 (d, J = 6.4 Hz, 1H), 8.576-8.560 (d, J = 6.4 Hz, 1H), 4.461 (s, 2H), 3.817-3.788 (d, J = 11.6 Hz, 2H), 3.699-3.668 (t, J = 4.4 Hz, 4H), 3.401-3.358 (m, 4H), 3.310-3.241 (m, 2H), 2.938-2.910 (m, 1H), 2.099-2.045 (m, 4H); LCMS: 538 |
| 144 | 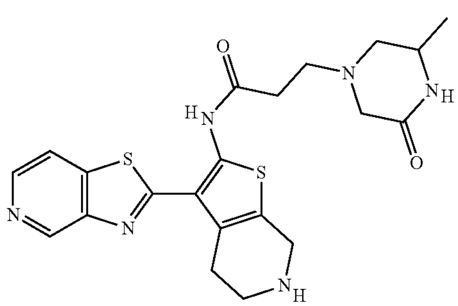 | ¹H NMR (400 MHz, MeOD) d 9.588 (s, 1H), 8.644-8.629 (d, J = 6 Hz, 1H), 8.538-8.524 (d, J = 5.6 Hz, 1H), 4.577 (s, 1H), 4.448-3.615 (m, 8H), 3.357-3.302 (m, 4H), 3.061-3.058 (m, 1H), 1.278-1.262 (d, J = 6.4 Hz, 3H); LCMS: 457.1 |

TABLE 1-continued

Exemplary Compounds and NMR/LCMS Data

| Compound | Structure | NMR/LCMS |
|---|---|---|
| 145 | 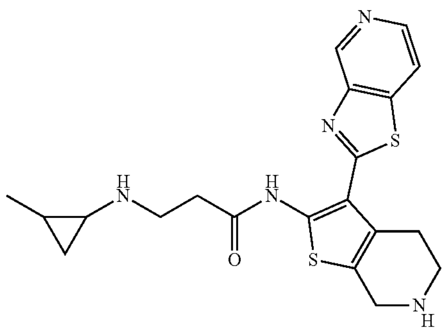 | ¹H NMR (400 MHz, MeOD) d 9.519 (s, 1H), 8.607-8.592 (d, J = 6 Hz, 1H), 8.456-8.441 (d, J = 6 Hz, 1H), 4.446 (s, 1H), 3.679-3.543 (m, 4H), 3.363-3.350 (m, 2H), 3.236-3.221 (t, J = 6 Hz, 2H), 2.562-2.527 (m, 1H), 1.335-1.295 (m, 2H), 1.131-1.061 (m, 3H), 0.728-0.622 (m, 1H); LCMS: 414.1 |
| 146 | 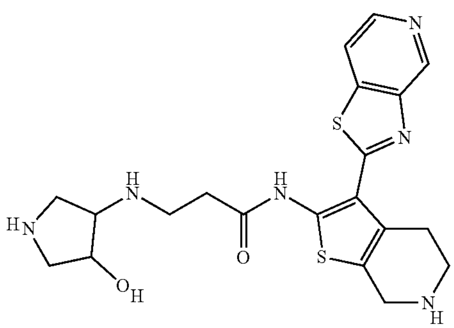 | ¹H NMR (400 MHz, MeOD) d ppm 9.607 (s, 1 H), 8.650-8.634 (d, J = 6.40 Hz, 1 H), 8.585-8.569 (d, J = 6.40 Hz, 1 H), 4.445 (s, 1 H), 3.958 (s, 2 H), 3.958-3.938 (m, 2 H), 3.686-3.621 (m, 7 H), 3.383-3.339 (m, 4 H); LCMS: 445.1 |
| 147 | 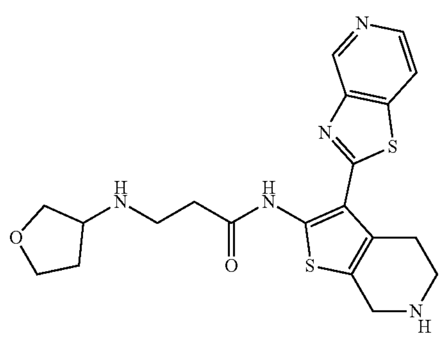 | ¹H NMR (400 MHz, MeOD), d 9.496 (s, 1H) 8.583-8.570 (d, 5.2 Hz, 1H) 8.414-8.399 (d, 6 Hz, 1H) 4.448 (s, 2H), 4.082-4.058 (m, 4H) 3.682-3.651 (m, 3H) 3.507-3.492 (t, 3 Hz, 2H) 3.353-3.339 (t, 5.6 Hz, 2H) 3.239-3.224 (t, 6 Hz, 2H) 2.449-2.401 (m, 1H) 2.154-2.112 (m, 1H); LCMS: 430.1 |
| 148 | 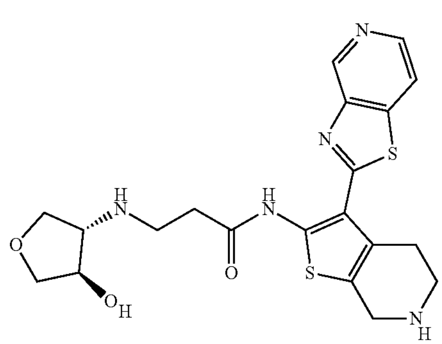 | ¹H NMR (400 MHz, MeOD), d 9.620 (s, 1H) 8.663-8.648 (d, 6 Hz, 1H) 8.613-8.598 (d, 6 Hz, 1H) 4.569 (br. s., 1H) 4.450 (s, 2H) 4.146-3.995 (m, 2H) 3.995 (d, 1H) 3.709-3.586 (m, 6H) 3.354 (br. s. 2H) 3.301-3.269 (m, 2H); LCMS: 446.1 |

TABLE 1-continued

Exemplary Compounds and NMR/LCMS Data

| Compound | Structure | NMR/LCMS |
|---|---|---|
| 149 | 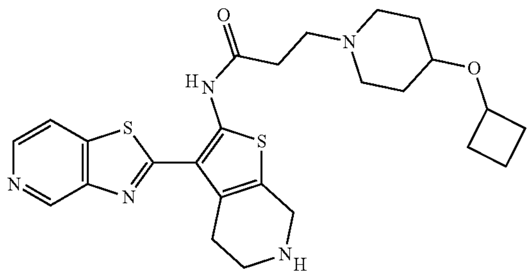 | $^1$H NMR (400 MHz, MeOD), d 9.615 (s, 1H) 8.653-8.639 (d, 5.6 Hz, 1H) 8.580-8.566 (d, 5.6 Hz, 1H) 4.446 (s, 2H) 4.063 (br. s., 1H) 4.063 (br. s., 1H) 3.748-3.573 (m, 7H) 3.353-3.3 (m, 4H) 3.127 (br. s., 1H) 2.249-2.192 (m, 3H) 2.015-1.963 (m, 5H) 1.718-1.512 (m, 3H); LCMS: 498.2 |
| 150 | 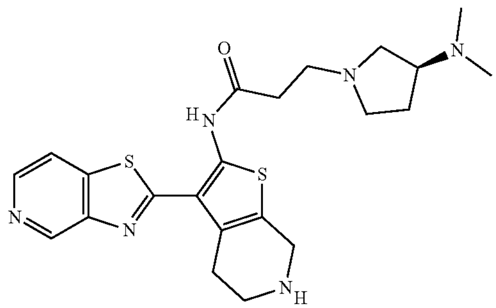 | $^1$H NMR (400 MHz, MeOD), d 9.540 (s, 1H) 8.581-8.567 (d, 5.6 Hz, 1H) 8.516-8.502 (d, 5.6 Hz, 1H) 4.371 (s, 2H) 4.174-4.135 (m, 1H) 3.914-3.895 (d, 7.6 Hz, 2H) 3.699-3.579 (m, 6H) 3.280-3.224 (m, 4H) 2.902 (s, 6H) 2.597-2.565 (m, 1H) 2.374-2.338 (m, 1H); LCMS: 457.2 |
| 151 | 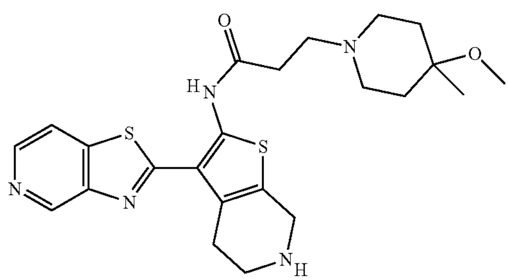 | $^1$H NMR (400 MHz, MeOD) d 9.577 (s, 1H), 8.603-5-8.619 (d, J = 6.40 Hz, 1H), 8.519-8.533 (d, J = 5.60 Hz, 1H), 4.423 (s, 2H), 3.566-3.660 (m, 6H), 3.205-3.341 (m, 9H), 2.023-2.060 (d, J = 14.8, 2H), 1.208 (s, 3H); LCMS: 472.1 |
| 152 | 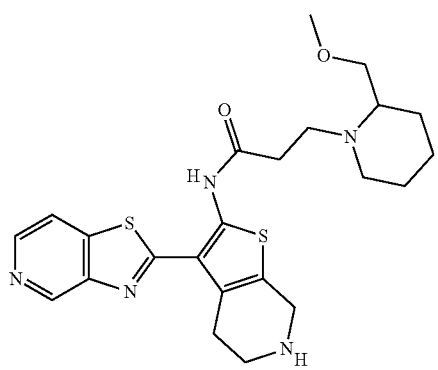 | $^1$H NMR (400 MHz, MeOD) d 9.586 (s, 1H), 8.634-5-8.648 (d, J = 5.60 Hz, 1H), 8.533-8.547 (d, J = 5.60 Hz, 1H), 4.449 (s, 2H), 3.568-3.872 (m, 7H), 3.146-3.442 (m, 9H), 1.611-1.948 (m, 6H); LCMS: 472.1 |
| 153 | 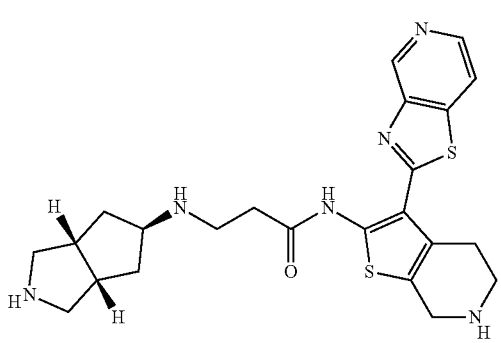 | $^1$H NMR (400 MHz, MeOD) d 9.449 (br, s, 1H), 8.575-8.561 (d, J = 5.6 Hz, 1H), 8.340-8.326 (d, J = 5.6 Hz, 1H), 4.446 (s, 2H), 3.678-3.662 (m, 2H), 3.570-3.496 (m, 4H), 3.355-3.341 (m, 2H), 3.246-3.229 (m, 2H), 3.103-3.025 (m, 5H), 2.167-2.1052 (m, 4H); LCMS: 469.1 |

TABLE 1-continued

Exemplary Compounds and NMR/LCMS Data

| Compound | Structure | NMR/LCMS |
|---|---|---|
| 154 | 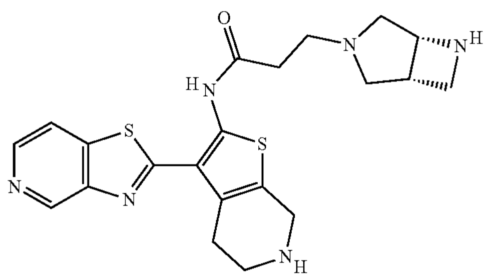 | $^1$H NMR (400 MHz, MeOD) d 9.463 (br. S, 1H), 8.590-8.576 (d, J = 5.6 Hz, 1H), 8.359-8.344 (d, J = 6.0 Hz, 1H), 4.447 (br, s, 2H), 4.124-4.098 (m, 1H), 3.697-3.630 (m, 4H), 3.459-3.336 (m, 6H), 3.147-3.117 (m, 3H), 2.650-2.630 (d, J = 8.0 Hz, 1H), 2.528-2.503 (d, J =10.0 Hz, 1H); LCMS: 441.2 |
| 155 | 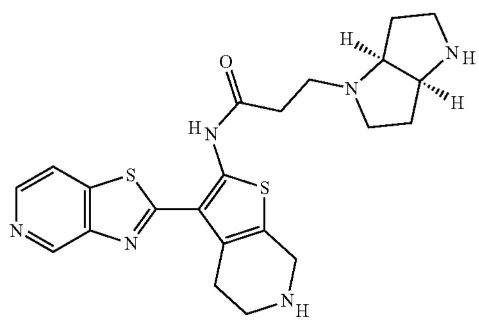 | $^1$H NMR (400 MHz, MeOD) d 9.528-9.519 (br. S, 1H), 8.607-8.594 (d, J = 5.2 Hz, 1H), 8.429-8.417 (d, J = 4.8 Hz, 1H), 4.482-4.438 (m, 3H), 4.085 (br, s, 1H), 3.753-3.651 (m, 4H), 3.462-3.451 (m, 2H), 3.357-3.220 (m, 4H), 3.066-3.053 (d, J = 5.2 Hz, 1H), 2.560-2.434 (m, 2H), 2.280-2.107 (m, 2H); LCMS: 455.2 |
| 156 | 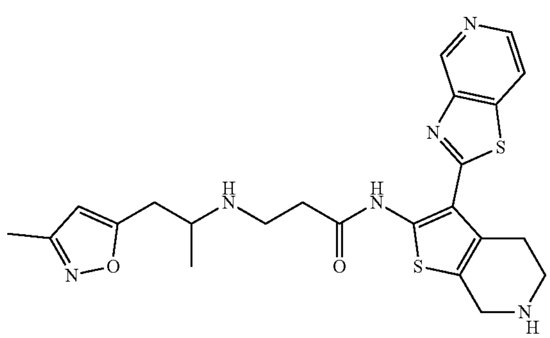 | $^1$H NMR (400 MHz, MeOD) d 9.474 (s, 1H), 8.578-8.567 (d, J = 4.4 Hz, 1H), 8.349-8.334 (d, J = 6 Hz, 1H), 6.278 (s, 1H), 4.452 (s, 2H), 3.773-3.546 (m, 5H), 3.358-3.328 (m, 3H), 3.258-3.123 (m, 3H), 2.273 (s, 3H), 1.403-1.386 (d, J = 6.8 Hz, 3H); LCMS: 483.1 |
| 157 | 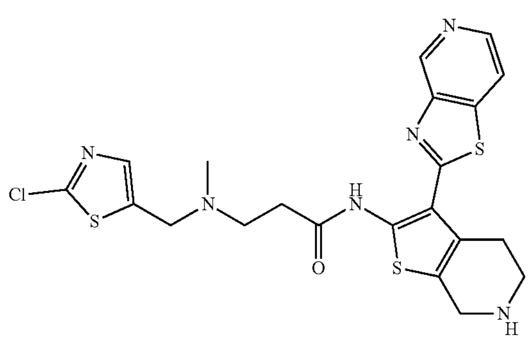 | $^1$H NMR (400 MHz, MeOD) d 9.643 (s, 1H), 8.664-8.651 (d, J = 5.2 Hz, 2H), 8.612-8.598 (d, J = 5.6 Hz, 1H), 7.854 (s, 1H), 4.923 (s, 2H), 4.448 (s, 2H), 3.682-3.635 (m, 4H), 3.387-3.341 (m, 4H), 2.964 (s, 3H); LCMS: 505.1 |

TABLE 1-continued

Exemplary Compounds and NMR/LCMS Data

| Compound | Structure | NMR/LCMS |
|---|---|---|
| 158 | 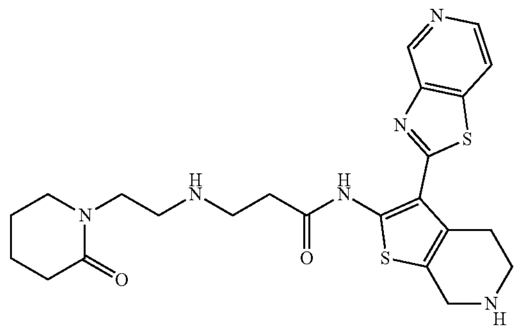 | ¹H NMR (400 MHz, MeOD) d 9.539 (s, 1H), 8.613-8.600 (d, J = 5.2 Hz, 1H), 8.461-8.448 (d, J = 5.2 Hz, 1H), 4.449 (s, 2H), 3.721-3.666 (m, 4H), 3.510-3.438 (m, 2H), 3.426-3.411 (m, 2H), 3.353-3.343 (d, J = 4 Hz, 4H), 3.225 (m, 2H), 2.413-2.383 (t, J = 12 Hz, 2H), 1.854 (s, 4H); LCMS: 485.2 |
| 159 | 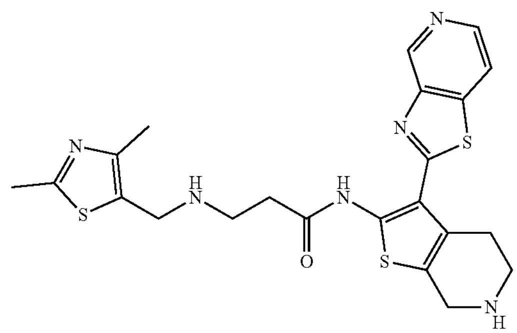 | ¹H NMR (400 MHz, MeOD) d 9.607 (s, 1H), 8.670-8.655 (d, J = 6 Hz, 1H), 8.599-8.583 (d, J = 6.4 Hz, 1H), 4.510 (s, 2H), 4.451 (s, 2H), 3.683-3.654 (t, J = 5.8 Hz, 2H), 3.534-3.502 (t, J = 6.4 Hz, 2H), 3.376-3.363 (t, J = 5.2 Hz, 2H), 3.267-3.235 (t, J = 6.4 Hz, 2H), 2.674 (s, 3H), 2.449 (s, 3H); LCMS: 485.2 |
| 160 | 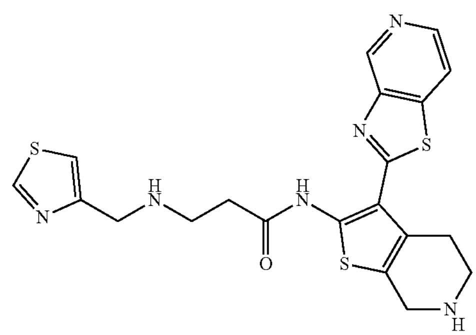 | ¹H NMR (400 MHz, MeOD) d 9.456 (s, 1H), 9.086 (s, 1H), 8.586-8.571 (d, J = 6 Hz, 1H), 8.362-8.348 (d, J = 5.6 Hz, 1H), 7.808 (s, 1H), 4.497 (s, 2H), 4.447 (s, 2H), 3.679-3.648 (t, J = 6.2 Hz, 2H), 3.553-3.521 (t, J = 6.4 Hz, 2H), 3.370-3.356 (m, 2H), 3.251-3.220 (t, J = 6.2 Hz, 2H); LCMS: 457.2 |
| 161 | 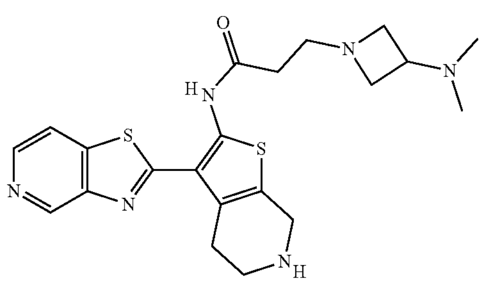 | ¹H NMR (400 MHz, MeOD) d 9.598 (s, 1H), 8.656-8.642 (d, J = 5.6 Hz, 1H), 8.568-8.553 (d, J = 6 Hz, 1H), 4.652-4.633 (d, J = 7.6 Hz, 4H), 4.446 (s, 2H), 4.328 (m, 1H), 3.799-3.768 (t, J = 6.2 Hz, 2H), 3.681-3.651 (t, J = 6 Hz, 2H), 3.372-3.344 (t, J = 5.6 Hz, 2H), 3.225-3.193 (t, J = 6.4 Hz, 2H), 2.873 (s, 6H); LCMS: 443.2 |
| 162 | 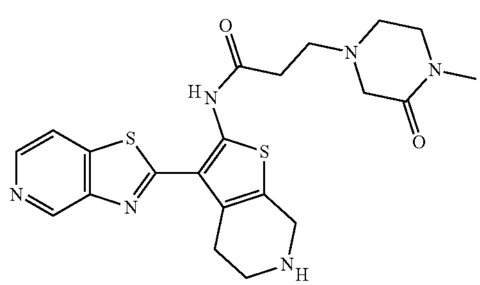 | ¹H NMR (400 MHz, MeOD), d 9.487 (br. s., 1H), 8.542 (br. s., 1H), 8.395-8.382 (d, 5.2 Hz, 1H), 4.439 (s, 2H), 3.951 (s, 2H), 3.675-3.623 (m, 8H), 3.315 (br. s. 2H), 3.009 (s. 2H), 2.994 (s, 3H); LCMS: 457.3 |

TABLE 1-continued

Exemplary Compounds and NMR/LCMS Data

| Compound | Structure | NMR/LCMS |
|---|---|---|
| 163 | 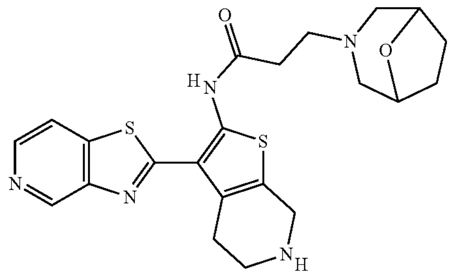 | $^1$H NMR (400 MHz, MeOD) d 9.660 (s, 1H), 8.658-5-8.673 (d, J = 6.00 Hz, 1H), 8.607-8.622 (d, J = 6.00 Hz, 1H), 4.550 (s, 2H), 4.446 (s, 2H), 3.590-3.684 (m, 4H), 3.514-3.545 (d, J = 12.40, 2H), 3.274-3.357 (m, 6H), 2.138 (s, 4H); LCMS: 456.2 |
| 164 | 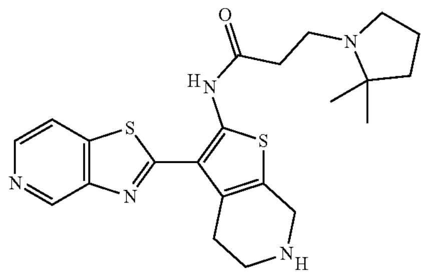 | $^1$H NMR (400 MHz, MeOD) d 9.468 (s, 1H), 8.532-5-8.545 (d, J = 5.20 Hz, 1H), 8.330-8.344 (d, J = 5.60 Hz, 1H), 4.445 (s, 2H), 3.649-3.679 (t, J = 6.00, 2H), 3.286-3.339 (m, 6H), 2.076 (s, 4H), 1.375-1.591 (m, 6H); LCMS: 442.2 |
| 165 | 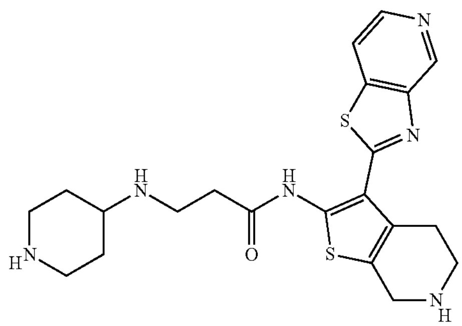 | $^1$H NMR (400 MHz, MeOD) d 9.4441 (s, 1H), 8.570-8.558 (d. J = 4.8 Hz, 1H), 8.318-8.304 (d, J = 5.6 hZ, 1H), 4.445 (s, 2H), 3.660-3.590 (t. J = 2.8 Hz, 2H), 3.560-3.531 (m, 5H), 3.368-3.356 (m, 2H), 3.259-3.229 (m, 2H), 3.118 (m, 2H), 2.434-2.402 (m, 2H), 1.959-1.928 (m, 2H); LCMS: 443.2 |
| 166 | 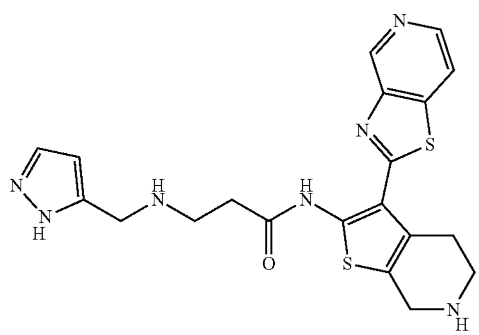 | $^1$H NMR (400 MHz, MeOD) d 9.452 (s, 1H), 8.587-8.572 (d, J = 6 Hz, 1H), 8.360-8.346 (d, J = 5.6 Hz, 1H), 7.740-7.734 (d, J = 6.4 Hz, 1H), 6.500-6.495 (d, J = 6 Hz, 1H), 4.447 (s, 2H), 4.350 (s, 2H), 3.664-3.648, (t, J = 6.4 Hz, 2H), 3.515-3.482 (t, J = 6.4 Hz, 2H), 3.305-3.298 (m, 2H), 3.228-3.212 (t, J = 6.4 Hz, 2H); LCMS: 440.1 |
| 167 | 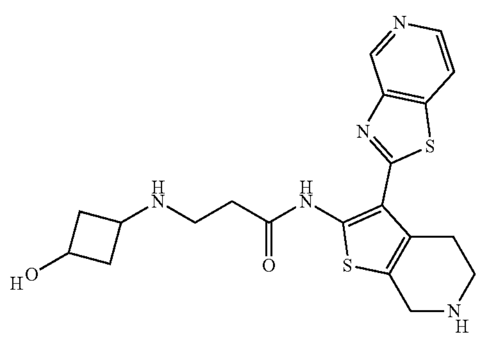 | $^1$H NMR (400 MHz, MeOD) d 9.561 (s, 1H), 8.637-8.623 (d, J = 5.6 Hz, 1H), 8.515-8.501 (d, J = 5.6 Hz, 1H), 4.450 (s, 2H), 4.116-4.099 (m, 1H), 3.682-3.652 (t, J = 6 Hz, 2H), 3.400-3.357 (m, 4H), 3.213-3.182 (m, 2H), 2.772-2.743 (m, 2H), 2.700-2.650 (m, 1H), 2.141-2.069 (m, 2H); LCMS: 430.1 |

TABLE 1-continued

Exemplary Compounds and NMR/LCMS Data

| Compound | Structure | NMR/LCMS |
|---|---|---|
| 168 | 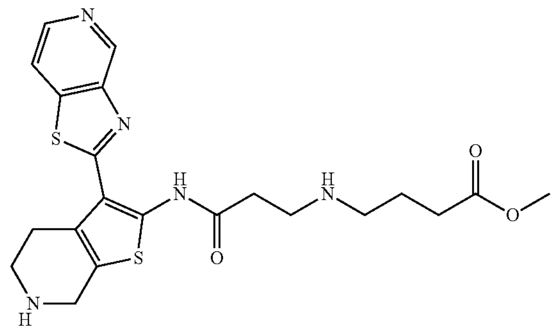 | ¹H NMR (400 MHz, MeOD) d 9.575 (s, 1H), 8.642-8.628 (d, J = 5.6 Hz, 1H), 8.526-8.511 (d, J = 6 Hz, 1H), 4.449 (s, 2H), 3.686-3.652 (m, 4H), 3.478-3.463 (m, 2H), 3.359-3.300 (m, 2H), 3.243-3.162 (m, 5H), 2.531-2.486 (m, 2H), 2.041-2.003 (m, 2H); LCMS: 460.1 |
| 169 | 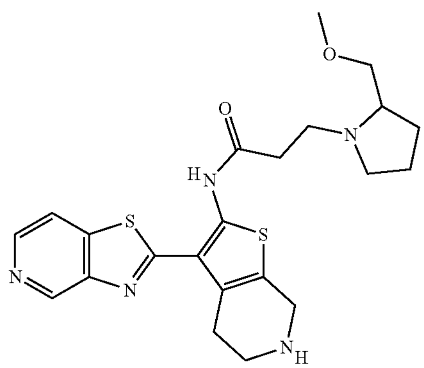 | ¹H NMR (400 MHz, MeOD) d 9.654 (s, 1H), 8.674-5-8.689 (d, J = 6.00 Hz, 1H), 8.633-8.648 (d, J = 6.00 Hz, 1H), 4.453 (s, 2H), 3.658-3.829 (m, 8H), 3.301-3.410 (m, 8H), 1.903-2.292 (m, 4H); LCMS: 458.1 |
| 170 | 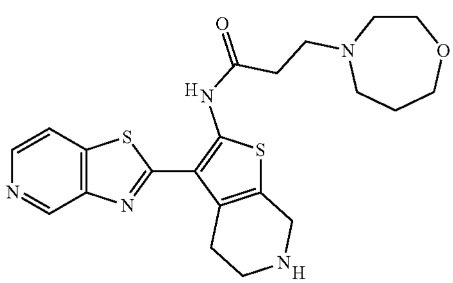 | ¹H NMR (400 MHz, MeOD) d 9.523 (s. 1H), 8.590-8.576 (d. J = 5.6 Hz, 1H), 8.430-8.415 (d. J = 6.0 Hz, 1H), 4.446 (s. 2H), 3.963-3.940 (T. J = 4.6 Hz, 2H), 3.853 (m. 8H), 3.710-3.650 (m. 8H), 3.357-3.301 (m. 4H), 2.221 (m. 2H); LCMS: 444.1 |
| 171 | 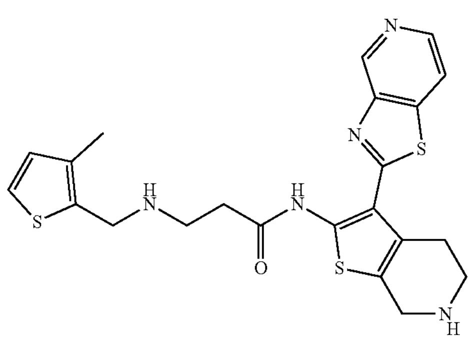 | ¹H NMR (400 MHz, MeOD) d 9.385 (s, 1H), 8.542 (s, 1H), 8.271-8.256 (d, J = 6 Hz 1H), 7.483-7.417 (d, J = 4.8 Hz, 1H), 6.974-6.962 (d, J = 4.8, 1H), 4.501 (s, 2H), 4.446 (s, 2H), 3.675-3.645 (m, 2H), 3.524-3.492 (m, 2H), 3.368-3.190 (m, 4H), 2.349 (s, 3H); LCMS: 470 |

TABLE 1-continued
Exemplary Compounds and NMR/LCMS Data
| Compound | Structure | NMR/LCMS |
|---|---|---|
| 172 | 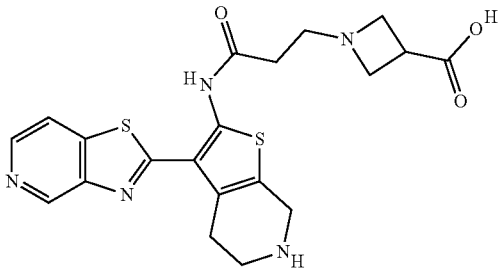 | ¹H NMR (400 MHz, MeOD) d 9.518 (s. 1H), 8.608 (s, 1H), 8.434-8.422 (d. J = 4.8 Hz, 1H), 4.445 (s, 4H), 3.790-3.647 (m. 5H), 3.368-3.339 (m. 4H), 3180-3.148 (m. 2H); LCMS: 444 |
| 173 | 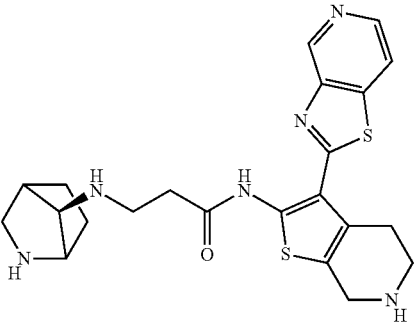 | ¹H NMR (400 MHz, MeOD) d 9.501 (br, s, 1H), 8.600-8.586 (d, J = 5.2 Hz, 1H), 8.404-8.390 (d, J = 5.6 Hz, 1H), 4.445 (s, 2H), 4.242 (s, 1H), 3.759 (s, 1H), 3.678-3.648 (t, J = 6.0 Hz, 2H), 3.557-3.357 (m, 3H), 3.257-3.183 (m, 3H), 2.911 (s, 1H), 2.171-1.976 (m, 3H), 1.816-1.771 (m, 4H); LCMS: 455.1 |
| 174 | 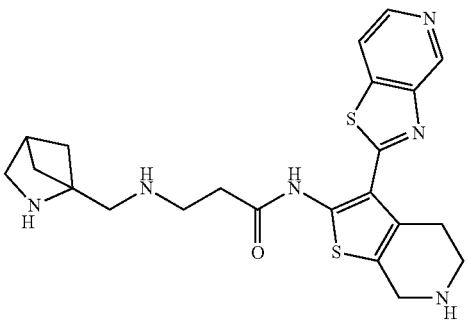 | ¹H NMR (400 MHz, MeOD) d 9.501 (br, s, 1H), 8.589 (br, s, 1H), 8.397-8.383 (d, J = 5.6 Hz, 1H), 4.442 (s, 2H), 3.747 (s, 2H), 3.662-3.579 (m, 2H), 3.563 (br, m, 2H), 3.488 (s, 2H), 3.369-3.272 (m, 4H), 2.992 (br, s, 1H), 2.296 (br, s, 2H), 1.766-1.747 (m, 2H); LCMS: 455.2 |
| 175 | 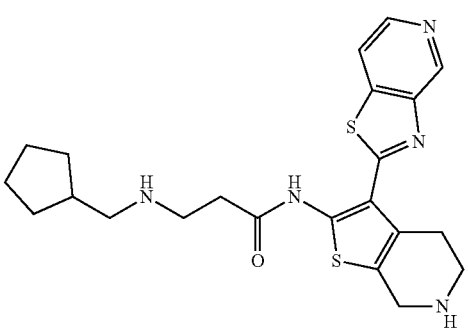 | ¹H NMR (400 MHz, MeOD) d 9.347 (s, 1H), 8.533-8.518 (d, J = 6 Hz, 1H), 8.193-8.179 (d, J = 5.6 Hz, 1H), 4.446 (s, 2H), 3.676-3.645 (t, J = 6.2 Hz, 2H), 3.481-3.464 (m, 2H), 3.369-3.355 (m, 2H), 3.215-3.182 (t, J = 6.6 Hz, 2H), 3.098-3.080 (d, J = 7.2 Hz, 2H), 1.943-1.927 (m, 2H), 1.730-1.651 (m, 4H), 1.329-1.281 (m, 3H); LCMS: 442.1 |

TABLE 1-continued

Exemplary Compounds and NMR/LCMS Data

| Compound | Structure | NMR/LCMS |
| --- | --- | --- |
| 176 | 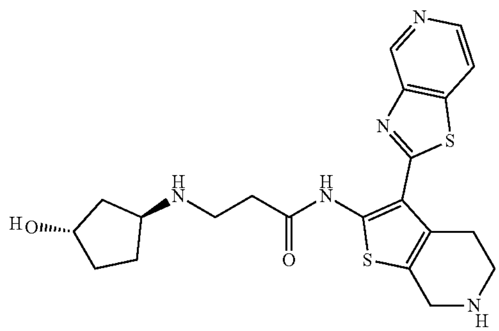 | ¹H NMR (400 MHz, MeOD) d 9.485 (s, 1H), 8.580-8.566 (d, J = 5.6 Hz, 1H), 8.347-8.332 (d, J = 6 Hz, 1H), 4.439 (s, 2H), 3.676-3.621 (m, 7H), 3.369-3.247 (m, 6H), 2.997 (s, 1H), 2.337 (s, 2H); LCMS: 444.1 |
| 177 | 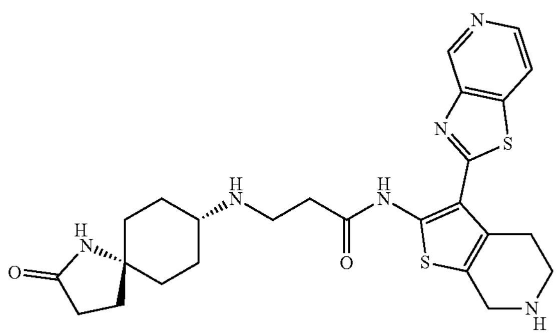 | ¹H NMR (400 MHz, MeOD) d 9.436 (s, 1H), 8.556-5-8.569 (d, J = 5.20 Hz, 1H), 8.292-8.305 (d, J = 5.20 Hz, 1H), 4.449 (s, 1H), 3.648-3.679 (t, J = 6.2 Hz, 2H), 3.499-3.515 (t, J = 6.40 Hz, 2H), 3.343-3.373 (t, J = 6.00 Hz, 3H), 3.215-3.247 (t, J = 6.40 Hz, 2H), 2.375-2.415 (t, J = 8.00 Hz, 2H), 2.120 (br. s., 2H), 1.889-1.981 (m, 4H), 1.652-1.675 (m, 4H); LCMS: 511.1 |
| 178 | 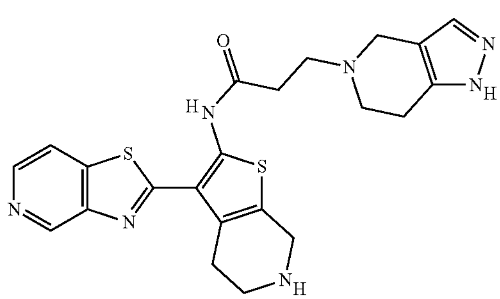 | ¹H NMR (400 MHz, MeOD) d 9.523 (s. 1H), 8.597-8.586 (d. J = 4.4 Hz, 1H), 8.406-8.392 (d. J = 5.6 Hz, 1H), 7.600 (s, 1H), 4.523-4.448 (m. 4H), 3.787-3.753 (m. 4H), 3.667-3.753 (T, J = 6.0 Hz, 2H), 3.421-3.340 (m. 4H), 3.172 (m. 2H); LCMS: 466.1 |
| 179 | 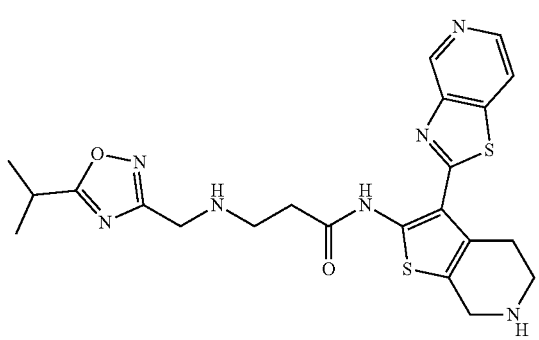 | ¹H NMR (400 MHz, MeOD) d 9.453 (s., 1H), 8.568-8.554 (d. J = 5.6 Hz, 1H), 8.330-8.316 (d. J = 5.6 Hz, 1H), 4.538 (s. 2H), 4.448 (s. 2H), 3.680-3.630 (m, 4H), 3.367-3.261 (m, 5H), 1.417-1.400 (d. J = 6.8 Hz, 6H); LCMS: 484.1 |

TABLE 1-continued

Exemplary Compounds and NMR/LCMS Data

| Compound | Structure | NMR/LCMS |
|---|---|---|
| 180 | 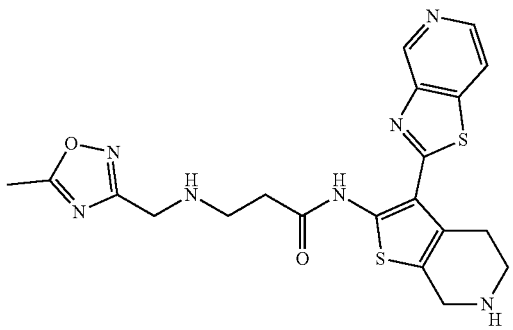 | ¹H NMR (400 MHz, MeOD) d 9.403 (s, 1H), 8.565-8.550 (d, J = 6 HZ, 1H), 8.283-8.256 (d, J = 10.8 Hz, 1H), 4.524 (s, 2H), 4.449 (s, 2H), 3.679-3.618 (m, 4H), 3.374-3.247 (m, 4H), 2.644 (s, 3H); LCMS: 456 |
| 181 | 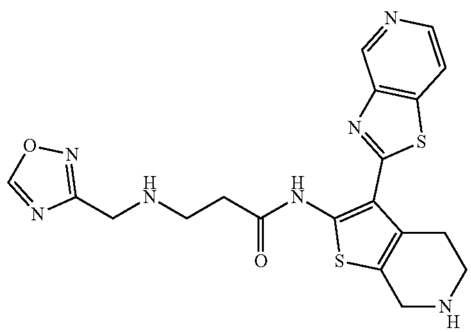 | ¹H NMR (400 MHz, MeOD) d 9.474-9.427 (m, 2H), 8.578 (s, 1H), 8.366-8.354 (d, J = 4.8 HZ, 1H), 4.636 (s, 2H), 4.446 (s, 2H), 3.675-3.647 (m, 4H), 3.365-3.337 (m, 4H); LCMS: 442 |
| 182 | 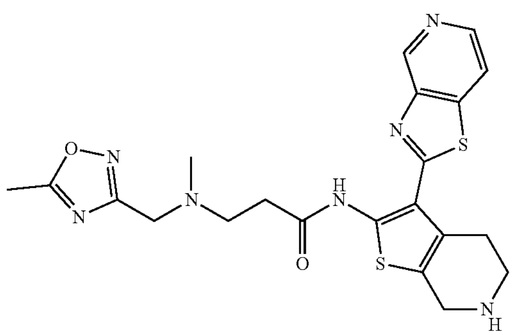 | ¹H NMR (400 MHz, MeOD) d 9.5 (s, 1H), 8.596-8.581 (d, J = 6 HZ 1H), 8.367-8.352 (d, J = 6 HZ, 1H), 4.652 (s, 2H), 4.458 (s, 2H), 3.736-3.660 (m, 4H), 3.361-3.351 (m, 4H), 3.060 (s, 3H), 2.656 (s, 3H); LCMS: 470.1 |
| 183 | 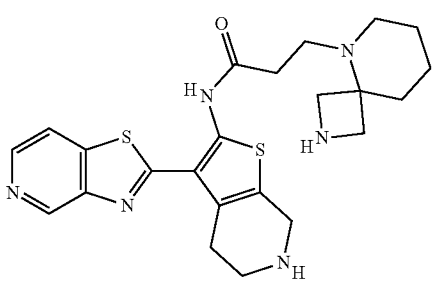 | ¹H NMR (400 MHz, MeOD) d 9.584 (s, 1H), 8.648-8.633 (d. J = 6 Hz, 1H), 8.537-8.522 (d, J = 6 Hz, 1H), 4.731-4.700 (d. J =12.4 Hz, 2H), 4.4440 (s, 2H), 4.126-4.094 (d. J =12.8 Hz, 2H), 3.684-3.685 (t. J = 6 Hz, 2H), 3.580-3.553 (t. J = 5.4 Hz, 2H), 3.380-3.353 (t, J = 5.4 Hz, 2H), 2.171-2.150 (t. J = 4.2 Hz, 2H), 1.820-1.743 (m, 4H); LCMS: 469.2 |
| 184 | 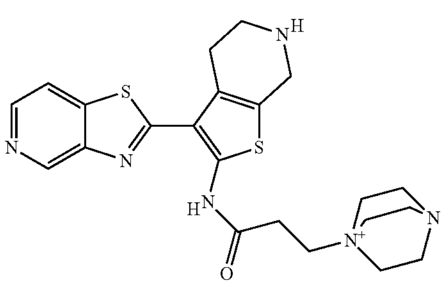 | ¹H NMR (400 MHz, MeOD) d 9.772 (s, 1H), 8.652-8.637 (d, J = 6.0 Hz, 1H), 8.546-8.531 (d, J = 6.0 Hz, 1H), 4.447 (s, 2H), 3.805-3.672 (t, J = 6.6 Hz, 2H), 3.658-3.558 (m, 2H), 3.540-3.467 (m, 7H), 3.376 (m, 2H), 1.280 (br. s., 5H); LCMS: 455.1 |

TABLE 1-continued

Exemplary Compounds and NMR/LCMS Data

| Compound | Structure | NMR/LCMS |
|---|---|---|
| 185 | 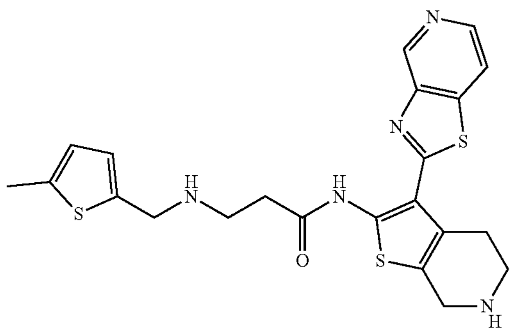 | $^1$H NMR (400 MHz, MeOD) d 9.402-9.377 (d, J = 10 Hz, 1H), 8.561-8.548 (d, J = 5.2 Hz, 1H), 8.292-8.277 (d, J = 6.0 Hz, 1H), 7.105-7.097 (d, J = 3.2 Hz, 1H), 6.781-6.775 (d, J = 2.4 Hz, 1H), 4.449 (s, 4H), 3.676-3.646 (t, J = 6.0 Hz, 2H), 3.486-3.454 (t, J = 6.4 Hz, 2H), 3.366-3.340 (t, J = 5.2 Hz, 2H), 3.207-3.191 (m, 2H), 2.485 (s, 3H); LCMS: 470 |
| 186 | 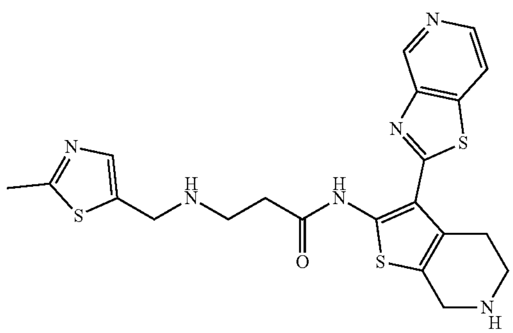 | $^1$H NMR (400 MHz, MeOD) d 9.476 (s, 1H), 8.585 (s, 1H), 8.382-8.369 (d, J = 5.2 Hz, 1H), 7.791 (s, 1H), 6.781-6.775 (d, J = 2.4 Hz, 1H), 4.568 (s, 2H), 4.445 (s, 2H), 3.676-3.646 (t, J = 6.0 Hz, 2H), 3.515-3.483 (t, J = 6.4 Hz, 2H), 3.366-3.339 (t, J = 5.0 Hz, 2H), 3.246-3.229 (m, 2H), 2.718 (s, 3H); LCMS: 471 |
| 187 | 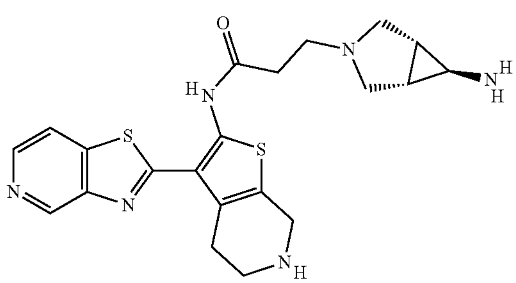 | $^1$H NMR (400 MHz, MeOD) d 9.485 (br, s, 1H), 8.568-8.555 (d, J = 5.6 Hz, 1H), 8.347-8.332 (d, J = 6.0 Hz, 1H), 4.439 (s, 2H), 3.676-3.644 (m, 8H), 3.355-3.247 (m, 4H), 2.997 (s, 1H), 2.337 (br, s, 2H); LCMS: 441.1 |
| 188 | 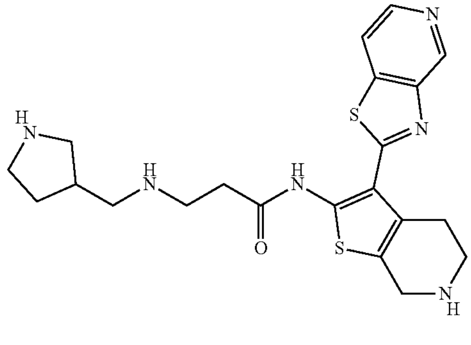 | $^1$H NMR (400 MHz, MeOD) d 9.445 (s, 1H), 8.522 (s, 1H), 8.323-8.310 (d, J = 5.2 Hz, 1H), 4.441 (s, 2H), 3.677-3.647 (m, 7H), 3.552-3.519 (m, 4H), 3.329-3.235 (m, 2H), 3.083 (m, 1H), 2.854-2.834 (d, J = 8 Hz, 1H), 2.387-2.343 (m, 1H), 1.890-1.836 (m, 1H); LCMS: 443.1 |

TABLE 1-continued

Exemplary Compounds and NMR/LCMS Data

| Compound | Structure | NMR/LCMS |
|---|---|---|
| 189 | 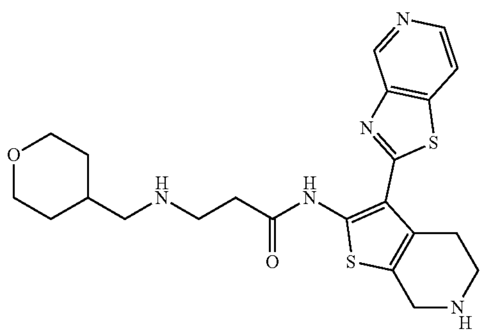 | $^1$H NMR (400 MHz, MeOD) d 9.486 (s, 1H), 8.598-8.585 (d, J = 5.6 Hz, 1H), 8.397-8.384 (d, J = 5.2 Hz, 1H), 4.448 (s, 2H), 3.960-3.951 (m, 2H), 3.680-3.665 (m, 2H), 3.494-3.437 (m, 6H), 3.298-3.232 (m, 2H), 3.042-3.025 (d, J = 6.8 Hz, 2H), 2.058-2.030 (m, 1H), 1.760-1.728 (m, 1H), 1.436-1.363 (m, 2H); LCMS: 458.1 |
| 190 | 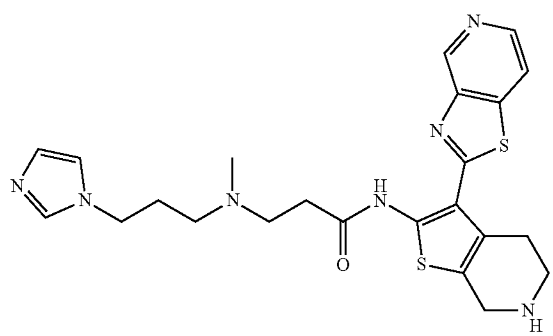 | $^1$H NMR (400 MHz, MeOD) d 9.662 (s, 1H), 9.026 (s, 1H), 8.689-8.674 (d, J = 6 Hz, 1H), 8.646-8.632 (d, J = 5.6 Hz, 1H), 4.450-4.404 (m, 4H), 3.688-3.658 (m, 4H), 3.383-3.352 (m, 6H), 2.985 (s, 3H), 2.489-2.451 (m, 2H); LCMS: 482.1 |
| 191 | 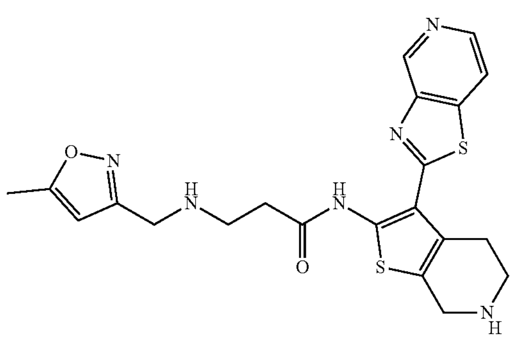 | $^1$H NMR (400 MHz, MeOD) d 9.618 (s, 1H), 8.670-8.656 (d, J = 5.6 Hz, 1H), 8.609-8.594 (d, J = 6 Hz, 1H), 6.302 (s, 1H), 4.447-4.408 (d, J = 15.6 Hz, 4H), 3.681-3.651 (t, J = 6 Hz, 2H), 3.585-3.553 (t, J = 6.4 Hz, 2H), 3.372-3.358 (m, 2H), 3.297-3.270 (m, 2H), 2.449 (s, 3H); LCMS: 455 |
| 192 | 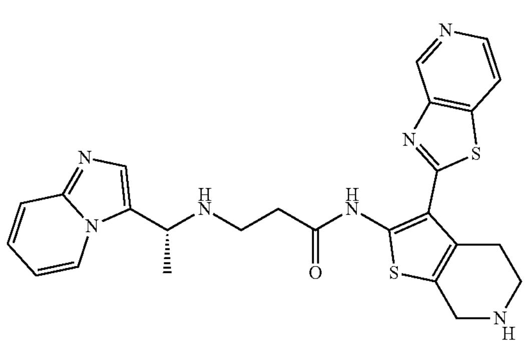 | $^1$H NMR (400 MHz, MeOD) d 9.445 (s, 1H), 9.040-9.022 (d, J = 7.2 Hz, 1H), 8.538-8.524 (d, J = 5.6 Hz, 1H), 8.402-8.357 (m, 2H), 8.044-7.964 (m, 2H), 7.581-7.548 (t, J = 6.2 Hz, 1H), 5.371-5.352 (m, 1H), 4.445 (s, 2H), 3.677-3.629 (m, 4H), 3.326-3.301 (m, 2H), 3.257-3.226 (t, J = 6.2 Hz, 2 Hz), 1.968-1.950 (d, J = 7.2 Hz, 3H); LCMS: 504.1 |

TABLE 1-continued

Exemplary Compounds and NMR/LCMS Data

| Compound | Structure | NMR/LCMS |
|---|---|---|
| 193 | 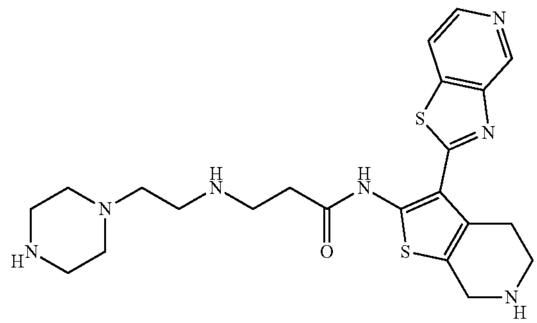 | $^1$H NMR (400 MHz, MeOD) d 9.522 (s, 1H), 8.589-8.575 (d, J = 5.6 Hz, 1H), 8.440-8.426 (d, J = 5.6 Hz, 1H), 4.454 (s, 2H), 3.684-3.655 (t, J = 5.8 Hz, 2H), 3.530-3.515 (t, J = 6 Hz, 2H), 3.357-3.329 (m, 6H), 3.316-3.272 (m, 4H), 2.833-2.821 (d, 6.4 Hz, 6H).; LCMS: 472.2 |
| 194 | 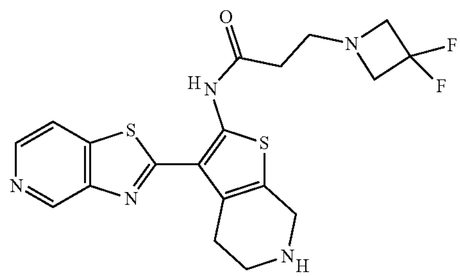 | $^1$H NMR (400 MHz, MeOD), d 9.593 (s, 1H) 8.643 (s, 1H) 8.557 (s, 1H) 4.881-4.785 (m, 4H) 4.445 (s, 2H) 3.8 (br. s., 2H) 3.680-3.649 (t, 6.2 Hz, 2H) 3.372-3.357 (d, 6 Hz, 2H) 3.238-3.206 (t, 6.4 Hz, 2H); LCMS: 436 |
| 195 | 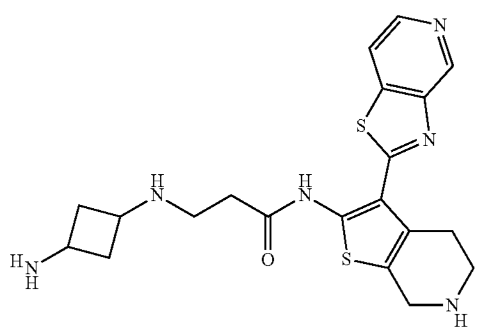 | $^1$H NMR (400 MHz, MeOD) d ppm 9.651 (s, 1 H), 8.682-8.666 (d, J6.40 Hz, 1 H), 8.642-8.626 (d, J = 6.40 Hz, 1 H), 4.449 (s, 2 H), 4.092-4.036 (m, 2 H), 3.687-3.657 (t, J = 6.00 Hz, 2 H), 3.405-3.363 (m, 4 H), 3.301-3.243 (m, 2 H), 2.811-2.797 (m, 2 H), 2.680-2.557 (m, 2 H); LCMS: 429 |
| 196 | 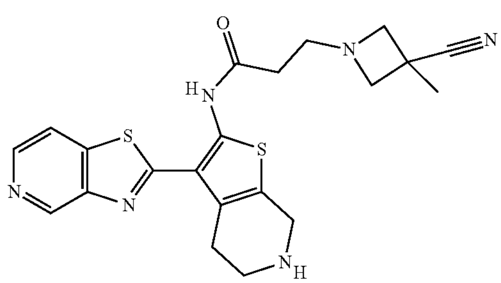 | $^1$H NMR (400 MHz, MeOD) d 9.579 (s. 1H), 8.647-8.632 (d, J = 6.0 Hz, 1H), 8.548-8.534 (d. J = 5.6 Hz, 1H), 4.680-4.653 (d. J = 10.8 Hz, 2H), 4.446 (s. 2H), 4.343-4.315 (d. J = 11.2 Hz, 2H), 3.777-3.745 (T. J = 6.4 Hz, 2H), 3.618-3.651 (T. J = 6 Hz, 2H), 3.354 (m. 2H), 3.196-3.181 (T. T = 6 Hz, 2H), 1.768 (s. 3H); LCMS: 439.1 |
| 197 | 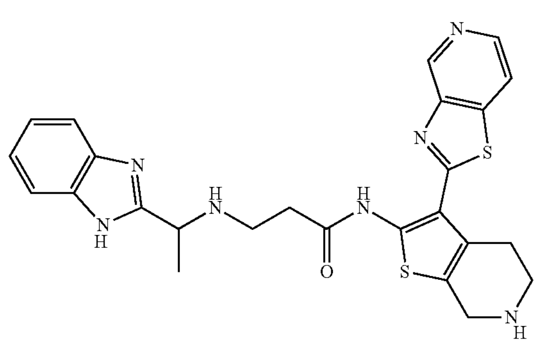 | $^1$H NMR (400 MHz, MeOD) d ppm 9.422 (s, 1 H), 8.598-8.583 (d, J = 6.00 Hz, 1 H), 8.405-8.391 (d, J = 5.60 Hz, 1 H), 7.535-7.512 (dd, J = 6.17, 3.09 Hz, 2 H), 7.258-7.235 (dd, J = 6.17, 3.09 Hz, 2 H), 4.798-4.781 (m, 1 H), 4.445 (s, 2 H), 3.681-3.651 (t, J = 6.00 Hz, 2 H), 3.569-3.552 (m, 1 H), 3.482-3.466 (m, 1 H), 3.333 (m, 2 H), 3.168-3.137 (t, J = 6.20 Hz, 2 H), 1.816-1.798 (d, J = 7.20 Hz, 3 H); LCMS: 504.1 |

TABLE 1-continued

Exemplary Compounds and NMR/LCMS Data

| Compound | Structure | NMR/LCMS |
|---|---|---|
| 198 | 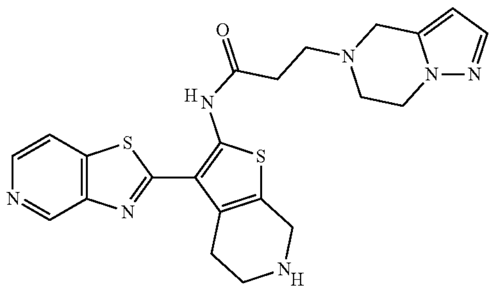 | ¹H NMR (400 MHz, MeOD) d 9.558 (br, s, 1H), 8.641-8.626 (d, J = 6.0 Hz, 1H), 8.505-8.490 (d, J = 6.0 Hz, 1H), 7.552-7.549 (d, J = 1.2 Hz, 1H), 6.267 (s, 1H), 4.596 (s, 2H), 4.445-4.421 (m, 4H), 3.857-3.829 (t, J = 5.6 Hz, 2H), 3.719-3.650 (m, 4H), 3.372-3.340 (t, J = 6.4 Hz, 1H); LCMS: 466 |
| 199 | 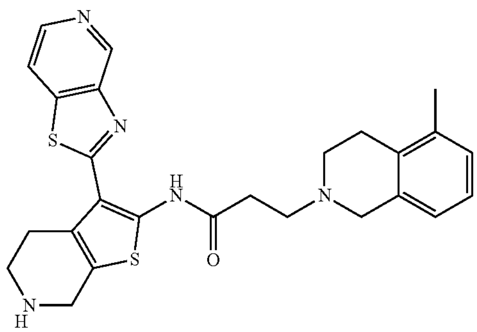 | ¹H NMR (400 MHz, MeOD) d 9.456 (s, 1H), 8.578-8.565 (d, J = 5.2 Hz, 1H), 8.321-8.308 (d, J = 5.2 Hz, 1H), 7.201-7.191 (m, 2H), 7.070-7.048 (t, J = 4.4 Hz, 1H), 4.579-4.448 (m, 4H), 3.780-3.746 (t, J = 6.8 Hz, 2H), 3.666-3.650 (t, J = 3.2 Hz, 2H), 3.422-3.363 (m, 4H), 3.136-3.119 (m, 2H), 2.284 (s, 3H); LCMS: 490 |
| 200 | 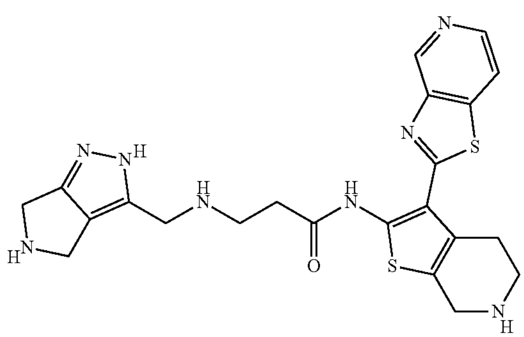 | ¹H NMR (400 MHz, MeOD) d 9.365 (br, s, 1H), 8.533-8.520 (d, J = 5.2 Hz, 1H), 8.222-8.209 (d, J = 5.2 Hz, 1H), 4.539-4.387 (m, 6H), 3.658-3.493 (m, 3H), 3.341-3.221 (m, 6H), 2.907 (s, 1H); LCMS: 481.2 |
| 201 | 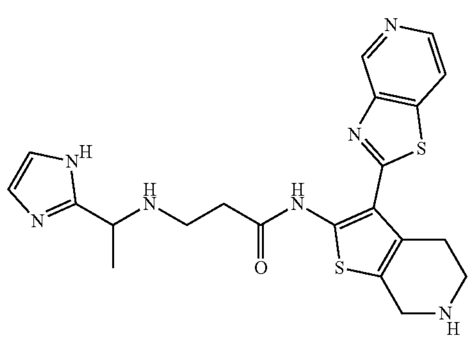 | ¹H NMR (400 MHz, MeOD) d 9.489 (s, 1H), 8.607-8.592 (d, J = 6.0 Hz, 1H), 8.427-8.413 (d, J = 5.6 Hz, 1H), 7.448 (s, 2H), 4.699-4.483 (m, 1H), 4.440 (s, 2H), 3.677-3.647 (t, J = 6.0 Hz, 2H), 3.366-3.229 (m, 4H), 3.128-3.097 (t, J = 6.2 Hz, 2H), 1.746-1.729 (d, J = 6.8 Hz, 3H); LCMS: 454.1 |

TABLE 1-continued
Exemplary Compounds and NMR/LCMS Data
| Compound | Structure | NMR/LCMS |
|---|---|---|
| 202 | 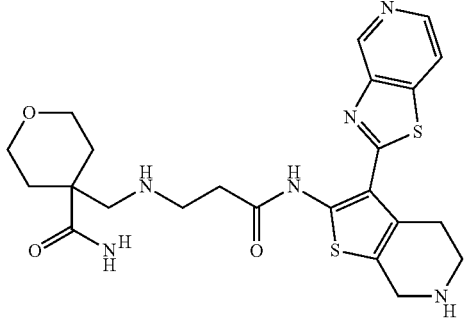 | ¹H NMR (400 MHz, MeOD) d 9.497 (s, 1H), 8.601-8.587 (d, J = 5.6, 1H), 8.417-8.410 (d, J = 5.6, 1H), 4.451 (s, 2H), 3.792-3.774 (m, 2H), 3.684-3.653 (m, 4H), 3.520-3.505 (m, 2H), 3.395-3.260 (m, 6H), 2.185-2.142 (m, 2H), 1.735-1.692 (m, 2H); LCMS: 501.1 |
| 203 | 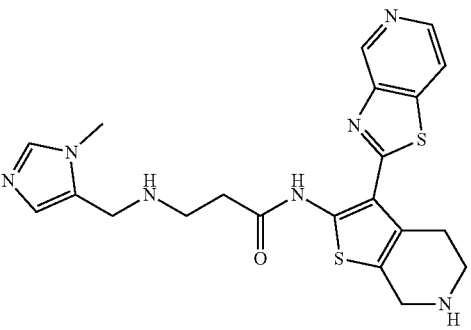 | ¹H NMR (400 MHz, MeOD) d 9.390 (s, 1H), 8.852 (s, 1H), 8.537-8.524 (d, J = 5.2 Hz, 1H), 8.246-8.233 (d, J = 5.2 Hz, 1H), 7.737 (s, 1H), 4.534 (s, 2H), 4.443 (s, 2H), 3.984 (s, 3H), 3.659-3.575 (m, 4H), 3.350-3.341 (m, 2H), 3.274-3.258 (t, J = 6.4 Hz, 2H); LCMS: 454.1 |
| 204 | 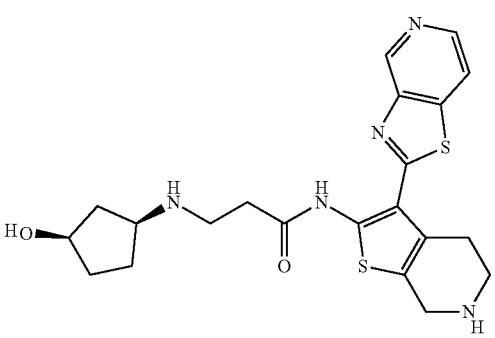 | ¹H NMR (400 MHz, MeOD) d ppm 9.359 (s, 1 H), 8.537-8.525 (d, J = 4.80 Hz, 1 H), 8.210-8.196 (d, J = 5.60 Hz, 1 H), 4.442 (s, 2 H), 4.366 (m, 1 H), 3.736-3.643 (m, 3 H), 3.471 (m, 2 H), 3.369-3.339 (m, 4 H), 3.231-3.174 (m, 2 H), 2.203-1.854 (m, 4 H); LCMS: 444 |
| 205 | 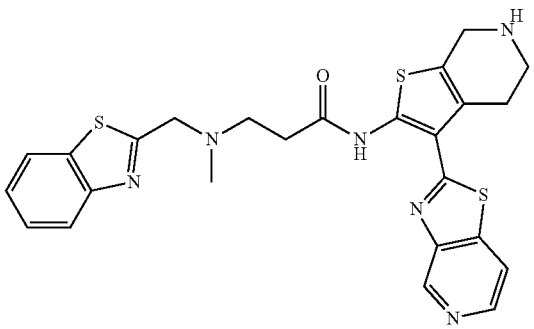 | ¹H NMR (400 MHz, MeOD) d 9.469 (s, 1H), 8.615-8.601 (d, J = 5.6 Hz, 1H), 8.464-8.451 (d, J = 5.6 Hz, 1H), 7.898-7.870 (t, J = 5.6 Hz, 2H), 7.436-7.357 (m, 2H), 4.913 (s, 2H), 4.453 (s, 2H), 3.810-3.777 (t, J = 6.6 Hz, 2H), 3.689-3.659 (t, J = 6.0 Hz, 2H), 3.340-3.322 (m, 4H), 3.108 (s, 3H); LCMS: 521.1 |

TABLE 1-continued

Exemplary Compounds and NMR/LCMS Data

| Compound | Structure | NMR/LCMS |
|---|---|---|
| 206 | 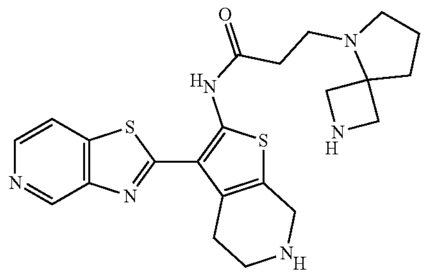 | $^1$H NMR (400 MHz, MeOD) d 9.625 (s, 1H), 8.664-8.648 (d, J = 6.4, 1H), 8.589-8.574 (d, J = 6 Hz, 1H), 4.635-4.603 (d, J = 12.8, 2H), 4.441 (s, 2H), 4.071-4.039 (d, J = 12.8 Hz, 2H), 3.668-3.652 (t, J = 6.4, 2H), 3.574-3.559 (t, J = 6 Hz, 2H), 3.377-3.324 (m, 4H), 3.215-3.201 (t, J = 5.6, 2H), 2.396-2.357 (t, J = 7.8, 2H), 2.004-1.967 (m, 2H); LCMS: 455.1 |
| 207 | 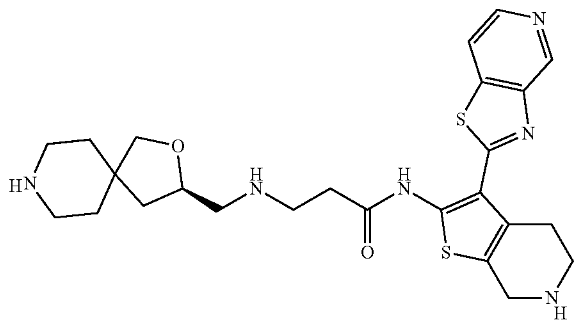 | $^1$H NMR (400 MHz, MeOD) d 9.446 (br. S, 1H), 8.580-8.565 (d, J = 6.0 Hz, 1H), 8.346-8.331 (d, J = 6.0 Hz, 1H), 4.445-4.351 (m, 3H), 3.376-3.721 (m, 4H), 3.661-3.647 (d, J = 5.6 Hz, 2H), 3.365-3.341 (m, 4H), 3.236-3.185 (m, 6H), 2.195-2.163 (m, 1H), 1.861-1.833 (m, 4H), 1.600-1.547 (m, 1H); LCMS: 513.2 |
| 208 | 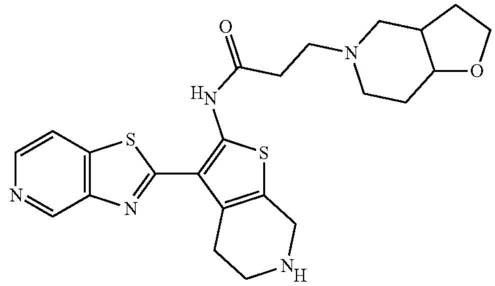 | $^1$H NMR (400 MHz, MeOD) d 9.493 (br, s, 1H), 8.600-8.586 (d, J = 5.2 Hz, 1H), 8.385-8.371 (d, J = 5.6 Hz, 1H), 4.448 (s, 2H), 4.026-3.966 (m, 3H), 3.681-3.651 (m, 5H), 3.393-3.334 (m, 7H), 2.334-2.305 (m, 1H), 2.145-2.130 (m, 1H), 1.912-1.1754 (m, 3H); LCMS: 470.1 |
| 209 | 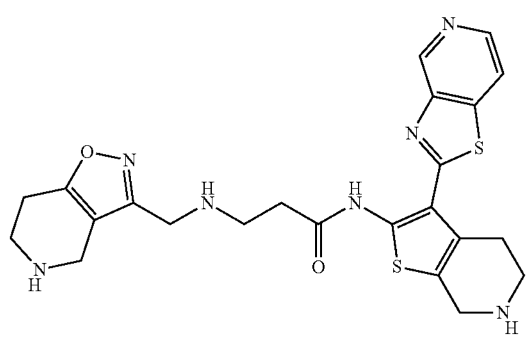 | $^1$H NMR (400 MHz, MeOD) d 9.415 (br, s, 1H), 8.565-8.550 (d, J = 6.0 Hz, 1H), 8.292-8.277 (d, J = 6.0 Hz, 1H), 4.507 (s, 2H), 4.447 (s, 2H), 4.321 (s, 2H), 3.662-3.602 (m, 6H), 3.357-3.263 (m, 4H), 3.201-3.185 (m, 2H); LCMS: 496.1 |
| 210 | 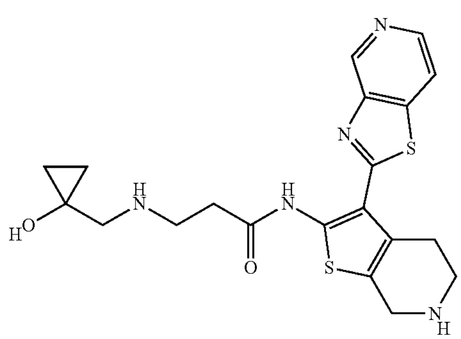 | $^1$H NMR (400 MHz, MeOD) d 9.478 (br, s, 1H), 8.603-8.589 (d, J = 5.6 Hz, 1H), 8.397-8.381 (d, J = 6.4 Hz, 1H), 4.451 (s, 2H), 3.684-3.653 (t, J = 6.2 Hz, 2H), 3.586-3.552 (t, J = 6.8 Hz, 2H), 3.363-3.224 (m, 6H), 0.928-0.897 (m, 2H), 0.770-0.757 (m, 2H); LCMS: 430 |

TABLE 1-continued
Exemplary Compounds and NMR/LCMS Data
| Compound | Structure | NMR/LCMS |
|---|---|---|
| 211 | 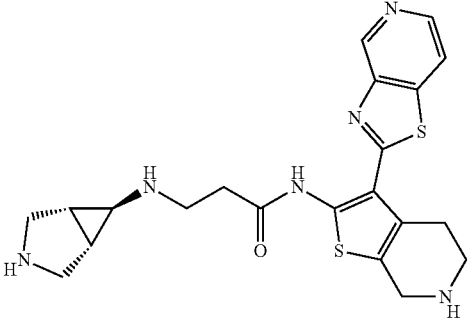 | $^1$H NMR (400 MHz, MeOD) d 9.480-9.430 (m, 1H), 8.568-8.555 (t, J = 5.2 Hz, 1H), 8.363-8.301 (m, 1H), 4.447 (s, 2H), 3.678-3.584 (m, 8H), 3.372-3.235 (m, 4H), 2.897-2.881 (d, J = 6.4 Hz, 1H), 2.465 (br, s, 1H); LCMS: 441.2 |
| 212 | 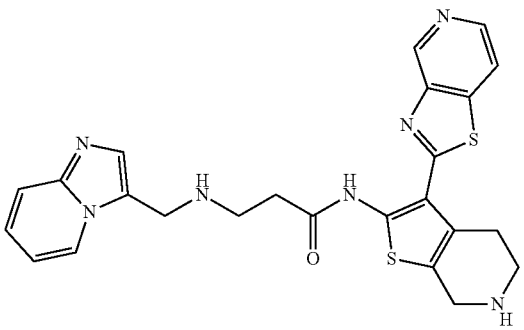 | $^1$H NMR (400 MHz, MeOD) d 9.432 (s, 1H), 8.984-8.968 (d, J = 6.4 Hz 1H), 8.569-8.555 (d, J = 5.6 Hz, 1H), 8.331-8.317 (d, J = 5.6, 1H), 8.262 (s, 1H), 7.994-7.959 (m, 2H), 7.548-7.516 (m, 2H), 4.896 (s, 2H), 4.446 (s, 2H), 3.677-3.621 (m, 4H), 3.351-3.255 (m, 4H); LCMS: 490.1 |
| 213 | 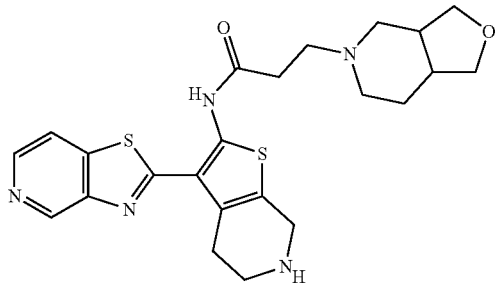 | $^1$H NMR (400 MHz, MeOD) d ppm 9.575 (s, 1 H), 8.636-8.623 (d, J = 5.20 Hz, 1 H), 8.498-8.482 (d, J = 6.40 Hz, 1 H), 4.448 (s, 2 H), 3.972-3.610 (m, 11 H), 3.377-3.326 (m, 6 H), 3.303-2.840 (m, 2 H), 2.716-2.650 (m, 1 H); LCMS: 470.1 |
| 214 | 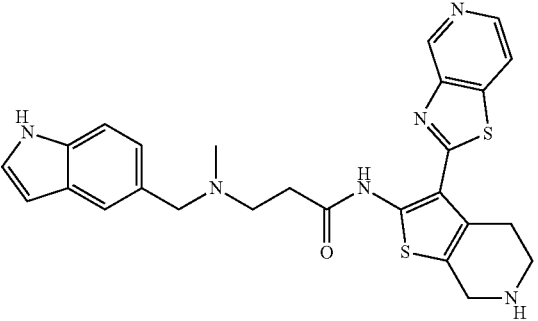 | N/A |

TABLE 1-continued

Exemplary Compounds and NMR/LCMS Data

| Compound | Structure | NMR/LCMS |
|---|---|---|
| 215 | 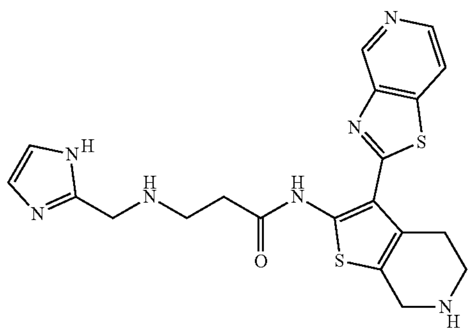 | ¹H NMR (400 MHz, MeOD) d 9.479 (s, 1H), 8.590-8.577 (d, J = 5.2 Hz, 1H), 8.397-8.384 (d, J = 5.2 Hz, 1H), 7.481 (s, 2H), 4.532 (s, 2H), 4.440 (s, 2H), 3.675-3.646 (t, J = 5.8 Hz, 2H), 3.478-3.449 (t, J = 5.8 Hz, 2H), 3.366-3.339 (t, J = 5.0 Hz, 2H), 3.203-3.188 (m, 2H); LCMS: 440.1 |
| 216 | 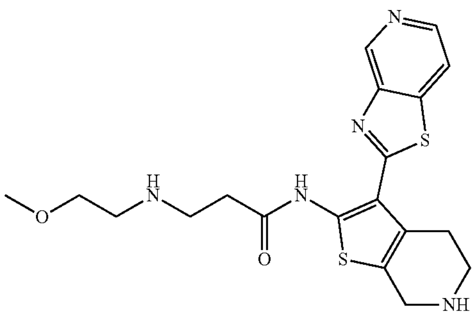 [SMILES: COCCNCCC(=O)Nc1sc2c(c1-c1nc3cnccc3s1)CCNC2] | N/A |
| 217 | 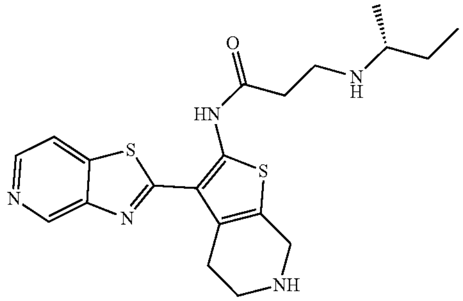 [SMILES: CC[C@@H](C)NCCC(=O)Nc1sc2c(c1-c1nc3cnccc3s1)CCNC2] | ¹H NMR (400 MHz, DMSO-d6) δ 12.24 (s, 1H), 9.61 (br. s, 2H), 9.56 (s, 1H), 8.80-8.99 (m, 2H), 8.64 (d, J = 5.38 Hz, 1H), 8.43 (d, J = 4.89 Hz, 1H), 4.35 (br. s, 2H), 3.46-3.54 (m, 3H), 3.27-3.31 (m, 2H), 3.16 (d, J = 7.34 Hz, 4H), 1.80-1.82 (m, 1H), 1.51 (td, J = 7.21, 13.94 Hz, 1H), 1.25 (d, J = 6.85 Hz, 3H), 0.92 (t, J = 7.34 Hz, 3H).; LCMS: 416.05 |
| 218 | 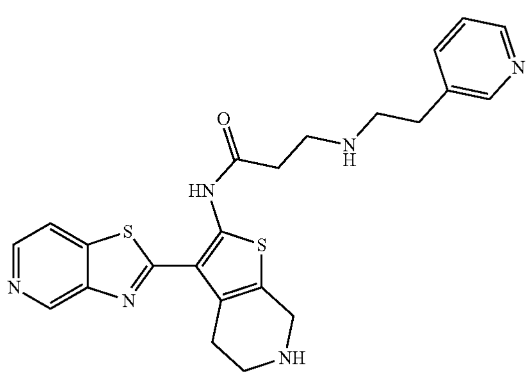 [SMILES: O=C(CCNCCc1cccnc1)Nc1sc2c(c1-c1nc3cnccc3s1)CCNC2] | ¹H NMR (400 MHz, DMSO-d6) δ 12.26 (s, 1H), 9.72 (s, 2H), 9.63 (s, 1H), 9.45 (s, 2H), 8.86 (d, J = 2.2 Hz, 1H), 8.78 (d, J = 5.5 Hz, 1H), 8.66 (d, J = 5.7 Hz, 1H), 8.49 (d, J = 5.7 Hz, 1H), 8.40 (d, J = 8.1 Hz, 1H), 7.91 (dd, J = 8.0, 5.4 Hz, 1H), 4.34 (d, J = 4.9 Hz, 2H), 3.48-3.46 (m, 4H), 3.39-3.34 (m, 4H), 3.24-3.18 (m, 4H).; LCMS: 465.1 |

TABLE 1-continued

Exemplary Compounds and NMR/LCMS Data

| Compound | Structure | NMR/LCMS |
|---|---|---|
| 219 | 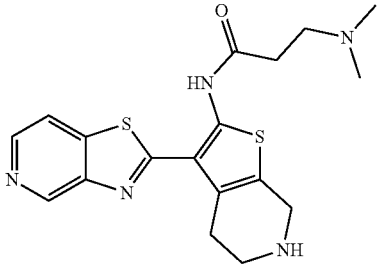 [SMILES: CN(C)CCC(=O)Nc1sc2c(c1-c1nc3cnccc3s1)CCNC2] | ¹H NMR (400 MHz, DMSO-d6) δ 9.33 (s, 1H), 8.51 (d, J = 5.4 Hz, 1H), 8.21 (d, J = 5.4 Hz, 1H), 3.87-38.5 (m, 2H), 3.06 (t, J = 5.5 Hz, 2H), 2.84 (t, J = 5.7 Hz, 2H), 2.76-2.62 (m, 4H), 2.19 (s, 6H). ; LCMS: 388.15 |
| 220 | 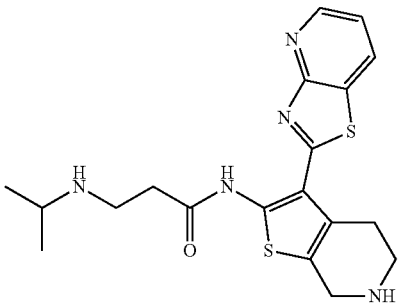 [SMILES: CC(C)NCCC(=O)Nc1sc2c(c1-c1nc3ncccc3s1)CCNC2] | DMSO-d6, δ 12.61 (s, 1H), 9.78-9.58 (m, 2H), 9.02-8.82 (m, 2H), 8.75 (dd, J = 4.6, 1.5 Hz, 1H), 8.70 (dd, J = 8.0, 1.6 Hz, 1H), 7.53 (dd, J = 8.0, 4.6 Hz, 1H), 4.35 (s, 2H), 3.53-3.45 (m, 2H), 3.35 (hept, J = 5.8 Hz, 1H), 3.33-3.25 (m, 2H), 3.19 (t, J = 6.0 Hz, 2H), 3.09 (t, J = 7.2 Hz, 2H), 1.27 (d, J = 6.5 Hz, 6H); LCMS: 402.1 |
| 221 | 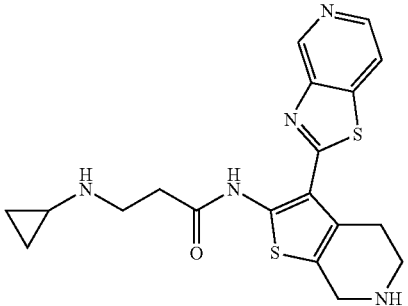 [SMILES: O=C(CCNC1CC1)Nc1sc2c(c1-c1nc3cnccc3s1)CCNC2] | ¹H NMR (400 MHz, DMSO-d6) δ 9.35 (s, 1H), 8.51 (d, J = 5.38 Hz, 1H), 8.21 (d, J = 5.87 Hz, 1H), 8.19 (s, 1H), 3.89 (s, 2H), 3.10 (t, J = 5.38 Hz, 2H), 3.02 (t, J = 6.36 Hz, 2H), 2.88 (br. s, 2H), 2.71 (t, J = 6.36 Hz, 2H), 2.55 (br. s, 1H), 2.33 (br. s, 1H), 2.10-2.14 (m, 1H), 0.30-0.35 (m, 2H), 0.13-0.17 (m, 2H).; LCMS: 400.35 |
| 222 | 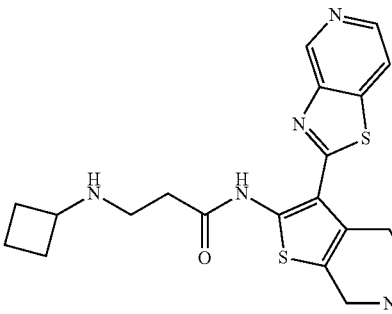 | ¹H NMR (400 MHz, DMSO-d6) δ = 9.28 (s, 1H), 8.47 (d, J = 5.38 Hz, 1H), 8.22 (s, 2H), 8.16 (d, J = 5.38 Hz, 1H), 3.92 (s, 2H), 3.36 (td, J = 7.64, 15.53 Hz, 2H), 3.14 (t, J = 5.62 Hz, 2H), 2.95 (t, J = 6.60 Hz, 4H), 2.70 (t, J = 6.60 Hz, 2H), 1.99-2.10 (m, 2H), 1.70-1.82 (m, 2H), 1.54-1.64 (m, 2H).; LCMS: 414.3 |
| 223 | 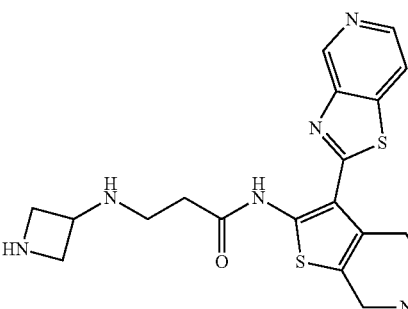 | ¹H NMR (DMSO-d6/D2O, 400 MHz): δ 9.43 (s, 1H), 8.56 (d, J = 5.38 Hz, 1H), 8.29 (d, J = 5.87 Hz, 1H), 4.33 (br. s, 2H), 4.14-4.29 (m, 5H), 3.48 (d, J = 5.87 Hz, 2H), 3.38 (s, 1H), 3.25 (t, J = 6.60 Hz, 2H), 3.15-3.19 (m, 2H), 3.09 (t, J = 6.60 Hz, 2H); LCMS: 415 |

TABLE 1-continued

Exemplary Compounds and NMR/LCMS Data

| Compound | Structure | NMR/LCMS |
|---|---|---|
| 224 | 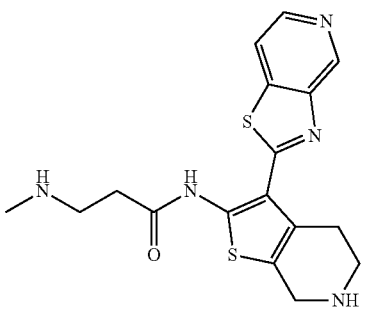 [SMILES: CNCCC(=O)Nc1sc2c(c1-c1nc3cnccc3s1)CCNC2] | $^1$H NMR (DMSO-d6, 400 MHz): δ 12.24 (s, 1H), 9.91 (br. s, 2H), 9.71 (br. s, 1H), 9.19 (br. s, 2H), 8.68 (d, J = 5.87 Hz, 1H), 8.58 (d, J = 4.89 Hz, 1H), 4.34 (br. s, 2H), 3.47 (br. s, 3H), 3.22-3.32 (m, 2H), 3.14-3.21 (m, 4H), 2.56-2.62 (m, 2H).; LCMS: 373.85 |
| 225 | 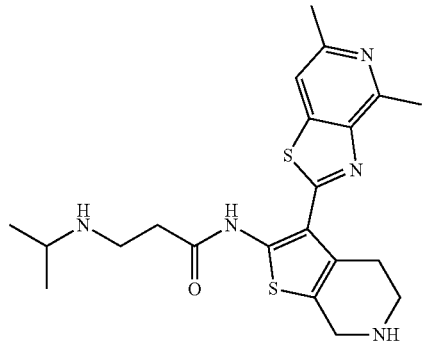 [SMILES: Cc1cc2sc(-c3c(NC(=O)CCNC(C)C)sc4c3CCNC4)nc2c(C)n1] | DMSO-d6 + D2O, δ 8.14 (s, 1H), 4.32 (br. s, 2H), 3.48 (t, J = 6.0 Hz, 2H), 3.33 (hept, J = 6.5 Hz, 1H), 3.26 (t, J = 6.8 Hz, 2H), 3.17 (t, J = 6.1 Hz, 2H), 3.04 (t, J = 6.9 Hz, 2H), 3.01 (s, 3H), 2.66 (s, 3H), 1.23 (d, J = 6.5 Hz, 6H). 5 NH missing due to D2O; LCMS: 430.1 |
| 226 | 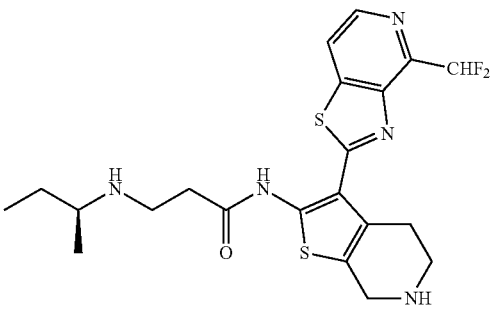 [SMILES: CC[C@H](C)NCCC(=O)Nc1sc2c(c1-c1nc3c(C(F)F)nccc3s1)CCNC2] | $^1$H NMR (400 MHz, DMSO-d6) δ 12.53 (s, 1H), 9.23 (s, 2H), 8.66 (d, J = 5.4 Hz, 1H), 8.49 (d, J = 5.6 Hz, 1H), 8.41 (s, 1H), 8.32 (s, 1H) 7.52 (t, J = 53.8 Hz, 1H), 4.37 (s, 2H), 3.53 (s, 2H), 3.11 (m, 5H), 1.79-1.71 (m, 1H), 1.48 (dt, J = 13.7, 7.5 Hz, 2H), 1.23 (d, J = 6.4 Hz, 3H), 1.25-1.20 (m, 2H), 0.92 (t, J = 7.4 Hz, 3H), 0.96-0.90 (m, 2H).; LCMS: not determined |
| 227 | 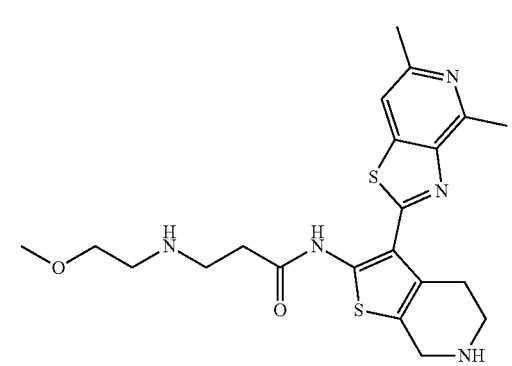 | DMSO-d6 + D2O, δ 8.21 (s, 1H), 4.32 (s, 2H), 3.57 (t, J = 5.2 Hz, 2H), 3.48 (t, J = 5.8 Hz, 2H), 3.32-3.27 (m, 2H), 3.29 (s, 3H), 3.20-3.13 (m, 4H), 3.09-3.02 (m, 2H), 3.04 (s, 3H), 2.69 (s, 3H). 5 NH missing due to D2O; LCMS: 446 |

TABLE 1-continued

Exemplary Compounds and NMR/LCMS Data

| Compound | Structure | NMR/LCMS |
|---|---|---|
| 228 | 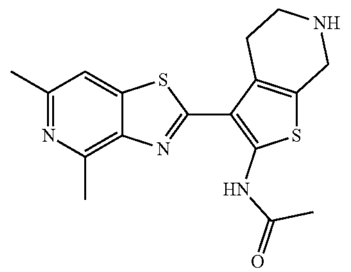 [SMILES: CC(=O)Nc1sc2c(c1-c1nc3c(C)nc(C)cc3s1)CCNC2] | DMSO-d6 + D2O, δ 8.24 (s, 1H), 4.29 (s, 2H), 3.47 (t, J = 5.9 Hz, 2H), 3.21-3.13 (m, 2H), 3.03 (d, J = 12.3 Hz, 3H), 2.70 (s, 3H), 2.30 (s, 3H). 3 NH missing due to D2O; LCMS: 358.9 |
| 229 | 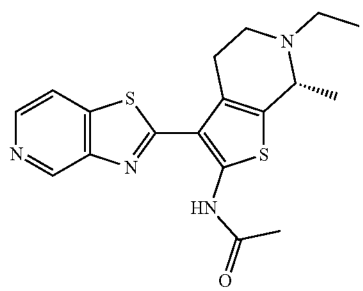 [SMILES: CCN1CCc2c(sc(NC(C)=O)c2-c2nc3cnccc3s2)[C@H]1C] | $^1$H NMR (DMSO-d6, 400 MHz): δ 12.32 (br. s, 1H), 9.40 (s, 1H), 8.52 (d, J = 5.38 Hz, 1H), 8.22 (d, J = 5.38 Hz, 1H), 3.71-3.93 (m, 1H), 3.06-3.19 (m, 1H), 2.56-2.97 (m, 5H), 2.33 (s, 3H), 1.30-1.42 (m, 3H), 1.02-1.13 (m, 3H).; LCMS: 373.13 |
| 230 | 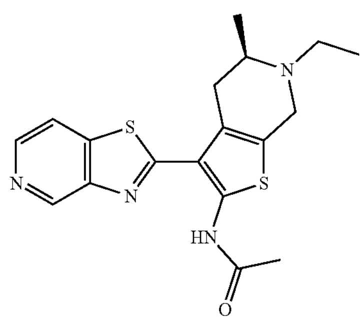 [SMILES: CCN1Cc2sc(NC(C)=O)c(-c3nc4cnccc4s3)c2C[C@H]1C] | $^1$H NMR (DMSO-d6, 400 MHz): δ 12.39 (s, 1H), 9.46 (s, 1H), 8.58 (d, J = 5.38 Hz, 1H), 8.28 (d, J = 5.38 Hz, 1H), 3.69-3.83 (m, 2H), 3.15-3.23 (m, 1H), 3.01-3.09 (m, 1H), 2.59-2.75 (m, 3H), 2.40 (s, 3H), 1.18 (d, J = 6.36 Hz, 3H), 1.12 (t, J = 7.09 Hz, 3H).; LCMS: 373.2 |
| 231 | 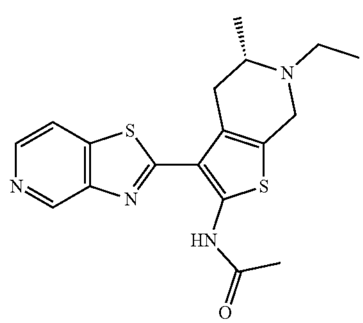 [SMILES: CCN1Cc2sc(NC(C)=O)c(-c3nc4cnccc4s3)c2C[C@@H]1C] | $^1$H NMR (DMSO-d6, 400 MHz): δ 12.30 (s, 1H), 9.40 (s, 1H), 8.53 (d, J = 5.38 Hz, 1H), 8.23 (d, J = 5.38 Hz, 1H), 3.68-4.01 (m, 2H), 2.63-3.19 (m, 5H), 2.34 (s, 3H), 1.09-1.27 (m, 6H).; LCMS: 373.13 |
| 232 | 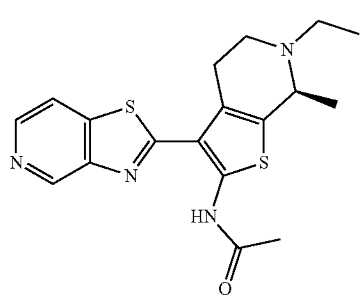 [SMILES: CCN1CCc2c(sc(NC(C)=O)c2-c2nc3cnccc3s2)[C@@H]1C] | $^1$H NMR (DMSO-d6, 400 MHz): δ 12.28 (br. s, 1H), 9.42 (s, 1H), 8.55 (d, J = 5.38 Hz, 1H), 8.25 (d, J = 5.38 Hz, 1H), 2.64-3.21 (m, 6H), 2.35 (s, 3H), 1.38-1.64 (m, 3H), 1.11-1.34 (m, 4H).; LCMS: 373.13 |

TABLE 1-continued

Exemplary Compounds and NMR/LCMS Data

| Compound | Structure | NMR/LCMS |
|---|---|---|
| 233 | 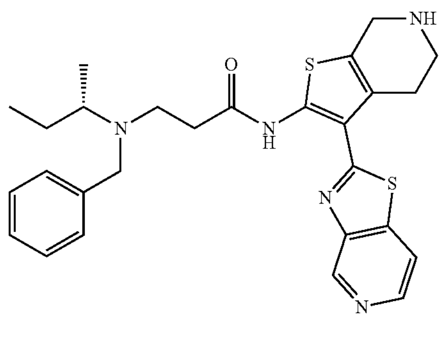 [SMILES: CC[C@H](C)N(CCC(=O)Nc1sc2c(c1-c1nc3cnccc3s1)CCNC2)Cc1ccccc1] | ¹H NMR (DMSO-d6/D2O, 400 MHz): δ 9.54 (br. s, 1H), 8.61 (d, J = 5.65 Hz, 1H), 8.40-8.44 (m, 1H), 7.57-7.62 (m, 2H), 7.40-7.46 (m, 3H), 4.35-4.44 (m, 2H), 4.31 (br. s, 2H), 3.43-3.50 (m, 2H), 3.10-3.38 (m, 5H), 1.84-2.08 (m, 2H), 1.51-1.68 (m, 2H), 1.33 (t, J = 6.06 Hz, 3H), 0.88 (d, J = 4.84 Hz, 3H); LCMS: 505.85 |
| 234 | 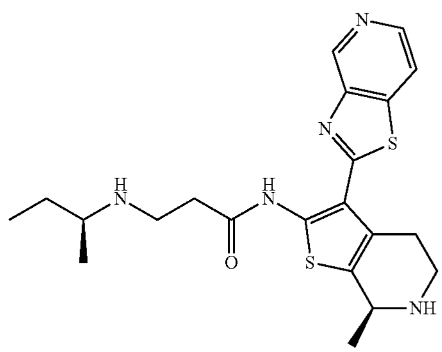 [SMILES: CC[C@H](C)NCCC(=O)Nc1sc2c(c1-c1nc3cnccc3s1)CCN[C@H]2C] | ¹H NMR (DMSO-d6/D2O, 400 MHz): δ 9.33 (s, 1H), 8.48 (d, J = 5.38 Hz, 1H), 8.14-8.19 (m, 1H), 4.58-4.65 (m, 1H), 3.58-3.68 (m, 1H), 3.23-3.38 (m, 3H), 3.11-3.18 (m, 2H), 3.02 (t, J = 6.11 Hz, 2H), 1.66-1.76 (m, 1H), 1.55 (d, J = 6.85 Hz, 3H), 1.40-1.51 (m, 2H), 1.19 (d, J = 6.85 Hz, 3H), 0.87 (t, J = 7.34 Hz, 3H).; LCMS: 429.7 |
| 235 | 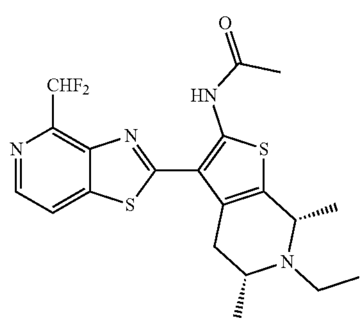 [SMILES: CCN1[C@H](C)Cc2c(sc(NC(C)=O)c2-c2nc3c(C(F)F)nccc3s2)[C@@H]1C] | ¹H NMR (DMSO-d6, 400 MHz): δ 12.59 (s, 1H), 8.64 (d, J = 5.4 Hz, 1H), 8.49 (d, J = 5.4 Hz, 1H), 7.48 (t, J = 53.7 Hz, 1H), 5.01 (s, 1H), 4.11 (d, J = 53.7 Hz, 1H), 3.01 (dd, J = 16.0, 8.6 Hz, 1H), 2.53 (s, 3H), 2.32 (s, 3H), 1.64 (dd, J = 47.2, 6.6 Hz, 3H), 1.47 (d, J = 6.5 Hz, 3H), 1.32 (t, J = 7.4 Hz, 3H).; LCMS: 437.21 |
| 236 | 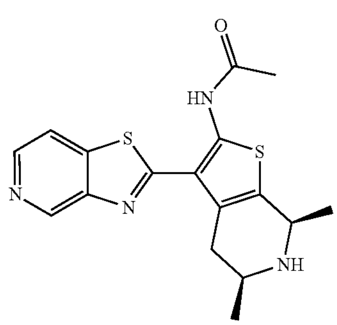 | ¹H NMR (DMSO-d6/D2O, 400 MHz): δ 9.31 (s, 1H), 8.46 (d, J = 5.38 Hz, 1H), 8.14 (d, J = 5.38 Hz, 1H), 4.00 (d, J = 5.87 Hz, 1H), 2.94-3.02 (m, 1H), 2.85-2.93 (m, 1H), 2.37-2.46 (m, 1H), 2.28 (s, 3H), 1.32 (d, J = 6.36 Hz, 3H), 1.21 (d, J = 6.36 Hz, 3H).; LCMS: 358.8 |

TABLE 1-continued

Exemplary Compounds and NMR/LCMS Data

| Compound | Structure | NMR/LCMS |
|---|---|---|
| 237 | 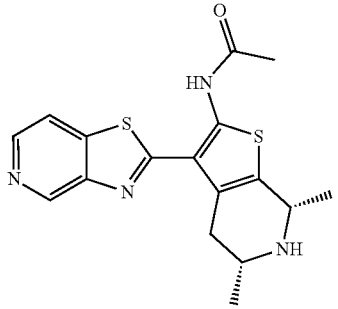 | $^1$H NMR (DMSO-d6/D2O, 400 MHz): δ 9.29 (s, 1H), 8.44 (d, J = 5.38 Hz, 1H), 8.12 (d, J = 5.38 Hz, 1H), 4.00 (d, J = 4.89 Hz, 1H), 2.93-3.01 (m, 1H), 2.89 (d, J = 15.16 Hz, 1H), 2.40 (d, J = 13.20 Hz, 1H), 2.27 (s, 3H), 1.31 (d, J = 6.85 Hz, 3H), 1.21 (d, J = 5.87 Hz, 3H).; LCMS: 358.71 |
| 238 | 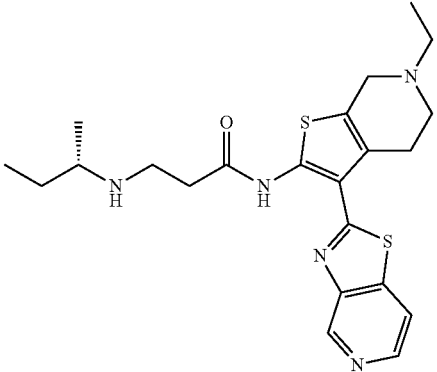 [SMILES: CC[C@H](C)NCCC(=O)Nc1sc2c(c1-c1nc3cnccc3s1)CCN(CC)C2] | $^1$H NMR (DMSO-d6/D2O, 400 MHz): δ 9.39 (s, 1H), 8.54 (d, J = 5.87 Hz, 1H), 8.28 (d, J = 5.87 Hz, 1H), 4.58 (d, J = 13.20 Hz, 1H), 4.25 (d, J = 12.72 Hz, 1H), 3.22-3.31 (m, 4H), 3.08-3.16 (m, 2H), 3.02 (t, J = 6.60 Hz, 2H), 1.65-1.73 (m, 1H), 1.39-1.51 (m, 1H), 1.28 (t, J = 7.34 Hz, 3H), 1.18 (d, J = 6.85 Hz, 3H), 0.87 (t, J = 7.34 Hz, 3H).; LCMS: 443.65 |
| 239 | 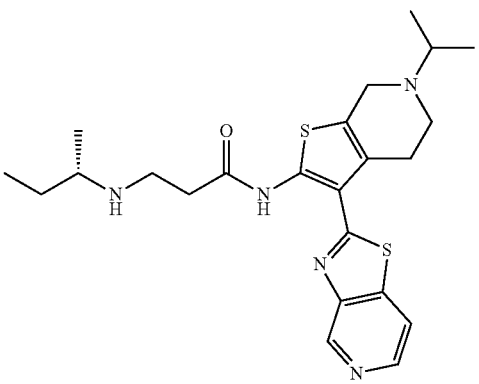 [SMILES: CC[C@H](C)NCCC(=O)Nc1sc2c(c1-c1nc3cnccc3s1)CCN(C(C)C)C2] | $^1$H NMR (DMSO-d6/D2O, 400 MHz): δ 9.37 (s, 1H), 8.54 (d, J = 5.38 Hz, 1H), 8.26 (d, J = 5.38 Hz, 1H), 4.33-4.52 (m, 3H), 3.10-3.41 (m, 8H), 3.03 (d, J = 5.87 Hz, 2H), 1.65-1.76 (m, 1H), 1.40-1.49 (m, 1H), 1.31 (d, J = 5.87 Hz, 6H), 1.18 (d, J = 6.36 Hz, 3H), 0.87 (t, J = 7.34 Hz, 3H).; LCMS: 457.75 |
| 240 | 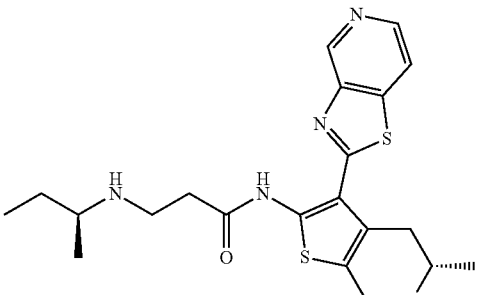 | $^1$H NMR (DMSO-d6/D2O, 400 MHz): δ 9.37 (br. s, 1H), 8.53 (d, J = 5.38 Hz, 1H), 8.25 (d, J = 5.38 Hz, 1H), 4.24-4.45 (m, 2H), 3.62 (br. s, 2H), 3.23-3.30 (m, 1H), 3.12-3.16 (m, 2H), 3.03 (t, J = 6.36 Hz, 2H), 2.85 (dd, J = 10.51, 15.41 Hz, 1H), 1.71 (d, J = 5.38 Hz, 1H), 1.46-1.51 (m, 1H), 1.43 (d, J = 6.36 Hz, 3H), 1.20 (d, J = 6.36 Hz, 3H), 0.89 (t, J = 7.09 Hz, 3H).; LCMS: 429.8 |

TABLE 1-continued

Exemplary Compounds and NMR/LCMS Data

| Compound | Structure | NMR/LCMS |
|---|---|---|
| 241 | 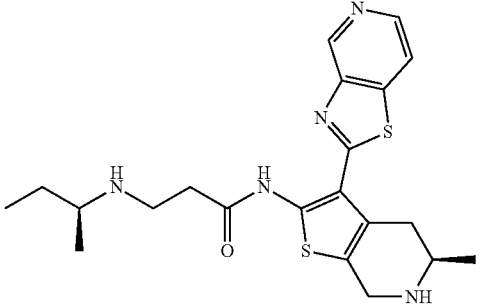 [SMILES: CC[C@H](C)NCCC(=O)Nc1sc2c(c1-c1nc3cnccc3s1)C[C@@H](C)NC2] | ¹H NMR (DMSO-d6/D2O, 400 MHz): δ 9.36 (s, 1H), 8.52 (d, J = 5.38 Hz, 1H), 8.25 (d, J = 5.38 Hz, 1H), 4.26-4.40 (m, 3H), 3.60 (br. s, 2H), 3.22-3.30 (m, 2H), 3.12 (d, J = 9.29 Hz, 1H), 3.00-3.05 (m, 2H), 2.84 (dd, J = 9.78, 15.65 Hz, 1H), 1.48 (d, J = 7.83 Hz, 1H), 1.42 (d, J = 5.87 Hz, 3H), 1.19 (d, J = 6.36 Hz, 3H), 0.88 (t, J = 7.09 Hz, 3H).; LCMS: 429.6 |
| 242 | 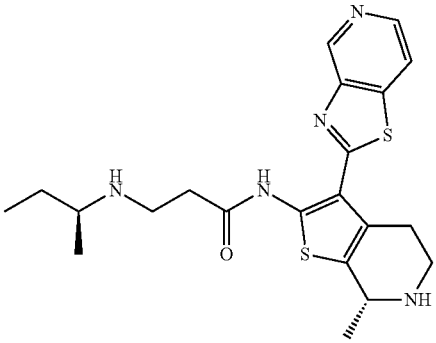 [SMILES: CC[C@H](C)NCCC(=O)Nc1sc2c(c1-c1nc3cnccc3s1)CCN[C@@H]2C] | ¹H NMR (DMSO-d6/D2O, 400 MHz): δ 9.17 (s, 1H), 8.38-8.44 (m, 1H), 8.03-8.10 (m, 1H), 4.31 (d, J = 5.87 Hz, 1H), 3.35-3.49 (m, 2H), 3.25-3.35 (m, 2H), 3.08-3.16 (m, 3H), 2.84-2.93 (m, 2H), 1.61-1.77 (m, 2H), 1.45 (d, J = 6.36 Hz, 3H), 1.18 (d, J = 6.36 Hz, 3H), 0.83-0.89 (m, 3H); LCMS: 429.7 |
| 243 | 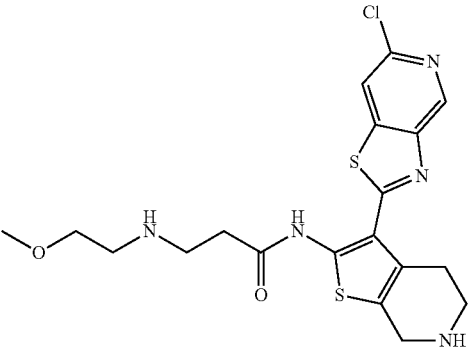 [SMILES: COCCNCCC(=O)Nc1sc2c(c1-c1nc3cnc(Cl)cc3s1)CCNC2] | DMSO-d6, δ 12.15 (s, 1H), 9.33 (s, 2H), 9.20 (d, J = 0.6 Hz, 1H), 8.69 (s, 2H), 8.44 (d, J = 0.7 Hz, 1H), 4.37 (s, 2H), 3.63-3.58 (m, 2H), 3.51 (t, J = 5.7 Hz, 2H), 3.32 (s, 3H), 3.24-3.18 (m, 2H), 3.14 (t, J = 5.9 Hz, 2H), 3.07 (t, J = 7.1 Hz, 2H). 2H hidden under water signal; LCMS: 452.0/453.8 |
| 244 | 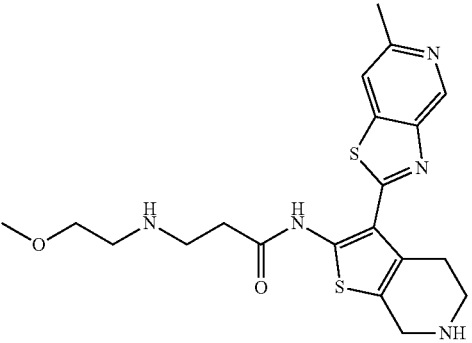 [SMILES: COCCNCCC(=O)Nc1sc2c(c1-c1nc3cnc(C)cc3s1)CCNC2] | DMSO-d6, δ 12.26 (s, 1H), 9.78 (s, 2H), 9.58 (s, 1H), 9.13 (s, 2H), 8.41 (s, 1H), 4.34 (s, 2H), 3.64 (t, J = 5.2 Hz, 2H), 3.52-3.44 (m, 2H), 3.36-3.28 (m, 2H), 3.32 (s, 3H), 3.21-3.13 (m, 6H), 2.74 (s, 3H).; LCMS: 432 |

TABLE 1-continued

Exemplary Compounds and NMR/LCMS Data

| Compound | Structure | NMR/LCMS |
|---|---|---|
| 245 | 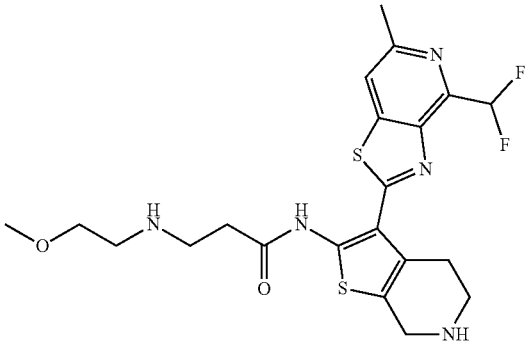 [SMILES: COCCNCCC(=O)Nc1sc2c(c1-c1nc3c(C(F)F)nc(C)cc3s1)CCNC2] | DMSO-d6, δ 12.53 (s, 1H), 9.28 (s, 2H), 8.65 (s, 2H), 8.31 (s, 1H), 7.47 (t, J = 53.9 Hz, 1H), 4.38 (s, 2H), 3.63-3.59 (m, 2H), 3.57-3.40 (m, 2H; overlap with water signal), 3.37-3.30 (m, 2H), 3.33 (s, 3H), 3.23-3.16 (m, 4H), 3.05 (t, J = 6.8 Hz, 2H), 2.68 (s, 3H); LCMS: 481.9 |
| 246 | 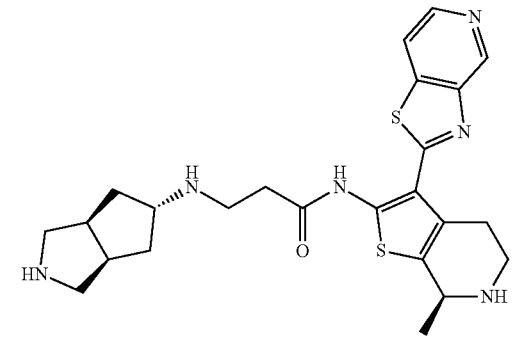 [SMILES: C[C@@H]1NCCc2c1sc(NC(=O)CCN[C@@H]1C[C@H]3CNC[C@H]3C1)c2-c1nc2cnccc2s1] | $^1$H NMR (DMSO-d6/D2O, 400 MHz): δ 9.54 (br. s, 1H), 8.60 (d, J = 4.89 Hz, 1H), 8.39 (d, J = 5.87 Hz, 1H), 4.30-4.44 (m, 3H), 3.77-3.82 (m, 1H), 3.31-3.36 (m, 2H), 3.27 (t, J = 7.09 Hz, 2H), 3.10-3.15 (m, 2H), 2.88-2.94 (m, 3H), 2.87 (d, J = 4.89 Hz, 2H), 1.88-2.04 (m, 5H), 1.44 (d, J = 6.36 Hz, 3H).; LCMS: 482.75 |
| 247 | 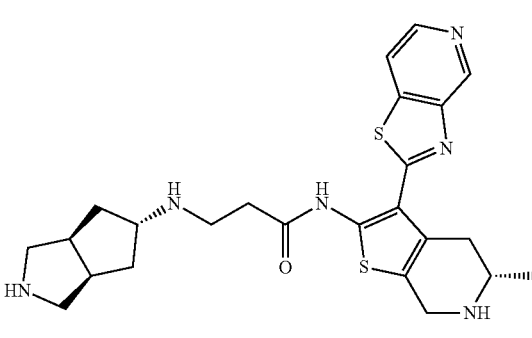 [SMILES: C[C@H]1Cc2c(sc(NC(=O)CCN[C@@H]3C[C@H]4CNC[C@H]4C3)c2-c2nc3cnccc3s2)CN1] | $^1$H NMR (DMSO-d6/D2O, 400 MHz): δ 9.55 (br. s, 1H), 8.61 (d, J = 5.38 Hz, 1H), 8.39 (d, J = 5.38 Hz, 1H), 4.69 (d, J = 6.85 Hz, 1H), 3.78-3.85 (m, 1H), 3.66 (d, J = 12.72 Hz, 2H), 3.32-3.40 (m, 3H), 3.24-3.30 (m, 2H), 3.15 (d, J = 6.85 Hz, 3H), 2.85-2.96 (m, 4H), 1.90-2.04 (m, 4H), 1.59 (d, J = 6.36 Hz, 3H).; LCMS: 482.8 |
| 248 | 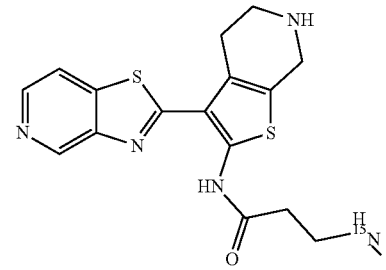 | $^1$H NMR (DMSO-d6/D2O, 400 MHz): δ 9.56 (s, 1H), 8.62 (d, J = 5.87 Hz, 1H), 8.45 (d, J = 5.87 Hz, 1H), 4.33 (br. s, 2H), 3.46-3.51 (m, 2H), 3.26 (t, J = 6.60 Hz, 2H), 3.17 (br. s, 2H), 3.09 (d, J = 5.38 Hz, 2H), 2.60 (s, 3H).; LCMS: 374.75 |

TABLE 1-continued

Exemplary Compounds and NMR/LCMS Data

| Compound | Structure | NMR/LCMS |
|---|---|---|
| 249 | 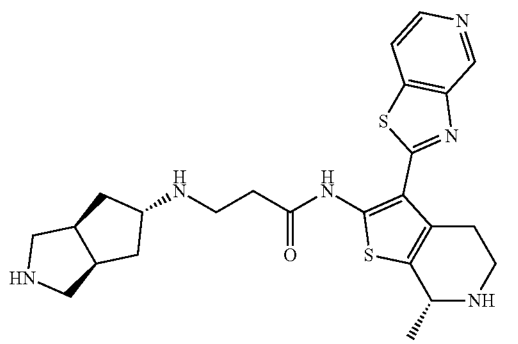 [SMILES: C[C@H]1NCCc2c1sc(NC(=O)CCN[C@@H]1C[C@H]3CNC[C@H]3C1)c2-c1nc2cnccc2s1] | ¹H NMR (DMSO-d6/D2O, 400 MHz): δ 9.25 (s, 1H), 8.43 (d, J = 5.38 Hz, 1H), 8.12 (d, J = 5.38 Hz, 1H), 3.86 (br. s, 2H), 3.10-3.25 (m, 4H), 2.88-3.05 (m, 5H), 2.67 (d, J = 6.85 Hz, 5H), 1.49-1.63 (m, 4H), 1.21 (d, J = 6.36 Hz, 3H).; LCMS: 482.75 |
| 250 | 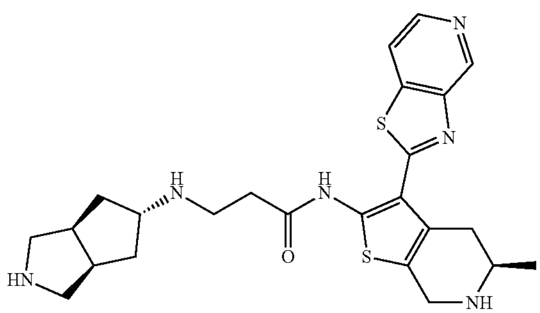 [SMILES: C[C@@H]1Cc2c(sc(NC(=O)CCN[C@@H]3C[C@H]4CNC[C@H]4C3)c2-c2nc3cnccc3s2)CN1] | ¹H NMR (DMSO-d6/D2O, 400 MHz): δ 9.25 (s, 1H), 8.43 (d, J = 5.38 Hz, 1H), 8.12 (d, J = 5.38 Hz, 1H), 3.97 (d, J = 3.91 Hz, 2H), 3.16-3.26 (m, 3H), 3.11 (br. s, 2H), 2.87-2.92 (m, 2H), 2.82-2.88 (m, 2H), 2.60-2.70 (m, 5H), 1.48-1.60 (m, 4H), 1.31 (d, J = 6.36 Hz, 3H).; LCMS: 482.7 |
| 251 | 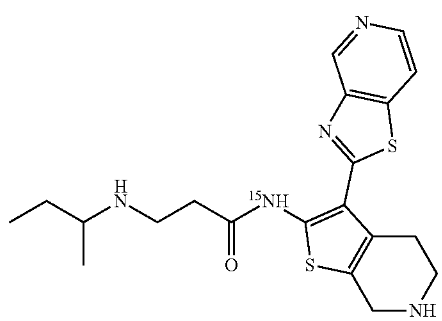 [SMILES: CCC(C)NCCC(=O)[15NH]c1sc2c(c1-c1nc3cnccc3s1)CCNC2] | ¹H NMR (DMSO-d6, 400 MHz): δ 12.36 (s, 1H), 12.13 (s, 1H), 9.65 (br. s, 2H), 8.86-9.04 (m, 2H), 4.32-4.39 (m, 2H), 3.48 (br. s, 2H), 3.26-3.31 (m, 2H), 3.08-3.22 (m, 5H), 2.55-2.68 (m, 2H), 1.76-1.88 (m, 1H), 1.45-1.55 (m, 1H), 1.25 (d, J = 6.36 Hz, 3H), 0.92 (t, J = 7.34 Hz, 3H).; LCMS: 416.8 |
| 252 | 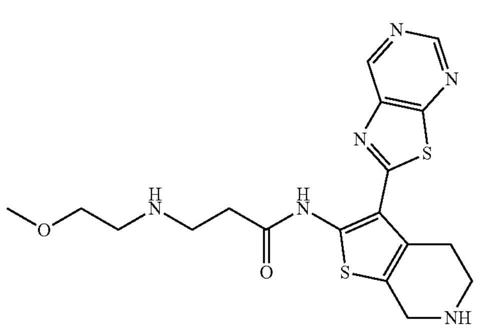 [SMILES: COCCNCCC(=O)Nc1sc2c(c1-c1nc3cncnc3s1)CCNC2] | DMSO-d6, δ 12.09 (s, 1H), 9.71 (br s, 2H), 9.59 (s, 1H), 9.20 (s, 1H), 9.06 (br s, 2H), 4.34 (s, 2H), 3.64-3.62 (m, 2H), 3.48-3.43 (m, 2H), 3.34-3.27 (m, 5H), 3.20-3.10 (m, 6H).; LCMS: 419.1 |

TABLE 1-continued

Exemplary Compounds and NMR/LCMS Data

| Compound | Structure | NMR/LCMS |
|---|---|---|
| 253 | 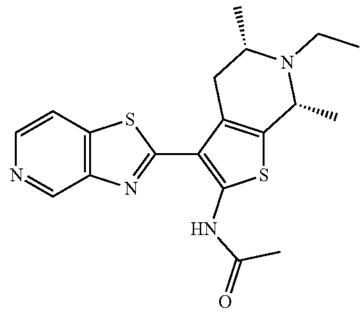 [SMILES: CCN1[C@H](C)c2sc(NC(C)=O)c(-c3nc4cnccc4s3)c2C[C@@H]1C] | CDCl3, δ 12.71 (br s, 1H), 9.26 (d, J = 0.8 Hz, 1H), 8.52 (d, J = 5.4 Hz, 1H), 7.84 (dd, J = 5.4, 0.9 Hz, 1H), 4.05 (dd, J = 13.3, 6.7 Hz, 1H), 3.19-3.11 (m, 1H), 2.96-2.82 (m, 3H), 2.74 (ddd, J = 15.4, 9.6, 2.5 Hz, 1H), 2.39 (s, 3H), 1.54 (d, J = 6.7 Hz, 3H), 1.37 (d, J = 6.5 Hz, 3H), 1.06 (t, J = 7.1 Hz, 3H).; LCMS: 387.2 |
| 254 | 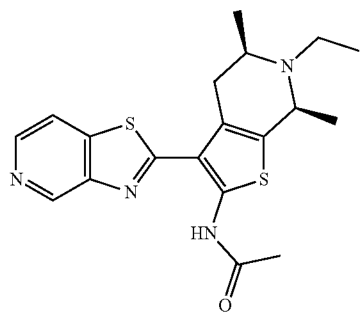 [SMILES: CCN1[C@H](C)Cc2c(sc(NC(C)=O)c2-c2nc3cnccc3s2)[C@@H]1C] | CDCl3, δ 12.71 (br s, 1H), 9.26 (d, J = 0.8 Hz, 1H), 8.52 (d, J = 5.4 Hz, 1H), 7.84 (dd, J = 5.4, 0.9 Hz, 1H), 4.05 (dd, J = 13.3, 6.7 Hz, 1H), 3.19-3.11 (m, 1H), 2.96-2.82 (m, 3H), 2.74 (ddd, J = 15.4, 9.6, 2.5 Hz, 1H), 2.39 (s, 3H), 1.54 (d, J = 6.7 Hz, 3H), 1.37 (d, J = 6.5 Hz, 3H), 1.06 (t, J = 7.1 Hz, 3H).; LCMS: 387.2 |

Pharmaceutical Compositions, Kits, and Administration

The present invention provides pharmaceutical compositions comprising a compound of Formula (I), e.g., Formulas (Ia), (Ib), (Ic), (Id), (Ie), (Ie-1), (Ie-2), (If), (Ig), (Ig-1), (Ig-2), (Ig-3), (Ih), (Ih-1), (Ih-2), (Ii), (Ii-1), (Ij), or (II) or a pharmaceutically acceptable salt, solvate, hydrate, tautomer, stereoisomer, or isotopically labeled derivative thereof, as described herein, and optionally a pharmaceutically acceptable excipient. In certain embodiments, the pharmaceutical composition of the invention comprises a compound Formula (I), e.g., Formulas (Ia), (Ib), (Ic), (Id), (Ie), (Ie-1), (Ie-2), (If), (Ig), (Ig-1), (Ig-2), (Ig-3), (Ih), (Ih-1), (Ih-2), (Ii), (Ii-1), (Ij), or (II) or a pharmaceutically acceptable salt thereof, and optionally a pharmaceutically acceptable excipient. In certain embodiments, the compound of Formula (I), e.g., Formulas (Ia), (Ib), (Ic), (Id), (Ie), (Ie-1), (Ie-2), (If), (Ig), (Ig-1), (Ig-2), (Ig-3), (Ih), (Ih-1), (Ih-2), (Ii), (Ii-1), (Ij), or (II) or a pharmaceutically acceptable salt, solvate, hydrate, tautomer, stereoisomer, or isotopically labeled derivative thereof, is provided in an effective amount in the pharmaceutical composition. In certain embodiments, the effective amount is a therapeutically effective amount. In certain embodiments, the effective amount is a prophylactically effective amount.

Pharmaceutical compositions described herein can be prepared by any method known in the art of pharmacology. In general, such preparatory methods include the steps of bringing the compound of Formula (I), e.g., a compound of Formulas (Ia), (Ib), (Ic), (Id), (Ie), (Ie-1), (Ie-2), (If), (Ig), (Ig-1), (Ig-2), (Ig-3), (Ih), (Ih-1), (Ih-2), (Ii), (Ii-1), (Ij), or (II) (the "active ingredient") into association with a carrier and/or one or more other accessory ingredients, and then, if necessary and/or desirable, shaping and/or packaging the product into a desired single- or multi-dose unit.

Pharmaceutical compositions can be prepared, packaged, and/or sold in bulk, as a single unit dose, and/or as a plurality of single unit doses. As used herein, a "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the pharmaceutically acceptable excipient, and/or any additional ingredients in a pharmaceutical composition of the invention will vary, depending upon the identity, size, and/or condition of the subject treated and further depending upon the route by which the composition is to be administered. By way of example, the composition may comprise between about 0.1% and about 100% (w/w) active ingredient.

The term "pharmaceutically acceptable excipient" refers to a non-toxic carrier, adjuvant, diluent, or vehicle that does not destroy the pharmacological activity of the compound with which it is formulated. Pharmaceutically acceptable excipients useful in the manufacture of the pharmaceutical compositions of the invention are any of those that are well known in the art of pharmaceutical formulation and include inert diluents, dispersing and/or granulating agents, surface active agents and/or emulsifiers, disintegrating agents, binding agents, preservatives, buffering agents, lubricating agents, and/or oils. Pharmaceutically acceptable excipients useful in the manufacture of the pharmaceutical compositions of the invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Compositions of the present invention may be administered orally, parenterally (including subcutaneous, intramuscular, intravenous and intradermal), by inhalation spray, topically, rectally, nasally, buccally, vaginally or via an implanted reservoir. In some embodiments, provided compounds or compositions are administrable intravenously and/or orally.

The term "parenteral" as used herein includes subcutaneous, intravenous, intramuscular, intraocular, intravitreal, intra-articular, intra-synovial, intrasternal, intrathecal, intrahepatic, intraperitoneal intralesional and intracranial injection or infusion techniques. Preferably, the compositions are administered orally, subcutaneously, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

Pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added. In some embodiments, a provided oral formulation is formulated for immediate release or sustained/delayed release. In some embodiments, the composition is suitable for buccal or sublingual administration, including tablets, lozenges and pastilles. A provided compound can also be in micro-encapsulated form.

Alternatively, pharmaceutically acceptable compositions of this invention may be administered in the form of suppositories for rectal administration. Pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For ophthalmic use, provided pharmaceutically acceptable compositions may be formulated as micronized suspensions or in an ointment such as petrolatum.

Pharmaceutically acceptable compositions of this invention may also be administered by nasal aerosol or inhalation.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

Compounds provided herein are typically formulated in dosage unit form, e.g., single unit dosage form, for ease of administration and uniformity of dosage. It will be understood, however, that the total daily usage of the compositions of the present invention will be decided by the attending physician within the scope of sound medical judgment. The specific therapeutically effective dose level for any particular subject or organism will depend upon a variety of factors including the disease being treated and the severity of the disorder; the activity of the specific active ingredient employed; the specific composition employed; the age, body weight, general health, sex and diet of the subject; the time of administration, route of administration, and rate of excretion of the specific active ingredient employed; the duration of the treatment; drugs used in combination or coincidental with the specific active ingredient employed; and like factors well known in the medical arts.

The exact amount of a compound required to achieve an effective amount will vary from subject to subject, depending, for example, on species, age, and general condition of a subject, severity of the side effects or disorder, identity of the particular compound(s), mode of administration, and the like. The desired dosage can be delivered three times a day, two times a day, once a day, every other day, every third day, every week, every two weeks, every three weeks, or every four weeks. In certain embodiments, the desired dosage can be delivered using multiple administrations (e.g., two, three, four, five, six, seven, eight, nine, ten, eleven, twelve, thirteen, fourteen, or more administrations).

In certain embodiments, an effective amount of a compound for administration one or more times a day to a 70 kg adult human may comprise about 0.0001 mg to about 3000 mg, about 0.0001 mg to about 2000 mg, about 0.0001 mg to about 1000 mg, about 0.001 mg to about 1000 mg, about 0.01 mg to about 1000 mg, about 0.1 mg to about 1000 mg, about 1 mg to about 1000 mg, about 1 mg to about 100 mg, about 10 mg to about 1000 mg, or about 100 mg to about 1000 mg, of a compound per unit dosage form.

In certain embodiments, the compounds of Formula (I), e.g., Formulas (Ia), (Ib), (Ic), (Id), (Ie), (Ie-1), (Ie-2), (If), (Ig), (Ig-1), (Ig-2), (Ig-3), (Ih), (Ih-1), (Ih-2), (Ii), (Ii-1), (Ij), or (II) may be at dosage levels sufficient to deliver from about 0.001 mg/kg to about 100 mg/kg, from about 0.01 mg/kg to about 50 mg/kg, preferably from about 0.1 mg/kg to about 40 mg/kg, preferably from about 0.5 mg/kg to about 30 mg/kg, from about 0.01 mg/kg to about 10 mg/kg, from about 0.1 mg/kg to about 10 mg/kg, and more preferably from about 1 mg/kg to about 25 mg/kg, of subject body weight per day, one or more times a day, to obtain the desired therapeutic effect.

It will be appreciated that dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

It will be also appreciated that a compound or composition, as described herein, can be administered in combination with one or more additional pharmaceutical agents. The compounds or compositions can be administered in combination with additional pharmaceutical agents that improve their bioavailability, reduce and/or modify their metabolism, inhibit their excretion, and/or modify their distribution within the body. It will also be appreciated that the therapy employed may achieve a desired effect for the same disorder, and/or it may achieve different effects.

The compound or composition can be administered concurrently with, prior to, or subsequent to, one or more additional pharmaceutical agents, which may be useful as, e.g., combination therapies. Pharmaceutical agents include therapeutically active agents. Pharmaceutical agents also include prophylactically active agents. Each additional pharmaceutical agent may be administered at a dose and/or on a time schedule determined for that pharmaceutical agent. The additional pharmaceutical agents may also be administered together with each other and/or with the compound or composition described herein in a single dose or administered separately in different doses. The particular combination to employ in a regimen will take into account compatibility of the inventive compound with the additional pharmaceutical agents and/or the desired therapeutic and/or prophylactic effect to be achieved. In general, it is expected that the additional pharmaceutical agents utilized in combination be utilized at levels that do not exceed the levels at which they are utilized individually. In some embodiments, the levels utilized in combination will be lower than those utilized individually.

Exemplary additional pharmaceutical agents include, but are not limited to, anti-proliferative agents, anti-cancer agents, anti-diabetic agents, anti-inflammatory agents, immunosuppressant agents, and a pain-relieving agent. Pharmaceutical agents include small organic molecules such as drug compounds (e.g., compounds approved by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells.

Also encompassed by the invention are kits (e.g., pharmaceutical packs). The inventive kits may be useful for preventing and/or treating a proliferative disease (e.g., cancer (e.g., leukemia, melanoma, multiple myeloma), benign neoplasm, angiogenesis, inflammatory disease, autoinflammatory disease, or autoimmune disease). The kits provided may comprise an inventive pharmaceutical composition or compound and a container (e.g., a vial, ampule, bottle, syringe, and/or dispenser package, or other suitable container). In some embodiments, provided kits may optionally further include a second container comprising a pharmaceutical excipient for dilution or suspension of an inventive pharmaceutical composition or compound. In some embodiments, the inventive pharmaceutical composition or compound provided in the container and the second container are combined to form one unit dosage form.

Thus, in one aspect, provided are kits including a first container comprising a compound described herein, or a pharmaceutically acceptable salt, solvate, hydrate, tautomer, stereoisomer, and isotopically labeled derivative, or a pharmaceutical composition thereof. In certain embodiments, the kit of the invention includes a first container comprising a compound described herein, or a pharmaceutically acceptable salt thereof, or a pharmaceutical composition thereof. In certain embodiments, the kits are useful in preventing and/or treating a proliferative disease in a subject. In certain embodiments, the kits further include instructions for administering the compound, or a pharmaceutically acceptable salt, solvate, hydrate, tautomer, stereoisomer, isotopically and labeled derivative thereof, or a pharmaceutical composition thereof, to a subject to prevent and/or treat a proliferative disease.

Methods of Treatment and Uses

The present invention also provides methods for the treatment or prevention of a proliferative disease (e.g., cancer, benign neoplasm, angiogenesis, inflammatory disease, autoinflammatory disease, or autoimmune disease) or an infectious disease (e.g., a viral disease) in a subject. Such methods comprise the step of administering to the subject in need thereof an effective amount of a compound of Formula (I), e.g., a compound of Formulas (Ia), (Ib), (Ic), (Id), (Ie), (Ie-1), (Ie-2), (If), (Ig), (Ig-1), (Ig-2), (Ig-3), (Ih), (Ih-1), (Ih-2), (Ii), (Ii-1), (Ij), or (II) or a pharmaceutically acceptable salt, solvate, hydrate, tautomer, stereoisomer, or isotopically labeled derivative thereof, or a pharmaceutical composition thereof. In certain embodiments, the methods described herein include administering to a subject an effective amount of a compound of Formula (I), e.g., a compound of Formulas (Ia), (Ib), (Ic), (Id), (Ie), (Ie-1), (Ie-2), (If), (Ig), (Ig-1), (Ig-2), (Ig-3), (Ih), (Ih-1), (Ih-2), (Ii), (Ii-1), (Ij), or (II) or a pharmaceutically acceptable salt thereof, or a pharmaceutical composition thereof.

In certain embodiments, the subject being treated is a mammal. In certain embodiments, the subject is a human. In certain embodiments, the subject is a domesticated animal, such as a dog, cat, cow, pig, horse, sheep, or goat. In certain embodiments, the subject is a companion animal such as a dog or cat. In certain embodiments, the subject is a livestock animal such as a cow, pig, horse, sheep, or goat. In certain embodiments, the subject is a zoo animal. In another embodiment, the subject is a research animal such as a rodent, dog, or non-human primate. In certain embodiments, the subject is a non-human transgenic animal such as a transgenic mouse or transgenic pig.

The proliferative disease to be treated or prevented using the compounds of Formula (I), e.g., a compound of Formulas (Ia), (Ib), (Ic), (Id), (Ie), (Ie-1), (Ie-2), (If), (Ig), (Ig-1), (Ig-2), (Ig-3), (Ih), (Ih-1), (Ih-2), (Ii), (Ii-1), (Ij), or (II) will typically be associated with deregulated activity of c-Myc. Deregulated activity of c-Myc may constitute an elevated and/or an inappropriate (e.g., abnormal) activity of c-Myc. In certain embodiments, c-Myc is not overexpressed, and the activity of c-Myc is elevated and/or inappropriate. In certain other embodiments, c-Myc is overexpressed, and the activity of c-Myc is elevated and/or inappropriate. The compounds Formula (I), e.g., the compound of Formulas (Ia), (Ib), (Ic), (Id), (Ie), (Ie-1), (Ie-2), (If), (Ig), (Ig-1), (Ig-2), (Ig-3), (Ih), (Ih-1), (Ih-2), (Ii), (Ii-1), (Ij), or (II) and pharmaceutically acceptable salts, solvates, hydrates, tautomers, stereoisomers, isotopically labeled derivatives, and compositions thereof, may inhibit the activity of c-Myc and be useful in treating and/or preventing proliferative diseases.

In other embodiments, the proliferative disease to be treated or prevented using the compounds of Formula (I), e.g., compounds of Formulas (Ia), (Ib), (Ic), (Id), (Ie), (Ie-1), (Ie-2), (If), (Ig), (Ig-1), (Ig-2), (Ig-3), (Ih), (Ih-1), (Ih-2), (Ii), (Ii-1), (Ij), or (II) may be associated with deregulated activity a Myc family member, e.g., N-Myc or L-Myc. Deregulated activity of a Myc family member (e.g., N-Myc or L-Myc) may constitute an elevated and/or an inappropriate (e.g., abnormal) activity of one or more Myc family members (e.g., N-Myc or L-Myc). In certain embodiments, a Myc family member (e.g., N-Myc or L-Myc) is not overexpressed, and the activity of said Myc family member (e.g., N-Myc or L-Myc) is elevated and/or inappropriate. In certain other embodiments, a Myc family member (e.g., N-Myc or L-Myc) is overexpressed, and the activity of said Myc family member (e.g., N-Myc or L-Myc) is elevated and/or inappropriate. The compounds of Formula (I), e.g., compounds of Formulas (Ia), (Ib), (Ic), (Id), (Ie), (Ie-1), (Ie-2), (If), (Ig), (Ig-1), (Ig-2), (Ig-3), (Ih), (Ih-1), (Ih-2), (Ii), (Ii-1), (Ij), or (II) and pharmaceutically acceptable salts, solvates, hydrates, tautomers, stereoisomers, isotopically labeled derivatives, and compositions thereof, may inhibit the activity of a Myc family members (e.g., N-Myc or L-Myc) and be useful in treating and/or preventing proliferative diseases.

A proliferative disease may also be associated with inhibition of apoptosis of a cell in a biological sample or subject. All types of biological samples described herein or known in the art are contemplated as being within the scope of the invention. Inhibition of the activity of c-Myc or other Myc family member (e.g., N-Myc or L-Myc) may cause cytotoxicity via induction of apoptosis. The compounds of Formula (I), e.g., compounds of Formulas (Ia), (Ib), (Ic), (Id), (Ie), (Ie-1), (Ie-2), (If), (Ig), (Ig-1), (Ig-2), (Ig-3), (Ih), (Ih-1), (Ih-2), (Ii), (Ii-1), (Ij), or (II) and pharmaceutically acceptable salts, solvates, hydrates, tautomers, stereoisomers, isotopically labeled derivatives, and compositions thereof, may induce apoptosis, and therefore, may be useful in treating and/or preventing proliferative diseases.

In certain embodiments, the proliferative disease to be treated or prevented using the compounds of Formula (I), e.g., compounds of Formulas (Ia), (Ib), (Ic), (Id), (Ie), (Ie-1), (Ie-2), (If), (Ig), (Ig-1), (Ig-2), (Ig-3), (Ih), (Ih-1), (Ih-2), (Ii), (Ii-1), (Ij), or (II) is cancer. All types of cancers disclosed herein or known in the art are contemplated as being within the scope of the invention. In certain embodiments, the proliferative disease is a cancer associated with dependence on BCL-2 anti-apoptotic proteins (e.g., MCL-1 and/or XIAP). In certain embodiments, the proliferative disease is a cancer associated with overexpression of Myc. In certain embodiments, the proliferative disease is a hematological malignancy. In certain embodiments, the proliferative disease is a blood cancer. In certain embodiments, the proliferative disease is leukemia. In certain embodiments, the proliferative disease is chronic lymphocytic leukemia (CLL). In certain embodiments, the proliferative disease is acute lymphoblastic leukemia (ALL). In certain embodiments, the proliferative disease is T-cell acute lymphoblastic leukemia (T-ALL). In certain embodiments, the proliferative disease is chronic myelogenous leukemia (CML). In certain embodiments, the proliferative disease is acute myelogenous leukemia (AML). In certain embodiments, the proliferative disease is lymphoma. In certain embodiments, the proliferative disease is melanoma. In certain embodiments, the proliferative disease is multiple myeloma. In certain embodiments, the proliferative disease is a bone cancer. In certain embodiments, the proliferative disease is osteosarcoma. In some embodiments, the proliferative disease is Ewing's sarcoma. In some embodiments, the proliferative disease is triple-negative breast cancer (TNBC). In some embodiments, the proliferative disease is a brain cancer. In some embodiments, the proliferative disease is neuroblastoma. In some embodiments, the proliferative disease is a lung cancer. In some embodiments, the proliferative disease is small cell lung cancer (SCLC). In some embodiments, the proliferative disease is large cell lung cancer. In some embodiments, the proliferative disease is a benign neoplasm. All types of benign neoplasms disclosed herein or known in the art are contemplated as being within the scope of the invention.

In some embodiments, the proliferative disease is associated with angiogenesis. All types of angiogenesis disclosed herein or known in the art are contemplated as being within the scope of the invention.

In certain embodiments, the proliferative disease is an inflammatory disease. All types of inflammatory diseases disclosed herein or known in the art are contemplated as being within the scope of the invention. In certain embodiments, the inflammatory disease is rheumatoid arthritis. In some embodiments, the proliferative disease is an autoinflammatory disease. All types of autoinflammatory diseases disclosed herein or known in the art are contemplated as being within the scope of the invention. In some embodiments, the proliferative disease is an autoimmune disease. All types of autoimmune diseases disclosed herein or known in the art are contemplated as being within the scope of the invention.

The cell described herein may be an abnormal cell. The cell may be in vitro or in vivo. In certain embodiments, the cell is a proliferative cell. In certain embodiments, the cell is a blood cell. In certain embodiments, the cell is a lymphocyte. In certain embodiments, the cell is a cancer cell. In certain embodiments, the cell is a leukemia cell. In certain embodiments, the cell is a CLL cell. In certain embodiments, the cell is a melanoma cell. In certain embodiments, the cell is a multiple myeloma cell. In certain embodiments, the cell is a benign neoplastic cell. In certain embodiments, the cell is an endothelial cell. In certain embodiments, the cell is an immune cell.

In another aspect, the present invention provides methods of down-regulating the expression of c-Myc or other Myc family member (e.g., N-Myc or L-Myc) in a biological sample or subject. In certain embodiments, the present invention provides methods of down-regulating the expression of c-Myc in a biological sample or subject. In another aspect, the present invention provides methods of down-regulating the expression of other bHLH transcription factors, such as MITF, TWIST1, and Max, in a biological sample or subject.

In certain embodiments, the methods described herein comprise the additional step of administering one or more additional pharmaceutical agents in combination with the compounds of Formula (I), e.g., compounds of Formulas (Ia), (Ib), (Ic), (Id), (Ie), (Ie-1), (Ie-2), (If), (Ig), (Ig-1), (Ig-2), (Ig-3), (Ih), (Ih-1), (Ih-2), (Ii), (Ii-1), (Ij), or (II) a pharmaceutically acceptable salt thereof, or compositions comprising such compound or pharmaceutically acceptable salt thereof. Such additional pharmaceutical agents include, but are not limited to, anti-proliferative agents, anti-cancer agents, anti-diabetic agents, anti-inflammatory agents, immunosuppressant agents, and a pain-relieving agent. The additional pharmaceutical agent(s) may synergistically augment inhibition of c-Myc or other Myc family member (e.g., N-Myc or L-Myc) induced by the inventive compounds or compositions of this invention in the biological sample or subject. In certain embodiments, the additional pharmaceutical agent is flavopiridol, triptolide, SNS-032 (BMS-387032), PHA-767491, PHA-793887, BS-181, (S)-CR8, (R)-CR8, ABT-737, or NU6140. In certain embodiments, the additional pharmaceutical agent is an inhibitor of a mitogen-activated protein kinase (MAPK). In certain embodiments, the additional pharmaceutical agent is an inhibitor of a Bcl-2 protein. In certain embodiments, the additional pharmaceutical agent is an inhibitor of a glycogen synthase kinase 3 (GSK3). In certain embodiments, the additional pharmaceutical agent is an inhibitor of an AGC kinase. In certain embodiments, the additional pharmaceutical agent is an inhibitor of a CaM kinase. In certain embodiments, the additional pharmaceutical agent is an inhibitor of a casein kinase 1. In certain embodiments, the additional pharmaceutical agent is an inhibitor of a STE kinase. In certain embodiments, the additional pharmaceutical agent is an inhibitor of a tyrosine kinase. Thus, the combination of the inventive compounds or compositions and the additional pharmaceutical agent(s) may be useful in treating proliferative diseases resistant to a treatment using the additional pharmaceutical agent(s) without the inventive compounds or compositions.

In yet another aspect, the present invention provides the compounds of compounds of Formula (I), e.g., compounds of Formulas (Ia), (Ib), (Ic), (Id), (Ie), (Ie-1), (Ie-2), (If), (Ig), (Ig-1), (Ig-2), (Ig-3), (Ih), (Ih-1), (Ih-2), (Ii), (Ii-1), (Ij), or (II) and pharmaceutically acceptable salts, solvates, hydrates, tautomers, stereoisomers, isotopically labeled derivatives, and compositions thereof, for use in the treatment of a proliferative disease in a subject. In certain embodiments, provided by the invention are the compounds described herein, and pharmaceutically acceptable salts and compositions thereof, for use in the treatment of a proliferative disease in a subject. In certain embodiments, provided by the invention are the compounds described herein, and pharmaceutically acceptable salts and compositions thereof, for use in inhibiting cell growth. In certain embodiments, provided by the invention are the compounds described herein, and pharmaceutically acceptable salts and compositions thereof, for use in inducing apoptosis in a cell. In certain embodiments, provided by the invention are the compounds described herein, and pharmaceutically acceptable salts and compositions thereof, for use in inhibiting transcription.

EXAMPLES

In order that the invention described herein may be more fully understood, the following examples are set forth. The synthetic and biological examples described in this application are offered to illustrate the compounds, pharmaceutical compositions, and methods provided herein and are not to be construed in any way as limiting their scope.

The compounds provided herein can be prepared from readily available starting materials using modifications to the specific synthesis protocols set forth below that would be well known to those of skill in the art. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvents used, but such conditions can be determined by those skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in Greene et al., *Protecting Groups in Organic Synthesis*, Second Edition, Wiley, New York, 1991, and references cited therein.

NMR and LCMS data for exemplary compounds of the invention are summarized in Table 1.

TABLE 2

| Abbreviations | |
|---|---|
| Ac | acetyl |
| Ac$_2$O | acetic anyhydride |
| AcOH | acetic acid |
| ACN | acetonitrile |
| aq. | aqueous |
| atm | atmospheres |
| Boc | tert-butoxy carbonyl |
| Boc$_2$O | di-t-butyl dicarbonate |
| Bn | benzyl |
| DCM | bichloromethane |
| DIPEA | N,N-diisopropyl ethylamine |
| DMF | dmethylformamide |
| DMSO | dimethylsulfoxide |
| DPPA | diphenoxyphosphoryl azide |
| EDTA | ethylenediamine tetraacetic acid |
| ELS, | evaporative light scattering |
| ELSD | detector |
| eq(s). | equivalent(s) |
| EtOAc | ethyl acetate |
| Et | ethyl |
| EtOH | ethanol |
| Et$_3$N, TEA | triethylamine |
| g | gram(s) |
| h | hour(s) |
| Hex | hexanes |
| HOBt | 1-Hydroxybenzotriazole |
| HPLC | high pressure liquid chromatography |
| IPA | isopropanol |
| LCMS; | liquid chromatography mass |
| LC-MS | spectrometry |
| m-CPBA | 3-chloroperoxybenzoic acid |
| MeOH | methanol |
| mg | milligram(s) |
| MHz | megahertz |
| min | minute(s) |
| mL; ml | milliliter(s) |
| MS | mass spectrometry |
| mW | microwave |
| NMe | N-methyl |
| NMR | nuclear magnetic resonance |
| Ph | phenyl |
| pyr | pyridine |
| r.t.; rt; RT | room temperature |
| S., sat. | saturated |
| T$_3$P | propylphosphonic anydride |
| TFA | trifluoroacetic acid |
| THF | tetrahydrofuran |
| TLC | thin layer chromatography |

Example 1

Synthesis of N-(3-(Thiazolo[4,5-c]pyridin-2-yl)-4,5,6,7-tetrahydrothieno[2,3-c]pyridin-2-yl)acetamide (Compound 100)

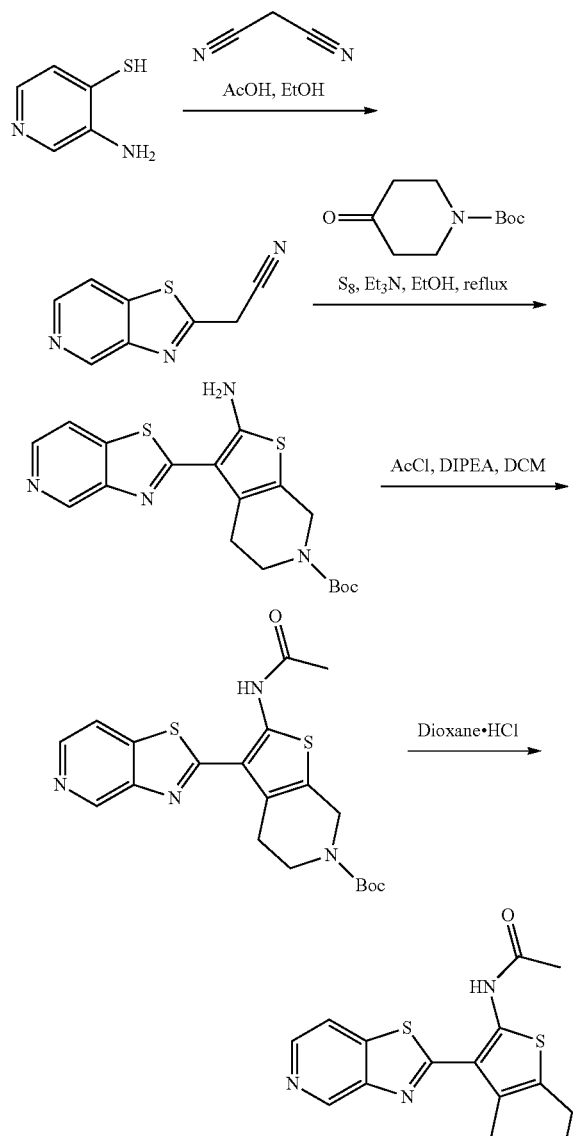

Step-1: 2-(Thiazolo[4,5-c]pyridin-2-yl)acetonitrile

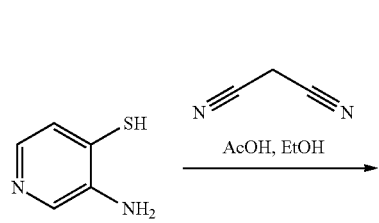

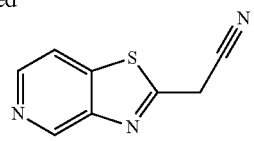

To the solution of 3-aminopyridine-4-thiol (500 mg, 3.96 mmol) in ethanol (5 mL) and AcOH (5 mL) was added malononitrile (392 mg, 5.94 mmol). After the addition, the resulting mixture was heated to reflux at 80° C. for 16 h. The reaction mixture was then evaporated under vacuum pressure to afford the title compound as a brown solid (650 mg crude). 1 H NMR (DMSO-$d_6$, 400 MHz): δ 9.30 (s, 1 H), 8.56 (d, J=5.38 Hz, 1 H), 8.22 (d, J=5.38 Hz, 1 H), 4.83 (s, 2 H). LCMS: [M+H]$^+$=176.00; $R_t$=1.49 min.

Step-2: tert-Butyl 2-amino-3-(thiazolo[4,5-c]pyridin-2-yl)-4,7-dihydrothieno[2,3-c]pyridine-6(5H)-carboxylate

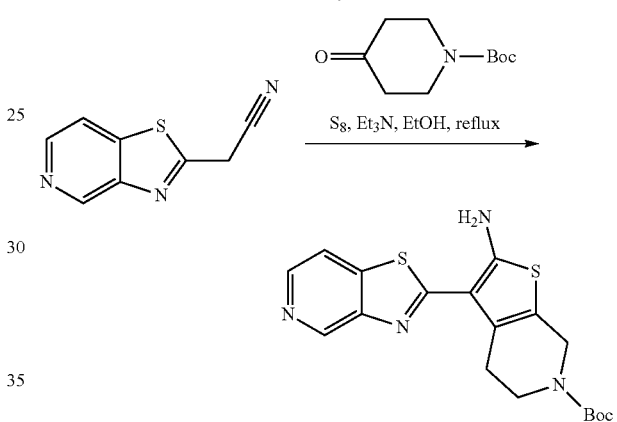

To the solution of 2-(thiazolo[4,5-c]pyridin-2-yl)acetonitrile (650 mg, 3.70 mmol) in ethanol (20 mL) were added tert-butyl 4-oxopiperidine-1-carboxylate (739 mg, 3.70 mmol), elemental sulfur (119 g, 3.70 mmol), and morpholine (0.32 mL, 3.70 mmol). After the addition, the resulting mixture was heated to reflux at 80° C. for 4 h, followed by concentration of the mixture. The resulting crude compound was purified by silica gel column chromatography with 0-20% ethyl acetate in n-hexane to afford the title compound as light brown solid (500 mg, yield 35%). $^1$H NMR (DMSO-$d_6$, 400 MHz): δ 9.13 (s, 1 H), 8.39 (d, J=5.38 Hz, 1 H), 8.26 (s, 2 H), 8.07 (d, J=5.15 Hz, 1 H), 4.36 (br. s, 2 H), 3.66 (t, J=5.27 Hz, 2 H), 2.81-2.86 (m, 2 H), 1.43 (s, 9 H). LCMS: [M+H]$^+$=389.05; $R_t$=2.83 min.

Step-3: tert-Butyl 2-acetamido-3-(thiazolo[4,5-c]pyridin-2-yl)-4,7-dihydrothieno[2,3-c]pyridine-6(5H)-carboxylate

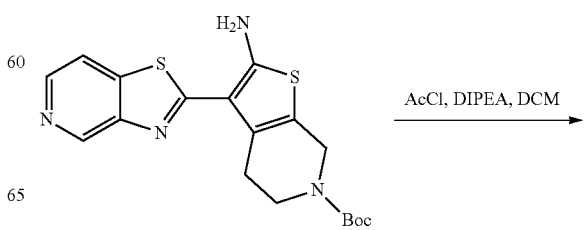

115
-continued

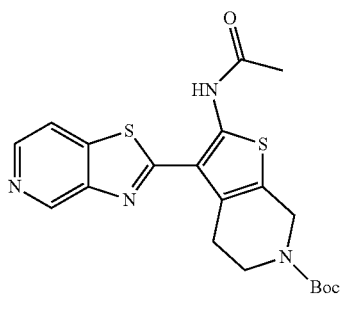

To the solution of tert-butyl 2-amino-3-(thiazolo[4,5-c] pyridin-2-yl)-4,7-dihydrothieno[2,3-c]pyridine-6(5H)-carboxylate (500 mg, 1.28 mmol) in DCM (20 mL) at 0° C. was added DIPEA (0.448 mL, 2.57 mmol), followed by drop wise addition of acetyl chloride (0.137 mL, 1.93 mmol). The reaction mixture was stirred at room temperature for 3h. After the reaction was complete, the mixture was diluted with water (30 mL) and extracted with dichloromethane (30 mL×3). The combined organic layers were washed with sat. NaHCO$_3$ and dried over Na$_2$SO$_4$. After removal of solvent, the crude residue was purified by column chromatography with 0-20% ethyl acetate in n-hexane to afford the title compound as a brown solid (210 mg, yield 38%). LCMS: [M+H]$^+$=431.05; R$_t$=3.32 min.

Step-4: N-(3-(Thiazolo[4,5-c]pyridin-2-yl)-4,5,6,7-tetrahydro thieno[2,3-c]pyridin-2-yl)acetamide

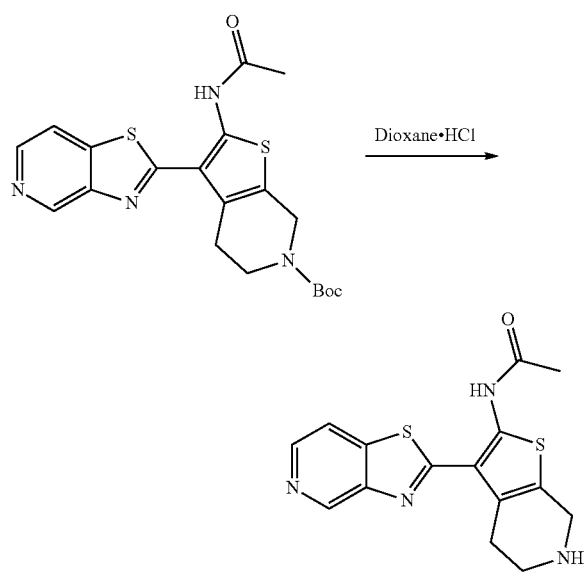

To a solution of 4M HCl in dioxane (5 mL) at 0° C. was added tert-butyl 2-acetamido-3-(thiazolo[4,5-c]pyridin-2-yl)-4,7-dihydrothieno[2,3-c]pyridine-6(5H)-carboxylate (200 mg, 0.46 mmol). After stirring at room temperature for 2 h, the reaction mixture was evaporated under vacuum pressure. The resultant crude residue was washed several times with acetonitrile to afford the title compound (HCl salt) as a brown solid (20 mg, yield 13%).

116
Example 2

Synthesis of N-(3-(thiazolo[5,4-b]pyridin-2-yl)-4,5,6,7-tetrahydrothieno[2,3-c]pyridin-2-yl)acetamide (Compound 101)

Step 1: 2-(Thiazolo[5,4-b]pyridin-2-yl)acetonitrile

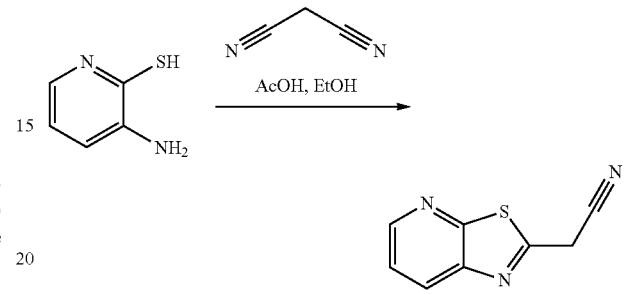

To a solution of 3-aminopyridine-2-thiol (500 mg, 0.39 mmol) in ethanol (10 mL) and AcOH (4 mL) was added malononitrile (207 mg, 3.12 mmol), and the resulting mixture was heated to reflux at 80° C. for 16 h. The reaction mixture was then concentrated under vacuum and the crude compound was purified by silica gel column chromatography using 0-40% ethyl acetate in n-hexane to afford the title compound as a brown solid (415 mg, yield 60%). 1H NMR (DMSO-d$_6$, 400 MHz): δ 8.65 (d, J=4.62 Hz, 1 H), 8.46 (d, J=8.32 Hz, 1 H), 7.63 (dd, J=4.62, 8.32 Hz, 1 H), 4.82 (s, 2 H). LCMS: [M+H]$^+$=175.85; R$_t$=1.78 min Step 2: tert-butyl 2-amino-3-(thiazolo[5,4-b]pyridin-2-yl)-4,5-dihydrothieno[2,3-c]pyridine-6(7H)-carboxylate

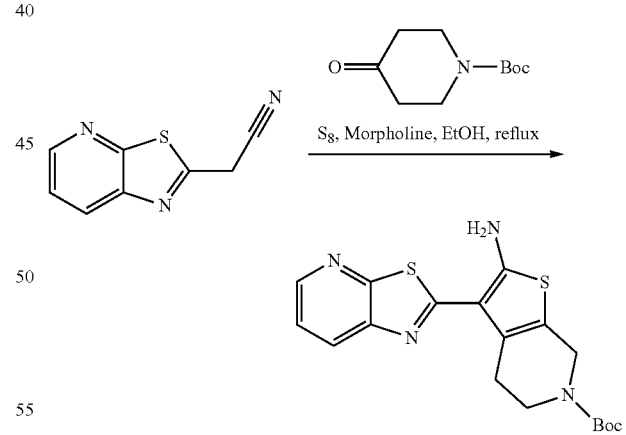

To a solution of 2-(thiazolo[5,4-b]pyridin-2-yl)acetonitrile (405 mg, 2.30 mmol) in ethanol (20 mL) were added tert-butyl 4-oxopiperidine-1-carboxylate (460 mg, 2.30 mmol), elemental sulfur (74 mg, 2.30 mmol), and morpholine (180 mg, 2.30 mmol). After the reaction was complete, the reaction mixture was concentrated under vacuum. The crude residue was washed with methanol and dried to afford the title compound as light brown solid (742 mg, yield 82%). 1H NMR (DMSO-d$_6$, 400 MHz): δ 8.44 (dd, J=1.64, 4.45 Hz, 1 H), 8.30 (s, 2 H), 8.20 (dd, J=1.40, 7.96 Hz, 1 H), 7.49

(dd, J=4.68, 8.43 Hz, 1 H), 4.35 (br. s, 2 H), 3.66 (t, J=5.38 Hz, 2 H), 2.81-2.86 (m, 2 H), 1.44 (s, 9 H). LCMS: [M+H]⁺=389.40; $R_t$=3.22 min.

Step 3: tert-Butyl 2-acetamido-3-(thiazolo[5,4-b]pyridin-2-yl)-4,7-dihydrothieno[2,3-c]pyridine-6(5H)-carboxylate

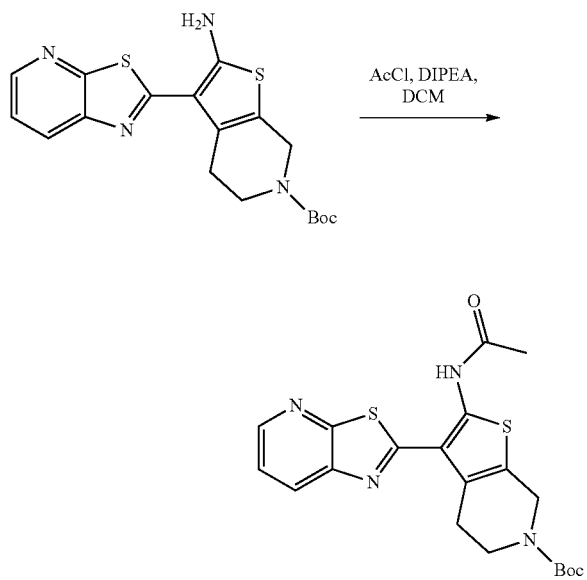 [SMILES: CC(C)(C)OC(=O)N1CCc2c(sc(N)c2-c2nc3cccnc3s2)C1 ; CC(=O)Nc1sc2c(c1-c1nc3cccnc3s1)CCN(C(=O)OC(C)(C)C)C2]

To a solution of tert-butyl 2-amino-3-(thiazolo[5,4-b]pyridin-2-yl)-4,7-dihydrothieno[2,3-c]pyridine-6(5H)-carboxylate (730 mg, 1.88 mmol) in DCM (20 mL) at 0° C. was added DIPEA (0.655 mL, 3.76 mmol), followed by drop wise addition of acetyl chloride (0.2 mL, 2.82 mmol). The reaction mixture was stirred at room temperature for 3h and after completion, was diluted with water (30 mL) and extracted with DCM (30 mL×3). The combined organic layers were washed with sat. NaHCO₃ and dried over Na₂SO₄. After removal of the solvent, the crude residue was purified by column chromatography using 0-50% ethyl acetate in n-hexane to afford the title compound as light brown solid (500 mg, yield 62%). LCMS: [M+H]⁺=431.40; $R_t$=3.36 min Step 4: N-(3-(Thiazolo[5,4-b]pyridin-2-yl)-4,5,6,7-tetrahydro thieno[2,3-c]pyridin-2-yl)acetamide

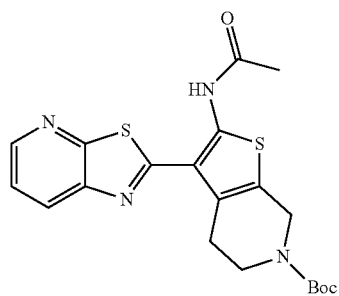

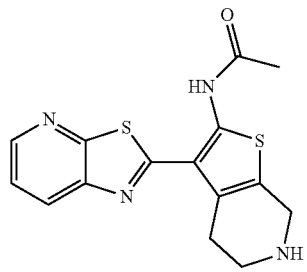

To a solution of 4M HCl in dioxane (7 mL) at 0° C. was added tert-butyl 2-acetamido-3-(thiazolo[5,4-b]pyridin-2-yl)-4,7-dihydrothieno[2,3-c]pyridine-6(5H)-carboxylate (500 mg, 1.16 mmol). The reaction mixture was stirred at room temperature for 2 h. After completion, the reaction mixture was concentrated under vacuum, and the crude residue obtained was diluted with DCM, washed with sat. NaHCO₃, and dried over Na₂SO₄. After removal of solvent, the crude residue was purified by preparative HPLC to afford the title compound as a yellow solid (157 mg, yield 41%).

Example 3

Synthesis of N-(3-(thiazolo[4,5-c]pyridin-2-yl)-5,6-dihydro-4H-thieno[2,3-c]pyrrol-2-yvl)acetamide (Compound 102)

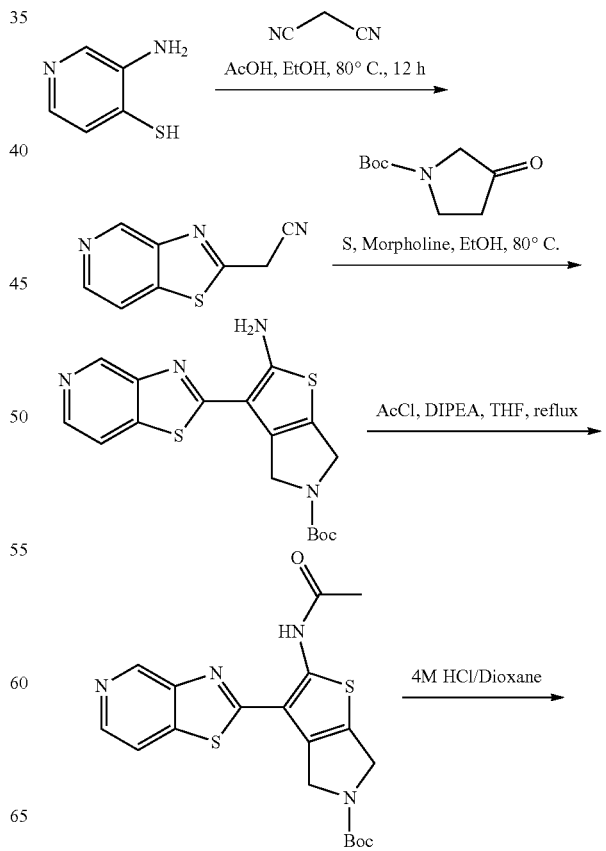

-continued

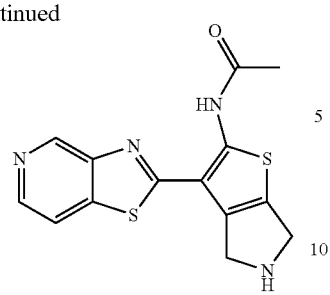

Step 1: 2-(Thiazolo[4,5-c]pyridin-2-yl)acetonitrile

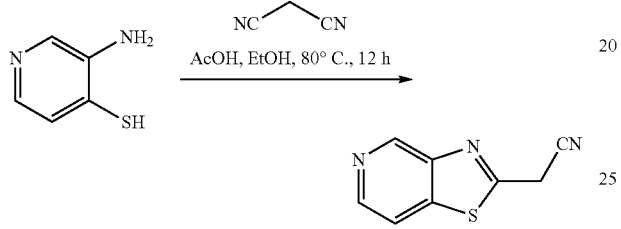

A stirred solution of 3-aminopyridine-4-thiol (2 g, 15.8 mmol) and malononitrile (1.6 g, 23.8 mmol) in ethanol (20 mL) was heated at 80° C. for 12 h. After the reaction was complete as monitored by TLC and LCMS, the reaction mixture was concentrated under reduced pressure and triturated with hexane. The solvent was decanted, and the crude solid was dried to afford 2 g of the crude title compound which was used in the next step without further purification. LCMS: [M+H]$^+$=175.85; $R_f$=1.49 min.

Step 2: tert-butyl 2-amino-3-(thiazolo[4,5-c]pyridin-2-yl)-4,6-dihydro-5H-thieno[2,3-c]pyrrole-5-carboxylate

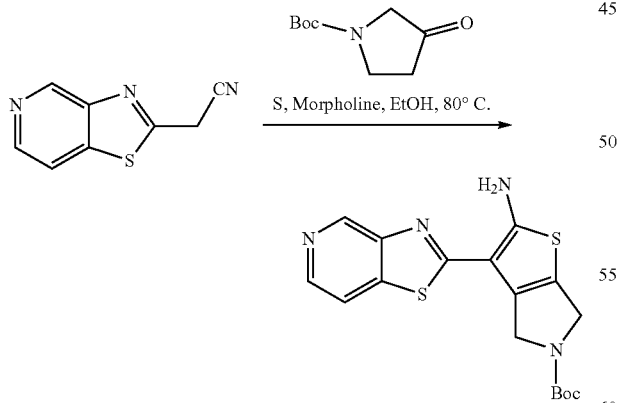

To a solution of 2-(thiazolo[4,5-c]pyridin-2-yl)acetonitrile (500 mg, 2.85 mmol) in ethanol (10 mL) was added tert-butyl 3-oxopyrrolidine-1-carboxylate (528 mg, 2.85 mmol), elemental sulphur (91 mg, 2.85 mmol) and morpholine (247 mg, 2.85 mmol) at room temperature. After the addition, the resulting mixture was heated to reflux at 85° C. for 3 h. After completion (monitored by TLC), the reaction mixture was evaporated under vacuum pressure. The crude residue obtained was stirred in methanol for 20 min, and the solid that precipitated was filtered and dried to afford the title compound (400 mg, crude). The crude compound was used in the next step without further purification. LCMS: [M+H]$^+$=374.90; $R_f$=2.93 min.

Step 3: tert-butyl 2-acetamido-3-(thiazolo[4,5-c]pyridin-2-yl)-4,6-dihydro-5H-thieno[2,3-c]pyrrole-5-carboxylate

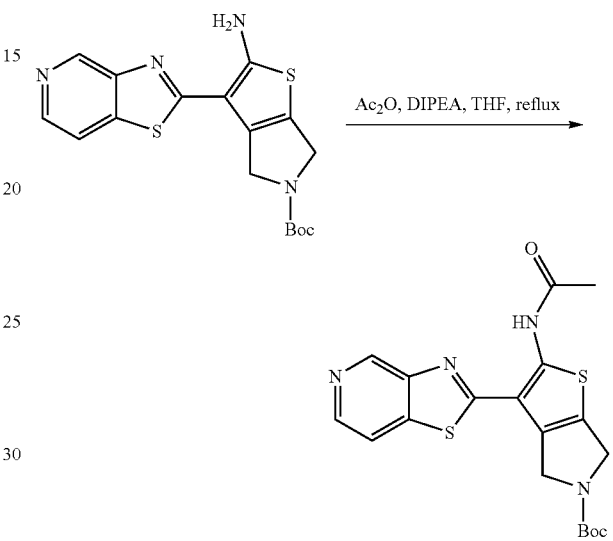

To a solution of tert-butyl 2-amino-3-(thiazolo[4,5-c]pyridin-2-yl)-4,6-dihydro-5H-thieno[2,3-c]pyrrole-5-carboxylate (200 mg, 0.53 mmol) in THF (10 mL) at 0° C. was added DIPEA (0.1 mL, 1.06 mmol) and acetyl anhydride (0.075 mL, 0.80 mmol). The reaction mixture was heated to 80° C. for 48 h, and the reaction was monitored by TLC. After the completion of reaction as indicated by LCMS, the reaction mixture was concentrated under reduced pressure to get a crude residue, which was taken up in 10% MeOH in CH$_2$Cl$_2$ and washed with sat. NaHCO$_3$ solution, dried with anhydrous Na$_2$SO$_4$, filtered, and concentrated to get a crude residue. The crude compound was purified by silica gel column chromatography, eluting with 0-20% ethyl acetate, to afford the title compound (100 mg, 45% yield). LCMS: [M+H]$^+$=417.0; $R_f$=3.41 min.

Step 4: N-(3-(thiazolo[4,5-c]pyridin-2-yl)-5,6-dihydro-4H-thieno[2,3-c]pyrrol-2-yl)acetamide

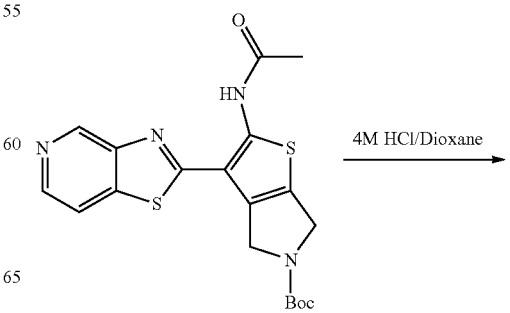

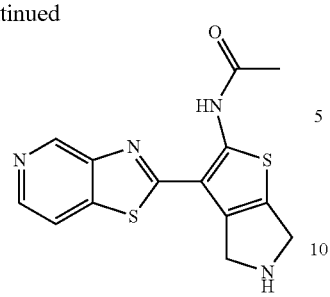

To tert-butyl 2-acetamido-3-(thiazolo[4,5-c]pyridin-2-yl)-4,6-dihydro-5H-thieno[2,3-c]pyrrole-5-carboxylate (100 mg, 0.24 mmol) at 0° C. was added 4M HCl in dioxane (5 mL). After the addition, the resulting mixture was stirred at room temperature for 2 h. The reaction was monitored by TLC. After TLC indicated the reaction was complete, the reaction mixture was evaporated under vacuum to give a crude residue which was purified by preparative HPLC to afford the title compound as a yellow solid (10 mg, 13% yield).

Example 4

Synthesis of 3-(sec-butylamino)-N-(3-(thiazolo[4,5-c]pyridin-2-yl)-4,5,6,7-tetrahydrothieno[2,3-c]pyridin-2-yl)propanamide (Compound 103)

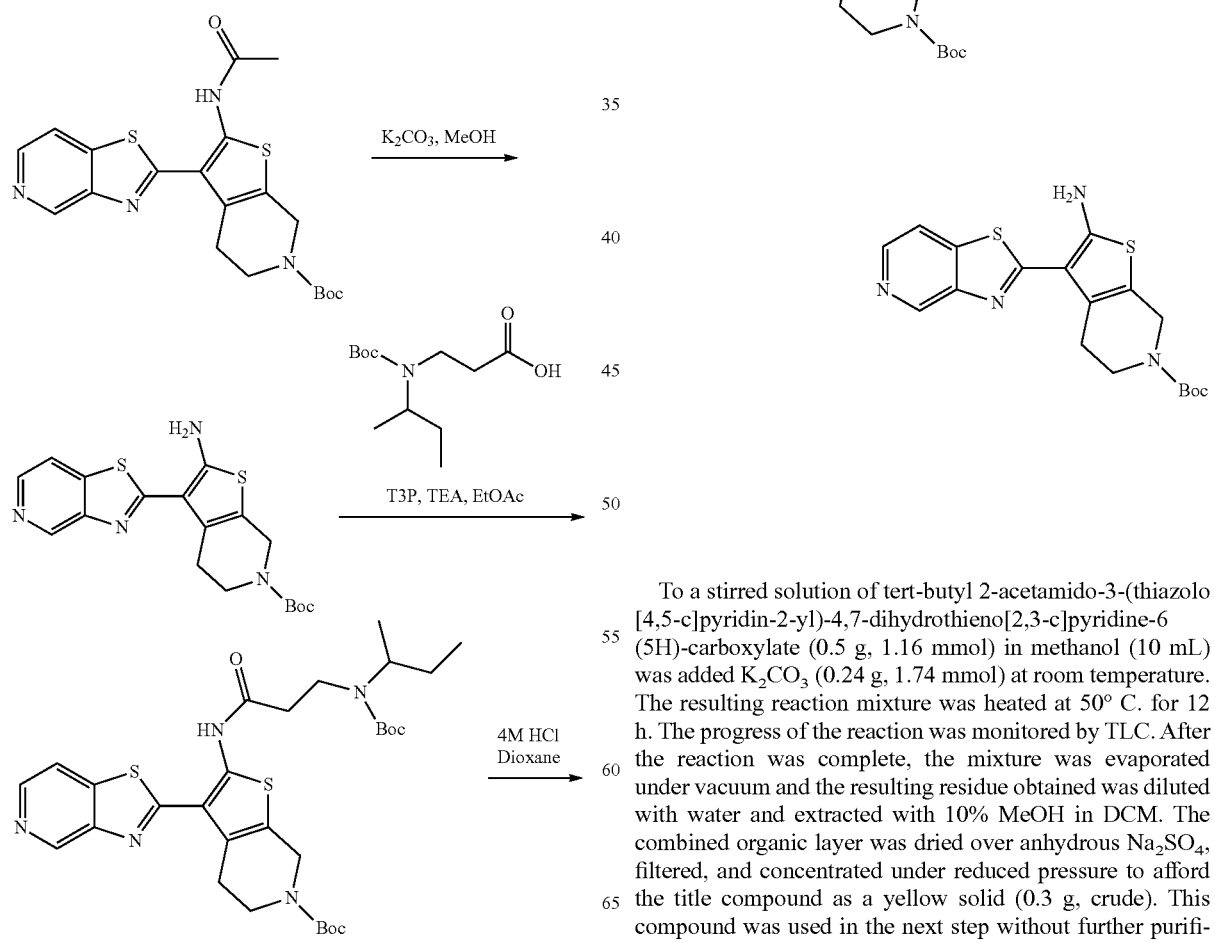

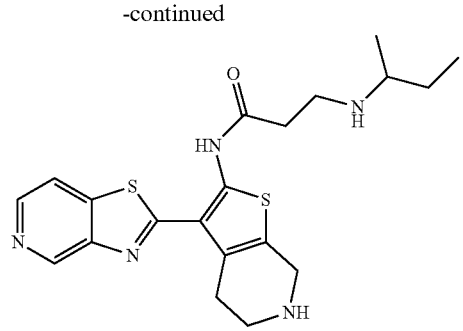

Step 1: tert-butyl 2-amino-3-(thiazolo[4,5-c]pyridin-2-yl)-4,7-dihydrothieno[2,3-c]pyridine-6(5H)-carboxylate

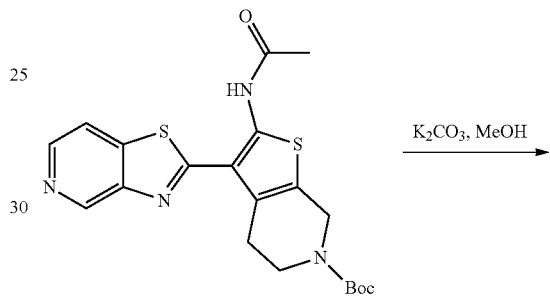

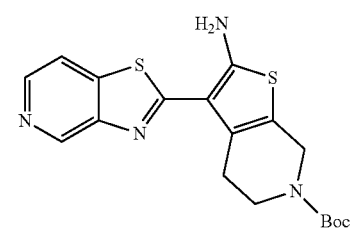

To a stirred solution of tert-butyl 2-acetamido-3-(thiazolo[4,5-c]pyridin-2-yl)-4,7-dihydrothieno[2,3-c]pyridine-6(5H)-carboxylate (0.5 g, 1.16 mmol) in methanol (10 mL) was added $K_2CO_3$ (0.24 g, 1.74 mmol) at room temperature. The resulting reaction mixture was heated at 50° C. for 12 h. The progress of the reaction was monitored by TLC. After the reaction was complete, the mixture was evaporated under vacuum and the resulting residue obtained was diluted with water and extracted with 10% MeOH in DCM. The combined organic layer was dried over anhydrous $Na_2SO_4$, filtered, and concentrated under reduced pressure to afford the title compound as a yellow solid (0.3 g, crude). This compound was used in the next step without further purification. LCMS: [M+H]+=388.90; $R_t$=2.99 min.

Step 2: tert-butyl 2-(3-((tert-butoxycarbonyl)(sec-butyl)amino)propanamido)-3-(thiazolo[4,5-c]pyridin-2-yl)-4,7-dihydrothieno[2,3-c]pyridine-6(5H)-carboxylate

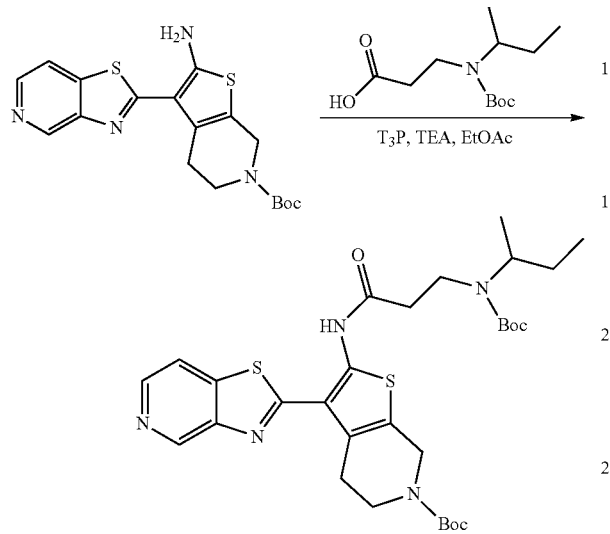

To a stirred solution of tert-butyl 2-amino-3-(thiazolo[4,5-c]pyridin-2-yl)-4,7-dihydrothieno[2,3-c]pyridine-6(5H)-carboxylate (0.15 g, 0.38 mmol) in ethyl acetate (10 mL) at 0° C., 3-((tert-butoxycarbonyl)(sec-butyl)amino)propanoic acid (0.14 g, 0.57 mmol), Et₃N (0.1 mL, 0.76 mmol), and T₃P (0.181 g, 0.57 mmol, 50 wt % solution in EtOAc) was added. The reaction was stirred at room temperature for 16 h, then heated to 60° C. for 12 h. The progress of the reaction was monitored by TLC and LCMS. After the reaction was complete, the reaction mixture was diluted with water and extracted with 10% MeOH in DCM and concentrated under reduced pressure to get a crude residue. The crude compound was purified by silica gel column chromatography eluting with 0-5% MeOH in DCM to afford the title compound which was repurified by preparative HPLC to afford the title compound (0.06 g, yield 25%). LCMS: [M+H]⁺=616.45; R$_f$=4.77 min.

Step 3: 3-(sec-butylamino)-N-(3-(thiazolo[4,5-c]pyridin-2-yl)-4,5,6,7-tetrahydrothieno[2,3-c]pyridin-2-yl)propanamide

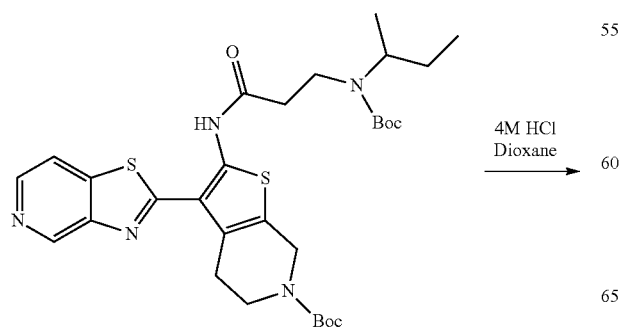

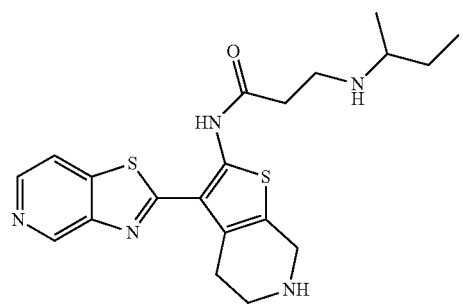

To a solution of tert-butyl 2-(3-((tert-butoxycarbonyl)(sec-butyl)amino)propanamido)-3-(thiazolo[4,5-c]pyridin-2-yl)-4,7-dihydrothieno[2,3-c]pyridine-6(5H)-carboxylate (0.06 g, 0.116 mmol) in dioxane (1 mL) at 0° C. was added 4M HCl in dioxane (0.5 mL). After the addition, the resulting mixture was stirred at room temperature for 2 h. After the reaction was complete, the reaction mixture was evaporated under vacuum pressure resulting in a crude residue which was purified by trituration in ether to afford the title compound as a yellow solid (0.025 g HCl salt, 52% yield).

Example 5

Synthesis of N-(4-methyl-3-(thiazolo[4,5-c]pyridin-2-yl)-4,5,6,7-tetrahydrothieno[2,3-c]pyridin-2-yl)acetamide (Compound 104)

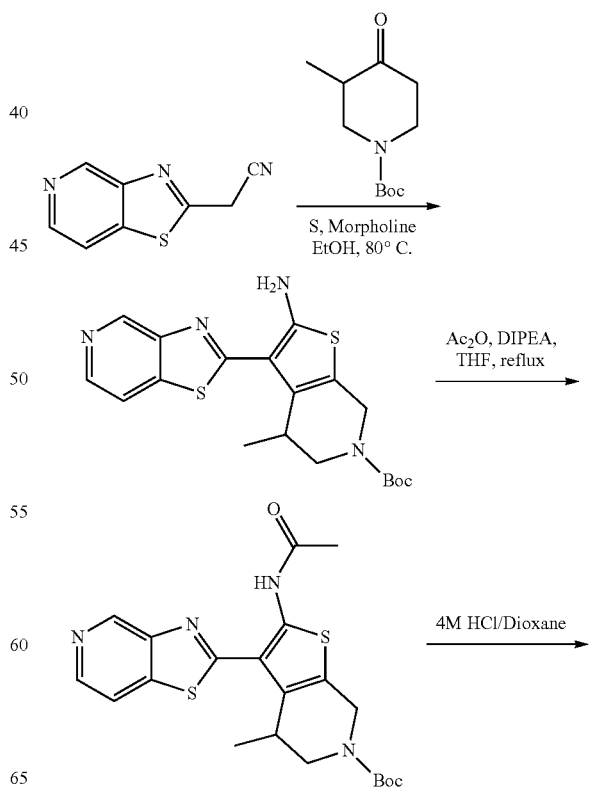

-continued

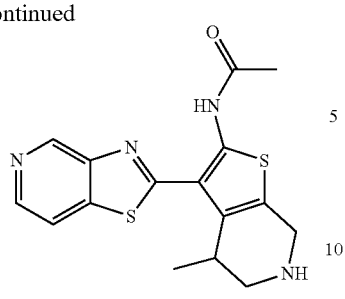

Step 1: tert-butyl 2-amino-4-methyl-3-(thiazolo[4,5-c]pyridin-2-yl)-4,7-dihydrothieno[2,3-c]pyridine-6(5H)-carboxylate

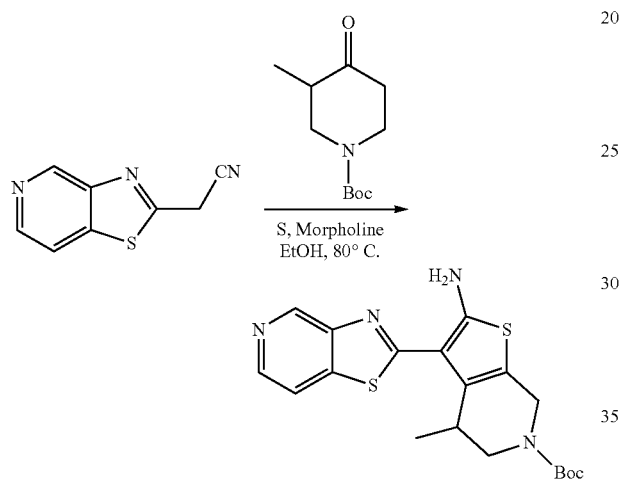

To a stirred solution of 2-(thiazolo[4,5-c]pyridin-2-yl)acetonitrile (1 g, 5.70 mmol) in ethanol (10 mL) was added tert-butyl 3-methyl-4-oxopiperidine-1-carboxylate (1.2 g, 5.70 mmol), elemental sulphur (0.216 g, 5.70 mmol) and morpholine (0.495 g, 5.70 mmol) at room temperature. After the addition, the resulting mixture was heated to reflux at 80° C. for 3 h. Progress of the reaction was monitored by TLC. After completion, the reaction mixture was evaporated under vacuum pressure. After removal of solvent, the crude compound was purified by triturating with methanol to afford the title compound as a yellow solid (1 g, crude). This compound was used in the next step without further purification.

Step 2: tert-butyl 2-acetamido-4-methyl-3-(thiazolo[4,5-c]pyridin-2-yl)-4,7-dihydrothieno[2,3-c]pyridine-6(5H)-carboxylate

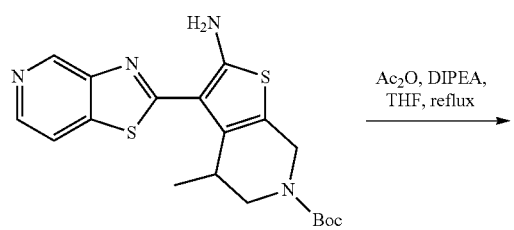

-continued

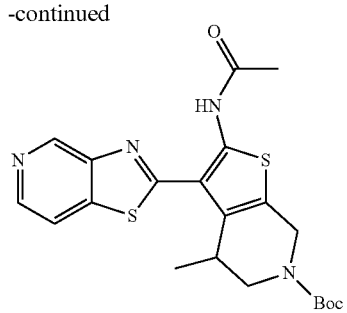

To a solution of tert-butyl 2-amino-4-methyl-3-(thiazolo[4,5-c]pyridin-2-yl)-4,7-dihydrothieno[2,3-c]pyridine-6(5H)-carboxylate (1 g, 2.40 mmol) in THF (20 mL) at 0° C. was added acetic anhydride (0.38 g, 3.70 mmol) and DIPEA (0.619 g, 4.80 mmol). The resulting mixture was heated to reflux at 80° C. for 48 h. Progress of the reaction was monitored by TLC. After the reaction was complete, the mixture was quenched with saturated $NaHCO_3$ solution and extracted with 10% MeOH in DCM. The combined organic layer was dried over $Na_2SO_4$, filtered, and concentrated to afford the title crude compound as yellow solid (1 g, crude). This compound was used in the next step without further purification. LCMS: $[M+H]^+$=445.05; $R_t$=3.52 min.

Step 3: N-(4-methyl-3-(thiazolo[4,5-c]pyridin-2-yl)-4,5,6,7-tetrahydrothieno[2,3-c]pyridin-2-yl)acetamide

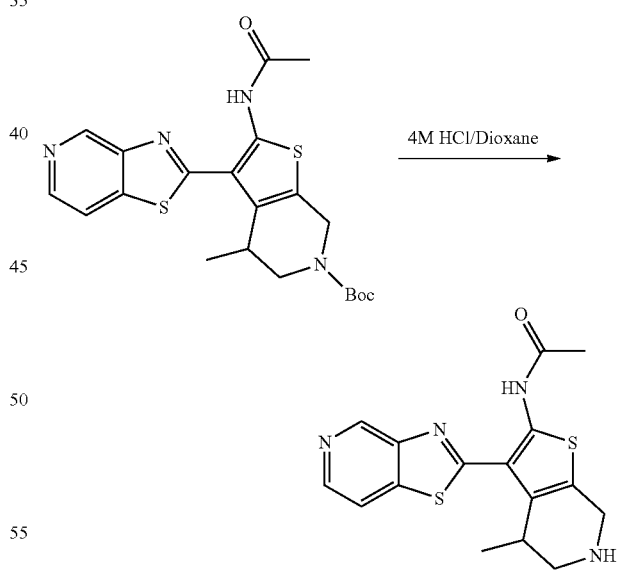

To a solution of tert-butyl 2-acetamido-4-methyl-3-(thiazolo[4,5-c]pyridin-2-yl)-4,7-dihydrothieno[2,3-c]pyridine-6(5H)-carboxylate (0.15 g, 0.22 mmol) in dioxane (2 mL) at 0° C. was added 4M HCl in dioxane (2 mL). After the addition, the resulting mixture was stirred at room temperature for 2 h. After completion, the reaction mixture was evaporated in vacuum resulting in a crude residue which was purified trituration in ether to afford the title compound as a yellow solid (0.1 g HCl salt, 78% yield).

Example 6

Synthesis of N-(6-(1-morpholinopropan-2-yl)-3-(thiazolo[4,5-c]pyridin-2-yl)-4,5,6,7-tetrahydrothieno[2,3-c]pyridin-2-yl)acetamide (Compound 105)

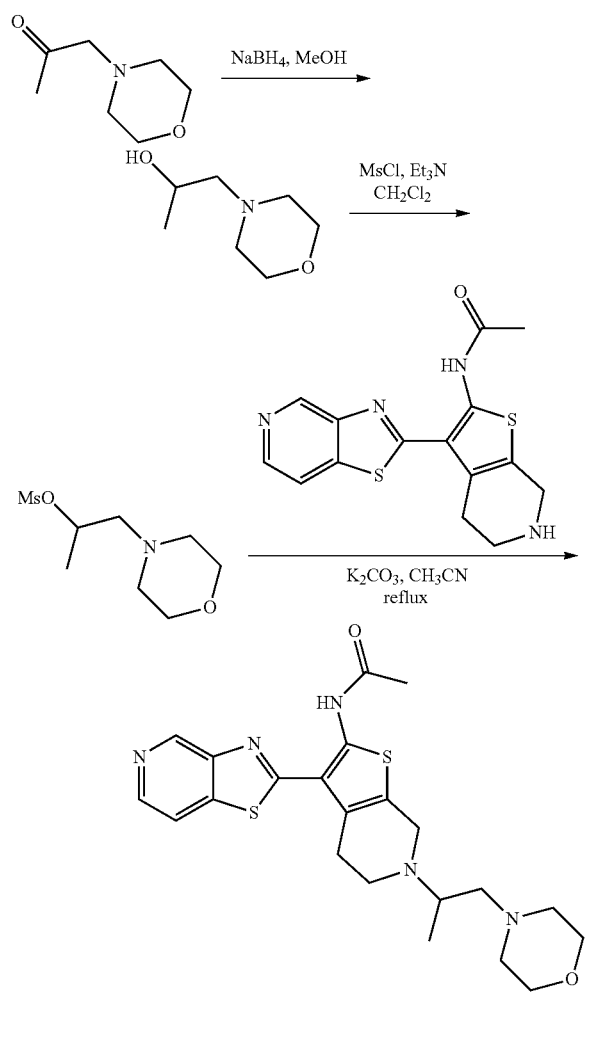

Step 1: 1-morpholinopropan-2-ol

To a solution of 1-morpholinopropan-2-one (0.4 g, 2.79 mmol) in MeOH (5 mL) at 0° C. was added NaBH₄ (0.159 g, 4.19 mmol). The resulting reaction mixture was stirred at room temperature for 12 h. Progress of the reaction was monitored by TLC. After TLC indicated the reaction was complete, the reaction mixture was concentrated to dryness under reduced pressure. The residue was diluted with water and extracted with DCM. The combined organic layer was dried over anhydrous Na₂SO₄, filtered, and concentrated to get a crude residue. The crude compound was purified by silica gel column chromatography eluting with 0-5% MeOH/DCM to afford the title compound as a yellow oil (0.18 g, yield 43.8%). $^1$H NMR (400 MHz, DMSO-d6) δ 4.26 (d, J=4.4 Hz, 1H), 3.78-3.72 (m, 1H), 3.55 (t, J=4.8 Hz, 4H), 2.37 (t, J=4.0 Hz, 4H), 2.25-2.11 (m, 2H), 1.02 (d, J=6.0 Hz, 3H).

Step 2: 1-morpholinopropan-2-yl methanesulfonate

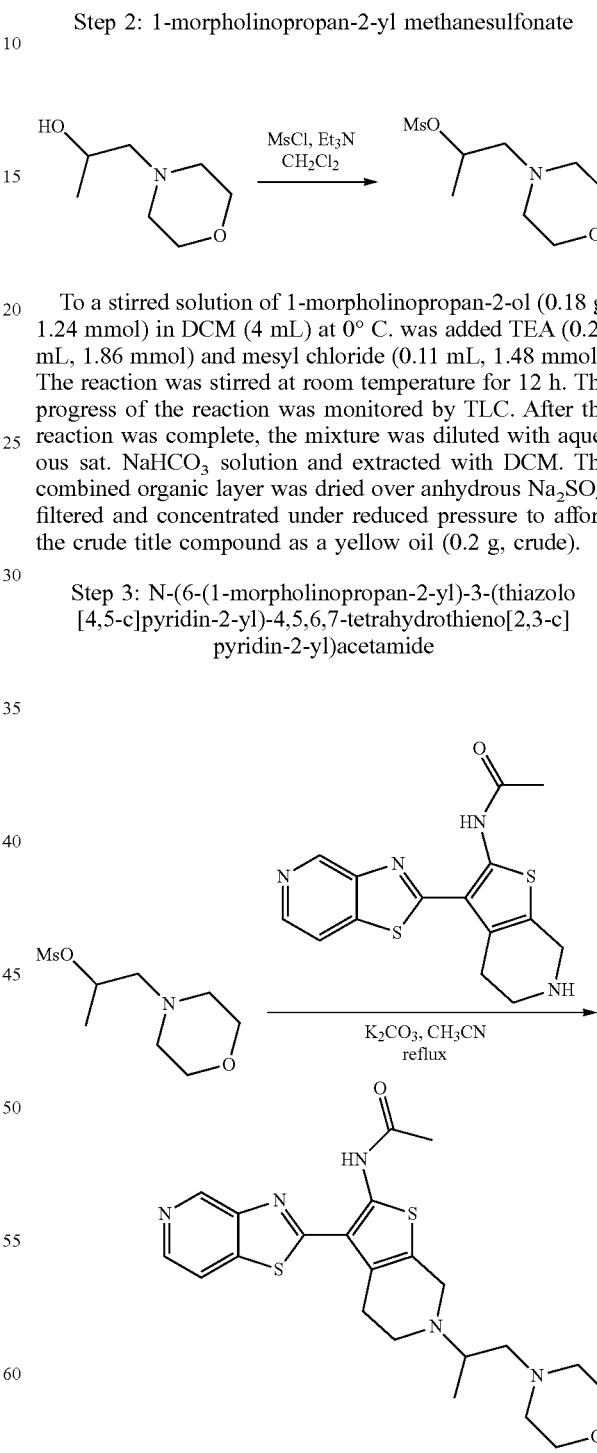

To a stirred solution of 1-morpholinopropan-2-ol (0.18 g, 1.24 mmol) in DCM (4 mL) at 0° C. was added TEA (0.25 mL, 1.86 mmol) and mesyl chloride (0.11 mL, 1.48 mmol). The reaction was stirred at room temperature for 12 h. The progress of the reaction was monitored by TLC. After the reaction was complete, the mixture was diluted with aqueous sat. NaHCO₃ solution and extracted with DCM. The combined organic layer was dried over anhydrous Na₂SO₄, filtered and concentrated under reduced pressure to afford the crude title compound as a yellow oil (0.2 g, crude).

Step 3: N-(6-(1-morpholinopropan-2-yl)-3-(thiazolo[4,5-c]pyridin-2-yl)-4,5,6,7-tetrahydrothieno[2,3-c]pyridin-2-yl)acetamide To a stirred solution of N-(3-(thiazolo[4,5-c]pyridin-2-yl)-4,5,6,7-tetrahydrothieno[2,3-c]pyridin-2-yl)acetamide (0.295 g, 0.895 mmol) in acetonitrile (4 mL) was added K₂CO₃ (0.185 g, 1.34 mmol) and 1-morpholinopropan-2-yl methanesulfonate (0.2 g, 0.895 mmol). After the addition, the resulting mixture was heated to reflux at 65° C. for 12 h. The progress of the reaction was monitored by TLC. After the reaction was complete, the mixture was concentrated to dryness under reduced pressure. The crude compound was purified by preparative HPLC to afford the title compound as a yellow solid (0.005 g, yield 1.22%).

Example 7

Synthesis of N-[3-[4-(difluoromethyl)thiazolo[4,5-c]pyridin-2-yl]-4,5,6,7-tetrahydrothieno[2,3-c]pyridin-2-yl]acetamide (Compound 106)

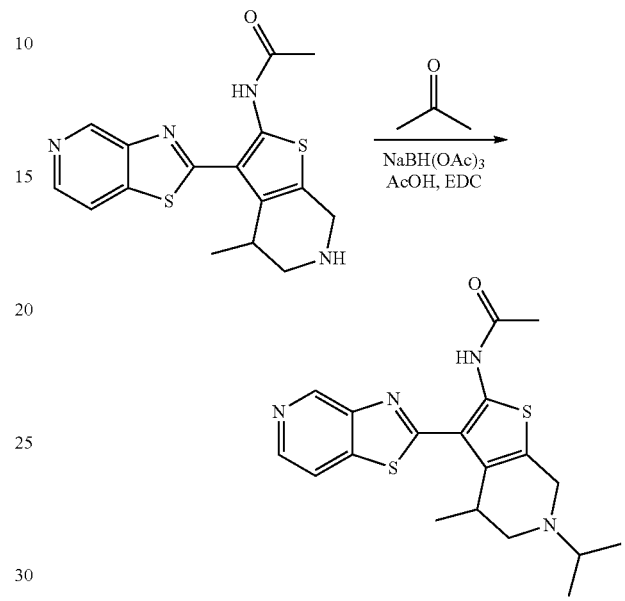

N-(3-thiazolo[4,5-c]pyridin-2-yl-4,5,6,7-tetrahydrothieno[2,3-c]pyridin-2-yl)acetamide (10.9 mg, 0.0300 mmol) N-(3-thiazolo[4,5-c]pyridin-2-yl-4,5,6,7-tetrahydrothieno[2,3-c]pyridin-2-yl)acetamide (10.9 mg, 0.0300 mmol) and bis(difluoromethylsulfinyloxy)zinc (24 mg, 0.0800 mmol) were dissolved in DMSO (300 uL) in a 4 mL vial and TFA (4 uL, 0.0500 mmol) was added. The solution was cooled to 0° C. followed by addition of TBHP (20 uL, 70 wt % in H2O, 0.0300 mmol). The reaction was stirred in a loosely capped vial at room temperature for 2 hrs until LC/MS indicated completion. The reaction was then quenched with an EDTA/saturated sodium bicarbonate solution (2 mL), and the aqueous layer was extracted with dichloromethane (3×5 mL). The combined organic layers were dried over Na₂SO₄, filtered, and concentrated, and the crude residue was purified by C18 reverse-phase MPLC (0-100% MeCN/H₂O) to afford the title compound (1.7 mg, 0.0045 mmol, 13.5% yield) as a yellow powder.

Example 8

Synthesis of N-(6-isopropyl-4-methyl-3-(thiazolo[4,5-c]pyridin-2-yl)-4,5,6,7-tetrahydrothieno[2,3-c]pyridin-2-yl)acetamide (Compound 107)

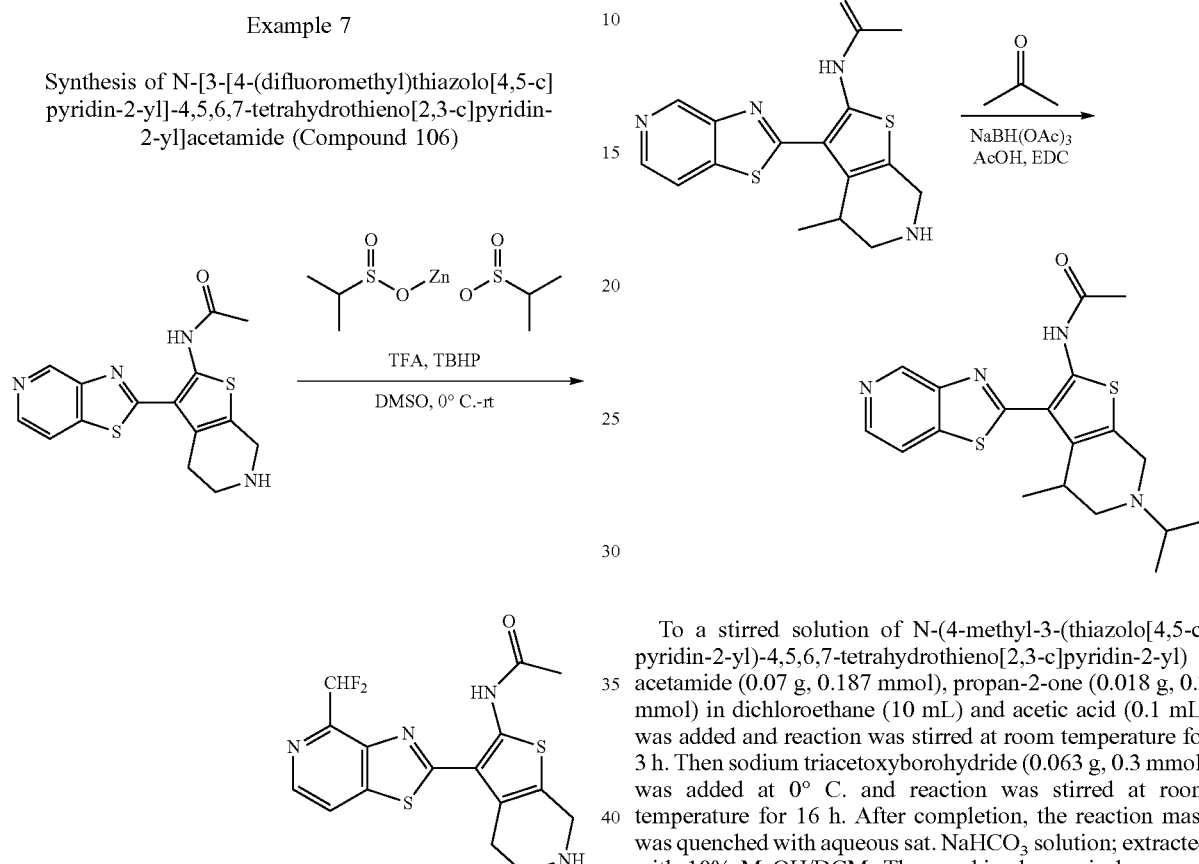

To a stirred solution of N-(4-methyl-3-(thiazolo[4,5-c]pyridin-2-yl)-4,5,6,7-tetrahydrothieno[2,3-c]pyridin-2-yl)acetamide (0.07 g, 0.187 mmol), propan-2-one (0.018 g, 0.3 mmol) in dichloroethane (10 mL) and acetic acid (0.1 mL) was added and reaction was stirred at room temperature for 3 h. Then sodium triacetoxyborohydride (0.063 g, 0.3 mmol) was added at 0° C. and reaction was stirred at room temperature for 16 h. After completion, the reaction mass was quenched with aqueous sat. NaHCO₃ solution; extracted with 10% MeOH/DCM. The combined organic layer was dried over anhydrous Na₂SO₄, filtered and concentrated to get a crude residue. The crude compound was purified by preparative HPLC to afford the title compound as a yellow solid (0.03 g, TFA salt, yield 38%).

Example 9

Synthesis of 2-(2-acetamido-4,5,6,7-tetrahydrothieno[2,3-c]pyridin-3-yl)thiazolo[4,5-c]pyridine 5-oxide (Compound 108)

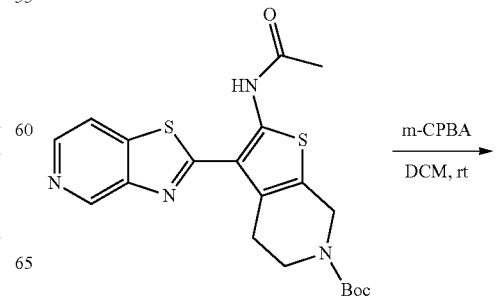

Step 1: 2-(2-acetamido-6-(tert-butoxycarbonyl)-4,5,6,7-tetrahydrothieno[2,3-c]pyridin-3-yl)thiazolo[4,5-c]pyridine 5-oxide

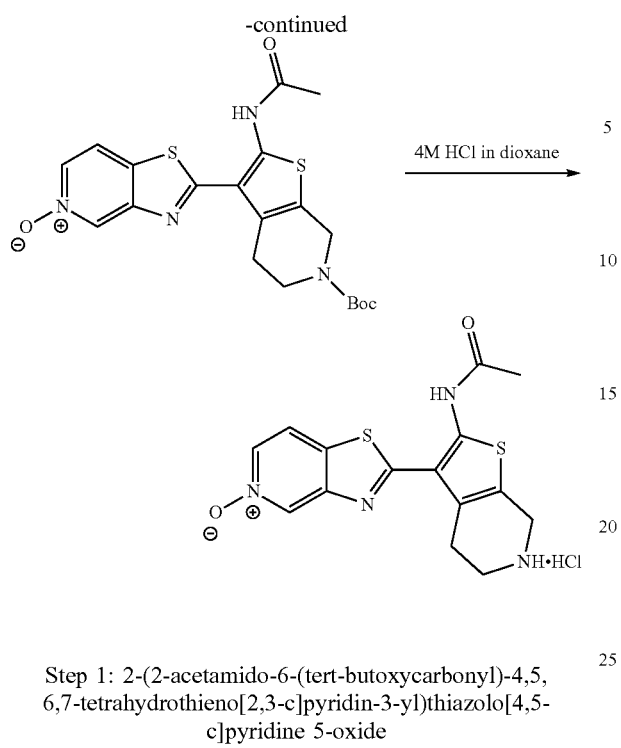

To a solution of tert-butyl 2-acetamido-3-(thiazolo[4,5-c]pyridin-2-yl)-4,7-dihydrothieno[2,3-c]pyridine-6(5H)-carboxylate (0.1 g, 0.232 mmol) in DCM (2 mL) at 0° C. was added m-CPBA (0.076 g, 0.44 mmol) and the reaction mixture was stirred at room temperature for 16 h. Progress of the reaction was monitored by TLC. After completion, the reaction mass was quenched with aqueous sat.Na$_2$CO$_3$ solution and stirred at room temperature for 1 h. The residue obtained was filtered and subsequently washed with DCM. The filtrate was concentrated under reduced pressure to afford the title compound as an off-white solid (0.03 g, yield 29.1%). LCMS: [M+H]$^+$=447.15; R$_t$=2.74 min.

Step 2: 2-(2-acetamido-4,5,6,7-tetrahydrothieno[2,3-c]pyridin-3-yl)thiazolo[4,5-c]pyridine 5-oxide

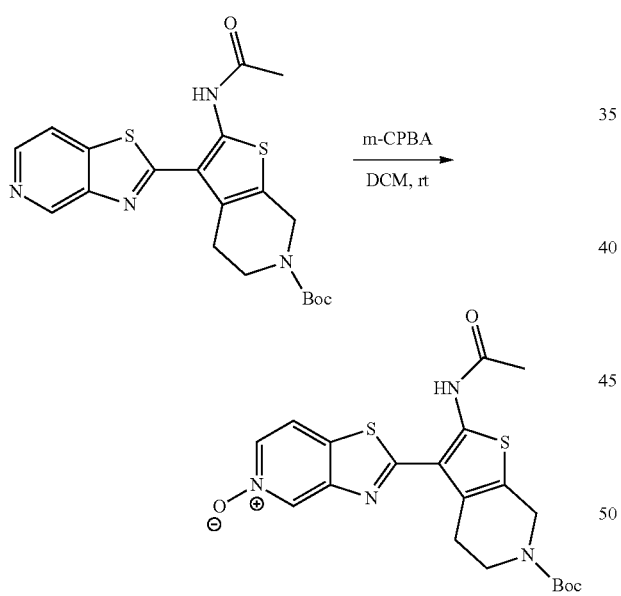

To a solution of 2-(2-acetamido-6-(tert-butoxycarbonyl)-4,5,6,7-tetrahydrothieno[2,3-c]pyridin-3-yl)thiazolo[4,5-c]pyridine 5-oxide (0.05 g, 0.112 mmol) in dioxane (0.5 mL) at 0° C. was added 4M HCl in dioxane (1 mL) and the reaction mixture was stirred at room temperature for 2 h. After the reaction was complete, the mixture was evaporated to dryness and the resulting crude residue was purified by trituration with ether to afford the title compound as a yellow solid (0.03 g, HCl salt, 71.4% yield).

Example 10

Synthesis of N-(5,7-dimethyl-3-(thiazolo[4,5-c]pyridin-2-yl)-4,5,6,7-tetrahydrothieno[2,3-c]pyridin-2-yl)acetamide (Compound 109)

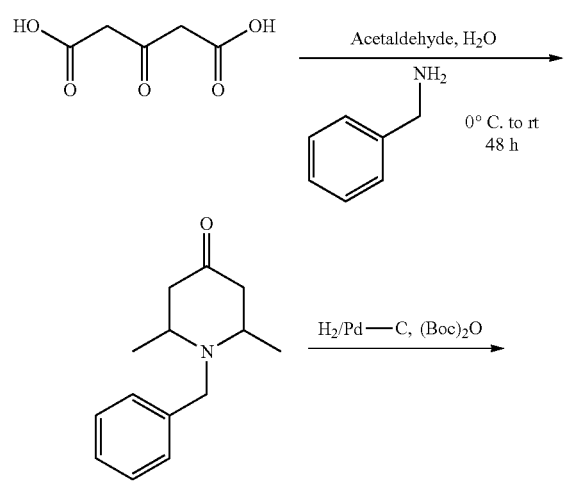

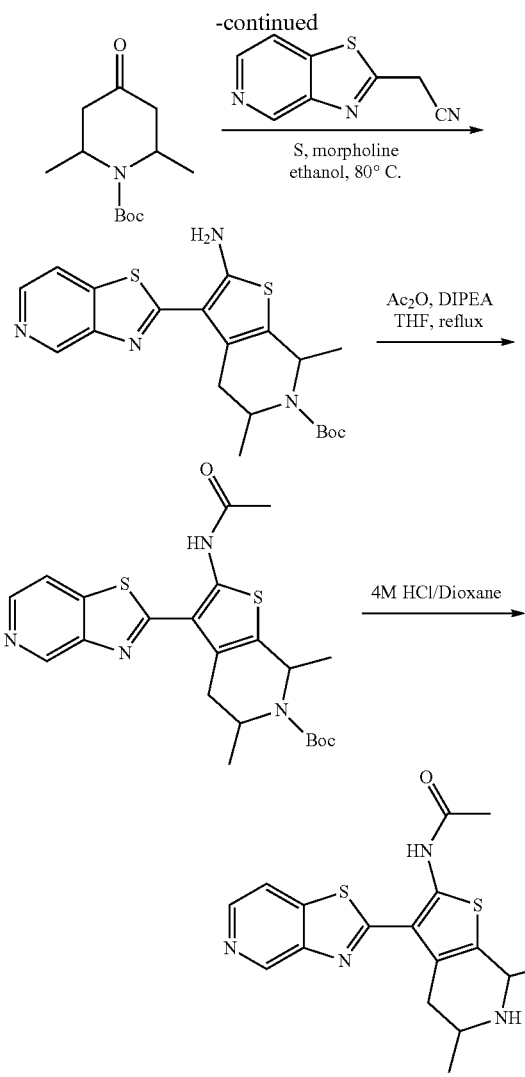

Step 1: 1-benzyl-2,6-dimethylpiperidin-4-one

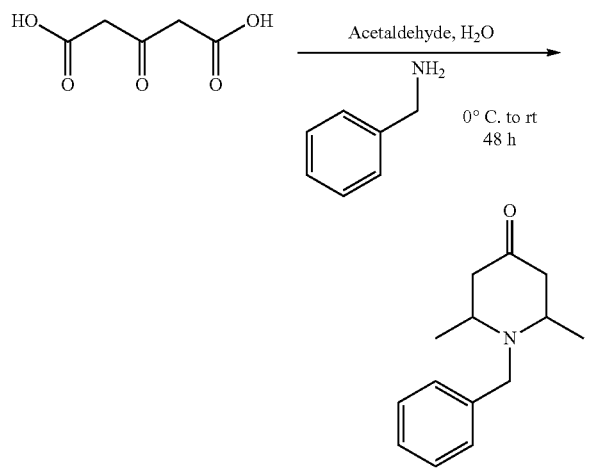

To a stirring solution of 3-oxopentanedioic acid (10 g, 68.44 mmol) in water (25 mL), acetaldehyde (6.02 g, 136.89 mmol) was added and stirred at room temperature for 20 min. To this solution, phenylmethanamine (7.33 g, 68.44 mmol) was added portionwise at 0° C. The resulting reaction mixture was stirred at room temperature for 48 h, and the progress was monitored by TLC. After completion, reaction mixture was acidified with 2N HCl to pH 2, neutralized with aqueous sat. NaHCO$_3$, and extracted with ethyl acetate. The combined organic layers were dried over Na$_2$SO$_4$, filtered, and concentrated to get a crude residue. This crude compound was purified by silica gel column chromatography eluting with 0-20% ethyl acetate in n-hexane to afford the title compound as a brown oil (7 g, yield 47%). LCMS: [M+H]$^+$=218.05; R$_f$=1.56 min.

Step 2: tert-butyl 2,6-dimethyl-4-oxopiperidine-1-carboxylate

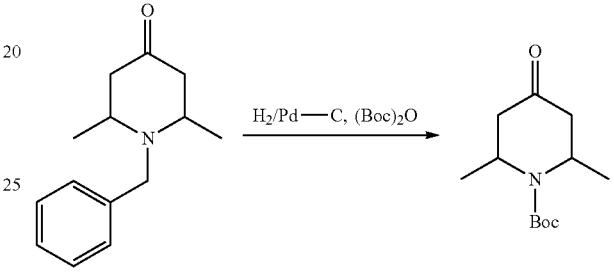

To a stirred solution of 1-benzyl-2,6-dimethylpiperidin-4-one (2 g, 9.17 mmol) in isopropyl alcohol (20 mL), 10% Pd/C (400 mg) and Boc anhydride (2.39 g, 11 mmol) were added and stirred at room temperature under hydrogen pressure (balloon) for 48 h. The progress of the reaction was monitored by TLC. After completion, the mixture was filtered through a pad of celite, washed with 10% MeOH/DCM, and filtrate was concentrated to yield a crude residue. The residue was purified by silica gel column chromatography eluting with 0-20% ethyl acetate in n-hexane to afford the title compound as a white solid (1.5 g, yield 71.2%). 1H NMR (400 MHz, chloroform-d) δ 4.41-4.33 (m, 2H), 2.85 (dd, J=17.9, 6.5 Hz, 2H), 2.37 (dd, J=17.8, 1.9 Hz, 2H), 1.49 (s, 9H), 1.25 (d, J=7.2 Hz, 6H).

Step 3: tert-butyl 2-amino-5,7-dimethyl-3-(thiazolo[4,5-c]pyridin-2-yl)-4,7-dihydrothieno[2,3-c]pyridine-6(5H)-carboxylate

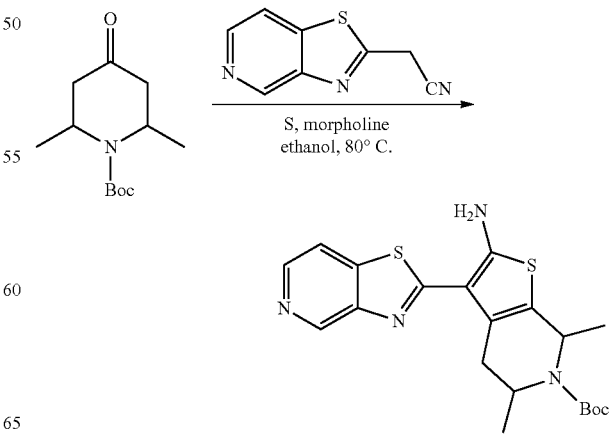

To a solution of 2-(thiazolo[4,5-c]pyridin-2-yl)acetonitrile (1.2 g, 6.85 mmol) in ethanol (60 mL) was added tert-butyl 2,6-dimethyl-4-oxopiperidine-1-carboxylate (1.56 g, 6.85 mmol), elemental sulphur (0.219 g, 6.85 mmol), and morpholine (0.596 g, 6.85 mmol) at rt. After the addition, the resulting mixture was heated to reflux at 80° C. for 15 h and the reaction progress was monitored by TLC. The reaction mixture was dried in vacuum and the crude compound was purified by triturating with methanol to afford the title compound as a brown solid (1.2 g, yield 42%). LCMS: [M+H]$^+$=417; R$_t$=2.99 min Step 4: tert-butyl 2-acetamido-5,7-dimethyl-3-(thiazolo[4,5-c]pyridin-2-yl)-4,7-dihydrothieno[2,3-c]pyridine-6(5H)-carboxylate

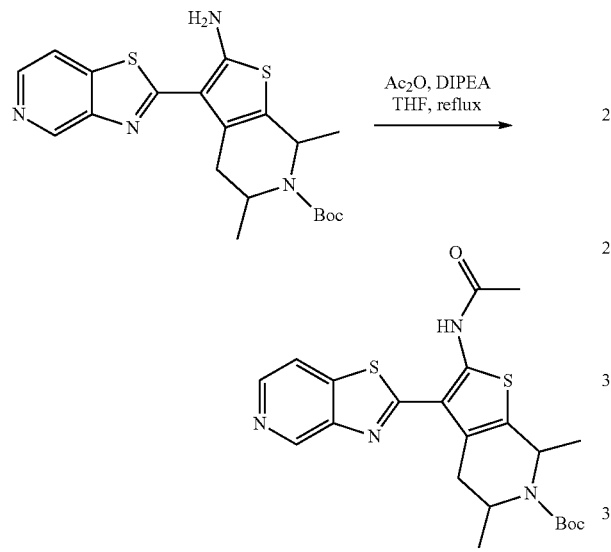

To a solution of tert-butyl 2-amino-5,7-dimethyl-3-(thiazolo[4,5-c]pyridin-2-yl)-4,7-dihydrothieno[2,3-c]pyridine-6(5H)-carboxylate (0.6 g, 1.44 mmol) in THF (10 mL) at 0° C. was added DIPEA (0.744 g, 5.77 mmol) and acetic anhydride (0.441 g, 4.33 mmol). The resulting reaction mixture was stirred at 65° C. for 24 h and the reaction progress was monitored by TLC. After completion, the mixture was concentrated to dryness under reduced pressure. The residue was diluted with water and extracted with ethyl acetate, and the combined organic layers were dried over Na$_2$SO$_4$, filtered, and concentrated to yield a crude residue. The crude residue was purified by silica gel column chromatography eluting with 0-70% ethyl acetate in n-hexane to afford the title compound as a yellow solid (0.45 g, yield 68.2%). LCMS: [M+H]$^+$=458.95; R$_t$=3.61 min.

Step 5: N-(5,7-dimethyl-3-(thiazolo[4,5-c]pyridin-2-yl)-4,5,6,7-tetrahydrothieno[2,3-c]pyridin-2-yl)acetamide

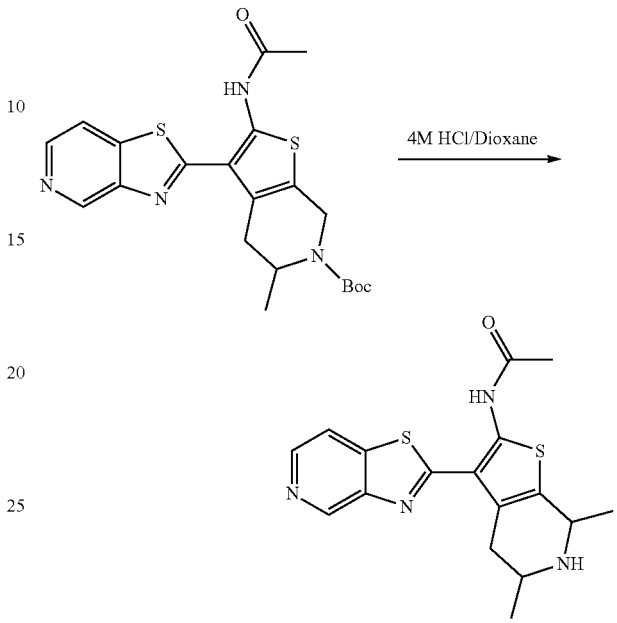

To a solution of tert-butyl 2-acetamido-5,7-dimethyl-3-(thiazolo[4,5-c]pyridin-2-yl)-4,7-dihydrothieno[2,3-c]pyridine-6(5H)-carboxylate (0.1 g, 0.218 mmol) in dioxane (3 mL) at 0° C. was added 4M HCl in dioxane (3 mL). After the addition, the resulting mixture was stirred at room temperature for 2 h. After completion, the reaction mixture was evaporated to dryness and to yield a crude residue which was purified by triturating with ether to afford a brown solid (0.07 g, HCl salt, 90% yield).

Example 11

Synthesis of tert-butyl (5R,7R)-2-acetamido-5,7-dimethyl-3-(thiazolo[4,5-c]pyridin-2-yl)-4,7-dihydrothieno[2,3-c]pyridine-6(5H)-carboxylate and tert-butyl (5S,7S)-2-acetamido-5,7-dimethyl-3-(thiazolo[4,5-c]pyridin-2-yl)-4,7-dihydrothieno[2,3-c]pyridine-6(5H)-carboxylate (Compound 110 and Compound 111)

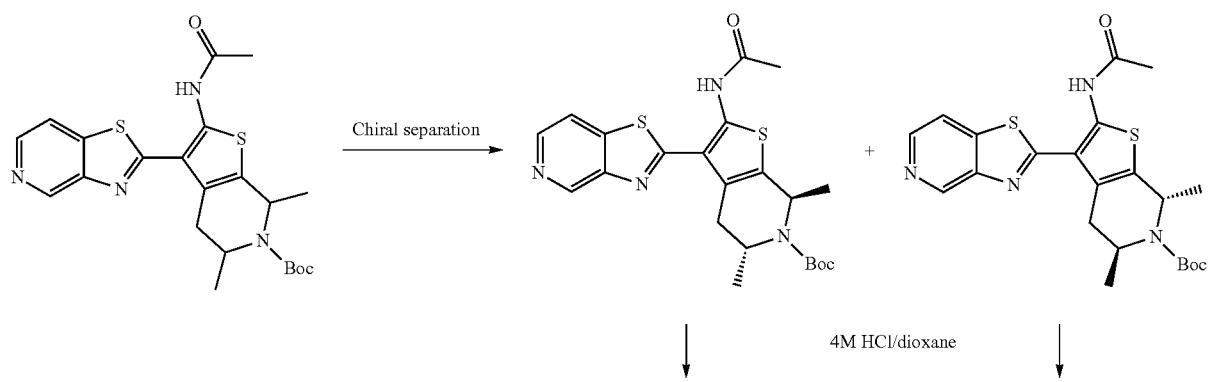

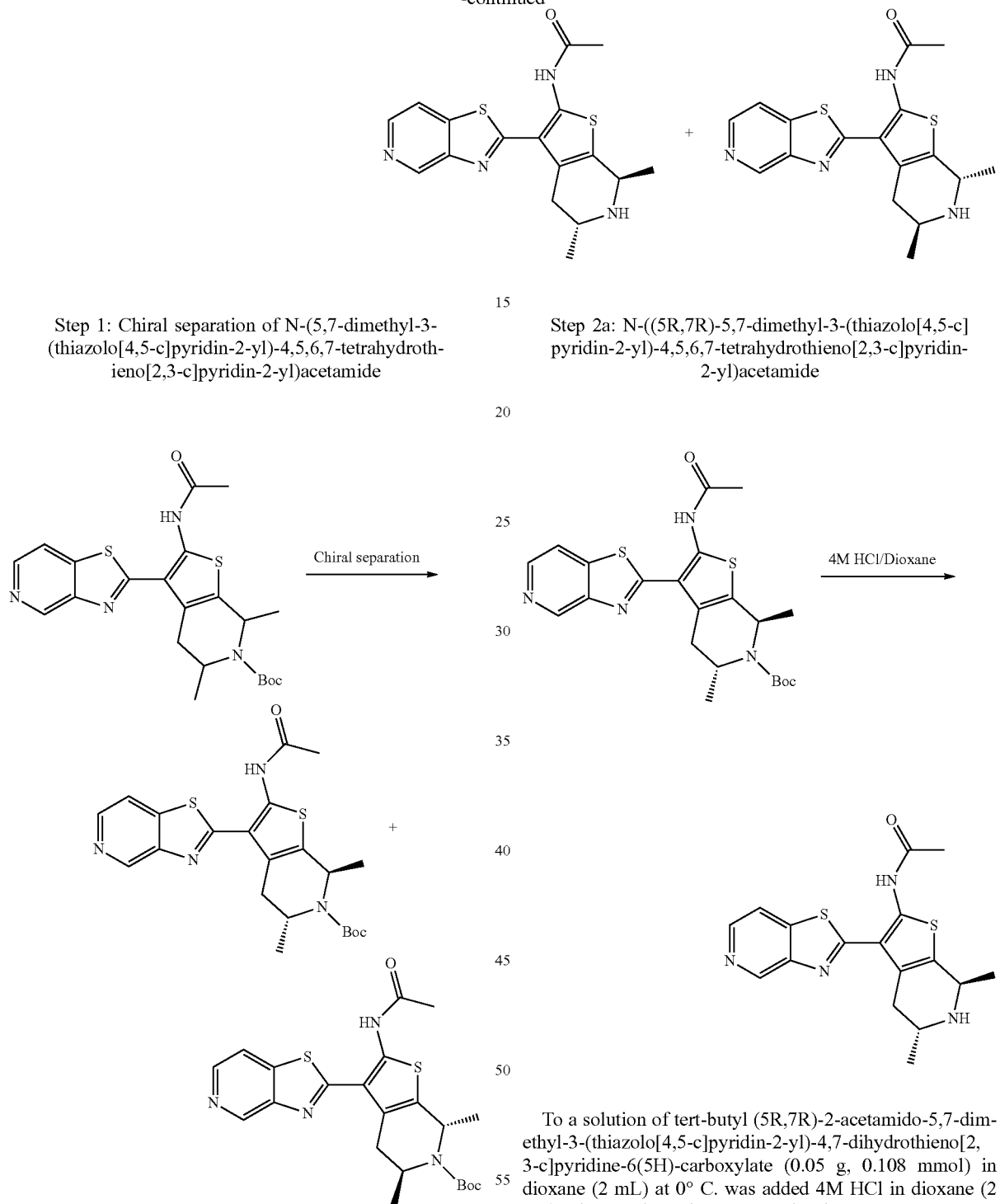

Step 1: Chiral separation of N-(5,7-dimethyl-3-(thiazolo[4,5-c]pyridin-2-yl)-4,5,6,7-tetrahydrothieno[2,3-c]pyridin-2-yl)acetamide Step 2a: N-((5R,7R)-5,7-dimethyl-3-(thiazolo[4,5-c]pyridin-2-yl)-4,5,6,7-tetrahydrothieno[2,3-c]pyridin-2-yl)acetamide The mixture of diastereomers of N-(5,7-dimethyl-3-(thiazolo[4,5-c]pyridin-2-yl)-4,5,6,7-tetrahydrothieno[2,3-c]pyridin-2-yl)acetamide prepared as described in the previous example was subjected to preparative chiral separation via HPLC to afford the individual enantiomers 1 (60 mg, 10% yield, off white solid) and 2 (60 mg, 10% yield, off white solid). LCMS: [M+H]⁺=458.10; $R_t$=3.52 min. The absolute stereochemistry of each enantiomer was not determined.

To a solution of tert-butyl (5R,7R)-2-acetamido-5,7-dimethyl-3-(thiazolo[4,5-c]pyridin-2-yl)-4,7-dihydrothieno[2,3-c]pyridine-6(5H)-carboxylate (0.05 g, 0.108 mmol) in dioxane (2 mL) at 0° C. was added 4M HCl in dioxane (2 mL). The reaction mixture was stirred at room temperature for 2 h. After the reaction was complete, the mixture was evaporated to dryness and the crude residue obtained was purified by trituration with ether to afford the title compound as a brown solid (0.03 g, HCl salt, 77% yield). ¹H NMR (400 MHz, DMSO-d6) δ 12.16 (s, 1H), 10.06 (d, J=10.3 Hz, 1H), 9.81 (d, J=10.9 Hz, 1H), 9.71 (s, 1H), 8.70 (d, J=5.9 Hz, 1H), 8.60 (d, J=5.9 Hz, 1H), 4.83-4.76 (m, 1H), 3.86 (dt, J=13.7, 7.6 Hz, 1H), 3.41-3.27 (m, 1H), 2.89 (dd, J=16.1, 8.3 Hz, 1H), 2.37 (s, 3H), 1.65 (d, J=6.7 Hz, 3H), 1.50 (dd, J=22.1, 6.4 Hz, 3H). LCMS: [M+H]⁺=358.90; $R_t$=2.60 min.

Step 2b: N-((5S,7S)-5,7-dimethyl-3-(thiazolo[4,5-c]pyridin-2-yl)-4,5,6,7-tetrahydrothieno[2,3-c]pyridin-2-yl)acetamide

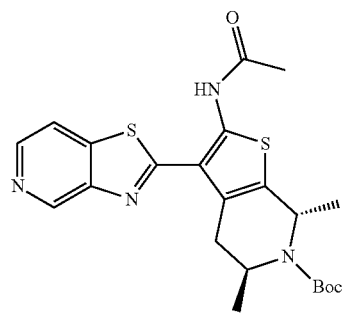

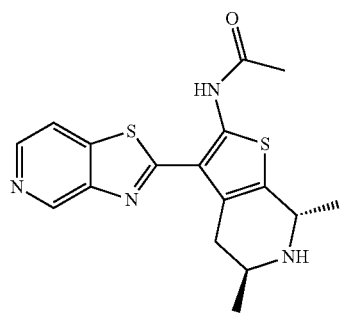

To a solution of tert-butyl (5S,7R)-2-acetamido-5,7-dimethyl-3-(thiazolo[4,5-c]pyridin-2-yl)-4,7-dihydrothieno[2,3-c]pyridine-6(5H)-carboxylate (0.04 g, 0.087 mmol) in dioxane (2 mL) at 0° C. was added 4M HCl in dioxane (2 mL) and the resulting mixture was stirred at room temperature for 2 h. After completion, the reaction mixture was evaporated to dryness and the crude residue obtained was purified by trituration with ether to afford the title compound as a yellow solid (0.025 g, HCl salt, 80% yield).

Example 12

Synthesis of 5-amino-N-((1S,3R)-3-(5-chloro-4-(1-methyl-1H-indol-3-yl)pyrimidin-2-ylamino)cyclohexyl)picolinamide (Compound 112)

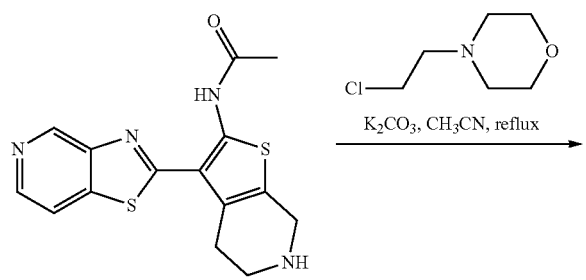

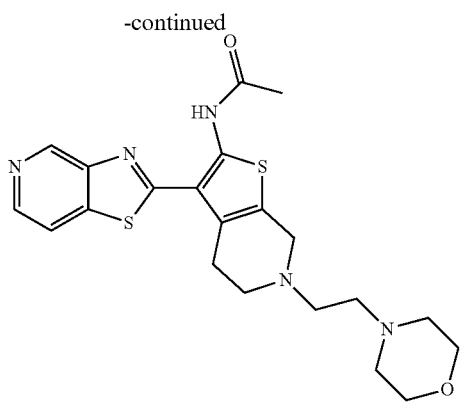

To a stirred solution of N-(3-(thiazolo[4,5-c]pyridin-2-yl)-4,5,6,7-tetrahydrothieno[2,3-c]pyridin-2-yl)acetamide (100 mg, 1 eq) in CH₃CN (3 mL) was added K₂CO₃ (83 mg, 2 eq) followed by 4-(2-chloroethyl)morpholine (67 mg, 1.5 eq). The resulting mixture was refluxed for 12 h. After TLC indicated the reaction was complete, the mixture was diluted with water and extracted with EtOAc. The combined organic fractions were dried over anhydrous Na₂SO₄ and concentrated in vacuo to get a crude residue which was purified by silica gel (100-200 mesh) column chromatography eluting with 0-5% methanol in DCM to afford the title compound (30 mg, yield 22%) as yellow solid.

Example 13

Synthesis of N-(6-amino-3-(thiazolo[4,5-c]pyridin-2-yl)-4,5,6,7-tetrahydrobenzo[b]thiophen-2-yl)acetamide (Compound 113)

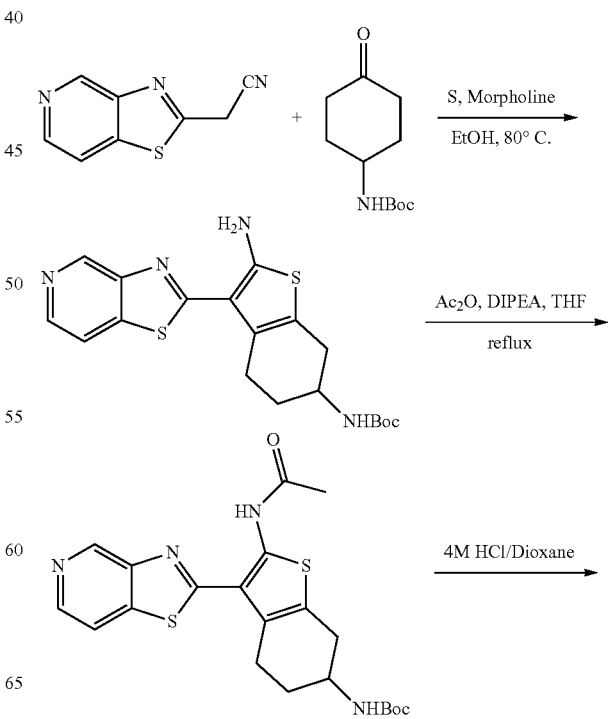

-continued

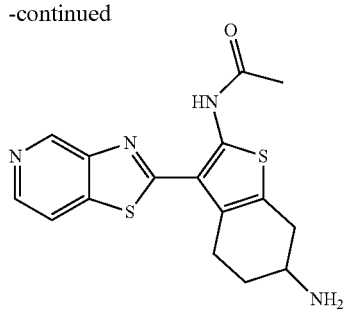

Step 1: tert-butyl (2-amino-3-(thiazolo[4,5-c]pyridin-2-yl)-4,5,6,7-tetrahydrobenzo[b]-thiophen-6-yl)carbamate

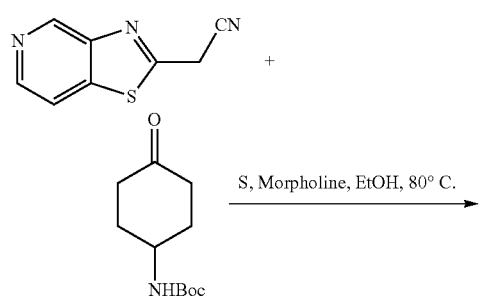

To a solution of 2-(thiazolo[4,5-c]pyridin-2-yl)acetonitrile (1 g, 5.71 mmol) in ethanol (15 mL) was added tert-butyl (4-oxocyclohexyl)carbamate (1.21 g, 5.71 mmol), elemental sulphur (182 mg, 5.71 mmol), and morpholine (497 mg, 5.71 mmol) at room temperature; the resulting reaction mixture was heated to reflux at 85° C. for 12 h. The reaction was monitored by TLC. After completion, the reaction mixture was evaporated to dryness and the crude compound was triturated in methanol and dried to afford the of title compound as an off white solid (1.5 g crude). LCMS: [M+H]$^+$=403.00; $R_t$=2.68 min.

Step 2: tert-butyl (2-acetamido-3-(thiazolo[4,5-c]pyridin-2-yl)-4,5,6,7-tetrahydrobenzo[b]thiophen-6-yl)carbamate

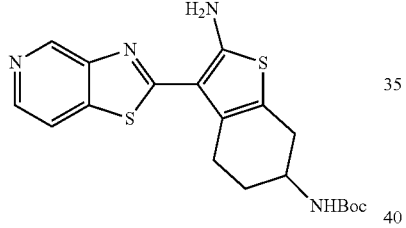

-continued

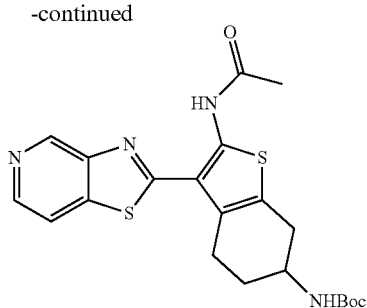

To a solution of tert-butyl (2-amino-3-(thiazolo[4,5-c]pyridin-2-yl)-4,5,6,7-tetrahydrobenzo[b]-thiophen-6-yl)carbamate (1 g, 2.48 mmol) in THF (10 mL) at 0° C. was added DIPEA (0.87 mL, 4.97 mmol), followed by acetic anhydride (0.35 mL, 3.73 mmol). The reaction mixture stirred at room temperature for 1 h and then heated at reflux for the next 48 h. The reaction was monitored by TLC. After TLC indicated the reaction was complete, the reaction mixture was evaporated to dryness and the resulting residue was taken up in 10% MeOH in DCM and washed with saturated NaHCO$_3$ solution and brine. The separated organic layer was dried over Na$_2$SO$_4$, filtered, and concentrated under vacuum to provide a crude residue which was purified by silica gel column chromatography eluting with 0-5% methanol in DCM to afford the title compound as an off white solid (440 mg, 36% yield). LCMS: [M+H]$^+$=445.15; $R_t$=3.17 min Step 3: N-(6-amino-3-(thiazolo[4,5-c]pyridin-2-yl)-4,5,6,7-tetrahydrobenzo[b]thiophen-2-yl)acetamide

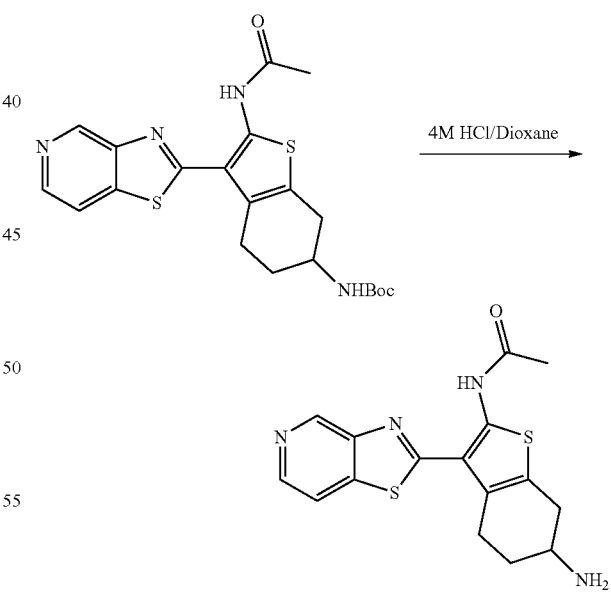

To a solution of tert-butyl (2-acetamido-3-(thiazolo[4,5-c]pyridin-2-yl)-4,5,6,7-tetrahydrobenzo[b]thiophen-6-yl)carbamate (100 mg, 0.22 mmol) in dioxane (1 mL) at 0° C. was added 4M HCl in dioxane (1 mL). The reaction mixture was stirred at room temperature for 12 h. After TLC indicated the reaction was complete, the reaction mixture was evaporated to dryness and the residue was purified by trituration in ether and pentane to give the HCl salt of the title compound as a brown solid (60 mg, 70% yield).

Example 14. Synthesis of N-(6-methyl-3-(thiazolo[4,5-c]pyridin-2-yl)-4,5,6,7-tetrahydrothieno[2,3-c]pyridin-2-yl)acetamide (Compound 114)

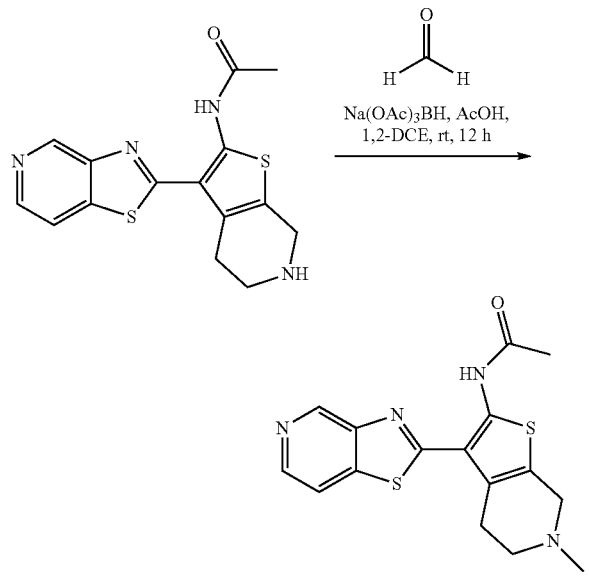

To the solution of formaldehyde (0.1 mL, 2.73 mmol, 37 wt % solution) and N-(3-(thiazolo[4,5-c]pyridin-2-yl)-4,5,6,7-tetrahydrothieno[2,3-c]pyridin-2-yl)acetamide (100 mg, 0.27 mmol) in 1,2-dichloroethane (3 mL) was added sodium triacetoxyborhydride (87 mg, 0.41 mmol) followed by AcOH (0.2 mL) and reaction was stirred at room temperature for 12 h. After the completion (the reaction was monitored by TLC) the reaction mixture was diluted with water (15 mL) and extracted with ethyl acetate (3×10 mL). The combined organic layers were dried over Na₂SO₄ and evaporated in vacuo resulting in the crude compound which was purified silica gel (100-200 mesh) column chromatography eluting with 0-5% methanol in DCM to give the title compound (70 mg, yield 74%) as yellow solid.

Example 15

Synthesis of N-(6-isopropyl-3-(thiazolo[4,5-c]pyridin-2-yl)-4,5,6,7-tetrahydrothieno[2,3-c]pyridin-2-yl)acetamide (Compound 115)

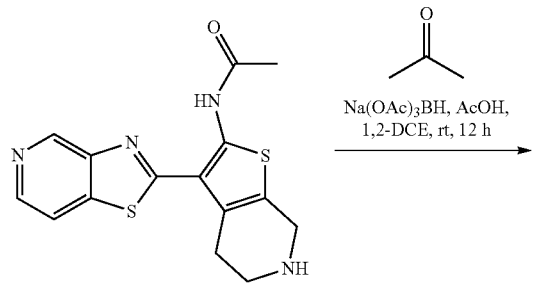

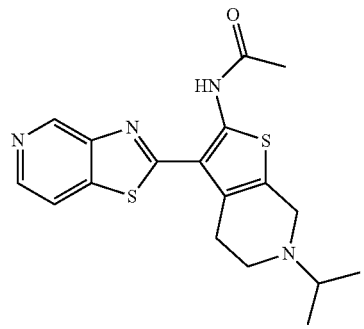

To the solution of N-(3-(thiazolo[4,5-c]pyridin-2-yl)-4,5,6,7-tetrahydrothieno[2,3-c]pyridin-2-yl)acetamide (100 mg, 0.30 mmol) and acetone (0.11 mL, 1.51 mmol) in 1,2-dichloroethane (3 mL) was added sodium triacetoxyborohydride (95 mg, 0.45 mmol) followed by AcOH (0.2 mL), and the reaction mixture was stirred at room temperature for 12 h. The reaction was monitored by TLC, and upon completion, was diluted with water (15 mL) and extracted with ethyl acetate (3×10 mL). The combined organic solvents were dried over Na₂SO₄ and evaporated in vacuum resulting in the crude compound. The crude compound was purified using silica gel flash column chromatography eluting with 0-5% methanol in DCM to afford the title compound (17 mg, yield 15%) as yellow solid.

Example 16

Synthesis of 3-(sec-butylamino)-N-(6-isopropyl-3-(thiazolo[4,5-c]pyridin-2-yl)-4,5,6,7-tetrahydrothieno[2,3-c]pyridin-2-yl)propanamide dihydrochloride (Compound 116)

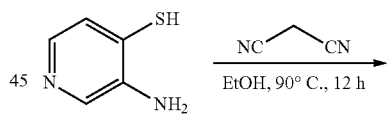

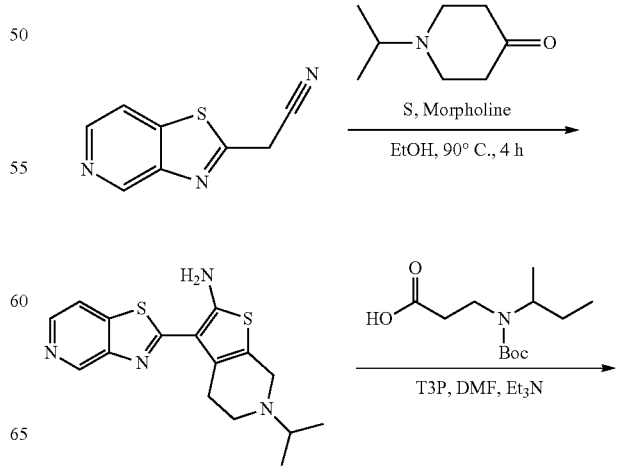

145

-continued

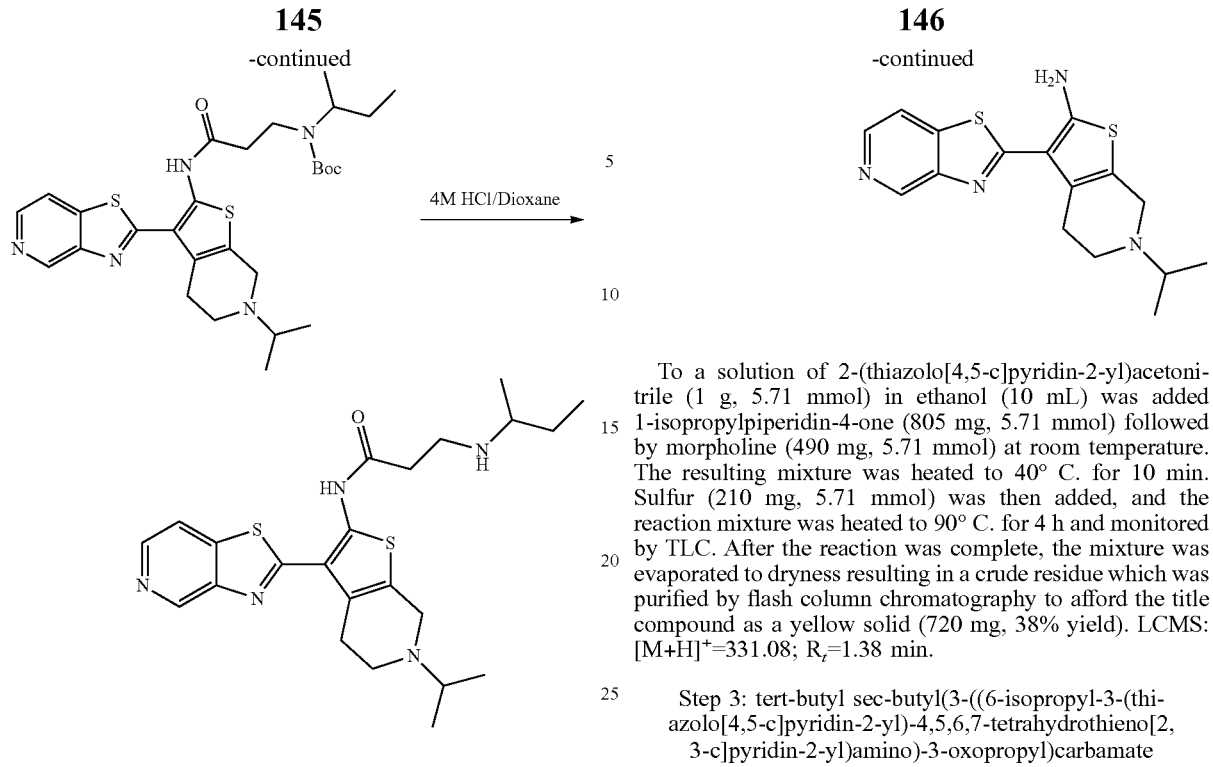

Step 1: 2-(thiazolo[4,5-c]pyridin-2-yl)acetonitrile

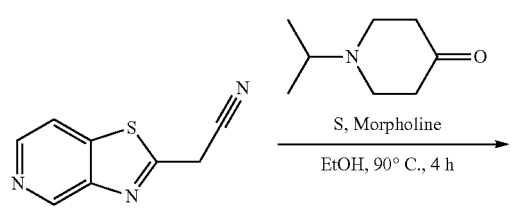

To a solution of 3-aminopyridine-4-thiol (1.5 g, 11.9 mmol) in ethanol (10 mL) was added acetic acid (10 mL) followed by malononitrile (790 mg, 11.9 mmol). The reaction mixture was heated to 90° C. for 12 h and monitored by TLC. After the reaction was complete, the solvent was removed under reduced pressure to give the product (3 g, crude) as a brown solid which was used in the next step without further purification. LCMS: [M+H]$^+$=175.90; R$_t$=1.50 min.

Step 2: 6-isopropyl-3-(thiazolo[4,5-c]pyridin-2-yl)-4,5,6,7-tetrahydrothieno[2,3-c]pyridin-2-amine

146

-continued

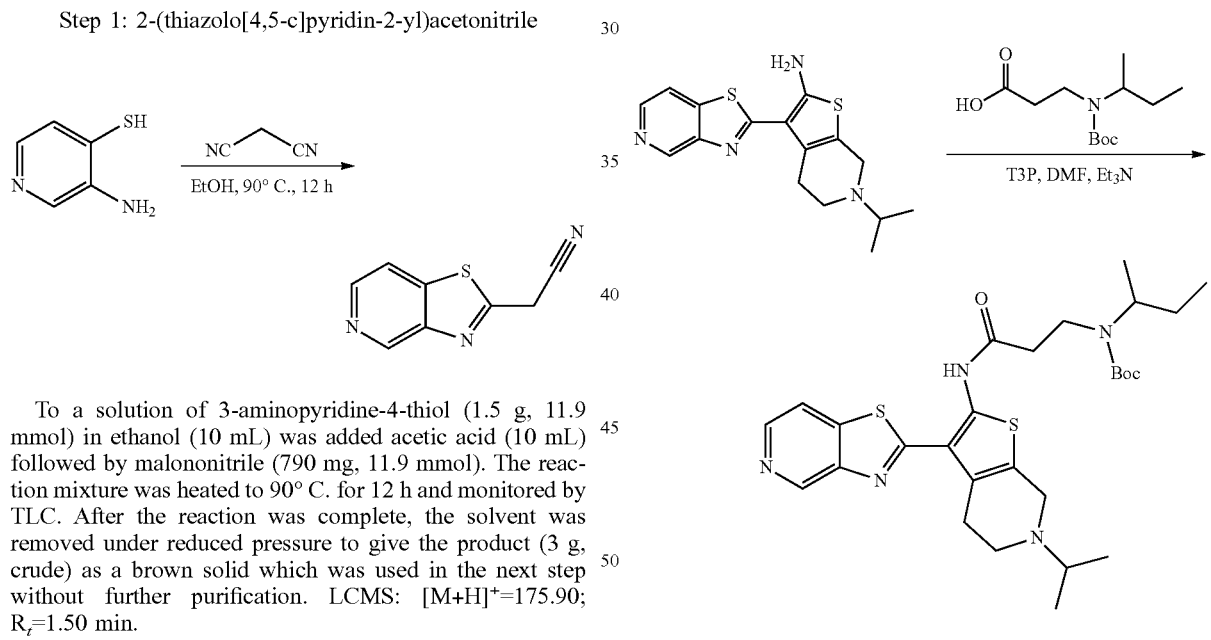

To a solution of 2-(thiazolo[4,5-c]pyridin-2-yl)acetonitrile (1 g, 5.71 mmol) in ethanol (10 mL) was added 1-isopropylpiperidin-4-one (805 mg, 5.71 mmol) followed by morpholine (490 mg, 5.71 mmol) at room temperature. The resulting mixture was heated to 40° C. for 10 min. Sulfur (210 mg, 5.71 mmol) was then added, and the reaction mixture was heated to 90° C. for 4 h and monitored by TLC. After the reaction was complete, the mixture was evaporated to dryness resulting in a crude residue which was purified by flash column chromatography to afford the title compound as a yellow solid (720 mg, 38% yield). LCMS: [M+H]$^+$=331.08; R$_t$=1.38 min.

Step 3: tert-butyl sec-butyl(3-((6-isopropyl-3-(thiazolo[4,5-c]pyridin-2-yl)-4,5,6,7-tetrahydrothieno[2,3-c]pyridin-2-yl)amino)-3-oxopropyl)carbamate To a solution of 6-isopropyl-3-(thiazolo[4,5-c]pyridin-2-yl)-4,5,6,7-tetrahydrothieno[2,3-c]pyridin-2-amine (500 mg, 1.51 mmol) in DMF (10 mL) at 0° C., was added 3-((tert-butoxycarbonyl) (sec-butyl)amino)propanoic acid (560 mg, 2.27 mmol) and TEA (0.62 mL, 4.54 mmol), followed by T$_3$P (50% w/v in EtOAc, 1.5 ml, 2.35 mmol). The reaction mixture was stirred at room temperature for 16 h and monitored by TLC. After the reaction was complete, the mixture was diluted with DCM and washed with 0.5 M HCl. The combined organic layer was dried over anhydrous Na$_2$SO$_4$ and concentrated to obtain a crude residue which was purified by basic alumina column chromatography to afford the title compound as a yellow solid (80 mg, 9.5% yield). LCMS: [M+1]$^+$=558.2; R$_t$=2.21 min.

147

Step 4: 3-(sec-butylamino)-N-(6-isopropyl-3-(thiazolo[4,5-c]pyridin-2-yl)-4,5,6,7-tetrahydrothieno[2,3-c]pyridin-2-yl)propanamide

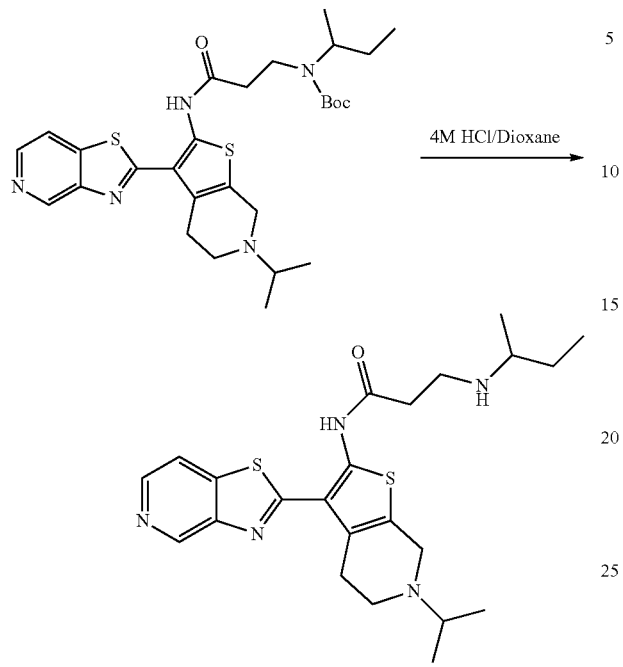

To a solution of tert-butyl sec-butyl(3-((6-isopropyl-3-(thiazolo[4,5-c]pyridin-2-yl)-4,5,6,7-tetrahydrothieno[2,3-c]pyridin-2-yl)amino)-3-oxopropyl)carbamate (50 mg, 0.08 mmol) in dioxane (1 mL) at 0° C. was added 4M HCl in dioxane (2 mL). After the addition, the resulting mixture was stirred at room temperature for 12 h and the reaction was monitored by TLC. After the reaction was complete, the mixture was evaporated to dryness resulting in a crude residue which was purified by triturating with ether and pentane to afford the HCl salt of the title compound as a yellow solid (40 mg, 92% yield).

Example 17

Synthesis of N-(6-ethyl-5,7-dimethyl-3-(thiazolo[4,5-c]pyridin-2-yl)-4,5,6,7-tetrahydrothieno[2,3-c]pyridin-2-yl)acetamide (Compound 117), N-((5R,7R)-6-ethyl-5,7-dimethyl-3-(thiazolo[4,5-c]pyridin-2-yl)-4,5,6,7-tetrahydrothieno[2,3-c]pyridin-2-yl)acetamide (Compound 119) and N-((5S,7S)-6-ethyl-5,7-dimethyl-3-(thiazolo[45-c]pyridin-2-yl)-4,5,6,7-tetrahydrothieno[2,3-c]pyridin-2-yl)acetamide (Compound 120)

Step 1. N-(6-ethyl-5,7-dimethyl-3-(thiazolo[4,5-c]pyridin-2-yl)-4,5,6,7-tetrahydrothieno[2,3-c]pyridin-2-yl)acetamide (Compound 117)

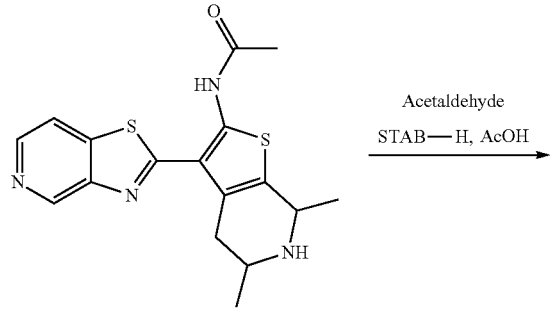

148

-continued

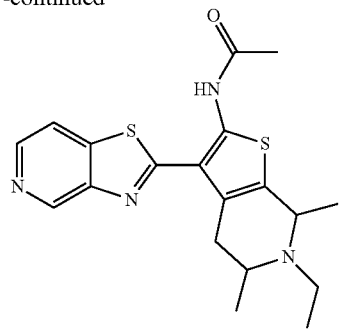

To a stirred solution of N-(5,7-dimethyl-3-(thiazolo[4,5-c]pyridin-2-yl)-4,5,6,7-tetrahydrothieno[2,3-c]pyridin-2-yl)acetamide (Compound 109; 0.25 g, 0.69 mmol) in 1,2-dichloroethane (3 mL) was added acetaldehyde (0.062 g, 1.39 mmol) followed by AcOH (0.207 g, 3.45 mmol) and the resulting solution was stirred at room temperature for 15 h. The solution was cooled to 0° C., sodium triacetoxy borohydride (0.74 g, 3.45 mmol) was added and the reaction mixture was stirred at room temperature for 3 h. The reaction was monitored by LCMS. After the completion, the reaction mixture was quenched with saturated sodium bicarbonate solution and extracted with 10% methanol in DCM. The combined organic solvents were dried over anhydrous $Na_2SO_4$ and evaporated in vacuum resulting in the crude compound. The crude compound was purified by prep HPLC to afford the title compound as yellow solid. (100 mg, yield 37%).

Step 2. Separation of Isomers to Yield N-((5R,7R)-6-ethyl-5,7-dimethyl-3-(thiazolo[4,5-c]pyridin-2-yl)-4,5,6,7-tetrahydrothieno[2,3-c]pyridin-2-yl)acetamide (Compound 119) and N-((5S,7S)-6-ethyl-5,7-dimethyl-3-(thiazolo[4,5-c]pyridin-2-yl)-4,5,6,7-tetrahydrothieno[2,3-c]pyridin-2-yl)acetamide (Compound 120)

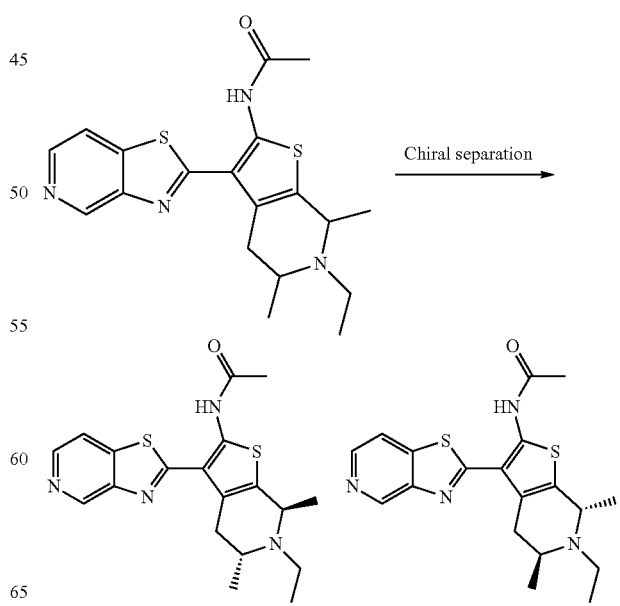

Example 18

Synthesis of N-(3-(4-methylthiazolo[4,5-c]pyridin-2-yl)-4,5,6,7-tetrahydrothieno[2,3-c]pyridin-2-yl)acetamide (Compound 118)

Step 1: 2-(2-acetamido-6-(tert-butoxycarbonyl)-4,5,6,7-tetrahydrothieno[2,3-c]pyridin-3-yl)thiazolo[4,5-c]pyridine 5-oxide

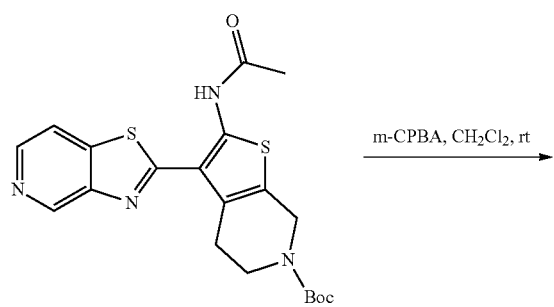

Chiral Separation of enantiomers was completed on 120 mg scale to afford 20 mg each of both the enantiomers using a Chiralpak IA (250×4.6 mm, 5 μm) column, Mobile Phase A: 0.1% DEA in n-Hexane; Mobile Phase B: EtOH: MeOH (50:50); A: B: 90:10; Flow Rate: 1.0 ml/min.

To a stirred solution of tert-butyl 2-acetamido-3-(thiazolo[4,5-c]pyridin-2-yl)-4,7-dihydrothieno[2,3-c]pyridine-6(5H)-carboxylate (1 g, 2.32 mmol) in DCM (10 mL) at 0° C. was added m-CPBA (400 mg, 2.55 mmol) and stirred at room temperature for 16 h. Reaction was monitored by TLC. After completion, the reaction mixture was quenched with solid NaHCO₃ and filtered. The filtrate was concentrated in vacuo resulting in the crude compound which was purified by flash column chromatography to afford the title compound 1 as pale yellow solid (900 mg, 87% yield).

Step 2: tert-butyl 2-acetamido-3-(4-methylthiazolo[4,5-c]pyridin-2-yl)-4,7-dihydrothieno[2,3-c]pyridine-6(5H)-carboxylate (2)

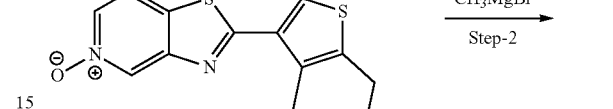

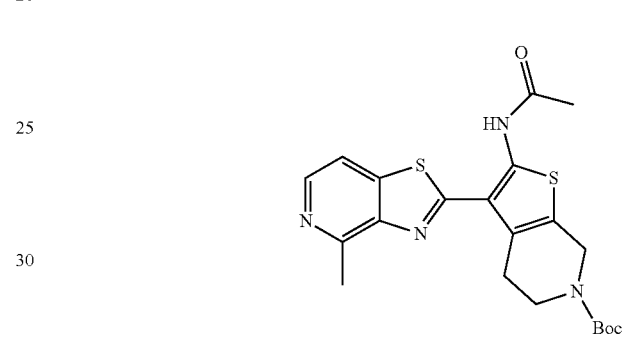

To a solution of 2-(2-acetamido-6-(tert-butoxycarbonyl)-4,5,6,7-tetrahydrothieno[2,3-c]pyridin-3-yl)thiazolo[4,5-c]pyridine 5-oxide 1 (500 mg, 1.11 mmol) in anhydrous THF (10 mL) at 0° C. were added methyl magnesium bromide (2 mL, 6.00 mmol) and stirred at room temperature for 16 h. Reaction was monitored by TLC. After the completion of reaction the reaction mixture was quenched by the addition of saturated NH₄Cl solution and extracted with ethyl acetate. The combined organic layer was dried over anhydrous Na₂SO₄, filtered and concentrated to get a crude residue which was purified by silica gel column chromatography and further followed by preparative HPLC to afford the title compound as yellow solid (40 mg, 8% yield).

Step 3: N-(3-(4-methylthiazolo[4,5-c]pyridin-2-yl)-4,5,6,7-tetrahydrothieno[2,3-c]pyridin-2-yl)acetamide (Compound 118)

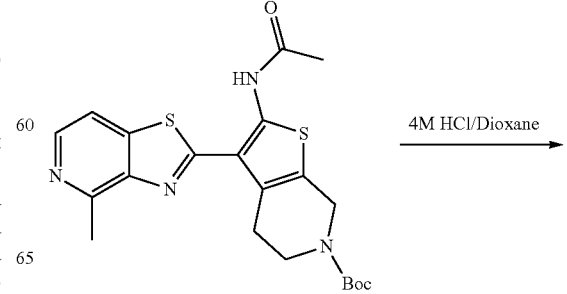

-continued

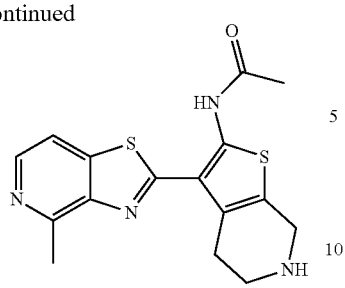

To a solution of tert-butyl 2-acetamido-3-(4-methylthiazolo[4,5-c]pyridin-2-yl)-4,7-dihydrothieno[2,3-c]pyridine-6(5H)-carboxylate 2 (40 mg, 0.09 mmol) in dioxane (1 mL) at 0° C. was added 4M HCl in dioxane (1.5 mL) and the resulting mixture was stirred at room temperature for 4 h. Reaction was monitored by TLC. After completion, the reaction mixture was evaporated to dryness resulting in a crude residue which was purified by triturating with ether and pentane to afford the title compound as yellow solid (20 mg, 64% yield).

Example 19

Synthesis of N-(6-(2-aminoethyl)-3-(thiazolo[4,5-c]pyridin-2-yl)-4,5,6,7-tetrahydrothieno[2,3-c]pyridin-2-yl)acetamide hydrochloride (Compound 121)

Step 1: tert-butyl (2-(2-acetamido-3-(thiazolo[4,5-c]pyridin-2-yl)-4,7-dihydrothieno[2,3-c]pyridin-6(5H)-yl)ethyl)carbamate

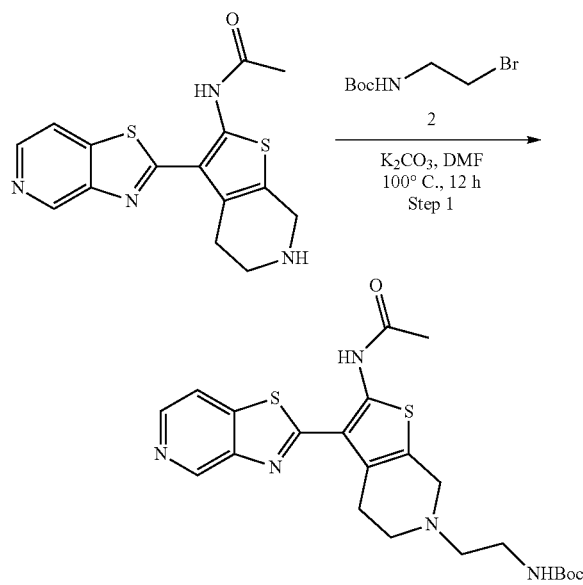

To a stirred solution of N-(3-(thiazolo[4,5-c]pyridin-2-yl)-4,5,6,7-tetrahydrothieno[2,3-c]pyridin-2-yl)acetamide 1 (200 mg, 0.6 mmol) in DMF (10 mL) was added tert-butyl (2-bromoethyl)carbamate 2 (202 mg, 0.9 mmol) followed by potassium carbonate (248 mg, 1.8 mmol) at room temperature and the resulting solution was heated at 100° C. for 12 h. Reaction was monitored by TLC. After completion, the reaction mass was diluted with water and ethyl acetate. The combined organic layer was dried over anhydrous $Na_2SO_4$ and concentrated to get a crude residue. The crude compound was purified by flash column chromatography to afford the title compound 3 as yellow solid (60 mg, 21% yield).

Step 2: N-(6-(2-aminoethyl)-3-(thiazolo[4,5-c]pyridin-2-yl)-4,5,6,7-tetrahydrothieno[2,3-c]pyridin-2-yl)acetamide (Compound 121)

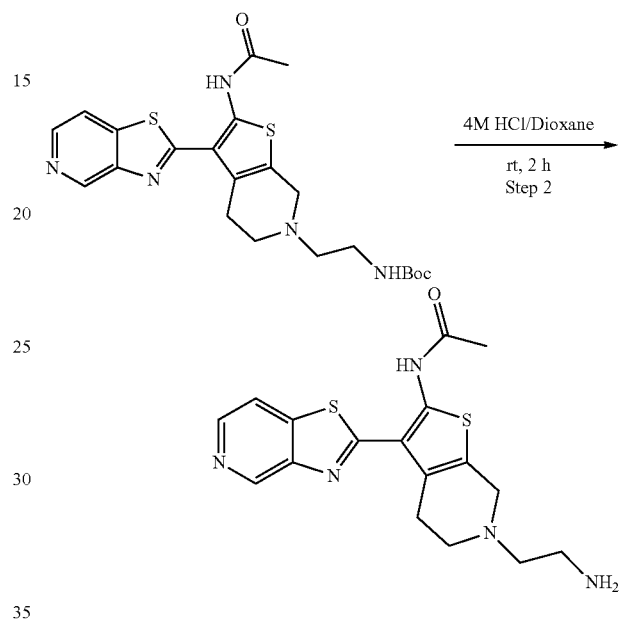

To a solution of tert-butyl (2-(2-acetamido-3-(thiazolo[4,5-c]pyridin-2-yl)-4,7-dihydrothieno[2,3-c]pyridin-6(5H)-yl)ethyl)carbamate 3 (60 mg, 0.12 mmol) in dioxane (3 mL) at 0° C. was added 4M HCl in dioxane (3 mL) and the resulting mixture was stirred at room temperature for 2 h. Reaction was monitored by TLC. After completion, the reaction mixture was evaporated to dryness resulting in a crude residue which was purified by triturating with ether and pentane to afford the HCl salt of the title compound as yellow solid (30 mg, 61% yield).

Example 20

Synthesis of (S)-3-(sec-butylamino)-N-(3-(thiazolo[4,5-c]pyridin-2-yl)-4,5,6,7-tetrahydrothieno[2,3-c]pyridin-2-yl)propanamide (Compound 122)

Step 1: 2-(thiazolo[4,5-c]pyridin-2-yl)acetonitrile

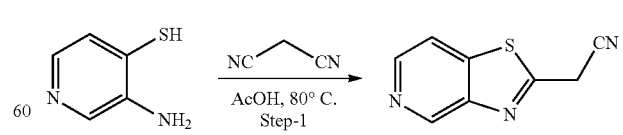

To a stirred solution of 3-aminopyridine-4-thiol 1 (1.5 g, 11.90 mmol) in ethanol (10 mL) malononitrile (0.79 g, 11.90 mmol) and acetic acid (10 mL) was added at room temperature. After the addition, the resulting mixture was heated to reflux at 80° C. for 12 h. Progress of the reaction was monitored by TLC. After completion, the reaction mass was diluted with ethyl acetate and washed with saturated NaHCO₃ solution and brine. The combined organic layer was dried over Na₂SO₄, filtered and concentrated to afford the title compound 2 as yellow solid (3 g, crude).

Step 2: tert-butyl 2-amino-3-(thiazolo[4,5-c]pyridin-2-yl)-4,7-dihydrothieno[2,3-c]pyridine-6(5H)-carboxylate

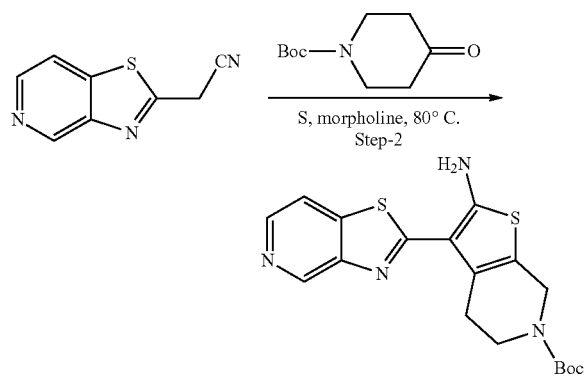

To a stirred solution of 2-(thiazolo[4,5-c]pyridin-2-yl)acetonitrile (8 g, 45.71 mmol) in ethanol (80 mL), tert-butyl 4-oxopiperidine-1-carboxylate (10.91 g, 54.85 mmol), elemental sulphur (1.75 g, 54.85 mmol) and morpholine (4.77 mL, 54.85 mmol) was added at room temperature. After the addition, the resulting mixture was heated to reflux at 80° C. for 3 h. Reaction was monitored by TLC. The reaction mixture was dried in vacuum and the crude compound was purified by triturating with methanol to afford the title compound as yellow solid (8 g, yield 45%).

Step 3: tert-butyl 2-acrylamido-3-(thiazolo[4,5-c]pyridin-2-yl)-4,7-dihydrothieno[2,3-c]pyridine-6(5H)-carboxylate(4)

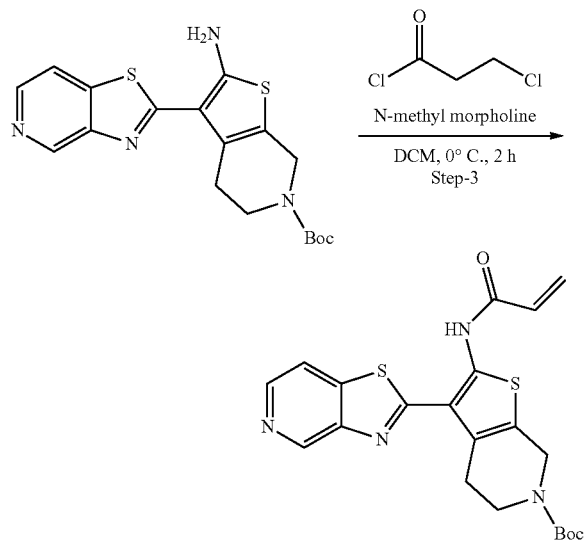

To a stirred solution of tert-butyl 2-amino-3-(thiazolo[4,5-c]pyridin-2-yl)-4,7-dihydrothieno[2,3-c]pyridine-6(5H)-carboxylate 3 (1 g, 2.57 mmol) in DCM (20 mL) at 0° C., N-methyl morpholine (0.8 mL, 6.44 mmol) was added and stirred at same temperature for 10 min. To this solution, 3-chloropropanoyl chloride (0.4 g, 3.86 mmol) was added at 0° C. and the resulting mixture was stirred at 0° C. for 2 h. Progress of the reaction was monitored by TLC. After completion, the reaction mass was diluted with DCM and washed with saturated NaHCO₃ solution and brine. The combined organic layer was dried over Na₂SO₄, filtered and concentrated to get a crude residue. This crude compound was purified by silica gel column chromatography eluting with 0-5% MeOH/DCM to afford the title compound 4 as brown oil (0.9 g, yield 40%).

Step 4: tert-butyl (S)-2-(3-(sec-butylamino)propanamido)-3-(thiazolo[4,5-c]pyridin-2-yl)-4,7-dihydrothieno[2,3-c]pyridine-6(5H)-carboxylate

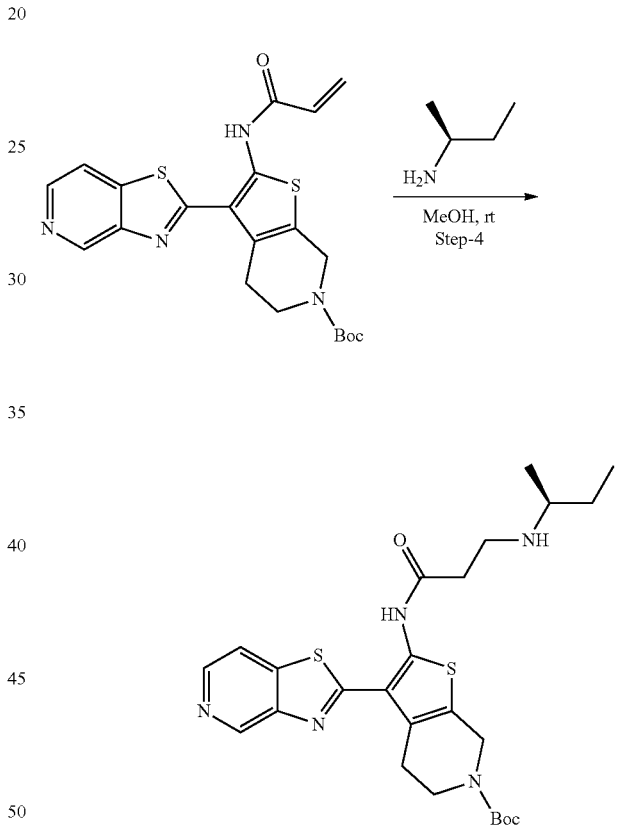

To a stirred solution of tert-butyl 2-acrylamido-3-(thiazolo[4,5-c]pyridin-2-yl)-4,7-dihydrothieno[2,3-c]pyridine-6(5H)-carboxylate 4 (0.5 g, 1.13 mmol) in MeOH (5 mL), (S)-butan-2-amine (0.165 g, 2.26 mmol) was added and the resulting mixture was stirred at room temperature for 16 h. Progress of the reaction was monitored by TLC. After completion, the reaction mass was concentrated to get a crude residue. This crude compound was purified by prep. HPLC to afford the title compound as yellow solid (0.1 g, yield 17.2%).

Step 5: (S)-3-(sec-butylamino)-N-(3-(thiazolo[4,5-c]pyridin-2-yl)-4,5,6,7-tetrahydrothieno[2,3-c]pyridin-2-yl)propanamide (Compound 122)

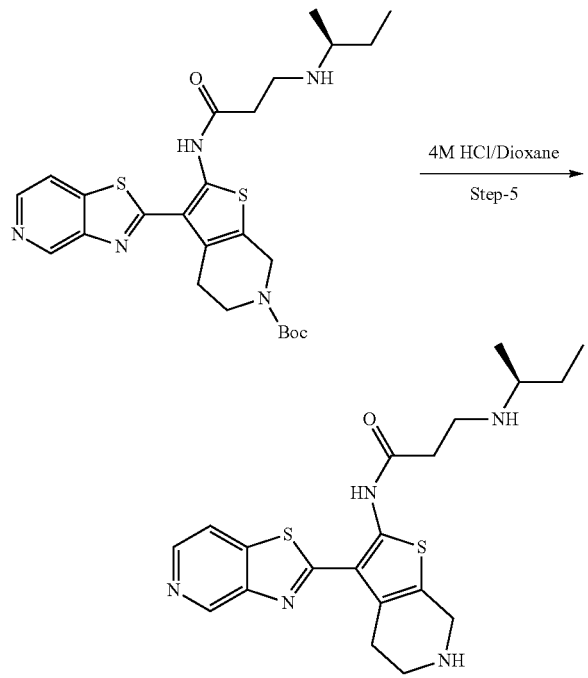

To a solution of tert-butyl (S)-2-(3-(sec-butylamino)propanamido)-3-(thiazolo[4,5-c]pyridin-2-yl)-4,7-dihydrothieno[2,3-c]pyridine-6(5H)-carboxylate 5 (0.1 g, 0.19 mmol) in dioxane (1 mL) at 0° C. was added 4M HCl in dioxane (1 mL) and the reaction mixture was stirred at room temperature for 2 h. After completion, the reaction mixture was evaporated to dryness and the resulting in a crude residue which was purified by trituration in ether to afford the title compound as yellow solid (0.1 g, HCl salt, 91% yield).

Example 21

Synthesis of Compounds 123-215

In the synthesis schemes below $R^B$ is selected from —$C_1$-$C_4$ alkyl, —$C_1$-$C_4$ alkylene-O-alkyl, —$C_1$-$C_4$ alkylene-C(O)—O-alkyl, —$C_1$-$C_4$ alkylene-cycloalkyl, -cycloalkyl, -heterocyclyl, —$C_1$-$C_4$ alkylene-heterocyclyl, —$C_1$-$C_4$ alkylene-heteroaryl, and —$C_1$-$C_4$ alkylene-aryl.

Step 1. tert-butyl 2-(prop-2-enoylamino)-3-thiazolo[4,5-c]pyridin-2-yl-5,7-dihydro-4H-thieno[2,3-c]pyridine-6-carboxylate

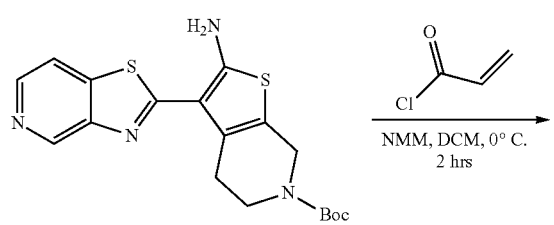

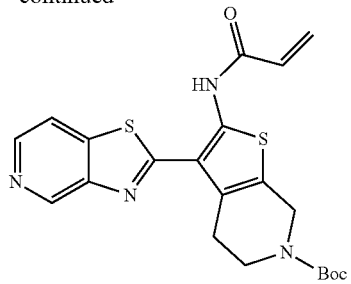

To a solution of tert-butyl 2-amino-3-thiazolo[4,5-c]pyridin-2-yl-5,7-dihydro-4H-thieno[2,3-c]pyridine-6-carboxylate (6.80 g, 17.50 mmol, 1.00 eq) in DCM (20.00 mL) and NMM (3.54 g, 35.00 mmol, 2.00 eq) was added prop-2-enoyl chloride (2.22 g, 24.50 mmol, 1.40 eq), The mixture was stirred at 0° C. for 3 hours. The starting material was consumed and the desired compound was detected by LCMS and then concentrated under reduced pressure to give a residue. Compound (7.50 g, crude) was obtained as a yellow solid and used directly.

Step 2. General Procedure for Preparation of the Library

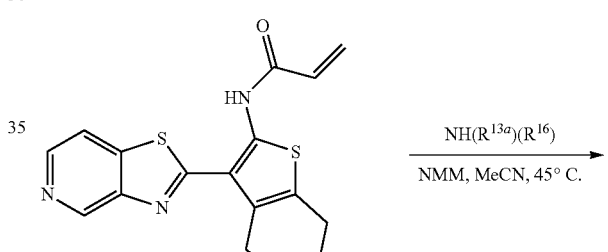

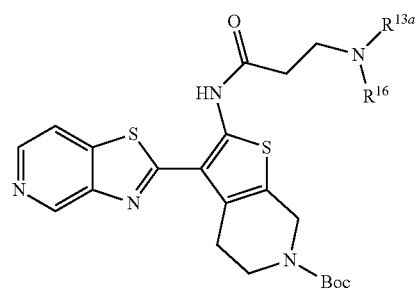

A mixture of tert-butyl-2-acrylamido-3-(thiazolo[4,5-c]pyridin-2-yl)-4,7-dihydrothieno[2,3-c]pyridine-6(5H)-carboxylate (150.00 mg, 0.44 mmol, 1.00 eq), an appropriate amine (NH($R^{13a}$)($R^{16}$); 1.20 eq) and NMM (2.00 eq) in MeCN (4.00 mL) was stirred at 45° C. for 12 hours. The reaction mixture was concentrated under reduced pressure to afford a crude residue. The crude product was purified by preparative HPLC to give the Boc-protected product, wherein variables $R^{16}$ and $R^{13a}$ are defined herein.

Step 3. Deprotection of the Boc-Protected Products

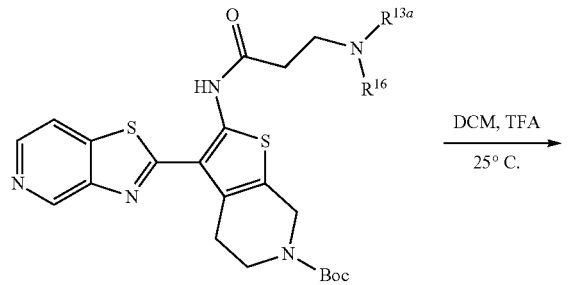

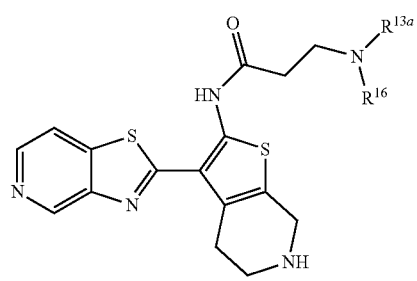

A solution of the Boc-protected product from the previous step in DCM/TFA (2.00 mL, 8/1) was stirred at 25° C. for 2 hour. LC-MS indicated complete reaction, the reaction mixture was concentrated under reduced pressure and the crude product was purified by preparative HPLC to give the final compound.

Example 22

Synthesis of 3-((2-methoxyethyl)amino)-N-(3-(thiazolo[4,5-c]pyridin-2-yl)-4,5,6,7-tetrahydrothieno[2,3-c]pyridin-2-yl)propanamide (Compound 216)

Step 1: tert-butyl 2-(3-((2-methoxyethyl)amino)propanamido)-3-(thiazolo[4,5-c]pyridin-2-yl)-4,7-dihydrothieno[2,3-c]pyridine-6(5H)-carboxylate

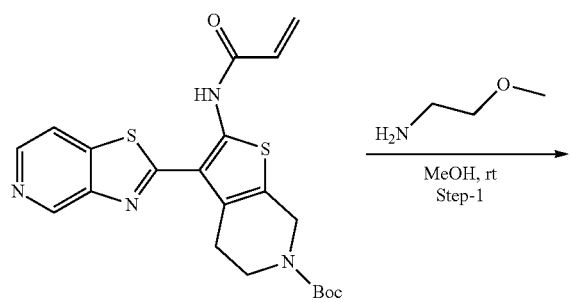

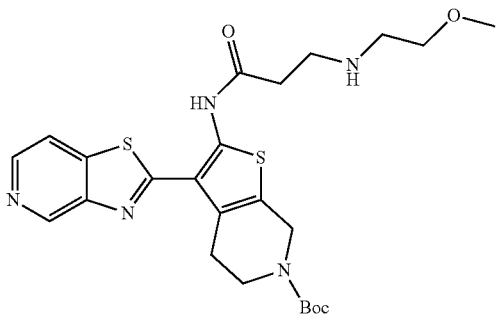

To a solution of tert-butyl 2-acrylamido-3-(thiazolo[4,5-c]pyridin-2-yl)-4,7-dihydrothieno[2,3-c]pyridine-6(5H)-carboxylate 1 (0.2 g, 0.452 mmol) in MeOH (4 mL), 2-methoxyethan-1-amine (0.051 g, 0.678 mmol) was added. The resulting reaction mixture was stirred at room temperature for 12 h. Progress of the reaction was monitored by TLC. After completion, the reaction mixture was concentrated to dryness under reduced pressure. The crude compound was purified by prep. HPLC to afford the title compound as yellow solid (0.065 g, yield 28%).

Step 2: 3-((2-methoxyethyl)amino)-N-(3-(thiazolo[4,5-c]pyridin-2-yl)-4,5,6,7-tetrahydrothieno[2,3-c]pyridin-2-yl)propanamide (Compound 216)

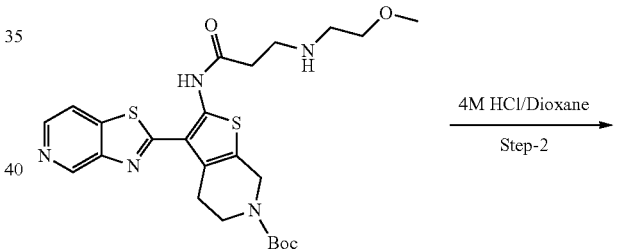

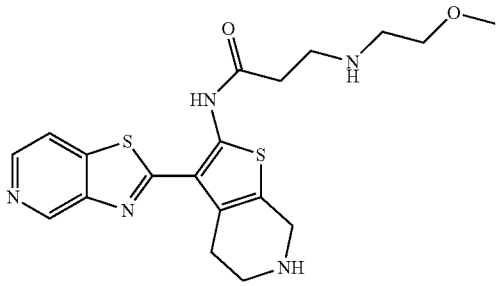

To a solution of tert-butyl 2-(3-((2-methoxyethyl)amino)propanamido)-3-(thiazolo[4,5-c]pyridin-2-yl)-4,7-dihydrothieno[2,3-c]pyridine-6(5H)-carboxylate 2 (0.065 g, 0.125 mmol) in dioxane (1 mL) at 0° C. was added 4M HCl in dioxane (2 mL). After the addition, the resulting mixture was stirred at room temperature for 3 h. Progress of the reaction was monitored by TLC. After completion, the reaction mixture was evaporated in vacuum resulting in a crude residue which was purified by trituration in ether and pentane to afford the HCl salt of the title compound as yellow solid (0.03 g, yield 49.2%).

Example 23

Synthesis of (R)-3-(sec-butylamino)-N-(3-(thiazolo[4,5-c]pyridin-2-yl)-4,5,6,7-tetrahydrothieno[2,3-c]pyridin-2-yl)propanamide (Compound 217)

Step 1: tert-butyl (R)-2-(3-(sec-butylamino)propanamido)-3-(thiazolo[4,5-c]pyridin-2-yl)-4,7-dihydrothieno[2,3-c]pyridine-6(5H)-carboxylate

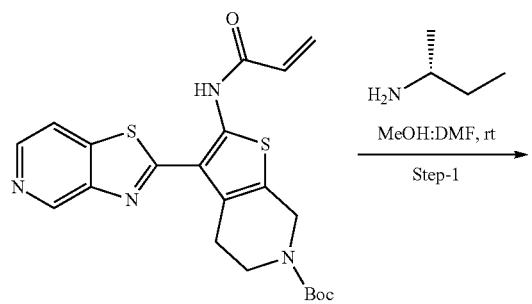

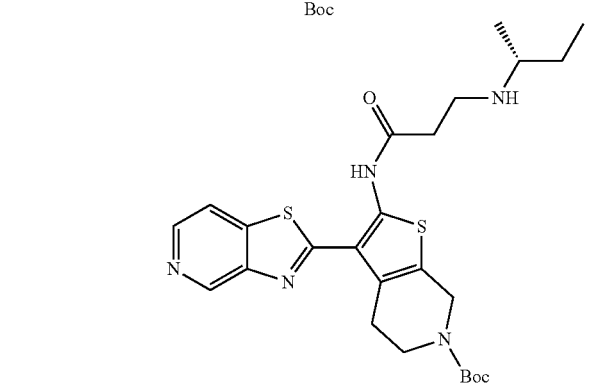

To a stirred solution of tert-butyl 2-acrylamido-3-(thiazolo[4,5-c]pyridin-2-yl)-4,7-dihydrothieno[2,3-c]pyridine-6(5H)-carboxylate SJMC0117-S Int-4 (4.3 g, 9.72 mmol) in MeOH:DMF (20:20 mL), (R)-butan-2-amine (1.06 g, 14.5 mmol) was added and the resulting mixture was stirred at room temperature for 16 h. Progress of the reaction was monitored by TLC. After completion, the reaction mass was concentrated to get a crude residue. This crude compound was purified by column chromatography on neutral silica gel eluting with 2-8% methanol in DCM to afford the title compound as yellow solid (3 g, yield 60%).

Step-2: (R)-3-(sec-butylamino)-N-(3-(thiazolo[4,5-c]pyridin-2-yl)-4,5,6,7-tetrahydrothieno[2,3-c]pyridin-2-yl)propanamide (Compound 217)

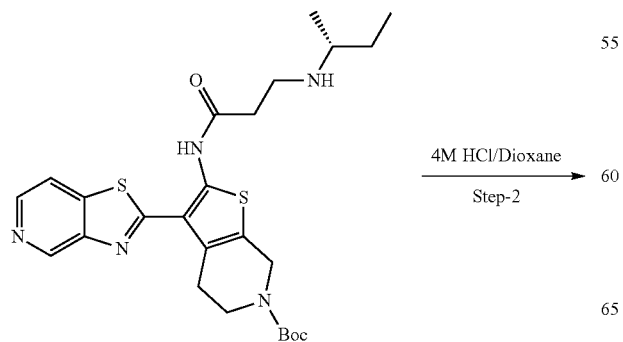

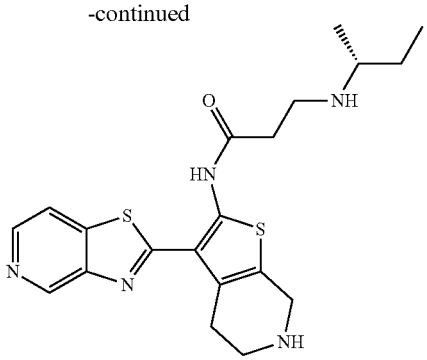

To a solution of tert-butyl (R)-2-(3-(sec-butylamino)propanamido)-3-(thiazolo[4,5-c]pyridin-2-yl)-4,7-dihydrothieno[2,3-c]pyridine-6(5H)-carboxylate 1 (3 g, 5.81 mmol) in dioxane (10 mL) at 0° C. was added 4M HCl in dioxane (30 mL) and the reaction mixture was stirred at room temperature for 2 h. After completion, the reaction mixture was evaporated to dryness and the resulting in the crude residue which was purified by trituration in pentane and diethyl ether to afford the HCl salt of the title compound as yellow solid (2.5 g, 88% yield).

Example 24

Synthesis of 3-((2-(pyridin-3-yl)ethyl)amino)-N-(3-(thiazolo[4,5-c]pyridin-2-yl)-4,5,6,7-tetrahydrothieno[2,3-c]pyridin-2-yl)propanamide (Compound 218)

Step 1: tert-butyl 2-(3-((2-(pyridin-3-yl)ethyl)amino)propanamido)-3-(thiazolo[4,5-c]pyridin-2-yl)-4,7-dihydrothieno[2,3-c]pyridine-6(5H)-carboxylate

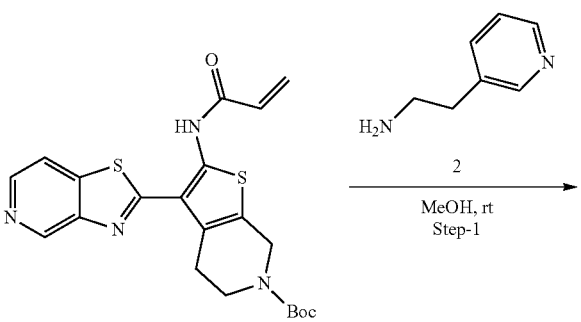

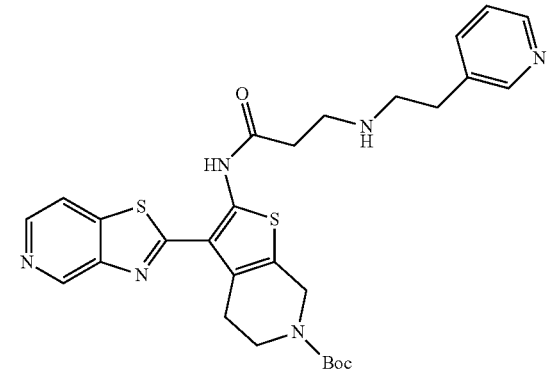

To a solution of tert-butyl 2-acrylamido-3-(thiazolo[4,5-c]pyridin-2-yl)-4,7-dihydrothieno[2,3-c]pyridine-6(5H)-carboxylate 1 (0.3 g, 0.678 mmol) in MeOH (5 mL), 2-(pyridin-3-yl)ethan-1-amine (0.124 g, 1.018 mmol) was added. The resulting reaction mixture was stirred at room temperature for 12 h. Progress of the reaction was monitored by TLC. After completion, the reaction mixture was concentrated to dryness under reduced pressure. The crude residue was purified by trituration with diethyl ether and pentane to afford the title compound as yellow solid (0.065 g, 17% yield).

Step 2: 3-((2-(pyridin-3-yl)ethyl)amino)-N-(3-(thiazolo[4,5-c]pyridin-2-yl)-4,5,6,7-tetrahydrothieno[2,3-c]pyridin-2-yl)propanamide (Compound 218)

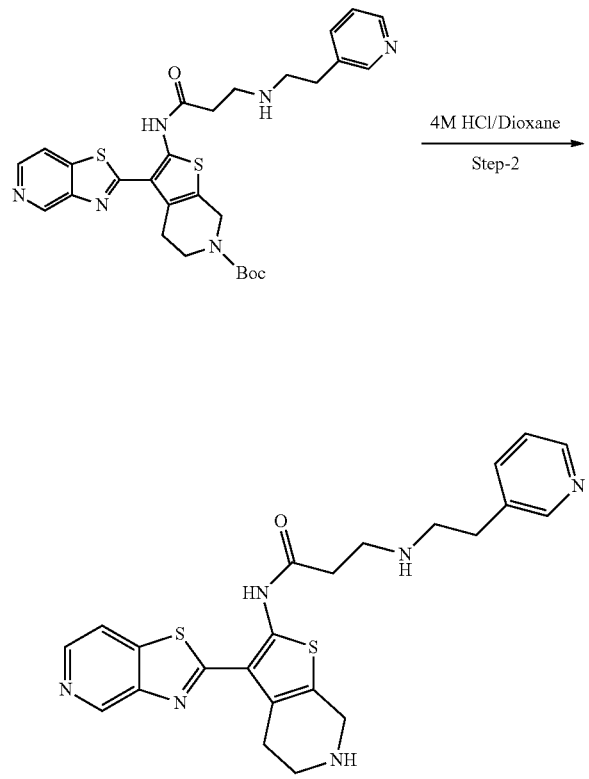

To a solution of tert-butyl 2-(3-((2-(pyridin-3-yl)ethyl)amino)propanamido)-3-(thiazolo[4,5-c]pyridin-2-yl)-4,7-dihydrothieno[2,3-c]pyridine-6(5H)-carboxylate 2 (0.065 g, 0.115 mmol) in dioxane (1 mL) at 0° C. was added 4M HCl in dioxane (2 mL). After the addition, the resulting mixture was stirred at room temperature for 3 h. Progress of the reaction was monitored by TLC. After completion, the reaction mixture was evaporated in vacuum resulting in a crude residue which was purified by trituration in ether and pentane to afford the title compound as yellow solid (0.058 g, yield 95.1%).

Example 25

Synthesis of 3-(dimethylamino)-N-(3-(thiazolo[4,5-c]pyridin-2-yl)-4,5,6,7-tetrahydrothieno[2,3-c]pyridin-2-yl)propanamide (Compound 219)

Step 1: tert-butyl 2-(3-(dimethylamino)propanamido)-3-(thiazolo[4,5-c]pyridin-2-yl)-4,7-dihydrothieno[2,3-c]pyridine-6(5H)-carboxylate

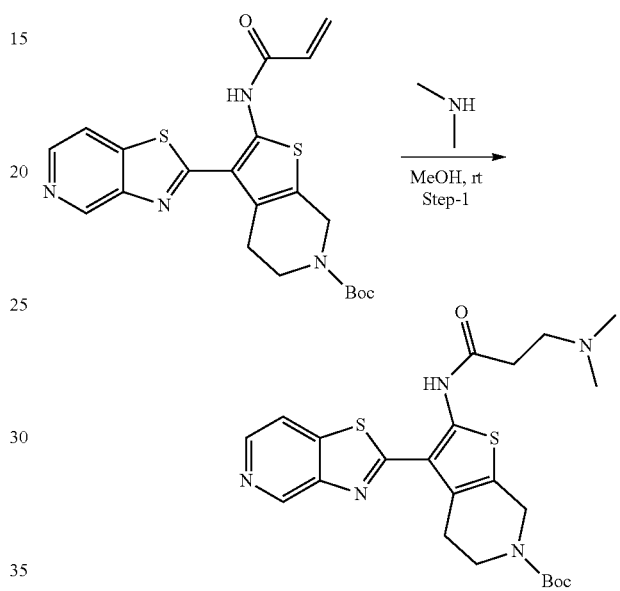

To a solution of tert-butyl 2-acrylamido-3-(thiazolo[4,5-c]pyridin-2-yl)-4,7-dihydrothieno[2,3-c]pyridine-6(5H)-carboxylate 1 (0.3 g, 0.678 mmol) in MeOH (6 mL), dimethylamine (2M in THF, 2.03 mL, 1.01 mmol) was added. The resulting reaction mixture was stirred at room temperature for 12 h. Progress of the reaction was monitored by TLC. After completion, the reaction mixture was concentrated to dryness under reduced pressure. The crude compound was purified by prep. HPLC to afford the title compound as yellow solid (0.16 g, yield 48.5%).

Step 2: 3-(dimethylamino)-N-(3-(thiazolo[4,5-c]pyridin-2-yl)-4,5,6,7-tetrahydrothieno[2,3-c]pyridin-2-yl)propanamide (Compound 219)

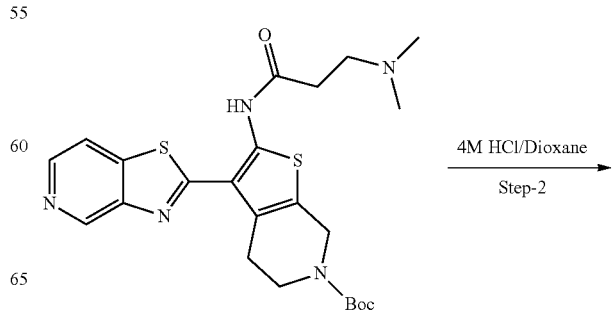

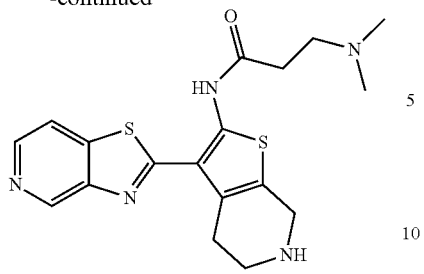

To a solution of tert-butyl 2-(3-(dimethylamino)propanamido)-3-(thiazolo[4,5-c]pyridin-2-yl)-4,7-dihydrothieno[2,3-c]pyridine-6(5H)-carboxylate 2 (0.16 g, 0.328 mmol) in dioxane (1 mL) at 0° C. was added 4M HCl in dioxane (2 mL). After the addition, the resulting mixture was stirred at room temperature for 2 h. Progress of the reaction was monitored by TLC. After completion, the reaction mixture was evaporated in vacuum resulting in a crude residue which was purified by trituration with diethyl ether and pentane to afford the title compound as yellow solid (0.07 g, yield 55.11%).

Example 26

Synthesis of 3-(cyclopropylamino)-N-(3-(thiazolo[4,5-c]pyridin-2-yl)-4,5,6,7-tetrahydrothieno[2,3-c]pyridin-2-yl)propanamide (Compound 221)

Step 1: 2-(thiazolo[4,5-c]pyridin-2-yl)acetonitrile

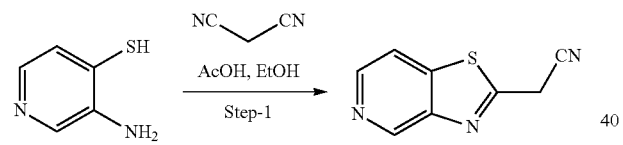

To a stirred solution of 3-aminopyridine-4-thiol 1 (2 g, 15.87 mmol) in EtOH (20 mL) was added malononitrile (1.05 g, 15.87 mmol) and acetic acid (2 mL). The resulting reaction mixture was stirred at 85° C. for 16 h. Progress of the reaction was monitored by TLC. After completion, the reaction mixture was evaporated in vacuum, diluted with water and extracted with ethyl acetate. The combined organic layer was dried over anhydrous Na$_2$SO$_4$; filtered and concentrated to afford the title compound as yellow solid (2.7 g crude).

Step 2: tert-butyl 2-amino-3-(thiazolo[4,5-c]pyridin-2-yl)-4,7-dihydrothieno[2,3-c]pyridine-6(5H)-carboxylate

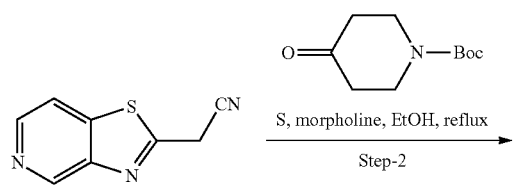

To a solution of 2-(thiazolo[4,5-c]pyridin-2-yl)acetonitrile 2 (2.7 g, 15.42 mmol) in ethanol (20 mL) was added tert-butyl 4-oxopiperidine-1-carboxylate (3.1 g, 15.42 mmol), elemental sulphur (493 mg, 15.42 mmol) and morpholine (1.3 g, 15.42 mmol) at room temperature. After the addition, the resulting mixture was heated to reflux at 85° C. for 16 h. Progress of the reaction was monitored by TLC. After completion, the reaction mixture was evaporated in vacuum, the crude compound was purified by silica gel column chromatography eluting with 5-10% methanol in DCM to afford the title compound as yellow solid (2 g, yield 34%).

Step 3: tert-butyl 2-acrylamido-3-(thiazolo[4,5-c]pyridin-2-yl)-4,7-dihydrothieno[2,3-c]pyridine-6(5H)-carboxylate

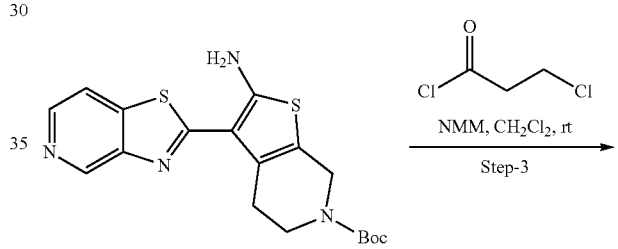

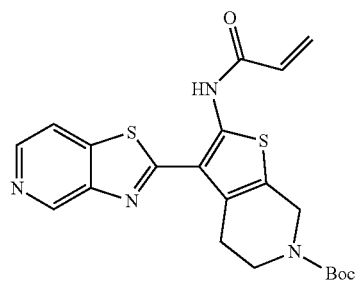

To a solution of tert-butyl 2-amino-3-(thiazolo[4,5-c]pyridin-2-yl)-4,7-dihydrothieno[2,3-c]pyridine-6(5H)-carboxylate 3 (1 g, 2.57 mmol) in DCM (20 mL) at 0° C. was added NMM (1.1 mL, mmol), 3-chloropropanoyl chloride (0.62 mL, 6.44 mmol). The reaction was stirred at room temperature for 16 h. Progress of the reaction was monitored by TLC. After completion, reaction mixture was diluted with water and extracted with ethyl acetate. The combined organic layer was dried over anhydrous Na$_2$SO$_4$; filtered and concentrated under reduced pressure to afford the title compound 4 (500 mg, yield 44%).

Step 4: tert-butyl 2-(3-(cyclopropylamino)propanamido)-3-(thiazolo[4,5-c]pyridin-2-yl)-4,7-dihydrothieno[2,3-c]pyridine-6(5H)-carboxylate

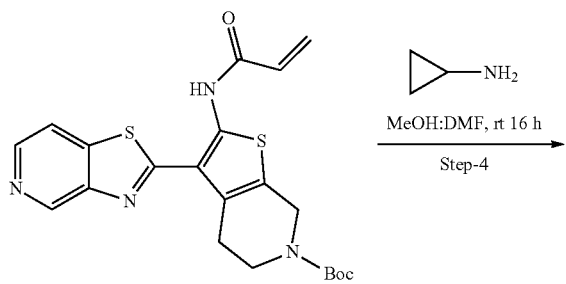

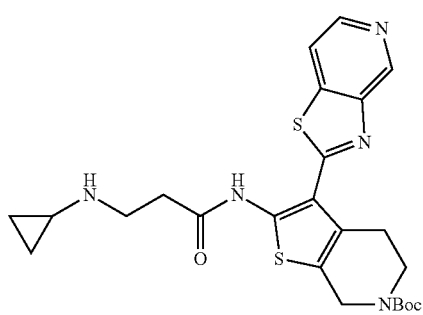

To a solution of tert-butyl 2-acrylamido-3-(thiazolo[4,5-c]pyridin-2-yl)-4,7-dihydrothieno[2,3-c]pyridine-6(5H)-carboxylate 4 (250 mg, 0.565 mmol) in methanol: DMF (1:1, 4 mL) was added cyclopropyl amine (0.08 mL, 1.13 mmol). After the addition, the resulting mixture was stirred at room temperature for 16 h. After completion (monitored by TLC), the reaction mixture was evaporated in vacuum resulting in the crude compound which was purified by silica gel column chromatography eluting with 0-5% methanol in DCM to afford the title compound as a yellow solid (160 mg, 57% yield).

Step 5: 3-(cyclopropylamino)-N-(3-(thiazolo[4,5-c]pyridin-2-yl)-4,5,6,7-tetrahydrothieno[2,3-c]pyridin-2-yl)propanamide (Compound 221)

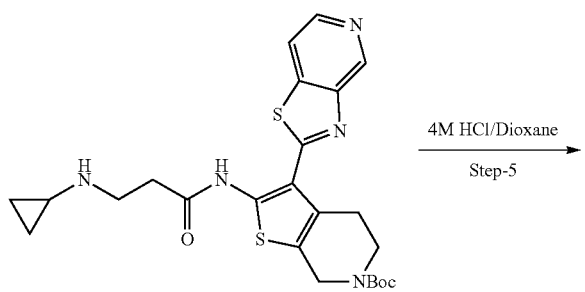

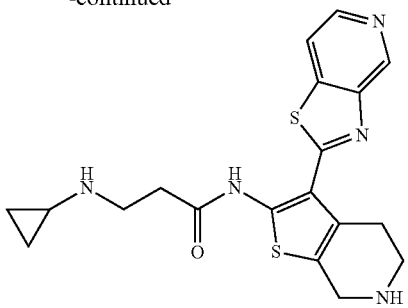

To a solution of tert-butyl 2-(3-(cyclopropylamino)propanamido)-3-(thiazolo[4,5-c]pyridin-2-yl)-4,7-dihydrothieno[2,3-c]pyridine-6(5H)-carboxylate 5 (0.15 g, 0.30 mmol) in dioxane (2 mL) at 0° C. was added 4M HCl in dioxane (2 mL). After the addition, the resulting mixture was stirred at room temperature for 2 h. After completion, the reaction mixture was evaporated in vacuum, washed with diethyl ether and filtered resulting in the crude compound which was purified by preparative HPLC to afford the formate salt of the title compound as a yellow solid (8 mg, 6% yield).

Example 27

Synthesis of 3-(cyclobutylamino)-N-(3-(thiazolo[4,5-c]pyridin-2-yl)-4,5,6,7-tetrahydrothieno[2,3-c]pyridin-2-yl)propanamide (Compound 222)

Step 1: tert-butyl 2-(3-(cyclobutylamino)propanamido)-3-(thiazolo[4,5-c]pyridin-2-yl)-4,7-dihydrothieno[2,3-c]pyridine-6(5H)-carboxylate

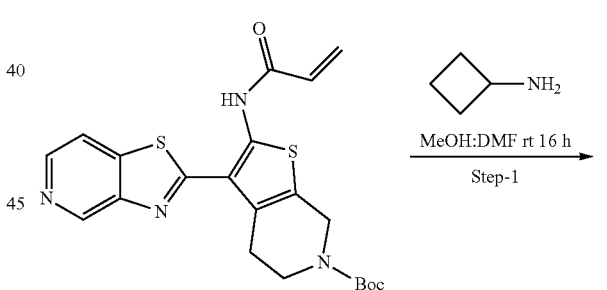

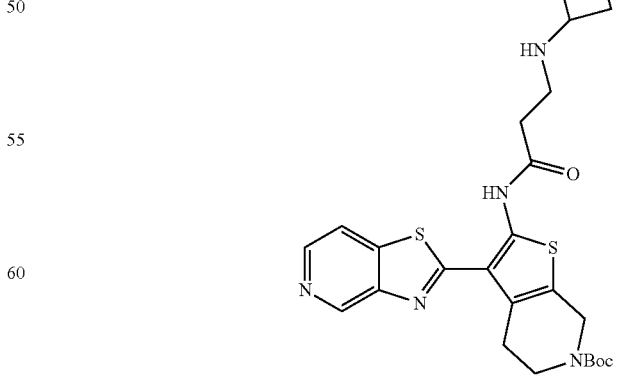

To a solution of tert-butyl 2-acrylamido-3-(thiazolo[4,5-c]pyridin-2-yl)-4,7-dihydrothieno[2,3-c]pyridine-6(5H)-carboxylate (250 mg, 0.565 mmol) in methanol: DMF (5:1 mL) was added cyclobutyl amine (0.09 mL, 1.11 mmol). After the addition, the resulting mixture was stirred at room temperature for 16 h. After completion (monitored by TLC), the reaction mixture was evaporated in vacuum resulting in the crude compound which was purified by silica gel column chromatography eluting with 0-5% methanol in DCM to afford the title compound as a yellow solid (130 mg, 45% yield).

Step 2: 3-(cyclobutylamino)-N-(3-(thiazolo[4,5-c]pyridin-2-yl)-4,5,6,7-tetrahydrothieno[2,3-c]pyridin-2-yl)propanamide (Compound 222)

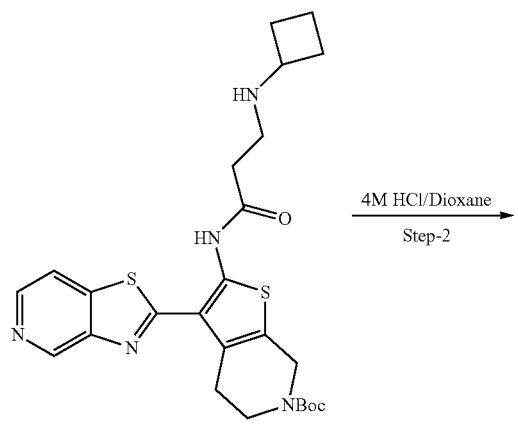

To a solution of tert-butyl 2-(3-(cyclobutylamino)propanamido)-3-(thiazolo[4,5-c]pyridin-2-yl)-4,7-dihydrothieno[2,3-c]pyridine-6(5H)-carboxylate 5 (0.15 g, 0.23 mmol) in dioxane (2 mL) at 0° C. was added 4M HCl in dioxane (2 mL). After the addition, the resulting mixture was stirred at room temperature for 2 h. After completion, the reaction mixture was evaporated in vacuum, washed with diethyl ether and filtered resulting in the crude compound which was purified by preparative HPLC to afford the formate salt of the title compound as a brown solid (10 mg, 9% yield).

Example 28

Synthesis of 3-(Azetidin-3-ylamino)-N-(3-(thiazolo[4,5-c]pyridin-2-yl)-4,5,6,7-tetrahydrothieno[2,3-c]pyridin-2-yl)propanamide (Compound 223)

Step 1: tert-Butyl 2-(3-(azetidin-3-ylamino)propanamido)-3-(thiazolo[4,5-c]pyridin-2-yl)-4,7-dihydrothieno[2,3-c]pyridine-6(5H)-carboxylate

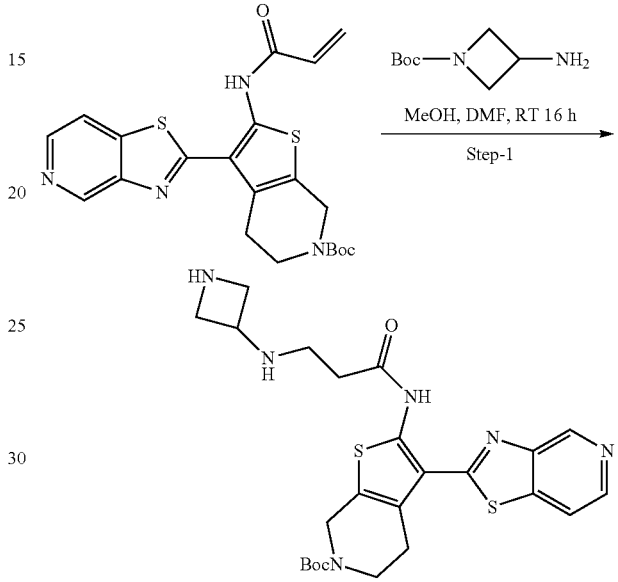

To a solution of 2-(6-(tert-butoxycarbonyl)-2-(3-(isopropylamino)propanamido)-4,5,6,7-tetrahydrothieno[2,3-c]pyridin-3-yl)thiazole-4-carboxylic acid 1 (200 mg, 0.452 mmol) in MeOH:DMF (1:1, 4 mL) was added tert-butyl 3-aminoazetidine-1-carboxylate (154 mg, 0.904 mmol). After the addition, the resulting mixture was stirred at room temperature for 16 h. After completion (monitored by TLC), the reaction mixture was evaporated to dryness resulting in a crude residue as thick oil. The crude compound was purified by silica gel column chromatography eluting with 0-5% methanol in DCM to afford the title compound as brown semi-solid (200 mg, 72% yield).

Step 2: 3-(Azetidin-3-ylamino)-N-(3-(thiazolo[4,5-c]pyridin-2-yl)-4,5,6,7-tetrahydrothieno[2,3-c]pyridin-2-yl)propanamide (Compound 223)

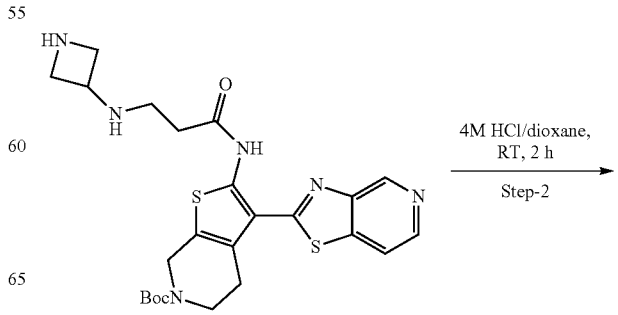

-continued

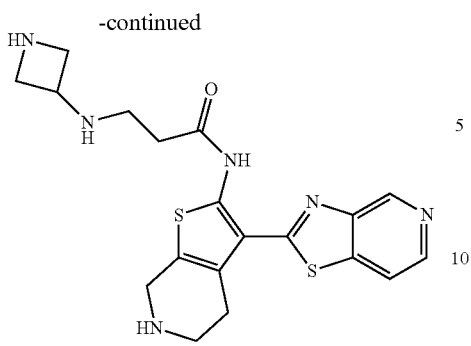

To a solution of tert-butyl 2-(3-(azetidin-3-ylamino)propanamido)-3-(thiazolo[4,5-c]pyridin-2-yl)-4,7-dihydrothieno[2,3-c]pyridine-6(5H)-carboxylate 2 (100 mg, 0.162 mmol) in dioxane (1 mL) at 0° C. was added 4M HCl in dioxane (2 mL). After the addition, the resulting mixture was stirred at room temperature for 2 h. After completion, the reaction mixture was evaporated to dryness and the resulting in a crude residue was purified by trituration in diethyl ether and pentane to afford the HCl salt of the title compound as yellow solid (70 mg HCl salt, 82% yield).

Example 29

Synthesis of 3-(Methylamino)-N-(3-(thiazolo[4,5-c]pyridin-2-yl)-4,5,6,7-tetrahydrothieno[2,3-c]pyridin-2-yl)propanamide (Compound 224)

Step 1: tert-Butyl 2-(3-(methylamino)propanamido)-3-(thiazolo[4,5-c]pyridin-2-yl)-4,7-dihydrothieno[2,3-c]pyridine-6(5H)-carboxylate

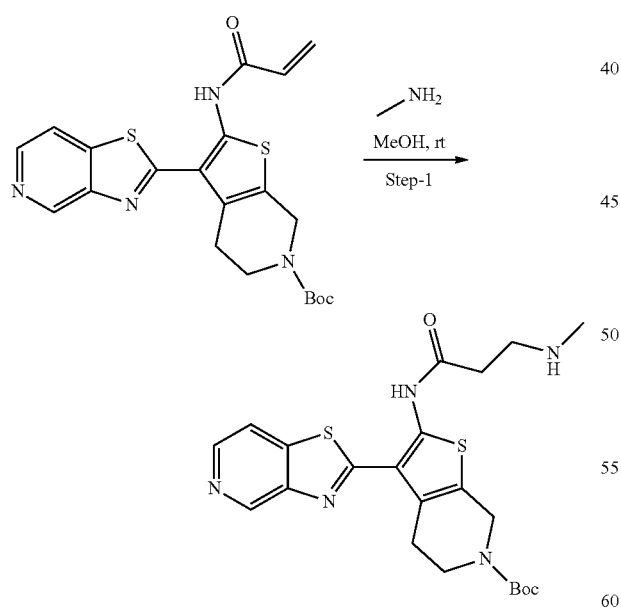

To a solution of tert-butyl 2-acrylamido-3-(thiazolo[4,5-c]pyridin-2-yl)-4,7-dihydrothieno[2,3-c]pyridine-6(5H)-carboxylate (200 mg, 0.452 mmol) in MeOH (2 mL) was added 1M solution of methyl amine in THF (0.9 mL, 0.904 mmol). The resulting reaction mixture was stirred at room temperature for 16 h. Progress of the reaction was monitored by TLC. After completion, the reaction mixture was concentrated to dryness under reduced pressure. The crude compound was purified by column chromatography eluting with 0-5% methanol in CH$_2$Cl$_2$ to afford the title compound as off white solid (80 mg, yield 39%).

Step 2: 3-(Methylamino)-N-(3-(thiazolo[4,5-c]pyridin-2-yl)-4,5,6,7-tetrahydrothieno[2,3-c]pyridin-2-yl)propanamide (Compound 224)

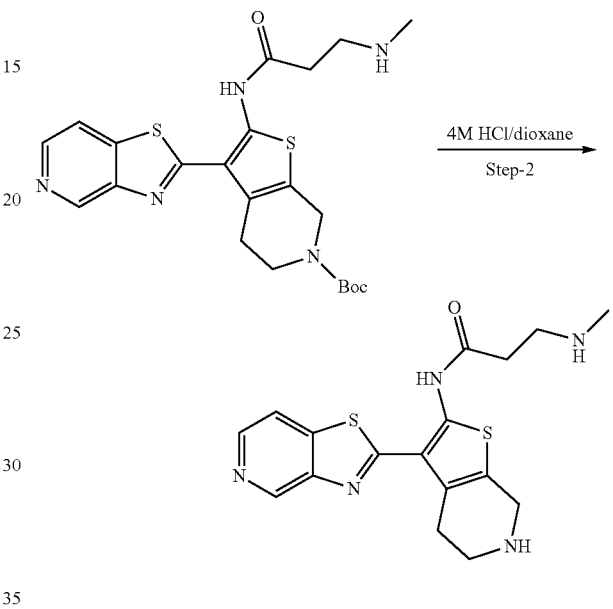

To a solution of tert-butyl 2-(3-(methylamino)propanamido)-3-(thiazolo[4,5-c]pyridin-2-yl)-4,7-dihydrothieno[2,3-c]pyridine-6(5H)-carboxylate 1 (80 mg, 0.168 mmol) in dioxane (2 mL) at 0° C. was added 4M HCl in dioxane (1 mL). After the addition, the resulting mixture was stirred at room temperature for 3 h. After completion, the reaction mixture was evaporated in vacuum resulting in a crude residue which was purified by trituration with methanol. The solid obtained was filtered and washed with diethyl ether and n-pentane to afford the HCl salt of the title compound as yellow solid (75 mg, HCl salt, yield 40%).

Example 30

Synthesis of N-(3-(4,6-dimethylthiazolo[4,5-c]pyridin-2-yl)-4,5,6,7-tetrahydrothieno[2,3-c]pyridin-2-yl)acetamide hydrochloride (Compound 228) and Structurally Related Compounds.

Step 1. 4-Chloro-2,6-dimethylpyridin-3-amine

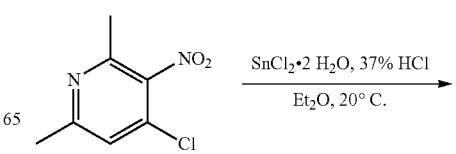

-continued

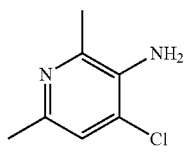

In a 2000 mL round-bottom flask was dissolved 4-chloro-2,6-dimethyl-3-nitropyridine (25.0 g, 134.0 mmol) in Et$_2$O (450 mL). Using an addition funnel, a solution of tin(II) chloride dihydrate (15.1 g, 669.9 mmol) in 37% HCl (134 mL, 1608 mmol) was added at 0-20° C. over 1 h. The resulting suspension was stirred for 3 h at 20° C. and water (150 mL) was added. Most of Et$_2$O was removed under reduced pressure and the resulting suspension was cooled at 0° C. The solid was filtered on Büchner and rinsed with cold water to afford the HCl salt of the desired compound (25.0 g) as a beige solid. A second crop (5.0 g) was obtained from the mother liquor. Both fraction were combined and suspended in MeOH (100 mL). A solution of NH$_4$OH (28% in water, 500 mL) was added and the resulting mixture was extracted with DCM (4×100 mL). Combined organic layers were washed with brine (150 mL), dried over anhydrous MgSO$_4$, filtered and concentrated to afford the title compound (14.9 g, 71% crude yield) as a yellow oil, which was used in the next step without further purification.

Step 2. 4,6-Dimethylthiazolo[4,5-c]pyridine-2(3H)-thione

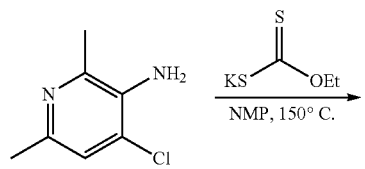

In a 2000 mL round-bottom flask equipped with a condenser under nitrogen were added 4-chloro-2,6-dimethylpyridin-3-amine (14.9 g, 95.2 mmol), potassium ethyl xanthate (30.5 g, 190.3 mmol) and NMP (270 mL). The mixture was heated in a 150° C. oil bath for 3.5 h and it was allowed to cool down at 20° C. Using a pH-meter, the solution was acidified to pH 1.4 with 1N HCl (400 mL). The mixture was washed with DCM (3×100 mL) and the pH of the aqueous layer was adjusted 6.6 with 5N NaOH (80 mL). The resulting suspension was filtered and the solid was rinsed with water (50 mL). Residual water was removed on high vacuum to afford the title compound (15.3 g, 82% crude yield) as a pale orange solid, which was used in the next step without further purification.

Step 3. 2-Chloro-4,6-dimethylthiazolo[4,5-c]pyridine

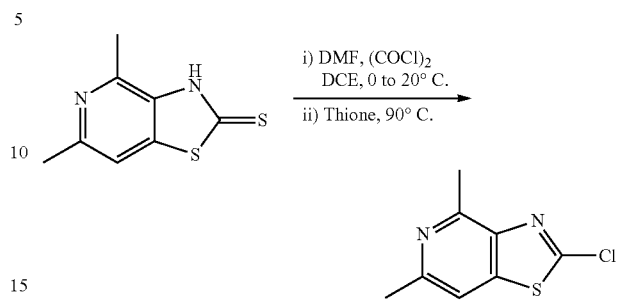

In a 2000 mL round-bottom flask under nitrogen were added DMF (13.8 mL, 178.3 mmol) and DCE (510 mL). Oxalyl chloride (15.1 mL, 178.3 mmol) was added dropwise at 0° C. and the white suspension was allowed to stir at 20° C. for 1 h. 4,6-Dimethylthiazolo[4,5-c]pyridine-2(3H)-thione (14.0 g, 71.3 mmol) was then added directly to the reaction mixture and the flask was mounted with a condenser. The suspension was heated in a 90° C. oil bath for 2.5 h and it was allowed to cool down at 20° C. After cooling at 0° C., the suspension was filtered and the solid was rinsed with DCE (75 mL). The HCl salt of the desired product was suspended in MeOH (25 mL) and EtOAc (250 mL). An aqueous solution of NaHCO$_3$ (350 mL) and water (100 mL) were added and the mixture was extracted with EtOAc (3×100 mL). The combined organic layers were washed with brine (75 mL), dried over anhydrous MgSO$_4$, filtered and concentrated. Trituration of the crude material with DCM (2×10 mL) followed by the removal of a volatile impurity on high vacuum afforded the title compound (13.1 g, 92%) as a brown solid.

Step 4. 2-(4,6-Dimethylthiazolo[4,5-c]pyridin-2-yl)acetonitrile

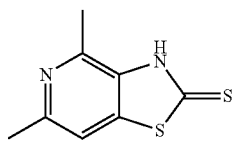

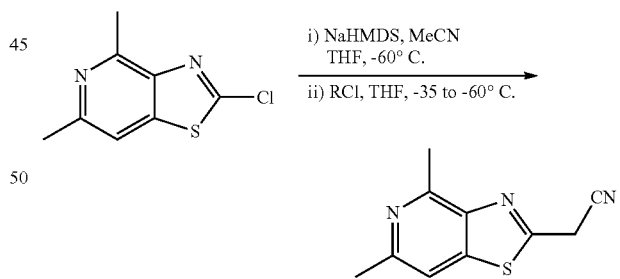

In a 1000 mL round-bottom flask equipped with a temperature probe were added NaHMDS (109 mL, 108.7 mmol) and THF (120 mL) under nitrogen. The solution was cooled at −60 OC. MeCN (5.7 mL, 108.7 mmol) was added dropwise and the mixture was stirred at the same temperature for 50 min. A solution of 2-chloro-4,6-dimethylthiazolo[4,5-c]pyridine (7.20 g, 36.2 mmol) in THF (50 mL) was then cannulated to the reaction flask over 5 min and the resulting mixture was stirred at −35/−60° C. for 40 min. A saturated aqueous solution of NH$_4$Cl (500 mL) and water (100 mL) were then added. The resulting mixture was extracted with EtOAc (3×100 mL) and the combined organic layers were washed with an aqueous solution of NH₄Cl (250 mL), water (200 mL), brine (200 mL), dried over anhydrous MgSO₄, filtered and concentrated. Trituration of the crude material with EtOAc (2×5 mL) afforded the title compound (6.73 g, 91%) as a brown solid.

Step 5. tert-Butyl 2-amino-3-(4,6-dimethylthiazolo[4,5-c]pyridin-2-yl)-4,5-dihydrothieno[2,3-c]pyridine-6(7H)-carboxylate

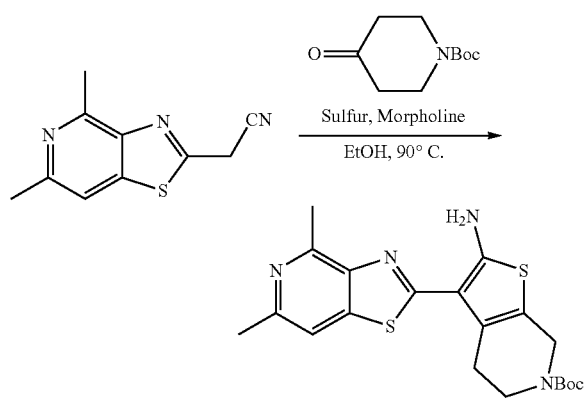

2-(4,6-Dimethylthiazolo[4,5-c]pyridin-2-yl)acetonitrile (6.73 g, 33.1 mmol), N-Boc-4-piperidone (6.60 g, 33.1 mmol) and sulfur (1.06 g, 33.1 mmol) were charged in a 1000 mL round-bottom flask equipped with a condenser under nitrogen. EtOH (220 mL) and morpholine (2.9 mL, 33.1 mmol) were successively added and the resulting mixture was stirred 14 h in a 90° C. oil bath. The obtained suspension was allowed to cool down at 20° C. and the solid was filtered on Büchner, rinsed with cold EtOH and air dried to afford the title compound (12.4 g, 90%) as a light beige solid.

Step 6. tert-Butyl 2-acetamido-3-(4,6-dimethylbenzo[d]thiazol-2-yl)-4,5-dihydrothieno[2,3-c]pyridine-6(7H)-carboxylate

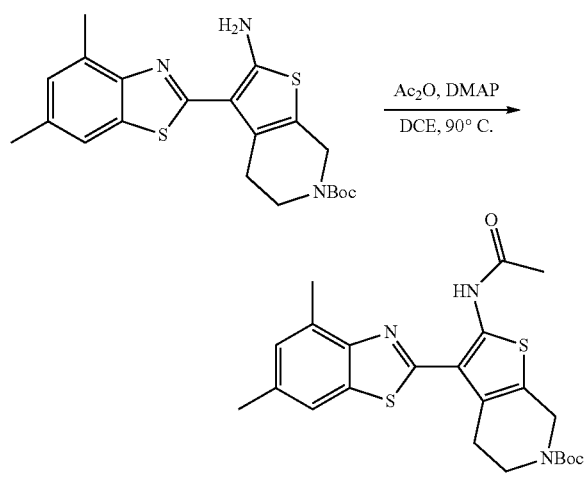

tert-Butyl 2-amino-3-(4,6-dimethylthiazolo[4,5-c]pyridin-2-yl)-4,5-dihydrothieno[2,3-c]pyridine-6(7H)-carboxylate (5.00 g, 12.0 mmol), DMAP (4.40 g, 36.0 mmol), DCE (92 mL) and acetic anhydride (2.3 mL, 24.0 mmol) were successively added in a 250 mL round-bottom flask equipped with a condenser. The reaction mixture was stirred in a 90° C. oil bath for 2 h. The resulting solution was allowed to cool down at 20° C. and N,N-dimethylethylenediamine (2 mL) was added. After 30 min, the suspension was dissolved with DCM (400 mL) and the mixture was washed with a saturated solution of aqueous NH₄Cl (2×150 mL), a saturated aqueous solution of NaHCO₃ (100 mL), brine (100 mL), dried over anh. MgSO₄, filtrated and concentrated. Trituration of the crude material with Et₂O (50 mL) afforded the title compound (5.30 g, 96%) as a light yellow solid.

Step 7. N-(3-(4,6-Dimethylthiazolo[4,5-c]pyridin-2-yl)-4,5,6,7-tetrahydrothieno[2,3-c]pyridin-2-yl)acetamide (Compound 228)

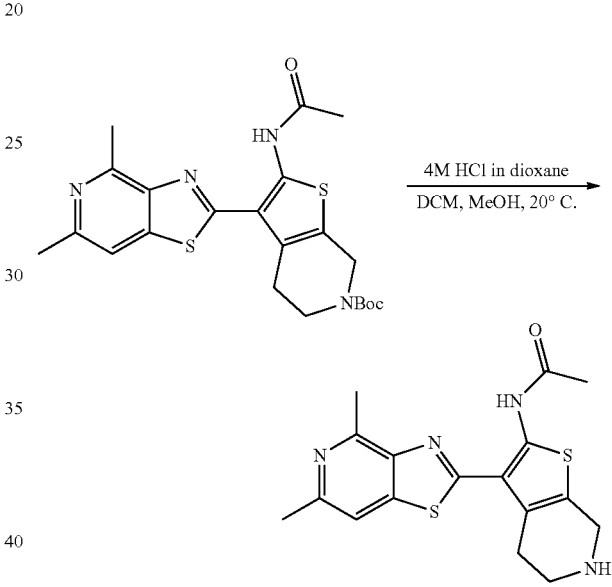

A solution of HCl (4 N in dioxane, 65 mL, 261.7 mmol) was added to a solution of tert-butyl 2-acetamido-3-(4,6-dimethylbenzo[d]thiazol-2-yl)-4,5-dihydrothieno[2,3-c]pyridine-6(7H)-carboxylate (4.00 g, 8.72 mmol) in DCM (79 mL) and MeOH (79 mL). The reaction mixture was stirred at 20° C. for 4 h and it was diluted with Et₂O (50 mL). The precipitated solid was collected by filtration and washed with Et₂O. Recrystallization of the material (water/isopropanol) afforded the title compound (2.23 g, 65%) as a yellowish solid.

Similar protocols were used to synthesize N-(3-(4,6-Dimethylthiazolo[4,5-c]pyridin-2-yl)-4,5,6,7-tetrahydrothieno[2,3-c]pyridin-2-yl)-3-(isopropylamino)propanamide dihydrochloride (Compound 225), N-(3-(4,6-Dimethylthiazolo[4,5-c]pyridin-2-yl)-4,5,6,7-tetrahydrothieno[2,3-c]pyridin-2-yl)-3-((2-methoxyethyl)amino)propanamide dihydrochloride (Compound 227), and, starting from 2-chlorothiazolo[4,5-b]pyridine, 3-(isopropylamino)-N-(3-(thiazolo[4,5-b]pyridin-2-yl)-4,5,6,7-tetrahydrothieno[2,3-c]pyridin-2-yl)propanamide dihydrochloride (Compound 220). The final deprotection of all compounds was been performed using 4N HCl in dioxane to afford the title compound.

Example 31

Synthesis of (R)—N-(6-ethyl-7-methyl-3-(thiazolo[4,5-c]pyridin-2-yl)-4,5,6,7-tetrahydrothieno[2,3-c]pyridin-2-yl)acetamide (Compound 229), (R)—N-(6-ethyl-5-methyl-3-(thiazolo[4,5-c]pyridin-2-yl)-4,5,6,7-tetrahydrothieno[2,3-c]pyridin-2-yl)acetamide (Compound 230), (S)—N-(6-ethyl-5-methyl-3-(thiazolo[4,5-c]pyridin-2-yl)-4,5,6,7-tetrahydrothieno[2,3-c]pyridin-2-yl)acetamide (Compound 231), and (S)—N-(6-ethyl-7-methyl-3-(thiazolo[4,5-c]pyridin-2-yl)-4,5,6,7-tetrahydrothieno[2,3-c]pyridin-2-yl)acetamide (Compound 232)

Step 1: tert-butyl-2-amino-5-methyl-3-(thiazolo[4,5-c]pyridin-2-yl) 4,7-dihydrothieno[2,3-c]pyridine-6(5H)-carboxylate and tert-butyl 2-amino-7-methyl-3-(thiazolo[4,5-c]pyridin-2-yl)-4,7-dihydrothieno[2,3-c]pyridine-6(5H)-carboxylate Step 2: tert-butyl 2-acetamido-5-methyl-3-(thiazolo[4,5-c]pyridin-2-yl)-4,7-dihydrothieno[2,3-c]pyridine-6(5H)-carboxylate and tert-butyl 2-acetamido-7-methyl-3-(thiazolo[4,5-c]pyridin-2-yl)-4,7-dihydrothieno[2,3-c]pyridine-6(5H)-carboxylate

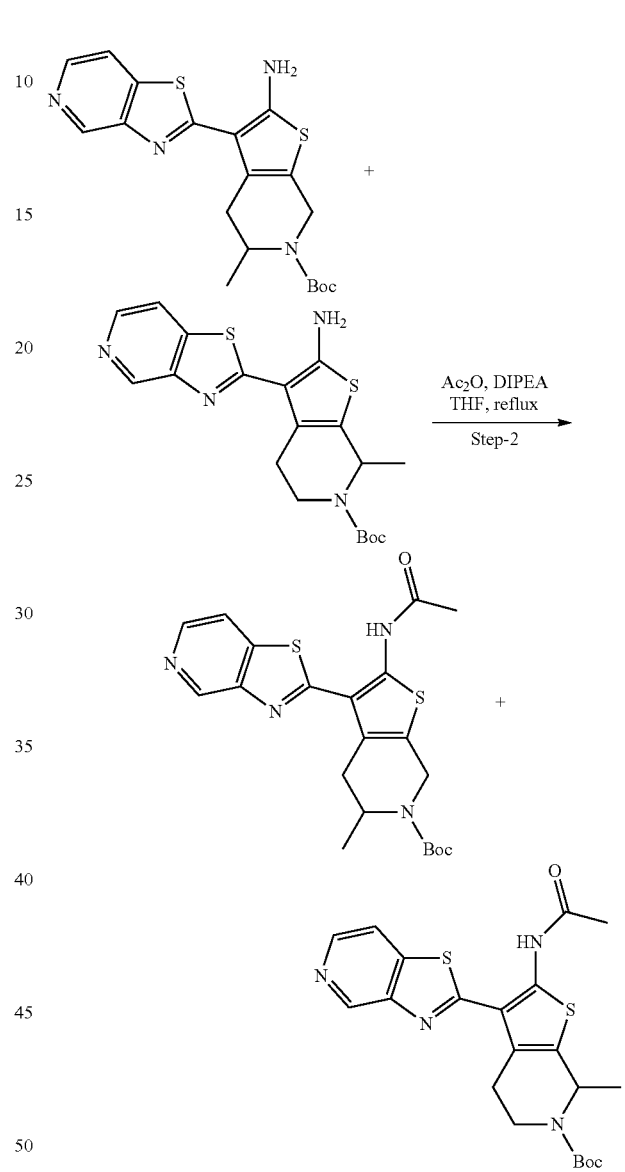

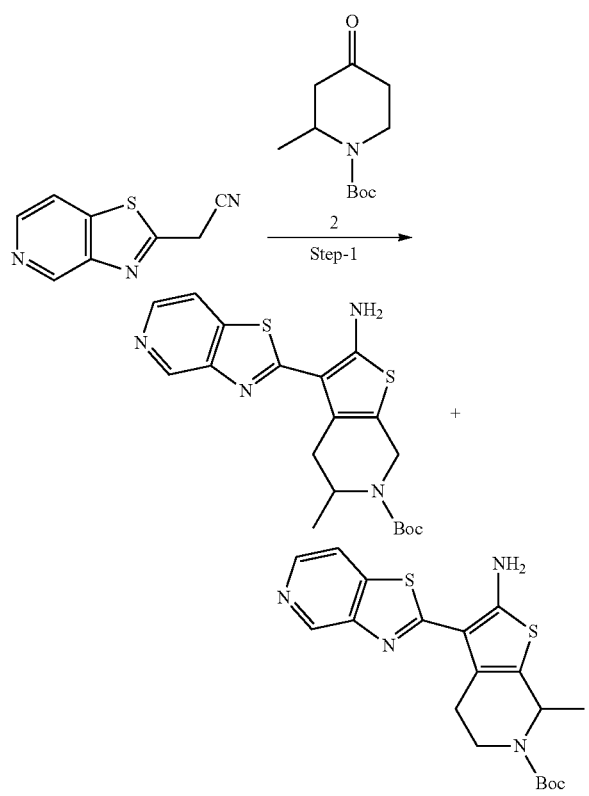

To a solution of 2-(thiazolo[4,5-c]pyridin-2-yl)acetonitrile 1 (0.5 g, 2.85 mmol) in ethanol (10 mL) was added tert-butyl 2-methyl-4-oxopiperidine-1-carboxylate 2 (0.61 g, 2.85 mmol), elemental sulphur (91 mg, 2.85 mmol) and morpholine (0.24 mg, 2.85 mmol) at room temperature and the resulting reaction mixture was heated to reflux at 85° C. for 3 h. Reaction was monitored by TLC. After the completion, reaction mixture was evaporated to dryness on rotavapour and the crude compound was triturated in methanol and dried to afford the mixture of title compounds as brown solid (1.3 g crude).

To a solution of the mixture of products from Step 1 (1.2 g, 2.98 mmol) in THF (10 mL) at 0° C. was added DIPEA (1.02 mL, 5.97 mmol) followed by acetic anhydride (0.45 mL, 4.47 mmol) at room temperature. Reaction mixture was heated under reflux for next 16 h. Reaction was monitored by TLC. After completion, the reaction mixture was evaporated to dryness on rota vapour and the resulting residue was taken in 10% MeOH/CH$_2$Cl$_2$ solution and washed with saturated NaHCO$_3$ solution and brine. The separated organic layer was dried over Na$_2$SO$_4$, filtered and concentrated in vacuum to get a crude residue which was purified by silica gel column chromatography eluting with 0-5% methanol in CH$_2$Cl$_2$ to afford the mixture of title compounds as yellow solid (1.0 g, 76% yield).

177

Step 3: N-(5-methyl-3-(thiazolo[4,5-c]pyridin-2-yl)-4,5,6,7-tetrahydrothieno[2,3-c]pyridin-2-yl)acetamide hydrochloride and N-(7-methyl-3-(thiazolo[4,5-c]pyridin-2-yl)-4,5,6,7-tetrahydrothieno[2,3-c]pyridin-2-yl)acetamide hydrochloride

178

Step 4: N-(6-ethyl-5-methyl-3-(thiazolo[4,5-c]pyridin-2-yl)-4,5,6,7-tetrahydrothieno[2,3-c]pyridin-2-yl)acetamide and N-(6-ethyl-7-methyl-3-(thiazolo[4,5-c]pyridin-2-yl)-4,5,6,7-tetrahydrothieno[2,3-c]pyridin-2-yl)acetamide

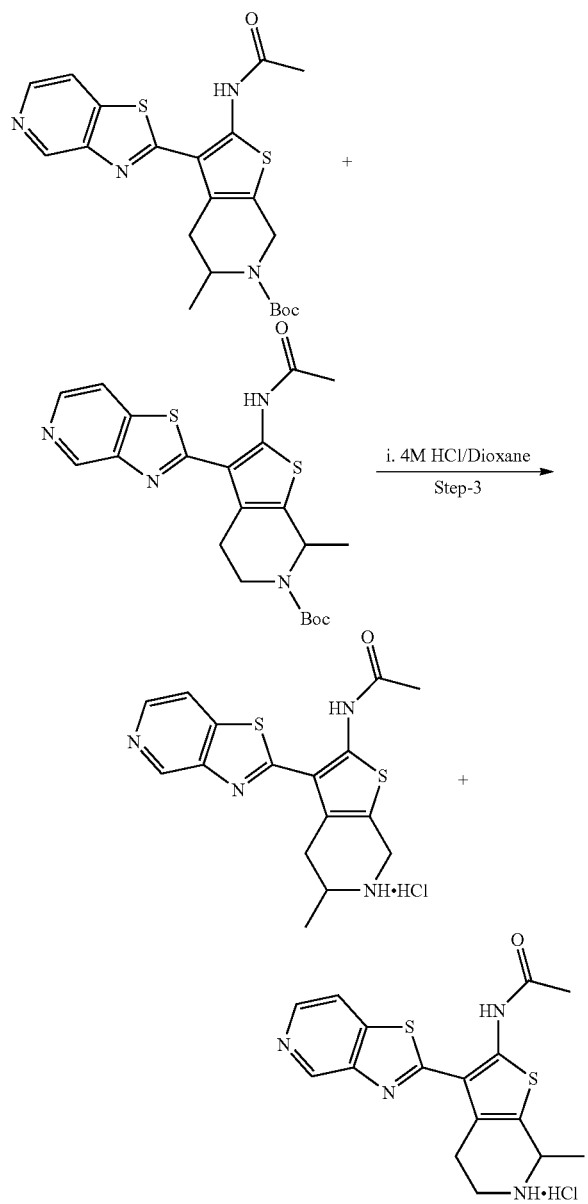

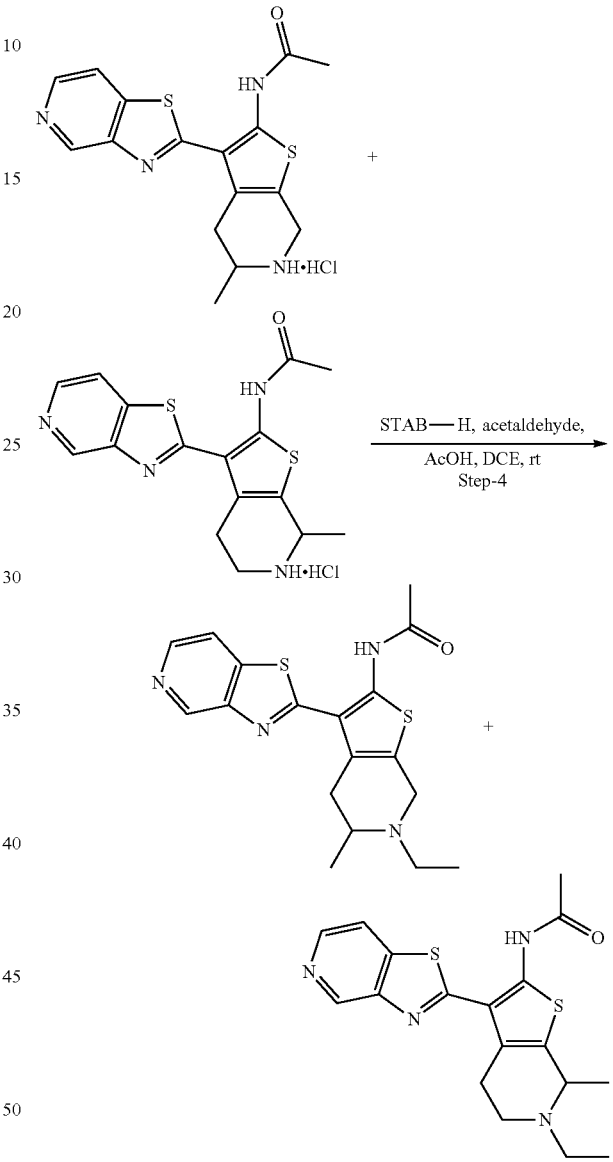

To a solution of the mixture of compounds from Step 2 (1.0 g, 2.25 mmol) in dioxane (10 mL) at 0° C. was added 4M HCl in dioxane (10 mL) and the reaction mixture was stirred at room temperature for 4 h. After completion of the reaction (monitored by TLC), the reaction mixture was evaporated to dryness on rotavapour and residue was purified by trituration in ether and pentane to give mixture of title compounds as HCl salts (800 mg, 96% yield).

To the solution of products from Step 3 (500 mg, 1.34 mmol) in CH$_2$Cl$_2$ (10 mL) triethylamine (0.28 mL, 2.02 mmol) was added. Reaction was stirred at room temperature for 1 h. Followed by addition of acetic acid (0.16 mL, 2.69 mmol) and acetaldehyde (0.11 g, 2.69 mmol) to the reaction mixture at room temperature and stirred for 2 h. The reaction mixture was cooled to 10 to 15° C. and sodium triacetoxyborohydride (1.09 g, 4.05 mmol) was added. Reaction mixture was stirred at room temperature for 16 h. The reaction was monitored by TLC. After the completion, the reaction mixture was diluted with water (15 mL) and extracted with dichloromethane (3×10 mL). The combined organic solvents were dried over Na$_2$SO$_4$ and evaporated in vacuum resulting in the crude compound. The crude compound was purified using silica gel flash column chromatography eluting with 0-5% methanol in CH₂Cl₂ to afford mixture of title compounds (300 mg, yield 60%) as yellow solid.

This mixture of compounds was purified by chiral preparative HPLC separation (YMC CHIRALART—CELLULOSE SC; 250 mm*4.6 mm*5 um; Mobile Phase: A: n-Hexane+0.1% TEA; B: ETOH: DCM (85:15)+0.1% TEA; Flow rate: 1.0 ml/min; Isocratic: 30% B) to afford Compound 231 (20 mg), Compound 230 (27 mg), Compound 229 (53 mg) and Compound 232 (56 mg).

Example 32

Synthesis of (S)-3-(Benzyl(sec-butyl)amino)-N-(3-(thiazolo[4,5-c]pyridin-2-yl)-4,5,6,7-tetrahydrothieno[2,3-c]pyridin-2-yl)propanamide hydrochloride (Compound 233)

Step 1: (S)—N-benzylbutan-2-amine

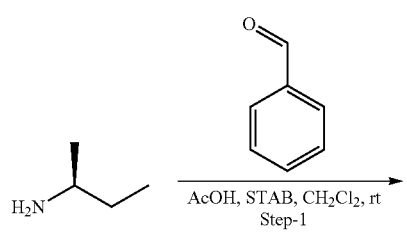

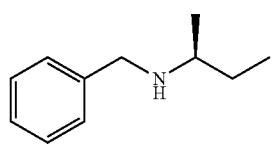

To a solution of (S) 2-amino butane 1 (0.13 g, 1.88 mmol) in CH₂Cl₂ (15 mL) at 0° C. was added benzaldehyde (0.1 g, 9.43 mmol) followed by acetic acid (0.1 mL) at room temperature. Reaction was stirred at room temperature for 2 hr. Sodium triacetoxy borohydride (0.6 g, 2.83 mmol) was added at 10° C. Reaction was stirred at room temperature for 16 h. Progress of the reaction was monitored by TLC. After completion, the reaction mixture was quenched with saturated solution of sodium carbonate and extracted with ethyl acetate (thrice). The combined organic layer was dried over anhydrous Na₂SO₄; filtered and concentrated under reduced pressure to afford the title compound as colourless oil (0.1 g, 66.6%).

Step 2: tert-Butyl (S)-2-(3-(benzyl(sec-butyl)amino)propanamido)-3-(thiazolo[4,5-c]pyridin-2-yl)-4,7-dihydrothieno[2,3-c]pyridine-6(5H)-carboxylate

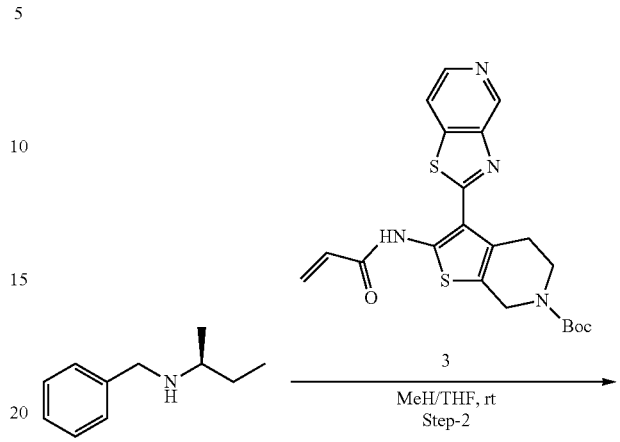

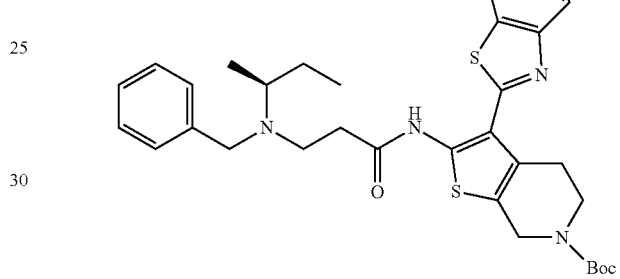

To a solution of tert-butyl 2-acrylamido-3-(thiazolo[4,5-c]pyridin-2-yl)-4,7-dihydrothieno[2,3-c]pyridine-6(5H)-carboxylate 3 (200 mg, 0.45 mmol) in MeOH:DMF (1:1, 10 mL) was added (S)—N-benzylbutan-2-amine (2) (148 mg, 0.902 mmol). The resulting reaction mixture was heated at 50° C. for 16 h. Progress of the reaction was monitored by TLC. After completion, the reaction mixture was concentrated to dryness under reduced pressure to obtain crude product. The crude compound was purified by column chromatography eluting with 0-5% methanol in CH₂Cl₂ to afford the title compound as yellow solid (200 mg, yield 74%).

Step 3: (S)-3-(benzyl(sec-butyl)amino)-N-(3-(thiazolo[4,5-c]pyridin-2-yl)-4,5,6,7-tetrahydrothieno[2,3-c]pyridin-2-yl)propanamide hydrochloride (Compound 233)

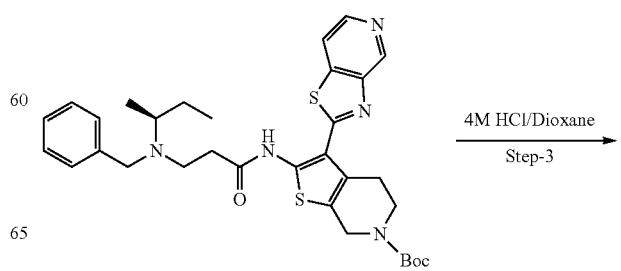

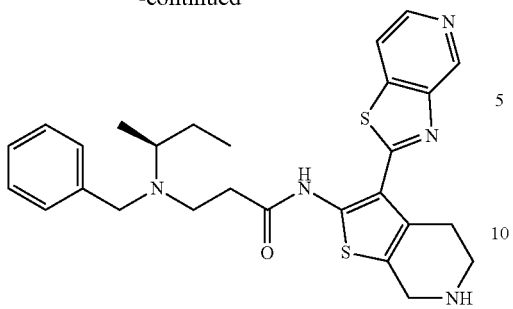

To a solution of tert-butyl (S)-2-(3-(benzyl(sec-butyl)amino)propanamido)-3-(thiazolo[4,5-c]pyridin-2-yl)-4,7-dihydrothieno[2,3-c]pyridine-6(5H)-carboxylate (4) (30 mg, 0.049 mmol) in dioxane (1 mL) at 0° C. was added 4M HCl in dioxane (1 mL). After the addition, the resulting mixture was stirred at room temperature for 3 h. After completion, the reaction mixture was evaporated in vacuum resulting in a crude residue which was purified by trituration with methanol. The solid obtained was filtered and washed with diethyl ether and n-pentane to afford the HCl salt of the title compound as yellow solid (25 mg, yield 78%).

Example 33

Synthesis of 3-(((S)-sec-butyl)amino)-N—((S)-4-methyl-3-(thiazolo[4,5-c]pyridin-2-yl)-4,5,6,7-tetrahydrothieno[2,3-c]pyridin-2-yl)propanamide (Compound 240) and 3-(((S)-sec-butyl)amino)-N—((S)-7-methyl-3-(thiazolo[4,5-c]pyridin-2-yl)-4,5,6,7-tetrahydrothieno[2,3-c]pyridin-2-yl)propanamide (Compound 234)

Step 1: tert-Butyl (S)-2-amino-5-methyl-3-(thiazolo[4,5-c]pyridin-2-yl)-4,7-dihydrothieno[2,3-c]pyridine-6(5H)-carboxylate and tert-Butyl (S)-2-amino-7-methyl-3-(thiazolo[4,5-c]pyridin-2-yl)-4,7-dihydrothieno[2,3-c]pyridine-6(5H)-carboxylate

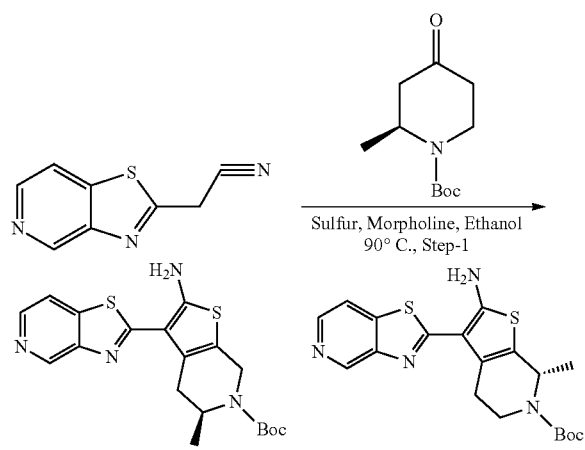

To a solution of 2-(thiazolo[4,5-c]pyridin-2-yl)acetonitrile (2.0 g, 11.4 mmol), elemental sulphur (0.36 g, 11.4 mmol) and morpholine (0.99 mL, 11.4 mmol) in ethanol (20 mL) was added tert-butyl (S)-2-methyl-4-oxopiperidine-1-carboxylate (2.43 g, 11.4 mmol) at room temperature and the resulting reaction mixture was heated to reflux at 85° C. for 3 h. Reaction was monitored by TLC. After the completion, reaction mixture was evaporated to dryness on rotavapour and the crude compound was purified by silica gel column chromatography. Product was eluted in 5% methanol in CH$_2$Cl$_2$ to afford the pure title compounds as brown solid (5.0 g, qunt. %).

Step-2: tert-butyl (S)-2-acrylamido-5-methyl-3-(thiazolo[4,5-c]pyridin-2-yl)-4,7-dihydrothieno[2,3-c]pyridine-6(5H)-carboxylate and tert-butyl (S)-2-acrylamido-7-methyl-3-(thiazolo[4,5-c]pyridin-2-yl)-4,7-dihydrothieno[2,3-c]pyridine-6(5H)-carboxylate

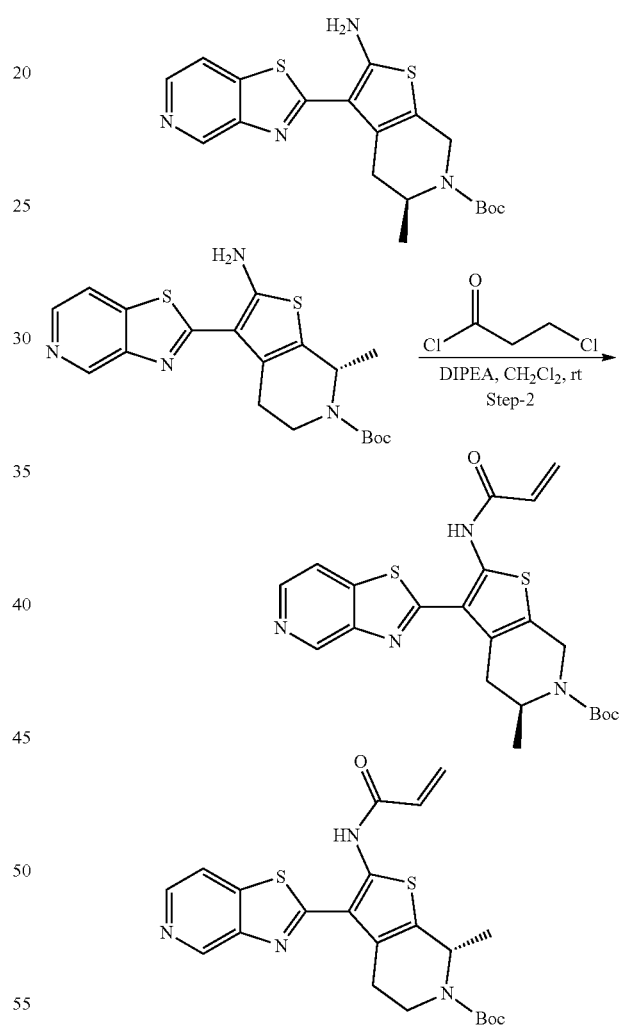

To a solution of mixture of the products from step 1 (1.0 g, 2.48 mmol) in CH$_2$Cl$_2$ (10 mL) at 0° C. was added N-methyl morpholine (0.62 g, 6.21 mmol) Followed by 3-chloro propionyl chloride (0.47 g, 3.73 mmol). Reaction mixture was stirred at room temperature for 3 h. Reaction was monitored by TLC. After completion, the reaction mixture was diluted with CH$_2$Cl$_2$ and washed with saturated NaHCO$_3$ solution and brine. The separated organic layer was dried over Na$_2$SO$_4$, filtered and concentrated in vacuum. Crude compound was purified by silica gel column chromatography. Product was eluted in 5% methanol in CH₂Cl₂ to afford the title compounds as brown solids (0.5 g, 98%).

Step 3: tert-Butyl (S)-2-(3-(((S)-sec-butyl)amino) propanamido)-5-methyl-3-(thiazolo[4,5-c]pyridin-2-yl)-4,7-dihydrothieno[2,3-c]pyridine-6(5H)-carboxylate and tert-Butyl (S)-2-(3-(((S)-sec-butyl)amino) propanamido)-7-methyl-3-(thiazolo[4,5-c]pyridin-2-yl)-4,7-dihydrothieno[2,3-c]pyridine-6(5H)-carboxylate

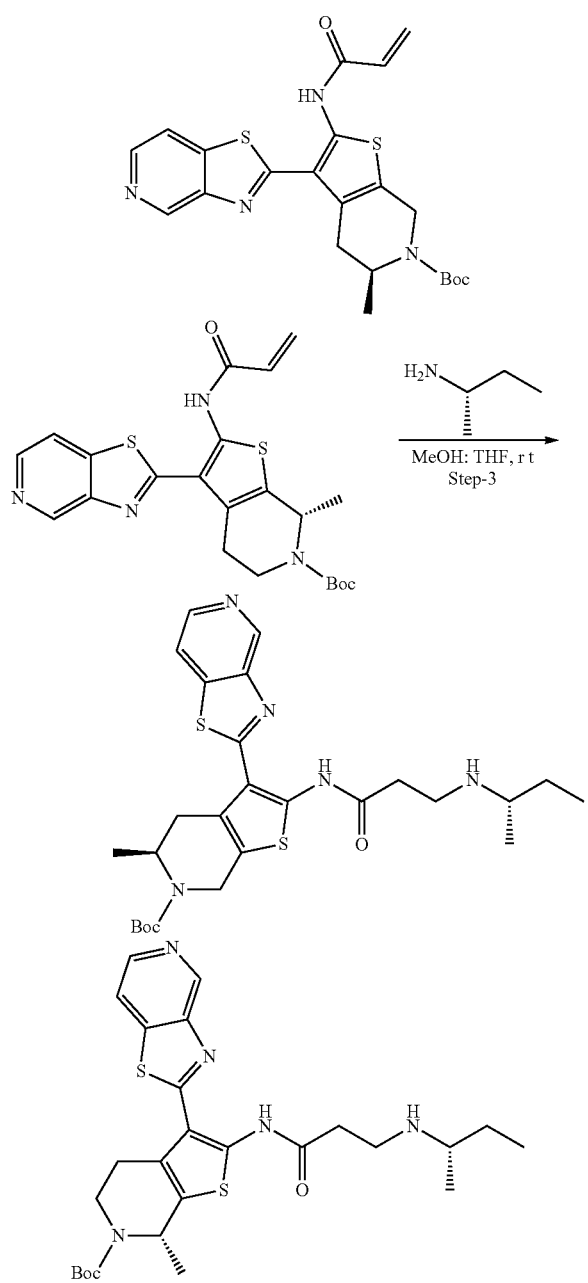

To a solution of a mixture of the products from step 2 (0.2 g, 0.43 mmol) in MeOH (2 mL) was added (S)-2-aminobutane (0.0075 mL, 0.657 mmol). The resulting reaction mixture was stirred at room temperature for 16 h. Progress of the reaction was monitored by TLC. After completion, the reaction mixture was concentrated to dryness under reduced pressure. The crude residue was dissolved in CH₂Cl₂ and washed with water. The combined organic layers were dried with anhydrous Na₂SO₄, filtered and concentrated to get a crude residue. This crude compound was purified by silica gel column chromatography eluting with 0-10% methanol in CH₂Cl₂ to afford title compounds as yellow solid (0.2 g, yield 86.9%).

Step 5: 3-(((S)-sec-butyl)amino)-N—((S)-4-methyl-3-(thiazolo[4,5-c]pyridin-2-yl)-4,5,6,7-tetrahydrothieno[2,3-c]pyridin-2-yl)propanamide (Compound 240) and 3-(((S)-sec-butyl)amino)-N—((S)-7-methyl-3-(thiazolo[4,5-c]pyridin-2-yl)-4,5,6,7-tetrahydrothieno[2,3-c]pyridin-2-yl)propanamide (Compound 234)

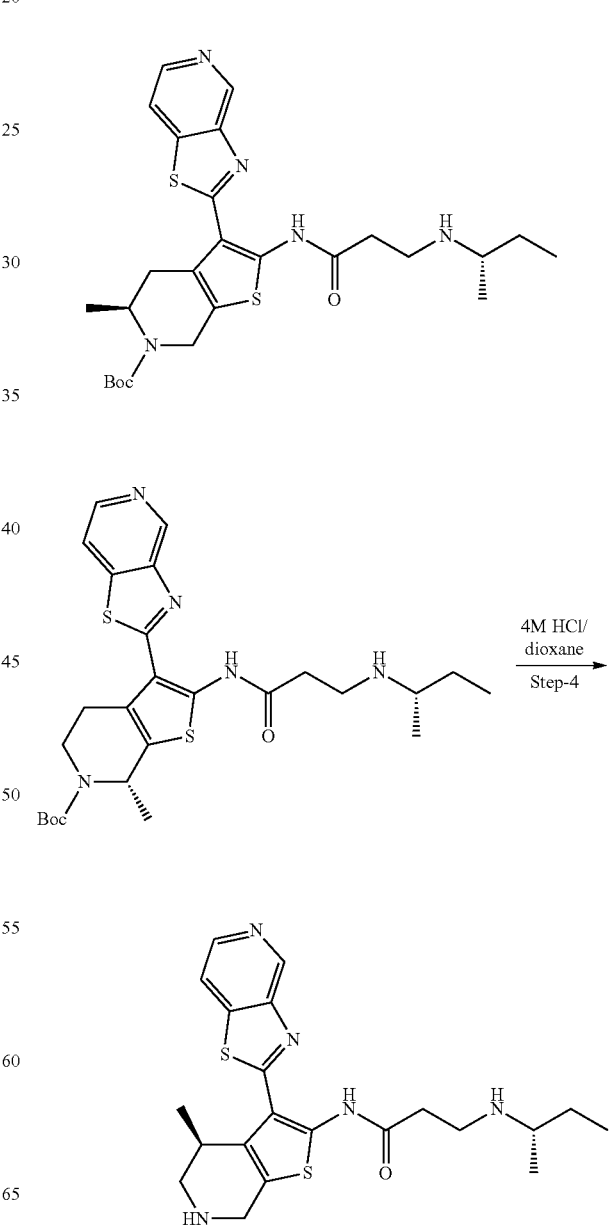

-continued

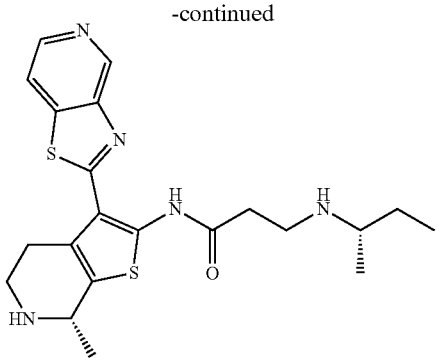

To a solution of mixture of products from step 4 (200 mg, 0.378 mmol) in dioxane (1 mL) at 0° C. was added 4M HCl in dioxane (5 mL). After the addition, the resulting mixture was stirred at room temperature for 3 h. After completion, the reaction mixture was evaporated in vacuum resulting in a crude residue which was purified by triturating with methanol. The solid obtained was filtered and washed with diethyl ether and n-pentane to afford a mixture of title compounds as yellow solid (180 mg). This mixture of compounds was purified by preparative HPLC separation (Column: YMC CHIRAL AMYLOSE-SA, 250 mm*4.6 mm, 5 um; Mobile Phase: A: 0.1% TEA in n-hexane; B: 0.1% TEA in ETOH:DCM (85:15); Flow rate:1.0 ml/min; Isocratic 50% B) to afford Compound 240 (25 mg, 12.5%) and Compound 234 (11.6 mg, 5.84%) as yellow solids.

Example 34

Synthesis of N-((5R,7R)-3-(4-(difluoromethyl)thi-azolo[4,5-c]pyridin-2-yl)-6-ethyl-5,7-dimethyl-4,5,6,7-tetrahydrothieno[2,3-c]pyridin-2-yl)acetamide (Compound 235)

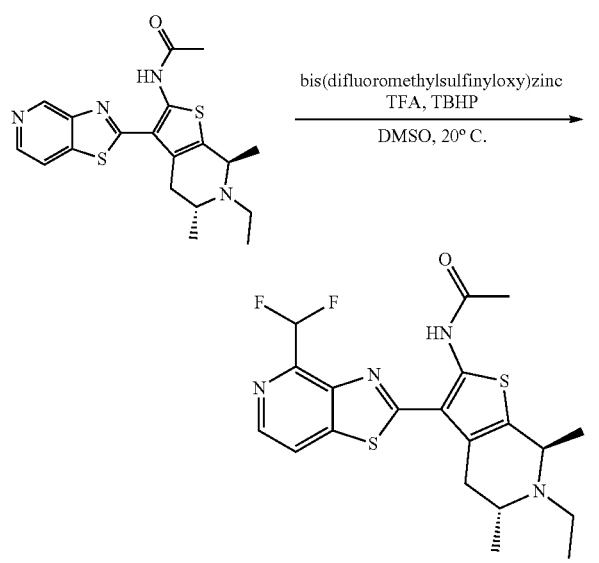

N-[(5R,7R)-6-ethyl-5,7-dimethyl-3-thiazolo[4,5-c]pyridin-2-yl-5,7-dihydro-4H-thieno[2,3-c]pyridin-2-yl]acetamide (5 mg, 0.0100 mmol) and bis(difluoromethylsulfinyloxy)zinc (15.29 mg, 0.0500 mmol) were dissolved in DMSO (150 uL). 2,2,2-trifluoroacetic acid (1 OL, 0.0100 mmol) was added, followed by tert-Butyl hydroperoxide (0.1 mL, 0.1000 mmol) and the reaction was stirred in a capped vial at 20° C. for 2 hours. LC/MS indicated complete reaction and the reaction mixture was purified by reverse phase MPLC (C18, 0-100% MeCN in H₂O, 0.1% TFA) to afford N-[(5R,7R)-3-[4-(difluoromethyl)thiazolo[4,5-c]pyridin-2-yl]-6-ethyl-5,7-dimethyl-5,7-dihydro-4H-thieno[2,3-c]pyridin-2-yl]acetamide (2.1 mg, 0.0048 mmol, 37.188% yield) as a yellow solid.

Example 35

Synthesis of tert-butyl (5R,7S)-2-acetamido-5,7-dimethyl-3-(thiazolo[4,5-c]pyridin-2-yl)-4,7-dihydrothieno[2,3-c]pyridine-6(5H)-carboxylate and tert-butyl Compound 237) and (5S,7R)-2-acetamido-5,7-dimethyl-3-(thiazolo[4,5-c]pyridin-2-yl)-4,7-dihydrothieno[2,3-c]pyridine-6(5H)-carboxylate (Compound 236)

Step 1: N-(5,7-dimethyl-3-(thiazolo[4,5-c]pyridin-2-yl)-4,5,6,7-tetrahydrothieno[2,3-c]pyridin-2-yl)acetamide

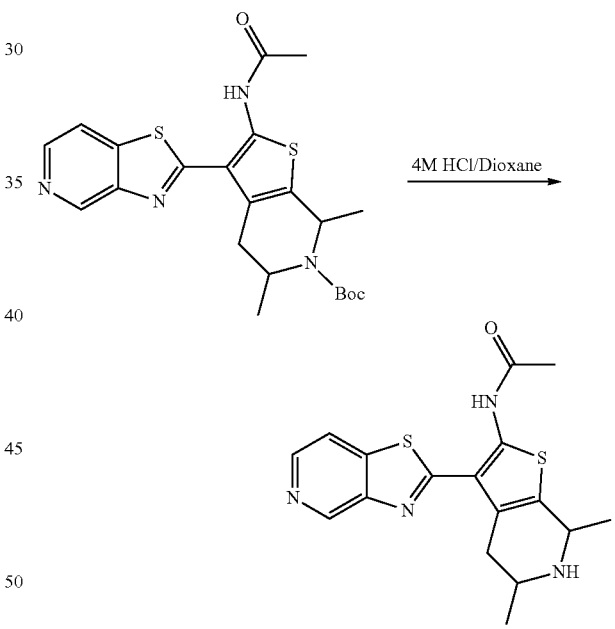

To a solution of tert-butyl 2-acetamido-5,7-dimethyl-3-(thiazolo[4,5-c]pyridin-2-yl)-4,7-dihydrothieno[2,3-c]pyridine-6(5H)-carboxylate 6 (0.5 g, 1.09 mmol) in dioxane (5 mL) at 0° C. was added 4M HCl in dioxane (5 mL). After the addition, the resulting mixture was stirred at room temperature for 2 h. After completion, the reaction mixture was evaporated to dryness and the resulting in a crude residue which was purified by triturating with ether to afford the title compound as brown solid (0.5 g, HCl salt,).

Step 2. Chiral Separation

The racemic compound from step 1 was purified by preparative HPLC separation to afford Compound 236 (40 mg) and Compound 237 (35 mg), as well as Compound 110 (30 mg) and Compound 111 (40 mg) all as yellow solids.

Example 36

Synthesis of (S)-3-(sec-butylamino)-N-(6-ethyl-3-(thiazolo[4,5-c]pyridin-2-yl)-4,5,6,7-tetrahydrothieno[2,3-c]pyridin-2-yl)propanamide (Compound 238)

Step 1: 3-(Benzo[d]thiazol-2-yl)-6-ethyl-4,5,6,7-tetrahydrothieno[2,3-c]pyridin-2-amine

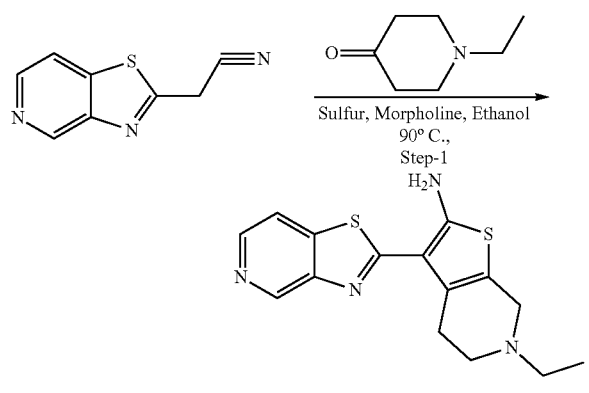

To a solution of 2-(benzo[d]thiazol-2-yl)acetonitrile 1 (500 mg, 2.85 mmol), elemental sulphur (91 mg, 2.85 mmol) and morpholine (0.248 mL, 2.85 mmol) in ethanol (5 mL) was added 1-ethyl-4-oxo-piperidine (360 mg, 2.85 mmol) at room temperature. The resulting solution was heated to reflux at 85° C. for 3 h. After the completion (monitored by TLC), the reaction mixture was evaporated to dryness on rotavapour. The crude compound was triturated in methanol and dried to afford the pure title compound as brown solid (700 mg, 77.7%).

Step 2: N-(6-ethyl-3-(thiazolo[4,5-c]pyridin-2-yl)-4,5,6,7-tetrahydrothieno[2,3-c]pyridin-2-yl)acrylamide

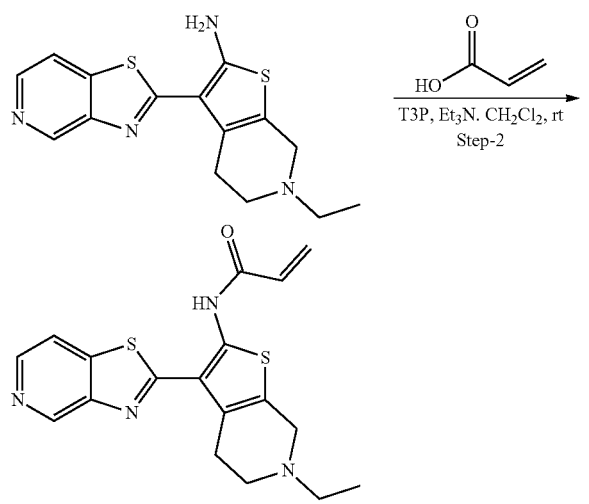

To a solution of triethyl amine (2.5 mL, 18.2 mmol) in $CH_2Cl_2$ (5 mL) at 0° C. was added acrylic acid (1.2 mL, 16.6 mmol) followed by $T_3P$ (1.5 mL, 2.22 mmol). The reaction mixture was stirred at room temperature for 1 h. Followed by addition of 3-(benzo[d]thiazol-2-yl)-6-ethyl-4,5,6,7-tetrahydrothieno[2,3-c]pyridin-2-amine 2 (300 mg, 9.49 mmol) at room temperature stirred for 16 h. After completion (monitored by TLC), the reaction mixture was diluted with $CH_2Cl_2$ and washed with saturated $NaHCO_3$ solution and brine. The separated organic layer was dried over $Na_2SO_4$, filtered and concentrated in vacuum to get a crude title compound as brown solid (400 mg, crude).

Step 3: (S)-3-(sec-butylamino)-N-(6-ethyl-3-(thiazolo[4,5-c]pyridin-2-yl)-4,5,6,7-tetrahydrothieno[2,3-c]pyridin-2-yl)propanamide (Compound 238)

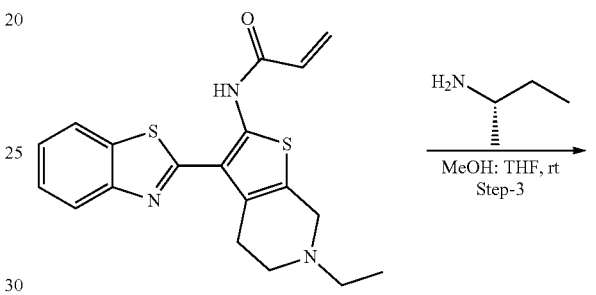

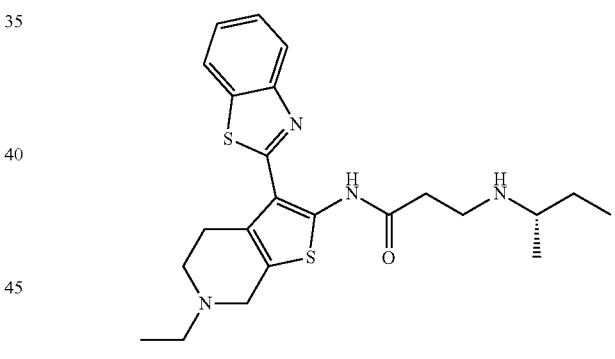

To a solution of N-(6-ethyl-3-(thiazolo[4,5-c]pyridin-2-yl)-4,5,6,7-tetrahydrothieno[2,3-c]pyridin-2-yl)acrylamide 3 (0.40 g, 1.07 mmol) in methanol (5 mL) was added (S) 2 aminobutane (0.16 g, 2.08 mmol). The resulting reaction mixture was stirred at room temperature for 16 h. Progress of the reaction was monitored by TLC. After completion, the reaction mixture was concentrated to dryness under reduced pressure. The crude residue was dissolved in $CH_2Cl_2$ and washed with water. The combined organic layers were dried with anhydrous $Na_2SO_4$, filtered and concentrated to get a crude residue. This crude compound was purified by silica gel column chromatography eluting with 0-10% methanol in $CH_2Cl_2$ to afford title compound as a yellow solid TFA salt (70 mg, yield 14.58%).

Example 37

Synthesis of (S)-3-(sec-butylamino)-N-(6-isopropyl-3-(thiazolo[4,5-c]pyridin-2-yl)-4,5,6,7-tetrahydrothieno[2,3-c]pyridin-2-yl)propanamide (Compound 239)

Step 1: 3-(Benzo[d]thiazol-2-yl)-6-isopropyl-4,5,6,7-tetrahydrothieno[2,3-c]pyridin-2-amine

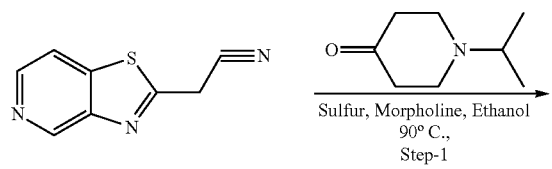

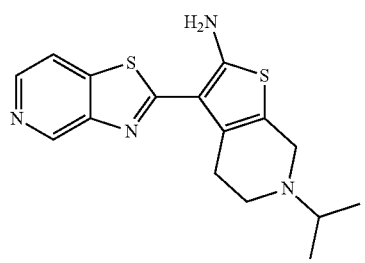

To a solution of 2-(benzo[d]thiazol-2-yl)acetonitrile (500 mg, 2.85 mmol), elemental sulphur (91 mg, 2.85 mmol) and morpholine (0.248 mL, 2.85 mmol) in ethanol (5 mL) was added 1-isopropyl-4-oxo-piperidine (400 mg, 2.85 mmol) at room temperature and the resulting reaction mixture was heated to reflux at 85° C. for 3 h. Reaction was monitored by TLC. After the completion, reaction mixture was evaporated to dryness on rotavapour and the crude compound was triturated in methanol and dried to afford the pure title compound as brown solid (800 mg, 85%).

Step 2: N-(6-Isopropyl-3-(thiazolo[4,5-c]pyridin-2-yl)-4,5,6,7-tetrahydrothieno[2,3-c]pyridin-2-yl)acrylamide

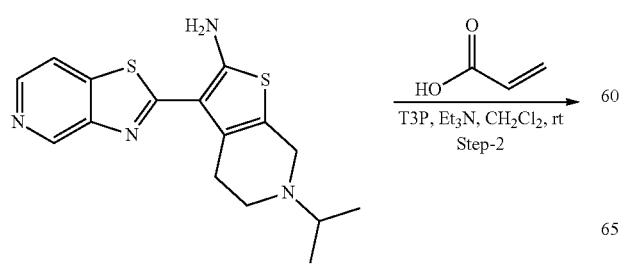

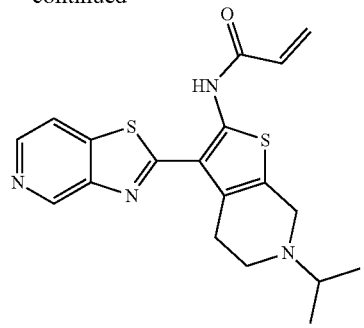

To a solution of triethyl amine (1.2 mL, 8.74 mmol) in $CH_2Cl_2$ (5 mL) at was 0 OC added acrylic acid (2.5 mL, 34.6 mmol) followed by $T_3P$ (1.5 mL, 2.35 mmol). Reaction was stirred at room temperature for 1 hr. Followed by addition of 3-(benzo[d]thiazol-2-yl)-6-ethyl-4,5,6,7-tetrahydrothieno[2,3-c]pyridin-2-amine (300 mg, 0.91 mmol) at room temperature and stirred at room temperature for another 16 h. Reaction was monitored by TLC. After completion, the reaction mixture was diluted with $CH_2Cl_2$ and washed with saturated $NaHCO_3$ solution and brine. The separated organic layer was dried over anhydrous $Na_2SO_4$, filtered and concentrated in vacuum to get a crude title compound as brown solid (400 mg, crude).

Step 3: (S)-3-(sec-butylamino)-N-(6-isopropyl-3-(thiazolo[4,5-c]pyridin-2-yl)-4,5,6,7-tetrahydrothieno[2,3-c]pyridin-2-yl)propanamide (Compound 239)

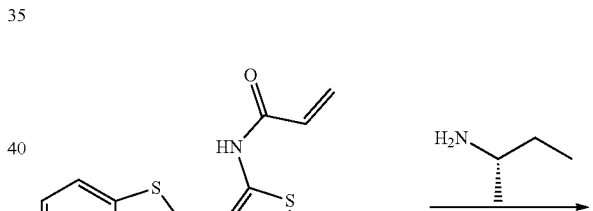

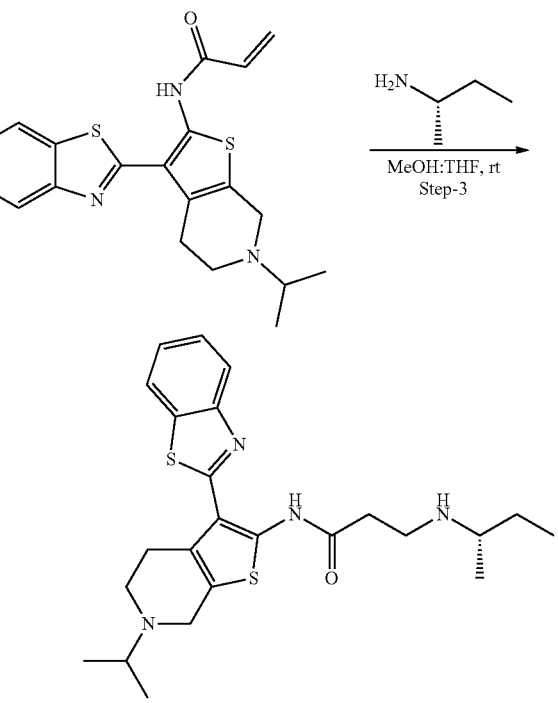

To a solution of N-(6-isopropyl-3-(thiazolo[4,5-c]pyridin-2-yl)-4,5,6,7-tetrahydrothieno[2,3-c]pyridin-2-yl)acrylamide 3 (0.40 g, 1.04 mmol) in methanol (5 mL) was added (S) 2 aminobutane (0.15 g, 2.08 mmol). The resulting reaction mixture was stirred at room temperature for 16 h. Progress of the reaction was monitored by TLC. After completion, the reaction mixture was concentrated to dryness under reduced pressure. The crude residue was dissolved in CH$_2$Cl$_2$ and washed with water. The combined organic layers were dried with anhydrous Na$_2$SO$_4$, filtered and concentrated to get a crude residue. This crude compound was purified by silica gel column chromatography eluting with 0-10% methanol in DCM to afford title compound as yellow solid TFA salt (200 mg, yield 42.55%).

Example 38

Synthesis of 3-(((S)-sec-butyl)amino)-N—((R)-5-methyl-3-(thiazolo[4,5-c]pyridin-2-yl)-4,5,6,7-tetrahydrothieno[2,3-c]pyridin-2-yl)propanamide (Compound 242) and 3-(((S)-sec-butyl)amino)-N—((R)-7-methyl-3-(thiazolo[4,5-c]pyridin-2-yl)-4,5,6,7-tetrahydrothieno[2,3-c]pyridin-2-yl)propanamide (Compound 241)

Step 1: tert-Butyl (R)-2-amino-5-methyl-3-(thiazolo[4,5-c]pyridin-2-yl)-4,7-dihydrothieno[2,3-c]pyridine-6(5H)-carboxylate and tert-Butyl (R)-2-amino-7-methyl-3-(thiazolo[4,5-c]pyridin-2-yl)-4,7-dihydrothieno[2,3-c]pyridine-6(5H)-carboxylate

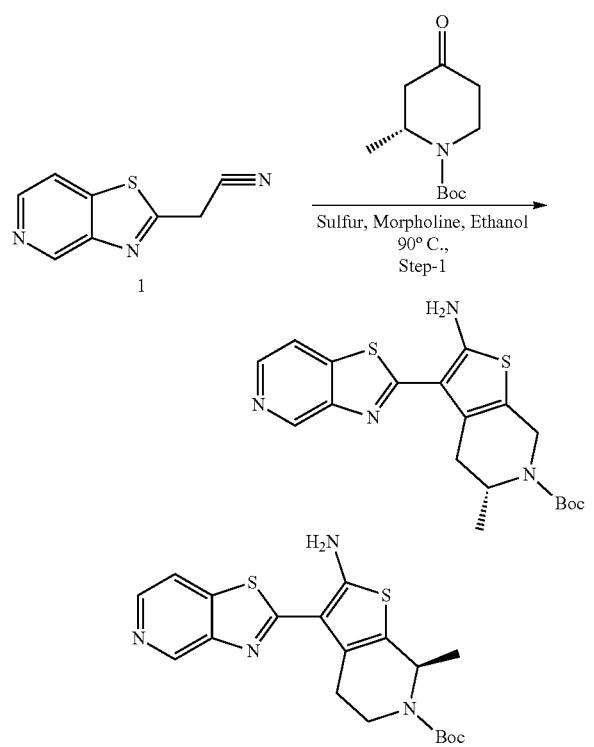

To a solution of 2-(thiazolo[4,5-c]pyridin-2-yl)acetonitrile 1 (2 g, 11.42 mmol), elemental sulphur (360 mg, 11.42 mmol) and morpholine (1 mL, 11.42 mmol) in ethanol (40 mL) was added tert-butyl (R)-2-methyl-4-oxopiperidine-1-carboxylate (2.43 g, 11.42 mmol) at room temperature and the resulting reaction mixture was heated to reflux at 85° C. for 3 h. Reaction was monitored by TLC. After the completion, reaction mixture was evaporated to dryness on rotavapour and the crude compound was purified by silica gel column chromatography. Product was eluted in 5% methanol in CH$_2$Cl$_2$ to afford a mixture of the pure title compounds as brown solid (4.3 g, yield 93%).

Step 2: tert-Butyl (R)-2-acrylamido-5-methyl-3-(thiazolo[4,5-c]pyridin-2-yl)-4,7-dihydrothieno[2,3-c]pyridine-6(5H)-carboxylate (4) and tert-Butyl (R)-2-acrylamido-7-methyl-3-(thiazolo[4,5-c]pyridin-2-yl)-4,7-dihydrothieno[2,3-c]pyridine-6(5H)-carboxylate

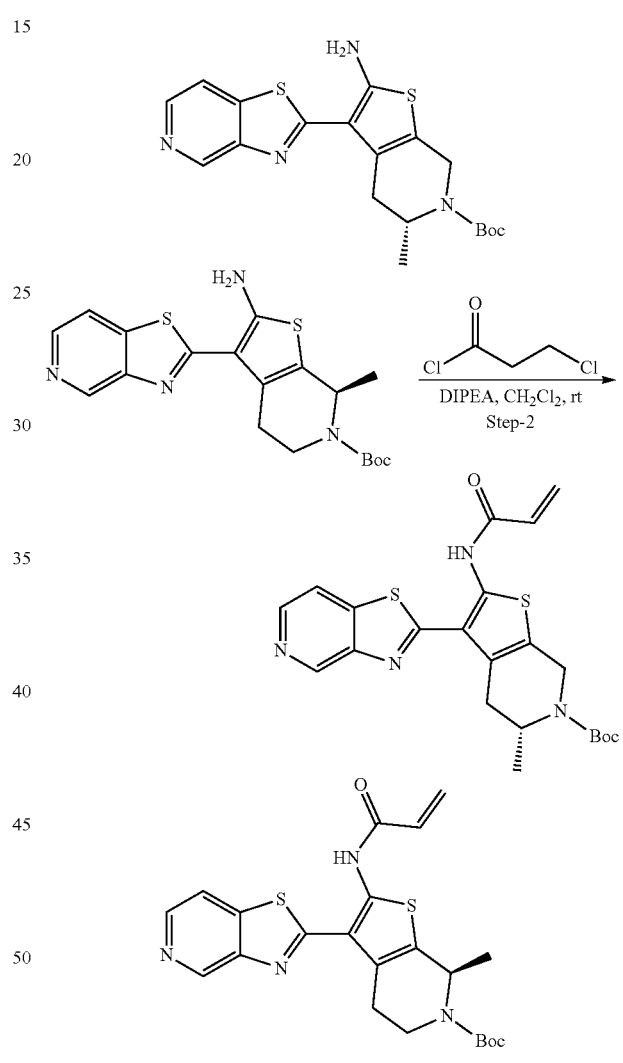

To a solution of products from Step 1 (1g, 2.57 mmol) in CH$_2$Cl$_2$ (10 mL) at 0° C. was added N-methyl morpholine (0.65 g, 6.44 mmol) followed by 3-chloropropionyl chloride (0.49 g, 3.86 mmol). Reaction mixture was stirred at room temperature for 3 h. Reaction was monitored by TLC. After completion, the reaction mixture was diluted with CH$_2$Cl$_2$ and washed with saturated NaHCO$_3$ solution and brine. The separated organic layer was dried over Na$_2$SO$_4$, filtered and concentrated in vacuum. Crude compound was purified by silica gel column chromatography. Product was eluted in 5% methanol in CH$_2$Cl$_2$ to afford a mixture of the title compounds as brown solid (0.6 g, 51.28%).

Step 3: tert-Butyl (R)-2-(3-(((S)-sec-butyl)amino)
propanamido)-5-methyl-3-(thiazolo[4,5-c]pyridin-2-
yl)-4,7-dihydrothieno[2,3-c]pyridine-6(5H)-carboxy-
late and tert-Butyl (R)-2-(3-(((S)-sec-butyl)amino)
propanamido)-7-methyl-3-(thiazolo[4,5-c]pyridin-2-
yl)-4,7-dihydrothieno[2,3-c]pyridine-6(5H)-
carboxylate

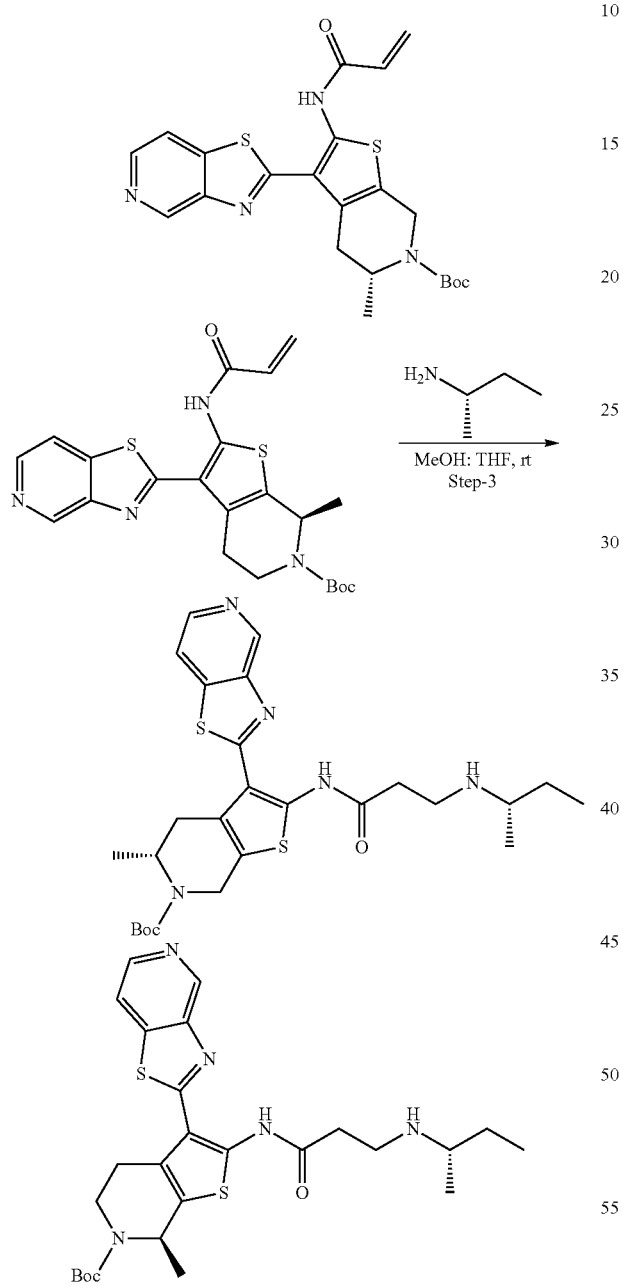

To the products from Step 2 (0.25 g, 0.548 mmol) in MeOH: THF (1:1 6 mL) was added (S) 2 aminobutane (48 mg, 0.657 mmol). The resulting reaction mixture was stirred at room temperature for 16 h. Progress of the reaction was monitored by TLC. After completion, the reaction mixture was concentrated to dryness under reduced pressure. The crude residue was dissolved in $CH_2Cl_2$ and washed with water. The combined organic layers were dried with anhydrous $Na_2SO_4$, filtered and concentrated to get a crude residue. This crude compound was purified by silica gel column chromatography eluting with 0-10% methanol in $CH_2Cl_2$ to afford a mixture of the title compounds as yellow solid (0.21 g, yield 72.41%).

Step 4: 3-(((S)-sec-butyl)amino)-N—((R)-5-methyl-
3-(thiazolo[4,5-c]pyridin-2-yl)-4,5,6,7-tetrahydroth-
ieno[2,3-c]pyridin-2-yl)propanamide (Compound
242) and 3-(((S)-sec-butyl)amino)-N—((R)-7-
methyl-3-(thiazolo[4,5-c]pyridin-2-yl)-4,5,6,7-tetra-
hydrothieno[2,3-c]pyridin-2-yl)propanamide (Com-
pound 241)

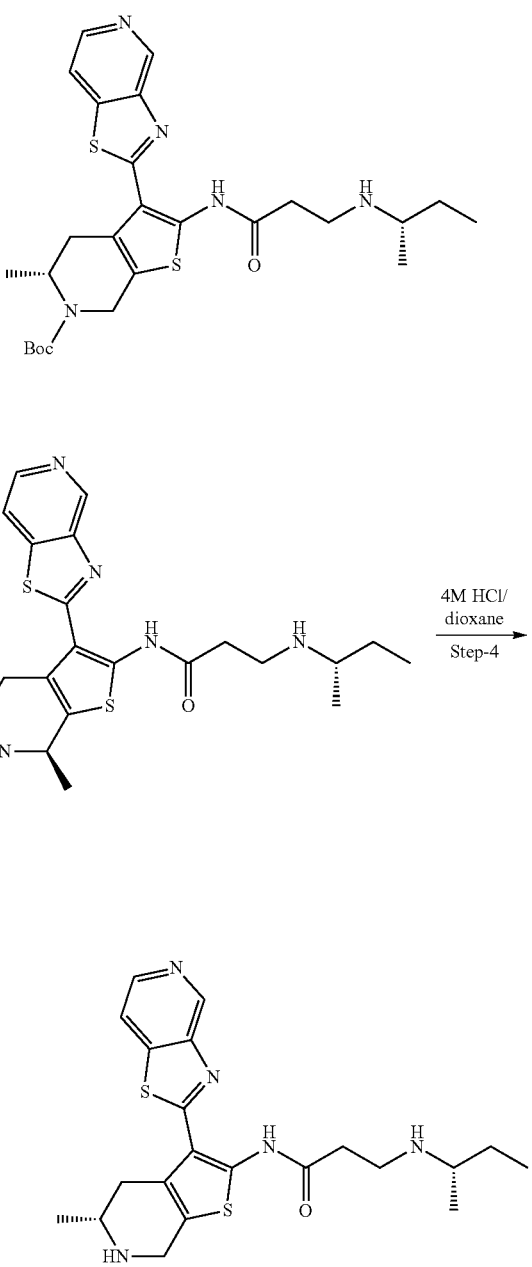

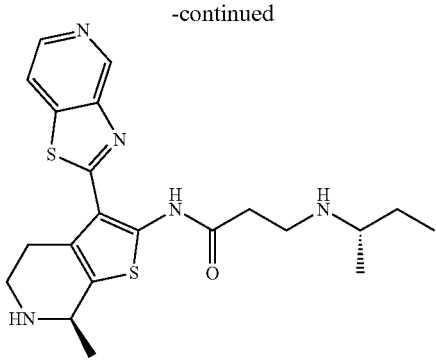

To a solution of the products from Step 3 (210 mg, 0.378 mmol) in dioxane (3 mL) at 0° C. was added 4M HCl in dioxane (2 mL). After the addition, the resulting mixture was stirred at room temperature for 3 h. After completion, the reaction mixture was evaporated in vacuum resulting in a crude residue which was purified by triturating with methanol. The solid obtained was filtered and washed with diethyl ether and n-pentane to afford a mixture of the title compounds as yellow solid (180 mg). This mixture of compounds was purified by preparative HPLC separation (CHIRALART—CELLULOSE SC; 250 mm*4.6 mm*5 um; Mobile Phase: A: n-Hexane+0.1% TEA; B: ETOH: DCM (85:15)+0.1% TEA; Flow rate: 1.0 ml/min; Isocratic: 10% B) to afford the separated title compounds (28 mg) as yellow solids.

Example 39

Synthesis of N—((S)-7-methyl-3-(thiazolo[4,5-c]pyridin-2-yl)-4,5,6,7-tetrahydrothieno[2,3-c]pyridin-2-yl)-3-(((3aR,5s,6aS)-octahydrocyclopenta[c]pyrrol-5-yl)amino)propanamide (Compound 246) and N—((S)-5-methyl-3-(thiazolo[4,5-c]pyridin-2-yl)-4,5,6,7-tetrahydrothieno[2,3-c]pyridin-2-yl)-3-(((3aR,5s,6aS)-octahydrocyclopenta[c]pyrrol-5-yl)amino)propanamide (Compound 247)

Step 1: tert-butyl (S)-7-methyl-2-(3-(((3aR,5s,6aS)-octahydrocyclopenta[c]pyrrol-5-yl)amino)propanamido)-3-(thiazolo[4,5-c]pyridin-2-yl)-4,7-dihydrothieno[2,3-c]pyridine-6(5H)-carboxylate and tert-butyl (S)-5-methyl-2-(3-(((3aR,5s,6aS)-octahydrocyclopenta[c]pyrrol-5-yl)amino)propanamido)-3-(thiazolo[4,5-c]pyridin-2-yl)-4,7-dihydrothieno[2,3-c]pyridine-6(5H)-carboxylate

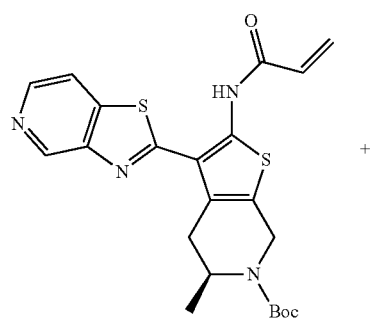 +

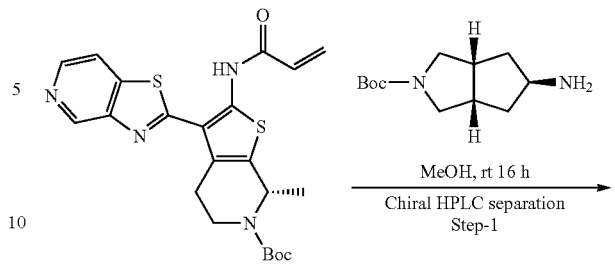

To the indicated starting compounds (250 mg, 0.548 mmol) in MeOH (5 mL) was added tert-butyl (3aR,5s,6aS)-5-aminohexahydrocyclopenta[c]pyrrole-2(1H)-carboxylate (180 mg, 0.822 mmol). The resulting reaction mixture was stirred at room temperature for 16 h. Progress of the reaction was monitored by TLC. After completion, the reaction mixture was concentrated to dryness under reduced pressure. The crude residue was dissolved in CH$_2$Cl$_2$ and washed with water. The combined organic layers were dried with anhydrous Na$_2$SO$_4$, filtered and concentrated to get a crude residue. This crude compound was purified by silica gel column chromatography eluting with 0-5% methanol in CH$_2$Cl$_2$ to afford mixture of title compounds as yellow solids (150 mg).

This mixture of compounds from Step 1 was purified by chiral HPLC separation (Column: Amylose-SA, 250 mm*4.6 mm, 5 um; Mobile Phase: A: 0.1% DEA in n-Hexane; B: 0.1% DEA in Ethanol: DCM (50:50); Flow rate: 1.0 ml/min; Isocratic: 20% B) to afford the separated title compounds as yellow solids.

Step 2a: N—((S)-7-methyl-3-(thiazolo[4,5-c]pyridin-2-yl)-4,5,6,7-tetrahydrothieno[2,3-c]pyridin-2-yl)-3-(((3aR,5s,6aS)-octahydrocyclopenta[c]pyrrol-5-yl)amino)propanamide (Compound 246)

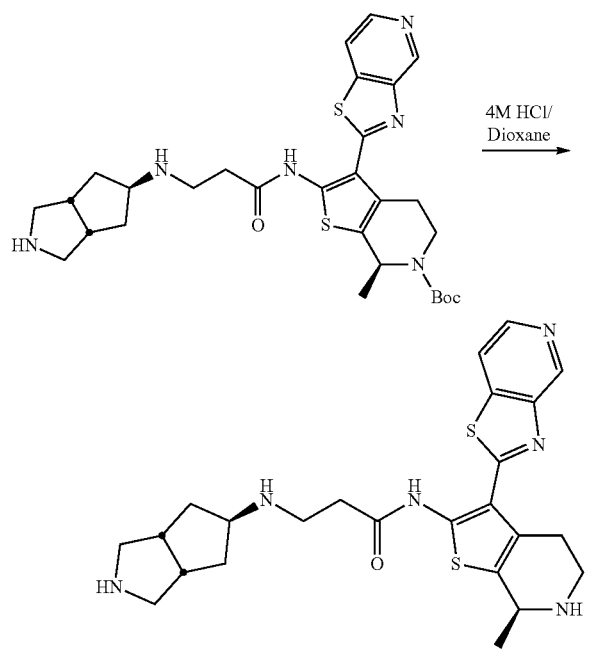

To a solution of tert-butyl (S)-7-methyl-2-(3-(((3aR,5s,6aS)-octahydrocyclopenta[c]pyrrol-5-yl)amino)propanamido)-3-(thiazolo[4,5-c]pyridin-2-yl)-4,7-dihydrothieno[2,3-c]pyridine-6(5H)-carboxylate 6 (20 mg, 0.029 mmol) in dioxane (1 mL) at 0° C. was added 4M HCl in dioxane (1 mL). After the addition, the resulting mixture was stirred at room temperature for 2 h. After completion, the reaction mixture was evaporated in vacuum resulting in a crude residue which was purified by trituration with methanol. The solid obtained was filtered and washed with diethyl ether and n-pentane to afford the title compound as yellow solid (15 mg, yield 86%).

Step 2b: N—((S)-5-methyl-3-(thiazolo[4,5-c]pyridin-2-yl)-4,5,6,7-tetrahydrothieno[2,3-c]pyridin-2-yl)-3-(((3aR,5s,6aS)-octahydrocyclopenta[c]pyrrol-5-yl)amino)propanamide (Compound 247)

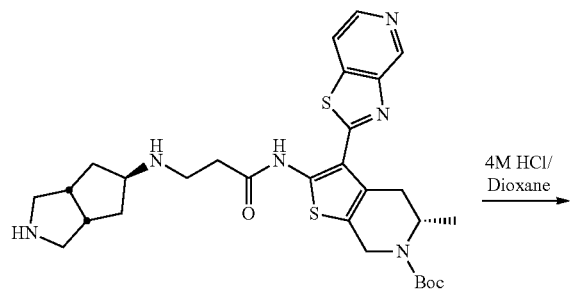

To a solution of tert-butyl (S)-5-methyl-2-(3-(((3aR,5s,6aS)-octahydrocyclopenta[c]pyrrol-5-yl)amino)propanamido)-3-(thiazolo[4,5-c]pyridin-2-yl)-4,7-dihydrothieno[2,3-c]pyridine-6(5H)-carboxylate 7 (40 mg, 0.058 mmol) in dioxane (1 mL) at 0° C. was added 4M HCl in dioxane (2 mL). After the addition, the resulting mixture was stirred at room temperature for 2 h. After completion, the reaction mixture was evaporated in vacuum resulting in a crude residue which was purified by trituration with methanol. The solid obtained was filtered and washed with diethyl ether and n-pentane to afford the title compound as yellow solid (25 mg, yield 72%).

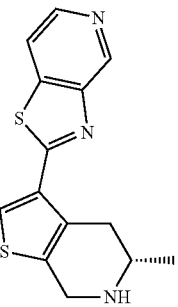

Example 40

Synthesis of 3-(Methyl-$N^{15}$-amino)-N-(3-(thiazolo[4,5-c]pyridin-2-yl)-4,5,6,7-tetrahydrothieno[2,3-c]pyridin-2-yl)propanamide (Compound 248)

Step 1: tert-Butyl 2-(3-(methylamino)propanamido)-3-(thiazolo[4,5-c]pyridin-2-yl)-4,7-dihydrothieno[2,3-c]pyridine-6(5H)-carboxylate

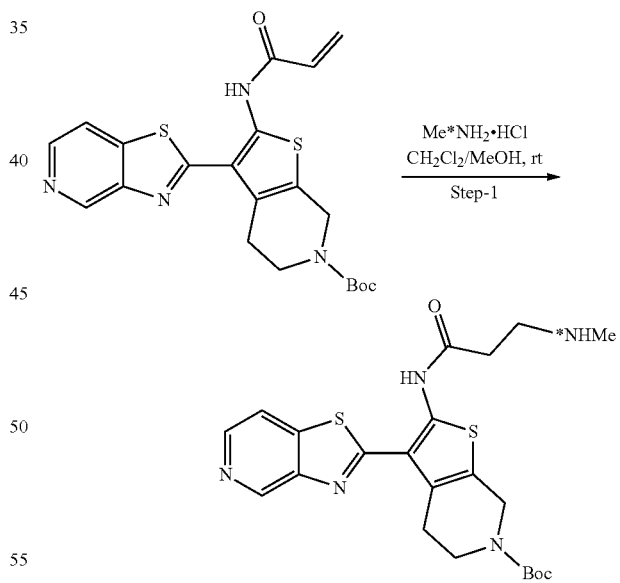

To a solution of tert-butyl 2-acrylamido-3-(thiazolo[4,5-c]pyridin-2-yl)-4,7-dihydrothieno[2,3-c]pyridine-6(5H)-carboxylate (200 mg, 0.452 mmol) in CH$_2$Cl$_2$: DMF (3:1 mL) was added 15N-methyl amine hydrochloride (46 mg, 0.678 mmol). The resulting reaction mixture was stirred at room temperature for 16 h. Progress of the reaction was monitored by TLC. After completion, the reaction mixture was concentrated to dryness under reduced pressure. The crude compound was purified by column chromatography eluting with 0-10% methanol in CH$_2$Cl$_2$ to afford the title compound as off white solid (110 mg, yield 51%).

Step 2: 3-(Methylamino)-N-(3-(thiazolo[4,5-c]pyridin-2-yl)-4,5,6,7-tetrahydrothieno[2,3-c]pyridin-2-yl)propanamide (Compound 248)

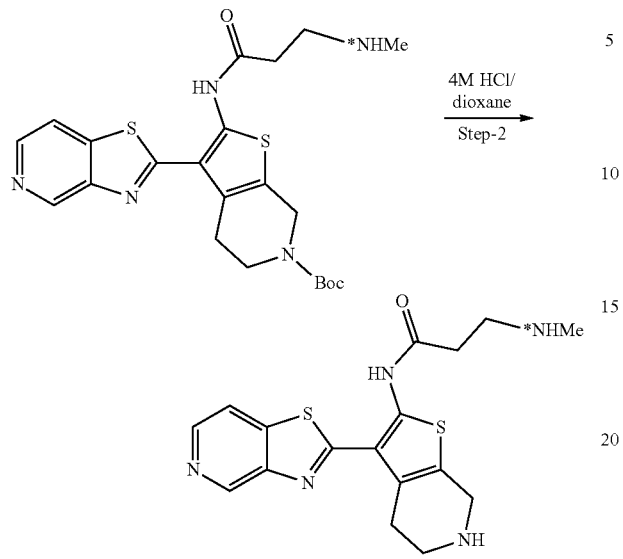

To a solution of tert-butyl 2-(3-(methylamino)propanamido)-3-(thiazolo[4,5-c]pyridin-2-yl)-4,7-dihydrothieno[2,3-c]pyridine-6(5H)-carboxylate 1 (110 mg, 0.232 mmol) in dioxane (2 mL) at 0° C. was added 4M HCl in dioxane (3 mL). After the addition, the resulting mixture was stirred at room temperature for 3 h. After completion, the reaction mixture was evaporated in vacuum resulting in a crude residue which was purified by trituration with methanol. The solid obtained was filtered and washed with diethyl ether and n-pentane to afford the title compound as yellow solid (100 mg, yield 97%).

Example 41

Synthesis of N—((R)-7-methyl-3-(thiazolo[4,5-c]pyridin-2-yl)-4,5,6,7-tetrahydrothieno[2,3-c]pyridin-2-yl)-3-(((3aR,5s,6aS)-octahydrocyclopenta[c]pyrrol-5-yl)amino)propanamide (Compound 249) and N—((R)-5-methyl-3-(thiazolo[4,5-c]pyridin-2-yl)-4,5,6,7-tetrahydrothieno[2,3-c]pyridin-2-yl)-3-(((3aR,5s,6aS)-octahydrocyclopenta[c]pyrrol-5-yl)amino)propanamide (Compound 250)

Step 1: tert-butyl (R)-7-methyl-2-(3-(((3aR,5s,6aS)-octahydrocyclopenta[c]pyrrol-5-yl)amino)propanamido)-3-(thiazolo[4,5-c]pyridin-2-yl)-4,7-dihydrothieno[2,3-c]pyridine-6(5H)-carboxylate and tert-butyl (R)-5-methyl-2-(3-(((3aR,5s,6aS)-octahydrocyclopenta[c]pyrrol-5-yl)amino)propanamido)-3-(thiazolo[4,5-c]pyridin-2-yl)-4,7-dihydrothieno[2,3-c]pyridine-6(5H)-carboxylate

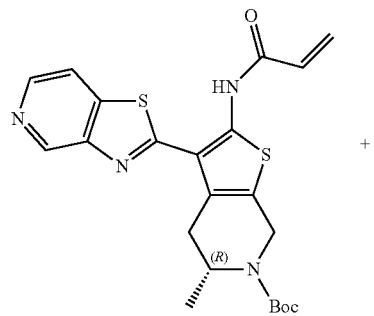

To the indicated starting compounds (250 mg, 0.548 mmol) in MeOH: THF (1:1 6 mL) was added tert-butyl (3 aR,5s, 6aS)-5-aminohexahydrocyclopenta[c]pyrrole-2(1H)-carboxylate (185 mg, 0.822 mmol). The resulting reaction mixture was stirred at room temperature for 16 h. Progress of the reaction was monitored by TLC. After completion, the reaction mixture was concentrated to dryness under reduced pressure. The crude residue was dissolved in $CH_2Cl_2$ and washed with water. The combined organic layers were dried with anhydrous $Na_2SO_4$, filtered and concentrated to get a crude residue. This crude compound was purified by silica gel column chromatography eluting with 0-5% methanol in $CH_2Cl_2$ to afford title compounds as yellow solids (320 mg racemic, yield 86%).

This mixture of compounds was purified by chiral HPLC separation (Column: YMC CHIRAL AMYLOSE SA, 250 mm*4.6 mm*5 um; Mobile Phase: A: n-Hexane+0.1% DEA; B: ETOH:MEOH (50:50); Flow rate: 1.0 ml/min; Isocratic: 30% B) to afford the separated title compounds as yellow solid.

Step 2a: N—((R)-7-methyl-3-(thiazolo[4,5-c]pyridin-2-yl)-4,5,6,7-tetrahydrothieno[2,3-c]pyridin-2-yl)-3-(((3aR,5s,6aS)-octahydrocyclopenta[c]pyrrol-5-yl)amino)propanamide (Compound 249)

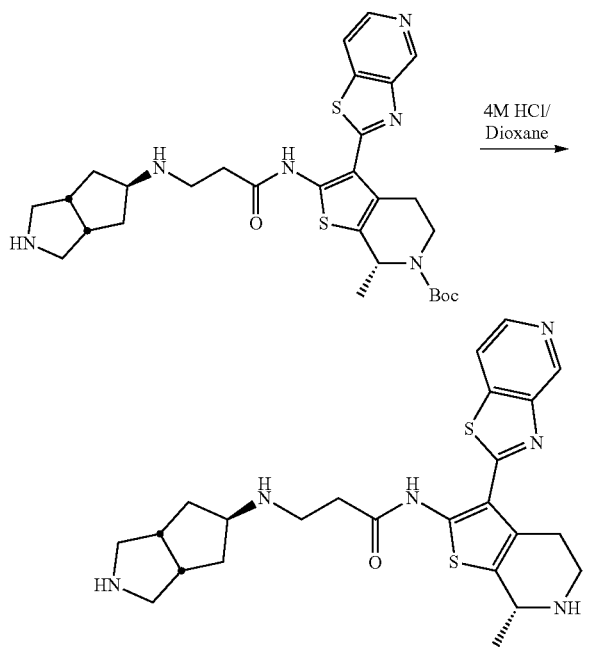

To a solution of tert-butyl (R)-7-methyl-2-(3-(((3aR,5s,6aS)-octahydrocyclopenta[c]pyrrol-5-yl)amino)propanamido)-3-(thiazolo[4,5-c]pyridin-2-yl)-4,7-dihydrothieno[2,3-c]pyridine-6(5H)-carboxylate 6 (65 mg, 0.095 mmol) in dioxane (1 mL) at 0° C. was added 4M HCl in dioxane (2 mL). After the addition, the resulting mixture was stirred at room temperature for 3 h. After completion, the reaction mixture was evaporated in vacuum resulting in a crude residue which was purified by trituration with methanol. The solid obtained was filtered and washed with diethyl ether and n-pentane to afford the title compound as yellow solid (44 mg, yield 95%).

Step 2b: N—((R)-5-methyl-3-(thiazolo[4,5-c]pyridin-2-yl)-4,5,6,7-tetrahydrothieno[2,3-c]pyridin-2-yl)-3-(((3aR,5s,6aS)-octahydrocyclopenta[c]pyrrol-5-yl)amino)propanamide (Compound 250)

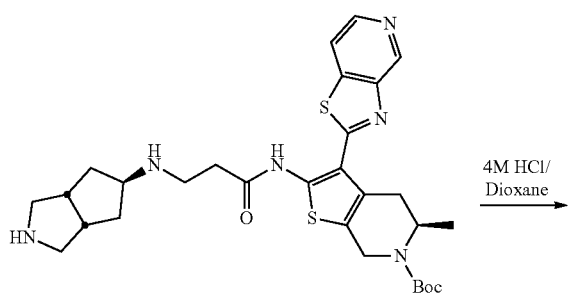

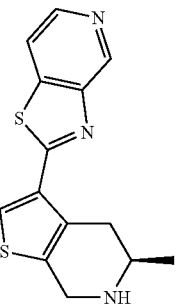

To a solution of tert-butyl (R)-5-methyl-2-(3-(((3aR,5s,6aS)-octahydrocyclopenta[c]pyrrol-5-yl)amino)propanamido)-3-(thiazolo[4,5-c]pyridin-2-yl)-4,7-dihydrothieno[2,3-c]pyridine-6(5H)-carboxylate 7 (75 mg, 0.109 mmol) in dioxane (1 mL) at 0° C. was added 4M HCl in dioxane (2 mL). After the addition, the resulting mixture was stirred at room temperature for 3 h. After completion, the reaction mixture was evaporated in vacuum resulting in a crude residue which was purified by trituration with methanol. The solid obtained was filtered and washed with diethyl ether and n-pentane to afford the title compound as yellow solid (45 mg, yield 85%).

Example 42

Synthesis of 3-(sec-Butyl-$N^{s1}$-amino)-N-(3-(thiazolo[4,5-c]pyridin-2-yl)-4,5,6,7-tetrahydrothieno[2,3-c]pyridin-2-yl)propanamide (Compound 251)

Step 1a: $^{15}$N-Labelled Malonamide

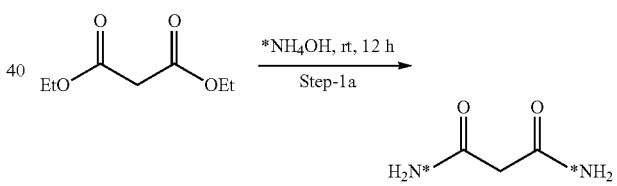

To diethyl malonate (3 mL, 19.68 mmol) was added ammonium hydroxide (10 mL) and was stirred at room temperature for 12 h. Progress of the reaction was monitored by TLC. After completion, the reaction mixture was concentrated under reduced pressure to dryness. The crude residue was washed with ethanol, filtered and dried to afford the title compound as yellow solid (1.2 g, yield 63%)

Step 1b: $^{15}$N-Labelled Malononitrile

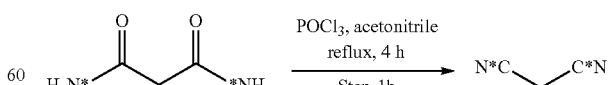

To a solution of 15N labelled malonamide 1b (1.2 g, 11.76 mmol) in acetonitrile (10 mL) at 0° C. was added POCl₃ (1 mL, 10.69 mmol) dropwise over a period of 15 min. The resulting reaction mixture was heated to 70° C. for 4 h. Progress of the reaction was monitored by TLC. After completion, the reaction mixture was concentrated under reduced pressure, quenched with saturated NaHCO₃ and extracted with 10% methanol in CH₂Cl₂ (thrice). The combined organic layer was dried over anhydrous sodium sulphate and concentrated up to dryness. The crude compound was purified by silica gel column chromatography eluting with 0-5% methanol in CH₂Cl₂ to afford the title compound as yellow oil (600 mg, yield 77%)

Step 1c: 2-(Thiazolo[4,5-c]pyridin-2-yl)acetonitrile

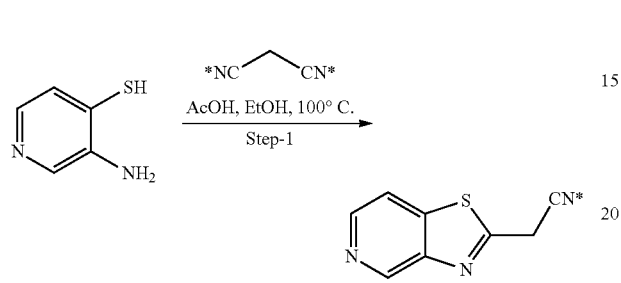

To a solution of 3-aminopyridine-4-thiol 1 (1 g, 7.936 mmol) in ethanol (5 mL) was added malononitrile 2 (523 mg, 7.936 mmol) and AcOH (5 mL). The resulting reaction mixture was stirred at 100° C. for 5 h. Progress of the reaction was monitored by TLC. After completion, the reaction mixture was quenched with saturated NaHCO₃ and extracted with 10% methanol in CH₂Cl₂ (thrice). The combined organic layer was dried over anhydrous sodium sulphate and concentrated up to dryness. The crude compound was purified by silica gel column chromatography eluting with 0-5% methanol in CH₂Cl₂ to afford the title compound as brown solid (500 mg, yield 26%).

Step 2: tert-Butyl 2-$^{15}$N-amino-3-(thiazolo[4,5-c]pyridin-2-yl)-4,7-dihydrothieno[2,3-c]pyridine-6(5H)-carboxylate

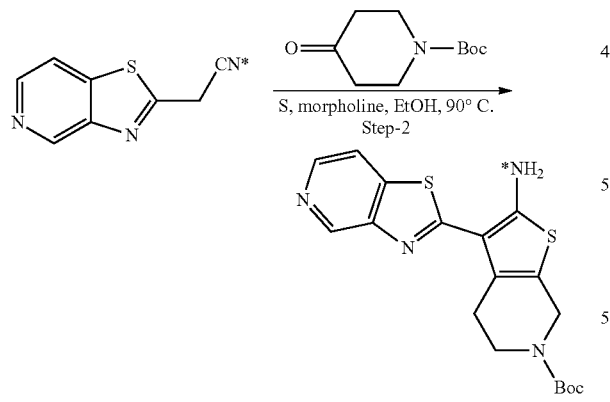

To a solution of 2-(thiazolo[4,5-c]pyridin-2-yl)acetonitrile (500 mg, 2.074 mmol) in ethanol (10 mL) was added tert-butyl 4-oxopiperidine-1-carboxylate (412 mg, 2.074 mmol), elemental sulphur (66.2 mg, 2.074 mmol) and morpholine (180 mg, 2.074 mmol) at room temperature. After the addition, the resulting mixture was heated to reflux at 90° C. for 4 h. Progress of the reaction was monitored by TLC. After completion, the reaction mixture was evaporated in vacuum up to dryness. The crude compound was purified by column chromatography eluting with 0-5% methanol in CH₂Cl₂ to afford the title compound as off white solid (200 mg, yield 25%).

Step 3: tert-Butyl 2-acryl-$^{15}$N-amido-3-(thiazolo[4,5-c]pyridin-2-yl)-4,7-dihydrothieno[2,3-c]pyridine-6(5H)-carboxylate

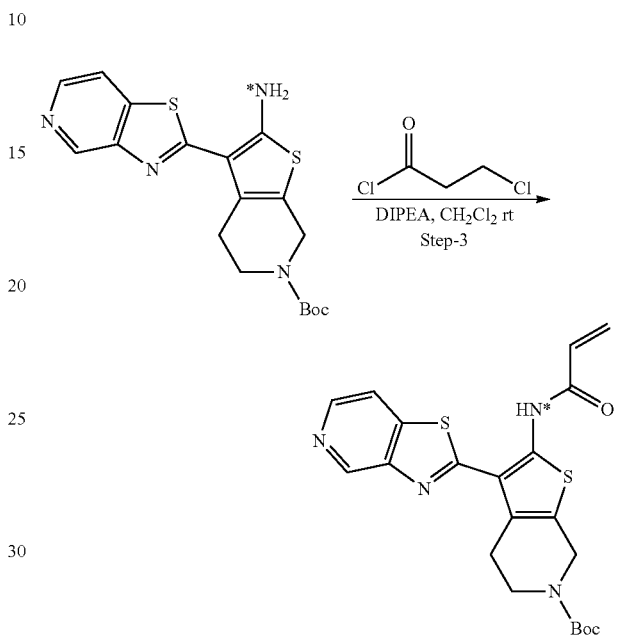

To a solution of tert-butyl 2-amino-3-(thiazolo[4,5-c]pyridin-2-yl)-4,7-dihydrothieno[2,3-c]pyridine-6(5H)-carboxylate 5 (200 mg, 0.515 mmol) in CH₂Cl₂ (10 mL) at 0° C. was added DIPEA (0.18 mL, 1.03 mmol) and 3-chloropropanoyl chloride (97.4 mg, 0.773 mmol). The reaction mixture was stirred at room temperature for 3 h. After completion (monitored by TLC), the reaction mixture was quenched with saturated NaHCO₃ and extracted with dichloromethane (thrice). The combined organic layer was dried over anhydrous sodium sulphate and concentrated up to dryness to afford the title compound as light brown solid (200 mg, yield 87%).

Step 4: tert-Butyl 2-(3-(sec-butylamino)propan-$^{15}$N-amido)-3-(thiazolo[4,5-c]pyridin-2-yl)-4,7-dihydrothieno[2,3-c]pyridine-6(5H)-carboxylate

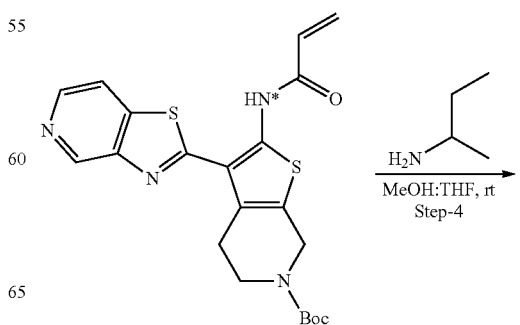

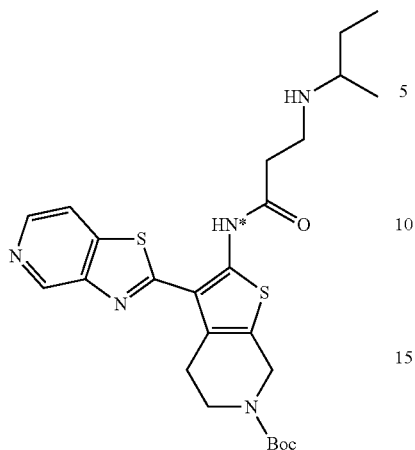

To a solution of tert-butyl 2-acrylamido-3-(thiazolo[4,5-c]pyridin-2-yl)-4,7-dihydrothieno[2,3-c]pyridine-6(5H)-carboxylate (200 mg, 0.451 mmol) in MeOH: THF (1:1, 10 mL) was added butan-2-amine (39 mg, 0.541 mmol). The resulting reaction mixture was stirred at room temperature for 12 h. Progress of the reaction was monitored by TLC. After completion, the reaction mixture was concentrated to dryness under reduced pressure. The residue was washed with water and extracted with $CH_2Cl_2$ (thrice). The combined organic layer was dried over anhydrous $Na_2SO_4$, filtered and concentrated. The crude compound was purified by column chromatography eluting with 0-3% methanol in $CH_2Cl_2$ to afford the title compound as yellow solid (100 mg, yield 43%).

Step 5: 3-(sec-Butylamino)-N-(3-(thiazolo[4,5-c]pyridin-2-yl)-4,5,6,7-tetrahydrothieno[2,3-c]pyridin-2-yl)propan-$^{15}$N-amide (Compound 251)

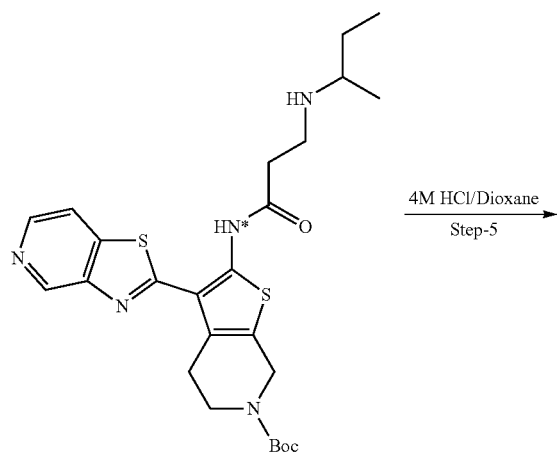

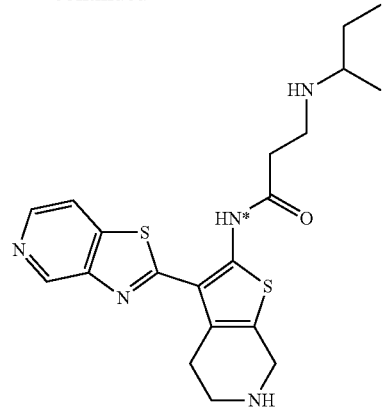

To a solution of tert-butyl 2-(3-(sec-butylamino)propanamido)-3-(thiazolo[4,5-c]pyridin-2-yl)-4,7-dihydrothieno[2,3-c]pyridine-6(5H)-carboxylate 7 (100 mg, 0.194 mmol) in dioxane (5 mL) at 0° C. was added 4M HCl in dioxane (5 mL). After the addition, the resulting mixture was stirred at room temperature for 3 h. After completion, the reaction mixture was evaporated in vacuum resulting in a crude residue which was purified by trituration with methanol. The solid obtained was filtered and washed with diethyl ether and methanol to afford the title compound as a yellow solid HCl salt (20 mg, yield 21%).

Example 43 c-Myc/Max/Ebox DNA AlphaScreen Assay

Compounds of the invention were assayed for c-Myc/Max/EBox activity as described in the following protocol. Human his$_6$-c-Myc and his$_6$-Max were used with biotinylated DNA containing a single Ebox sequence (biotinG-GAAGCAGACCACGTGGTCTGCTTCC) purchased from MWG Operon. Free c-Myc was generated from his$_6$-c-Myc through thrombin cleavage of the his$_6$ tag. For 384-well plate assays, 10 µL of a 2× solution of free c-Myc (20 nM final), $Ni^{2+}$ coated Acceptor Beads (25 µg/ml final), and biotinylated Ebox oligo (10 nM final) were added to 384-well plates with a Biotek EL406 liquid handler. 50 nL of compounds from stock plates were added by pin transfer using a Janus Workstation (PerkinElmer), allowing the compounds to interact with c-Myc prior to c-Myc binding with Max. In the current assay, DMSO was not allowed to exceed 2% v/v of the assay. 10 µl of 2× master mix containing streptavidin-coated donor beads (25 µg/ml final) and his$_6$-Max (5 nM) were added. AlphaScreen measurements were performed on an Envision plate reader (PerkinElmer) utilizing the manufacturer's protocol.

Both master mixes were made in room temperature assay buffer (50 mM HEPES, 150 mM NaCl, 0.2% w/v BSA, 0.02% w/v Tween20, 40 µg/ml glycogen, 500 µM DTT, pH 8.0, wherein both DTT and glycogen were added fresh). Alpha beads were added to respective master solutions. All subsequent steps were performed in low light conditions. Solution 1: 2× solution of components with final concentrations of c-Myc Ni-coated Acceptor Beads (25 jag/ml), and biotinylated Ebox oligo (10 nM). Solution 2: 2× solution of streptavidin-coated donor beads (25 µg/ml final) and his$_6$-Max 10 µL. Solution 1 was added to 384-well plate (AlphaPlate-384, PerkinElmer) with Biotek EL406 liquid handler and the plates were centrifuged very briefly. 50 nL of compounds from stock plates were added by pin transfer using a Janus Workstation. Solution 2 (10 μL) was added with the liquid handler. Plates were sealed with foil to block light exposure and prevent evaporation. Plates were very briefly centrifuged followed by 2 hour incubation. AlphaScreen measurements were performed on an Envision 2104 utilizing the manufacturer's protocol. Excitation was at 680 nm for donor bead release of singlet oxygen and emission was read with a bandpass filter from 520-620 nm. Glycogen: Roche Diagnostics#10901393001. Plate 1536: Perkin Elmer, 6004350. Plate 384: Perkin Elmer, 6005350. Nickel-His Alpha Beads: 6760619R. The data from this assay are summarized in Table 3 below (Myc/Max/DNA Activity).

Example 44

Cell Viability Assay

Compounds of the invention were assayed for cell viability using the human small lung cancer cell line H2171 as described in the following protocol. Cells were counted and adjusted to 20,000 cells/mL. Using a Biotek EL406, 50 μL of cells in media were distributed into 384 well white plates from Thermo. Immediately after plating, compound in DMSO was distributed to plates. Compounds were added to plates using a 50 nL 384 well pin transfer manifold on a Janus workstation. Stocks were arrayed in 10 point dose response in DMSO stock in 384 well Greiner compound plates. After the addition of compounds, plates were incubated for three days in a 37° C. incubator. Cell viability was read out using ATPlite from Perkin Elmer. Lyophilized powder was resuspended in lysis buffer and diluted 1:2 with deionized water. 25 μL of this solution was added to each well using the Biotek liquid handler. Plates were incubated for 15 minutes at room temperature before signal was read on an Envision Plate Reader. The data from this assay are summarized in Table 3 below (H2171 activity).

TABLE 3

Biological Assay Data of Selected Compounds of the Invention
The results of the assays described in Examples 43 and 44 are sumamrized in the following table, where "A" represents a calculated $IC_{50}$ of less than 500 nM; "B" represents a calculated $IC_{50}$ of between 500 nM and 5 μM; "C" represents a calculated $IC_{50}$ of between 5 μM and 25 μM; "D" represents a value of greater than 25 μM; "*" is a value above the assay detection limit; and "NT" represents a value that was not obtained.

| Compound No. | Myc/Max/DNA Activity | H2171 Activity |
|---|---|---|
| 100 | A | B |
| 101 | B | A |
| 102 | B | NT |
| 103 | A | A |
| 104 | B | * |
| 105 | B | B |
| 106 | A | A |
| 107 | B | B |
| 108 | B | B |
| 109 | B | NT |
| 110 | A | A |
| 111 | A | A |
| 112 | C | NT |
| 113 | B | A |
| 114 | B | B |
| 115 | B | NT |
| 116 | A | A |
| 117 | B | B |
| 118 | A | A |
| 119 | A | A |
| 120 | B | NT |
| 121 | B | NT |
| 122 | A | A |
| 123 | A | NT |
| 124 | A | NT |
| 125 | A | NT |
| 126 | A | NT |
| 127 | A | NT |
| 128 | B | NT |
| 129 | A | NT |
| 130 | A | NT |
| 131 | A | NT |
| 132 | B | NT |
| 133 | A | NT |
| 134 | A | B |
| 135 | A | NT |
| 136 | B | NT |
| 137 | A | NT |
| 138 | A | NT |
| 139 | B | NT |
| 140 | B | NT |
| 141 | A | NT |
| 142 | A | NT |
| 143 | B | NT |
| 144 | B | NT |
| 145 | A | NT |
| 146 | A | NT |
| 147 | A | NT |
| 148 | A | NT |
| 149 | A | NT |
| 150 | A | NT |
| 151 | A | NT |
| 152 | A | NT |
| 153 | A | A |
| 154 | A | NT |
| 155 | A | NT |
| 156 | A | NT |
| 157 | B | NT |
| 158 | A | NT |
| 159 | B | NT |
| 160 | A | NT |
| 161 | A | NT |
| 162 | B | NT |
| 163 | B | NT |
| 164 | A | NT |
| 165 | A | NT |
| 166 | A | NT |
| 167 | A | NT |
| 168 | A | NT |
| 169 | A | NT |
| 170 | A | NT |
| 171 | A | NT |
| 172 | A | A |
| 173 | A | NT |
| 174 | A | NT |
| 175 | A | NT |
| 176 | A | A |
| 177 | A | A |
| 178 | A | NT |
| 179 | B | NT |
| 180 | A | NT |
| 181 | A | NT |
| 182 | B | NT |
| 183 | B | A |
| 184 | A | NT |
| 185 | A | NT |
| 186 | B | NT |

TABLE 3-continued

Biological Assay Data of Selected Compounds of the Invention
The results of the assays described in Examples 43 and 44 are summarized in the following table, where "A" represents a calculated $IC_{50}$ of less than 500 nM; "B" represents a calculated $IC_{50}$ of between 500 nM and 5 μM; "C" represents a calculated $IC_{50}$ of between 5 μM and 25 μM; "D" represents a value of greater than 25 μM; "*" is a value above the assay detection limit; and "NT" represents a value that was not obtained.

| Compound No. | Myc/Max/DNA Activity | H2171 Activity |
|---|---|---|
| 187 | A | NT |
| 188 | A | NT |
| 189 | A | NT |
| 190 | A | A |
| 191 | B | NT |
| 192 | A | NT |
| 193 | A | NT |
| 194 | B | NT |
| 195 | A | NT |
| 196 | B | NT |
| 197 | C | NT |
| 198 | B | NT |
| 199 | B | NT |
| 200 | A | NT |
| 201 | A | NT |
| 202 | A | NT |
| 203 | A | B |
| 204 | A | NT |
| 205 | C | NT |
| 206 | A | B |
| 207 | A | NT |
| 208 | A | NT |
| 209 | B | NT |
| 210 | A | NT |
| 211 | A | NT |
| 212 | C | NT |
| 213 | A | NT |
| 214 | A | NT |
| 215 | A | NT |
| 216 | A | A |
| 217 | A | A |
| 218 | A | A |
| 219 | A | A |
| 220 | A | A |
| 221 | A | NT |
| 222 | A | NT |
| 223 | A | A |
| 224 | A | B |
| 225 | A | A |
| 226 | A | A |
| 227 | A | A |
| 228 | A | A |
| 229 | C | NT |
| 230 | B | A |
| 231 | B | A |
| 232 | A | A |
| 233 | C | B |
| 234 | A | A |
| 235 | A | A |
| 236 | A | A |
| 237 | B | B |
| 238 | A | A |
| 239 | A | A |
| 240 | A | A |
| 241 | A | A |
| 242 | A | A |
| 243 | A | A |
| 244 | A | A |
| 245 | A | A |
| 246 | B | A |
| 247 | C | A |
| 248 | A | A |
| 249 | A | A |
| 250 | B | A |
| 251 | A | A |
| 252 | D | NT |
| 253 | A | NT |
| 254 | D | NT |

EQUIVALENTS

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims are introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:
1. A compound of structural formula I:

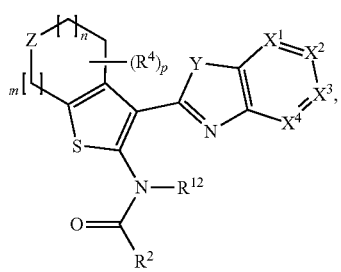

(I)

or a pharmaceutically acceptable salt, tautomer, or stereoisomer thereof, wherein:
each of $X^1$, $X^2$, $X^3$ and $X^4$ is independently selected from C(R), N and N(O), wherein one or two of $X^1$, $X^2$, $X^3$ and $X^4$ is N or one of $X^1$, $X^2$, $X^3$ and $X^4$ is N(O);
each R is independently selected from hydrogen, halogen, —CN, $C_1$-$C_8$ alkyl, $C_1$-$C_8$ heteroalkyl, $N(R^{3a})(R^{3b})$, $C(O)(C_1$-$C_6$ alkyl), $C(O)O(C_1$-$C_6$ alkyl), $(C_0$-$C_6$ alkylene)-carbocyclyl, $(C_1$-$C_6$ heteroalkylene)-carbocyclyl, $(C_0$-$C_6$ alkylene)-heterocyclyl, $(C_1$-$C_6$ heteroalkylene)-heterocyclyl, $(C_0$-$C_6$ alkylene)-aryl, $(C_1$-$C_6$ heteroalkylene)-aryl, and $(C_0$-$C_6$ alkylene)-heteroaryl, wherein any alkyl, alkylene, heteroalkyl, heteroalkylene, carbocyclyl, heterocyclyl, aryl or heteroaryl portion of R is optionally and independently substituted;
Y is selected from O, S and $N(R^{3a})$;
Z is selected from $C(R^{4a})(N(R^5)(R^6))$ and $N(R^1)$;
$R^1$ is selected from hydrogen, $C_1$-$C_6$ alkyl, $C_1$-$C_6$ heteroalkyl, $(C_0$-$C_6$ alkylene)-carbocyclyl, $(C_1$-$C_6$ heteroalkylene)-carbocyclyl, $(C_0$-$C_6$ alkylene)-heterocyclyl, $(C_1$-$C_6$ heteroalkylene)-heterocyclyl, $(C_0$-$C_6$ alkylene)-aryl, $(C_1$-$C_6$ heteroalkylene)-aryl, $(C_0$-$C_6$ alkylene)-heteroaryl, $(C_1$-$C_6$ heteroalkylene)-heteroaryl, $CH_2C(O)OR^7$, $CH_2C(O)N(R^{10})(R^{11})$, and $CH_2CH_2N(R^{10})(R^{11})$, wherein:
$R^{10}$ is hydrogen or $C_1$-$C_4$ alkyl;
$R^{11}$ is selected from hydrogen, $C_1$-$C_4$ alkyl, $C_1$-$C_4$ heteroalkyl, $(C_0$-$C_4$ alkylene)-carbocyclyl, $(C_0$-$C_4$ alkylene)-heterocyclyl, $(C_0$-$C_4$ alkylene)-aryl, $(C_0$-$C_4$ alkylene)-heteroaryl, $(C_1$-$C_4$ alkyl)-O—$(C_1$-$C_4$ alkyl), $(C_1$-$C_4$ alkyl)-N—$(C_1$-$C_4$ alkyl)$_2$, $(C_1$-$C_4$ alkyl)-NH—$(C_1$-$C_4$ alkyl), $C(O)$—$(C_1$-$C_4$ alkyl), and $C(O)$—$O$—$(C_1$-$C_4$ alkyl), or $R^{10}$ and $R^{11}$ are taken together with the nitrogen atom to which they are commonly bound to form a 4-11 membered heterocyclyl or heteroaryl; and any alkyl, alkylene, heteroalkyl, heteroalkylene, heterocyclyl, heteroaryl, aryl or carbocyclyl portion of $R^1$ is optionally substituted;
$R^2$ is selected from $C(R^{2a})(R^{2b})(R^{2c})$, carbocyclyl, aryl, heterocyclyl and heteroaryl, wherein any carbocyclyl, aryl, heterocyclyl and heteroaryl is optionally substituted;
$R^{2a}$ is selected from hydrogen, halogen, —CN, $C_1$-$C_4$ alkyl, $C_1$-$C_4$ heteroalkyl and $C_1$-$C_4$ haloalkyl, wherein any alkyl, heteroalkyl or haloalkyl is optionally substituted;
each of $R^{2a}$ and $R^{2c}$ is independently selected from hydrogen, halogen, —CN, $C_1$-$C_6$ alkyl, $C_1$-$C_6$ heteroalkyl, $C(O)(C_1$-$C_6$ alkyl), $C(O)(C_1$-$C_6$ heteroalkyl), $C(O)O$ $(C_1$-$C_6$ alkyl), $C(O)O(C_1$-$C_6$ heteroalkyl), $C(O)N(R^{3a})$ $(R^{3b})$, $(C_0$-$C_6$ alkylene)-carbocyclyl, $(C_1$-$C_6$ heteroalkylene)-carbocyclyl, $(C_0$-$C_6$ alkylene)-heterocyclyl, $(_1$-$C_6$ heteroalkylene)-heterocyclyl, $(C_0$-$C_6$ alkylene)-aryl, $(C_1$-$C_6$ heteroalkylene)-aryl, $(C_0$-$C_6$ alkylene)-heteroaryl and $(C_1$-$C_6$ heteroalkylene)-heteroaryl, wherein any alkyl, alkylene, heteroalkyl, heteroalkylene, carbocyclyl, heterocyclyl, aryl or heteroaryl portion of $R^{2b}$ and $R^{2c}$ is optionally and independently substituted;
each of $R^{3a}$ and $R^{3b}$ is independently selected from hydrogen, $C_1$-$C_6$ alkyl, or $C_1$-$C_6$ heteroalkyl, each of which is optionally substituted;
each $R^4$ is independently selected from halogen, —CN, $C_1$-$C_8$ alkyl, $C_1$-$C_8$ heteroalkyl, $N(R^{3a})(R^{3b})$, $C(O)(C_1$-$C_6$ alkyl), $C(O)(C_1$-$C_6$ heteroalkyl), $C(O)O(C_1$-$C_6$ alkyl), $C(O)N(R^{3a})(R^{3b})$, $(C_0$-$C_6$ alkylene)-carbocyclyl, $(C_1$-$C_6$ heteroalkylene)-carbocyclyl, $(C_0$-$C_6$ alkylene)-heterocyclyl, $(C_1$-$C_6$ heteroalkylene)-heterocyclyl, $(C_0$-$C_6$ alkylene)-aryl, $(C_1$-$C_6$ heteroalkylene)-aryl, $(C_0$-$C_6$ alkylene)-heteroaryl, and $(C_1$-$C_6$ heteroalkylene)-heteroaryl, wherein any alkyl, alkylene, heteroalkyl, heteroalkylene, carbocyclyl, heterocyclyl, aryl or heteroaryl portion of $R^4$ is optionally and independently substituted;
$R^{4a}$ is selected from hydrogen and $C_1$-$C_6$ alkyl;
each of $R^5$ and $R^6$ is independently selected from hydrogen, $C_1$-$C_6$ alkyl, $C_1$-$C_6$ heteroalkyl, $C(O)(C_1$-$C_6$ alkyl), $C(O)O(C_1$-$C_6$ alkyl), $(C_0$-$C_6$ alkylene)-carbocyclyl, $(C_1$-$C_6$ heteroalkylene)-carbocyclyl, $(C_0$-$C_6$ alkylene)-heterocyclyl, $(C_1$-$C_6$ heteroalkylene)-heterocyclyl, $(C_0$-$C_6$ alkylene)-aryl, $(C_1$-$C_6$ heteroalkylene)-aryl, $(C_0$-$C_6$ alkylene)-heteroaryl, and $(C_1C_6$ heteroalkylene)-heteroaryl, wherein any alkyl, alkylene, heteroalkyl, heteroalkylene, carbocyclyl, heterocyclyl, aryl or heteroaryl portion of each of $R^5$ and $R^6$ is optionally and independently substituted; or
$R^5$ and $R^6$ are taken together with the nitrogen atom to which they are commonly bound to form an optionally substituted heterocyclyl;
$R^7$ is hydrogen, $C_1$-$C_6$ alkyl, $C_1$-$C_6$ heteroalkyl, $(C_0$-$C_3$ alkylene)-carbocyclyl, $(C_0$-$C_3$ alkylene)-heterocyclyl;
$R^{12}$ is hydrogen, $C_1$-$C_6$ alkyl, $C_1$-$C_6$ heteroalkyl, $(C_0$-$C_3$ alkylene)-carbocyclyl, $(C_0$-$C_3$ alkylene)-heterocyclyl;
n is 0, 1 or 2;
m is 0, 1 or 2;
n+m=1, 2 or 3; and
p is 0, 1, 2, 3, 4, 5 or 6.

2. The compound of claim 1, wherein one of $X^1$, $X^2$, $X^3$, and $X^4$ is N or N(O), and the others of $X^1$, $X^2$, $X^3$, and $X^4$ are independently C(R).

3. The compound of claim 2, wherein $X^3$ is N, and each of $X^1$, $X^2$, and $X^4$ is independently C(R).

4. The compound of claim 1, wherein each R is independently selected from hydrogen, halogen, optionally substituted $C_1$-$C_4$ alkyl, optionally substituted $C_1$-$C_4$ heteroalkyl, $N(R^{3a})(R^{3b})$, $C(O)(C_1$-$C_4$ optionally substituted alkyl), and $C(O)O$(optionally substituted $C_1$-$C_4$ alkyl).

5. The compound of claim 1, wherein each R is independently selected from hydrogen, chloro, —$CH_3$ and —$CHF_2$.

6. The compound of claim 1, wherein Y is S.

7. The compound of claim 1, wherein Z is $N(R^1)$.

8. The compound of claim 7, wherein $R^1$ is selected from hydrogen, methyl, ethyl, isopropyl, ($C_0$-$C_6$ alkylene)-morpholin-4-yl, and $CH_2CH_2N(R^{10})(R^{11})$, wherein each of $R^{10}$ and $R^{11}$ is independently hydrogen or methyl.

9. The compound of claim 8, wherein $R^1$ is selected from hydrogen, isopropyl and ethyl.

10. The compound of claim 1, wherein $R^2$ is $C(R^{2a})(R^{2b})(R^{2c})$.

11. The compound of claim 10, wherein:
$R^{2a}$ is hydrogen;
$R^{2b}$ is hydrogen; and
$R^{2c}$ is selected from $C_1$-$C_6$ alkyl, $C_1$-$C_6$ heteroalkyl, ($C_1$-$C_6$ heteroalkylene)-carbocyclyl, ($C_1$-$C_6$ heteroalkylene)-heterocyclyl, ($C_1$-$C_6$ heteroalkylene)-aryl, and ($C_1$-$C_6$ heteroalkylene)-heteroaryl, any alkyl, alkylene, cycloalkyl, aryl, heterocyclyl, or heteroaryl portion of $R^{2c}$ is optionally substituted.

12. The compound of claim 10, wherein $R^{2c}$ is selected from $C_1$-$C_6$ alkyl, —$(CH_2)$—$N(R^{13})$—$C_1$-$C_4$ alkyl, —$(CH_2)$—$N(R^{13})$—$C_1$-$C_4$ alkylene-O-alkyl, —$(CH_2)$—$N(R^{13})$—$C_1$-$C_4$ alkylene-$C(O)$—O-alkyl, —$(CH_2)$—$N(R^{13})$—$C_1$-$C_4$ alkylene-cycloalkyl, —$(CH_2)$—$N(R^{13})$-cycloalkyl, —$(CH_2)_2$—N-linked heterocyclyl, —$(CH_2)$—$N(R^{13})$-heterocyclyl, —$(CH_2)$—$N(R^{13})$—$C_1$-$C_4$ alkylene-heterocyclyl, —$CH_2$—N-linked heterocyclyl, —$(CH_2)$—$N(R^{13})$—$C_1$-$C_4$ alkylene-heteroaryl, and —$(CH_2)$—$N(R^{13})$—$C_1$-$C_4$ alkylene-aryl, wherein $R^{13}$ is hydrogen or $C_1$-$C_4$ alkyl; and any alkyl, alkylene, cycloalkyl, aryl, heterocyclyl, or heteroaryl portion of $R^{2c}$ is optionally substituted.

13. The compound of claim 12, wherein any alkyl, alkylene, cycloalkyl, aryl, heterocyclyl, or heteroaryl portion of $R^{2c}$ is optionally substituted with one or more substituents independently selected from halo, hydroxy, oxo, —CN, —$NH_2$, —NH($C_1$-$C_4$ alkyl), —N($C_1$-$C_4$ alkyl)$_2$, —$C_1$-$C_4$ alkyl, —$C_1$-$C_4$ hydroxyalkyl, —$C(O)NH_2$, —$C(O)$OH, —$C(O)$O—$C_1$-$C_4$ alkyl, —$C_1$-$C_4$ alkyl-O—$C_1$-$C_4$ alkyl, —O—$C_1$-$C_4$ alkyl, —O—$C_3$-$C_6$ cycloalkyl, phenyl, and halo-substituted phenyl.

14. The compound of claim 1, wherein each $R^4$ is independently selected from halogen, $C_1$-$C_8$ alkyl, $C_1$-$C_8$ heteroalkyl, $N(R^{3a})(R^{3b})$, ($C_0$-$C_6$ alkylene)-heterocyclyl, and ($C_0$-$C_6$ alkylene)-heteroaryl, wherein any alkyl, alkylene, heteroalkyl, heterocyclyl or heteroaryl portion of each $R^4$ is optionally and independently substituted.

15. The compound of claim 14, wherein each $R^4$ is optionally substituted $C_1$-$C_4$ alkyl.

16. The compound of claim 15, wherein each $R^4$ is methyl.

17. The compound of claim 1, wherein p is 0, 1 or 2.

18. The compound of claim 1, wherein the compound of Formula (I) has the structure of Formula (II):

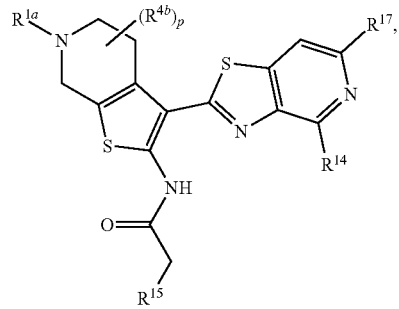

or a pharmaceutically acceptable salt thereof, wherein:
$R^{1a}$ is selected from hydrogen and $C_1$-$C_3$ alkyl;
each $R^{4b}$, if present, is $C_1$-$C_3$ alkyl;
$R^{17}$ and $R^{14}$ are independently selected from hydrogen, halo, $C_1$-$C_3$ alkyl and $C_1$-$C_3$ haloalkyl;
$R^{15}$ is selected from hydrogen, $C_1$-$C_3$ alkyl, and —$CH_2$—$N(R^{13a})(R^{16})$;
$R^{13a}$ is selected from hydrogen and $C_1$-$C_3$ alkyl;
$R^{16}$ is selected from $C_1$-$C_6$ alkyl, $C_1$-$C_6$ heteroalkyl, —($C_0$-$C_2$ alkylene)-heterocyclyl, —($C_0$-$C_2$ alkylene)-$C_3$-$C_6$ cycloalkyl, or ($C_1$-$C_2$ alkylene)-heteroaryl, wherein any heteroalkyl, alkylene, cycloalkyl, heterocyclyl or heteroaryl portion of $R^{11a}$ is optionally substituted; or
$R^{13a}$ and $R^{16}$ are taken together to form an optionally substituted heterocyclyl; and
p is 0, 1 or 2.

19. The compound of claim 18, wherein $R^{1a}$ is selected from hydrogen, ethyl and isopropyl.

20. The compound of claim 18, wherein each $R^{4b}$, if present, is —$CH_3$.

21. The compound of claim 18, wherein $R^{13a}$ is selected from hydrogen and —$CH_3$.

22. The compound of claim 18, wherein $R^{17}$ is selected from hydrogen, chloro, and —$CH_3$.

23. The compound of claim 18, wherein $R^{14}$ is selected from hydrogen, —$CH_3$ and —$CHF_2$.

24. The compound of claim 18, wherein $R^{15}$ is selected from hydrogen, $NHR^{16}$, and $N(CH_3)R^{16}$.

25. The compound of claim 18, wherein $R^{16}$ is selected from -heterocyclyl, —$CH_2$-heterocyclyl, —$(CH_2)_2$-heterocyclyl, —$CH_2$-heteroaryl, —$CH(CH_3)$-heteroaryl, —$(CH_2)_2$-heteroaryl, —$CH(CH_3)$—$CH_2$-heteroaryl, —$CH_3$, —$CH_2CH_3$, —$CH(CH_3)CH_2CH_3$, —$CH_2CH_2$—O—$CH_3$, —$(CH_2)_3$—$C(O)OCH_3$, —$CH(CH_2OH)CH_2CH(CH_3)_2$, —$CH(CH(CH_3)_2)CH_2OCH_3$, —($C_{3-5}$ cycloalkyl), —$CH_2$—($C_3$-$C_5$ cycloalkyl), and —$CH(CH_3)$—($C_3$-$C_5$ cycloalkyl); or
wherein $R^{16}$ is taken together with $R^{13a}$ and the nitrogen atom to which they are bound to form a N-linked heterocyclyl, and
wherein each heterocyclyl, heteroaryl and cycloalkyl portion of $R^{16}$ or the N-linked
heterocyclyl formed when $R^{16}$ is taken together with $R^{13a}$ is optionally substituted with one or more substituents independently selected from oxo, hydroxy, —$CH_3$, —$CH_2OCH_3$, —$OCH_3$, —$NH_2$, —$N(CH_3)_2$, —$C(O)$OH, and —O-cycloalkyl.

26. The compound of claim 1, wherein the compound is selected from the group consisting of

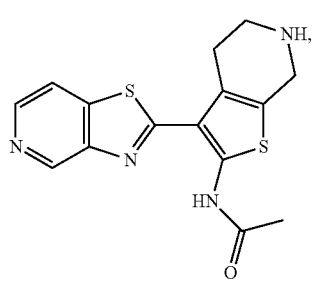
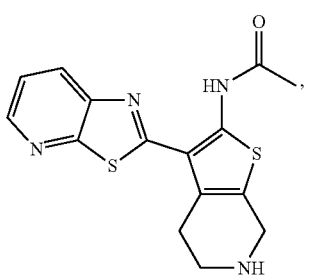
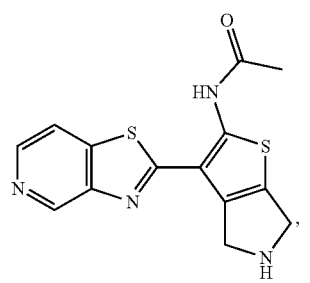
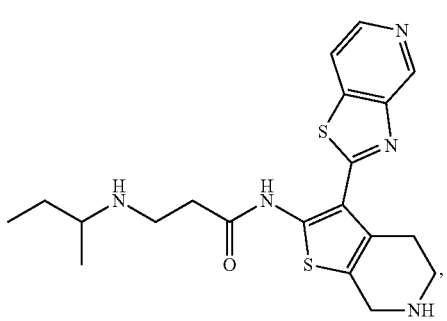
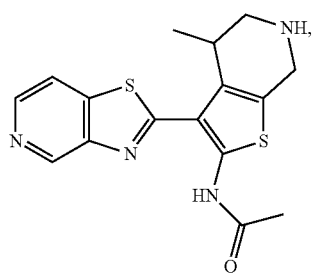
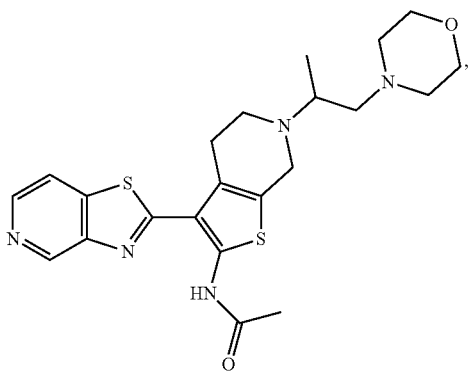
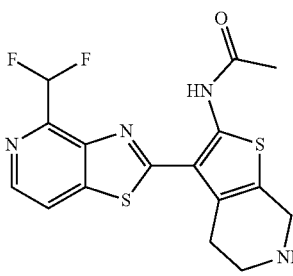
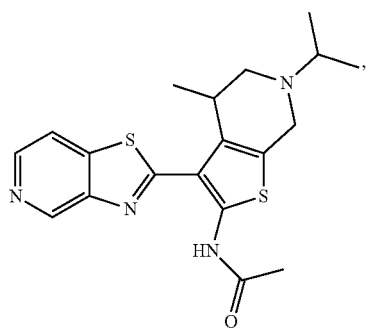
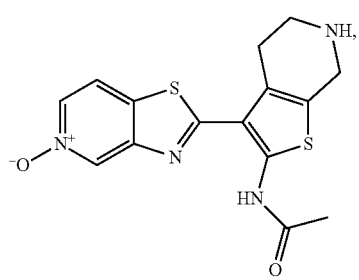
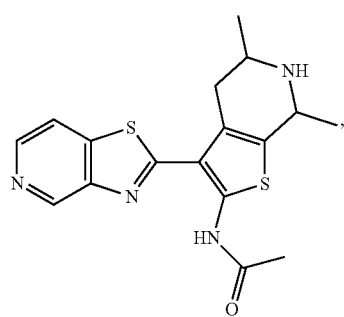

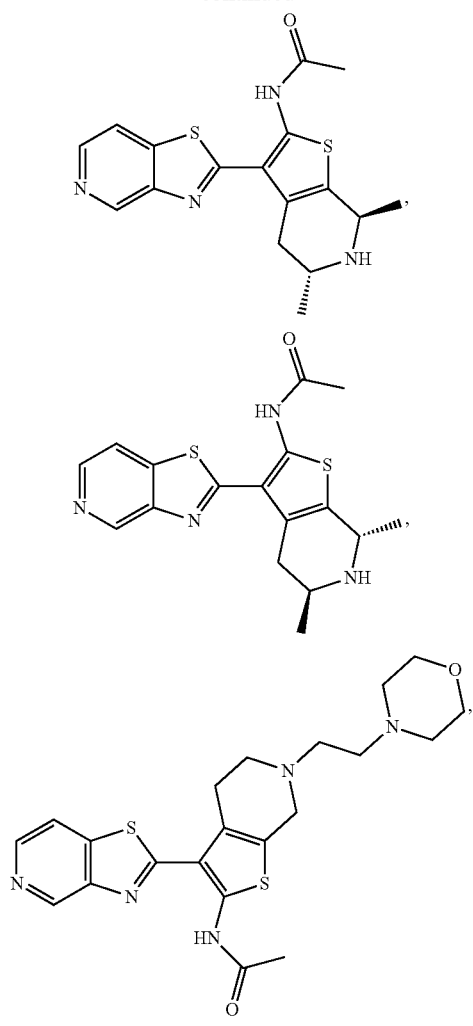
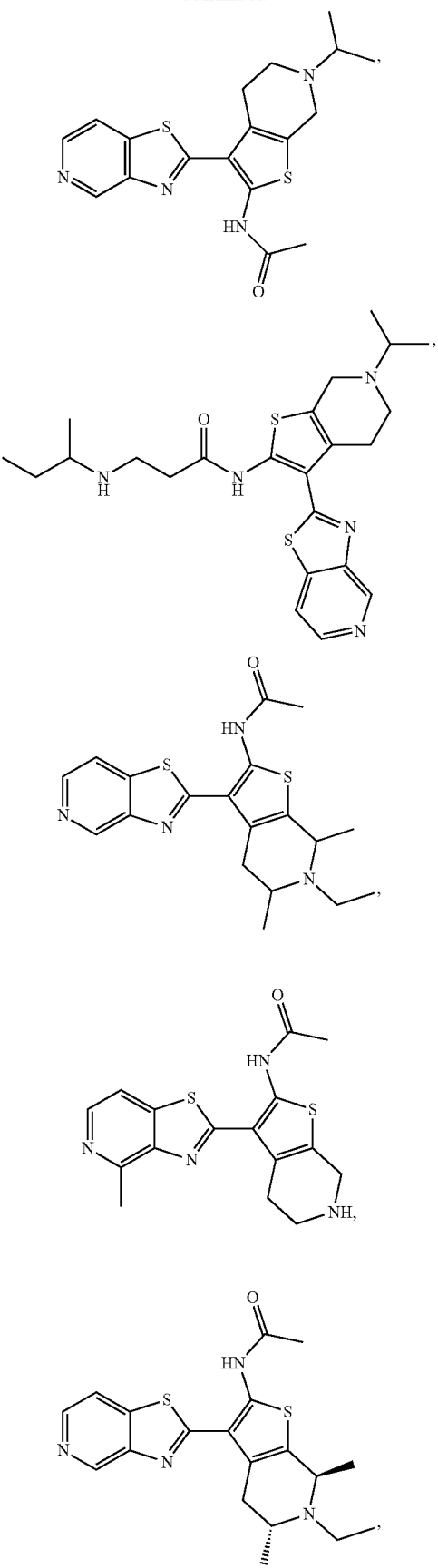

219
-continued
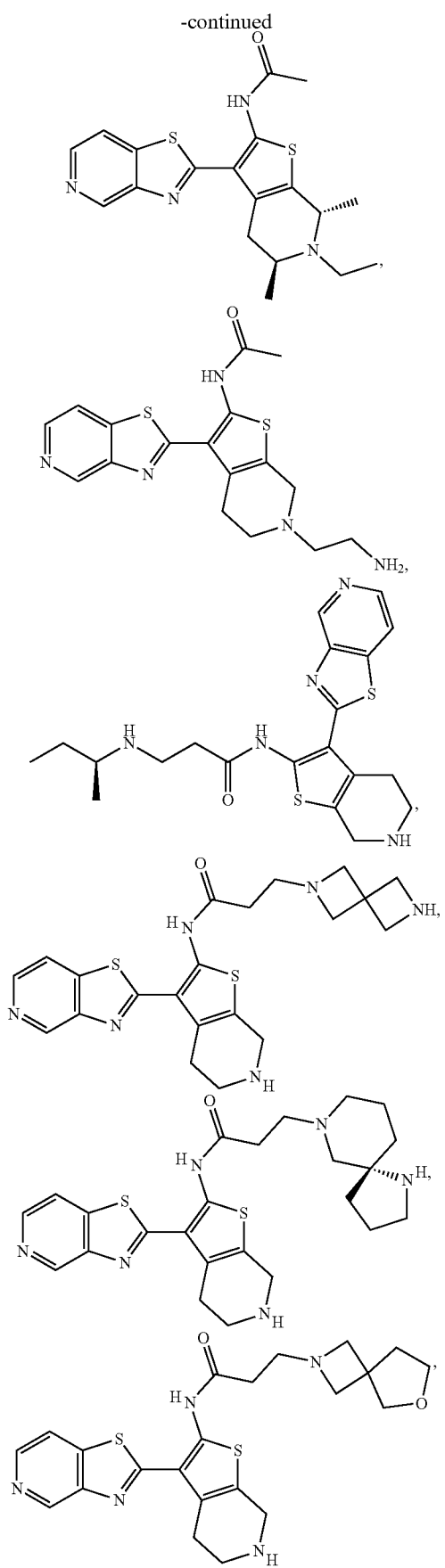
220
-continued
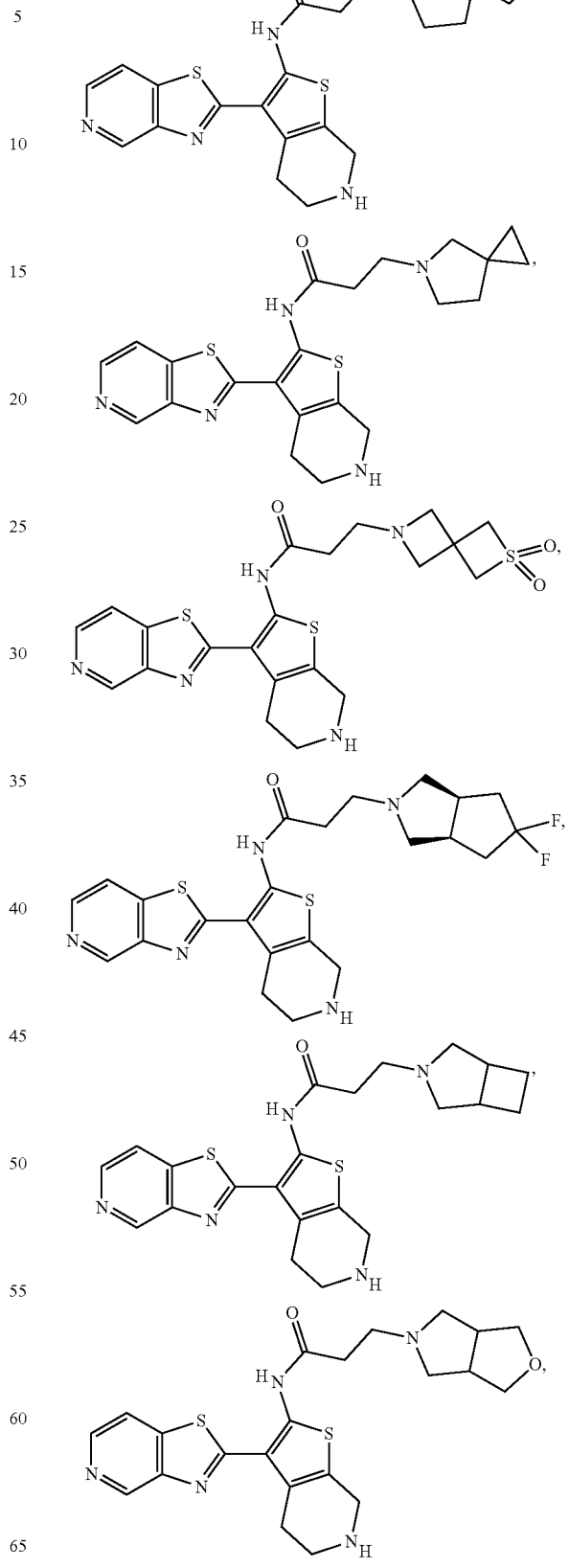

221
-continued
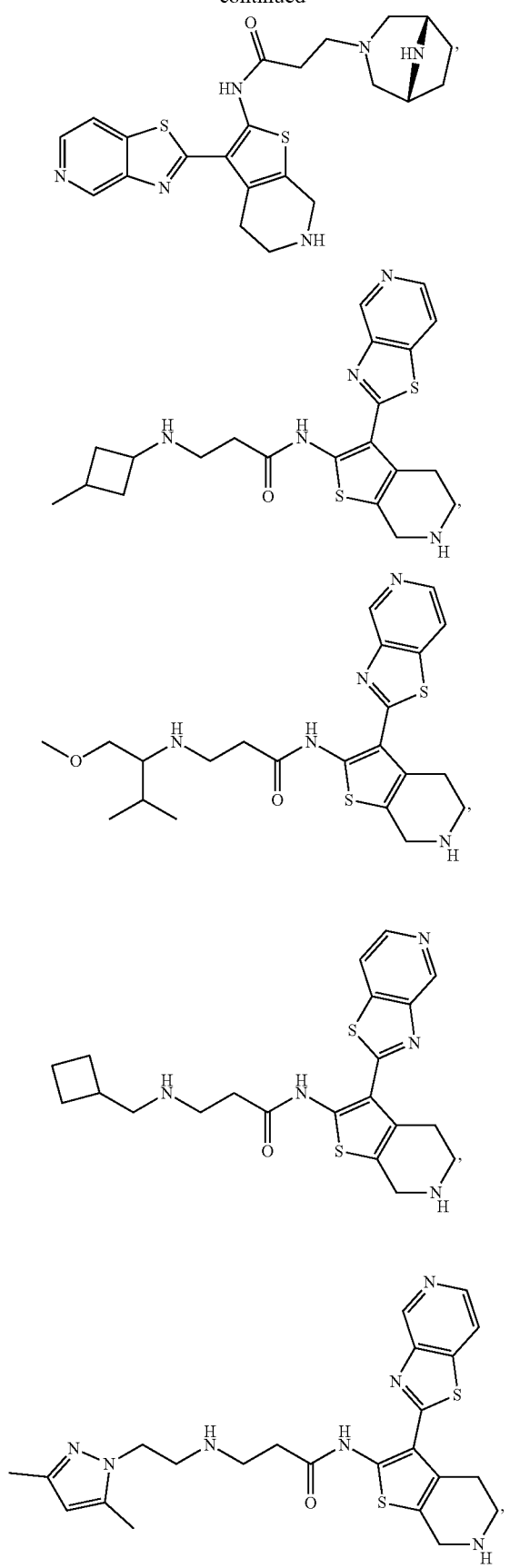
222
-continued
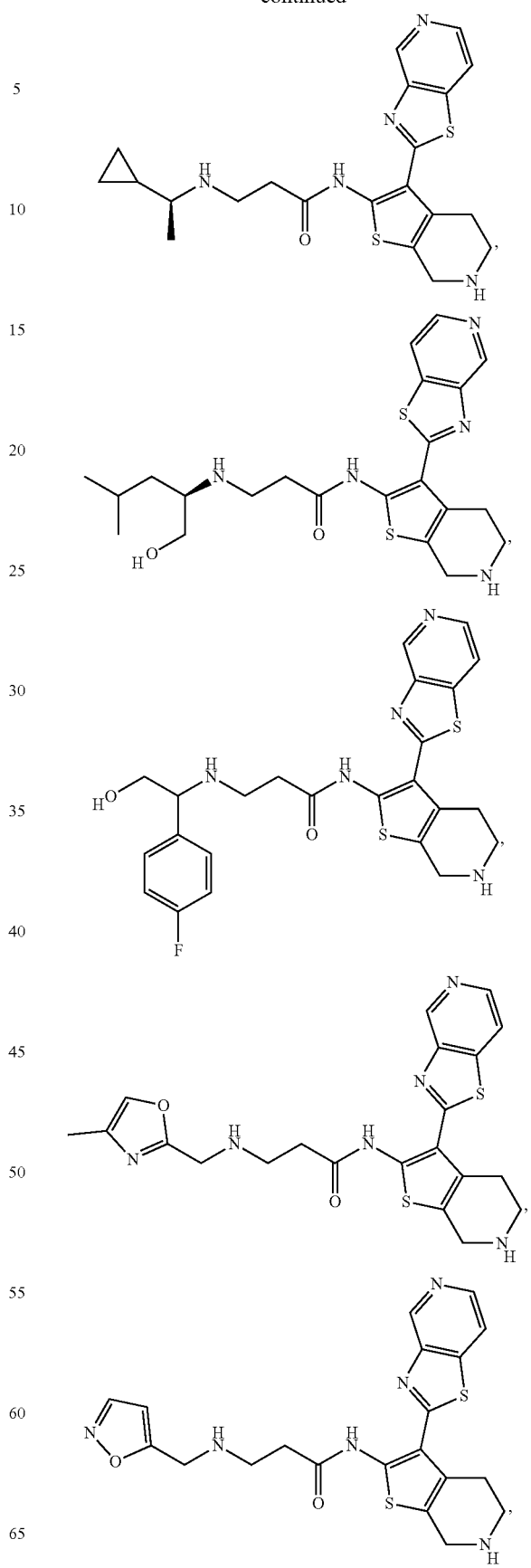

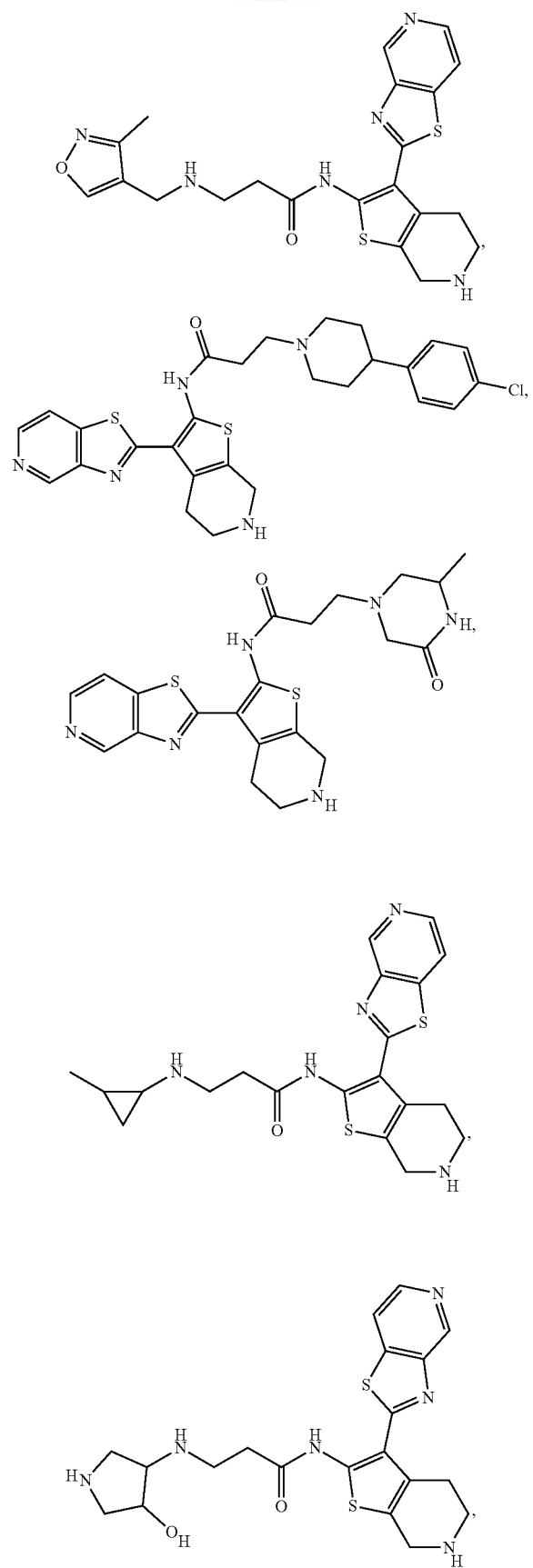
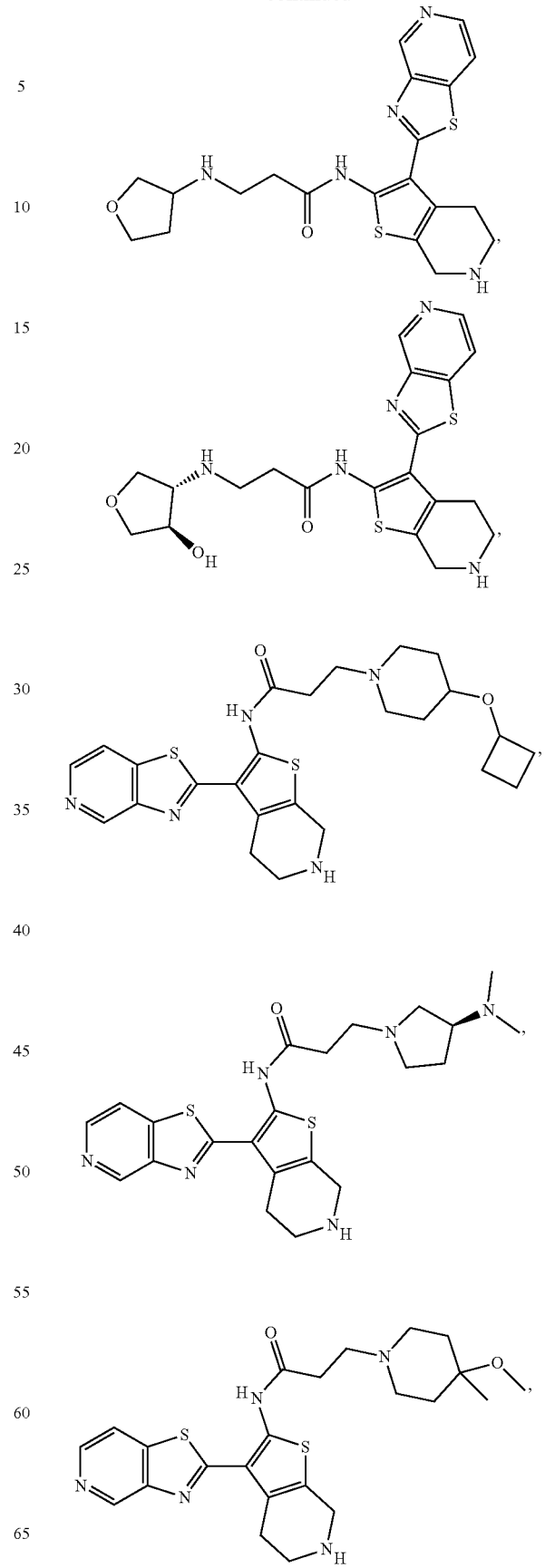

225
-continued
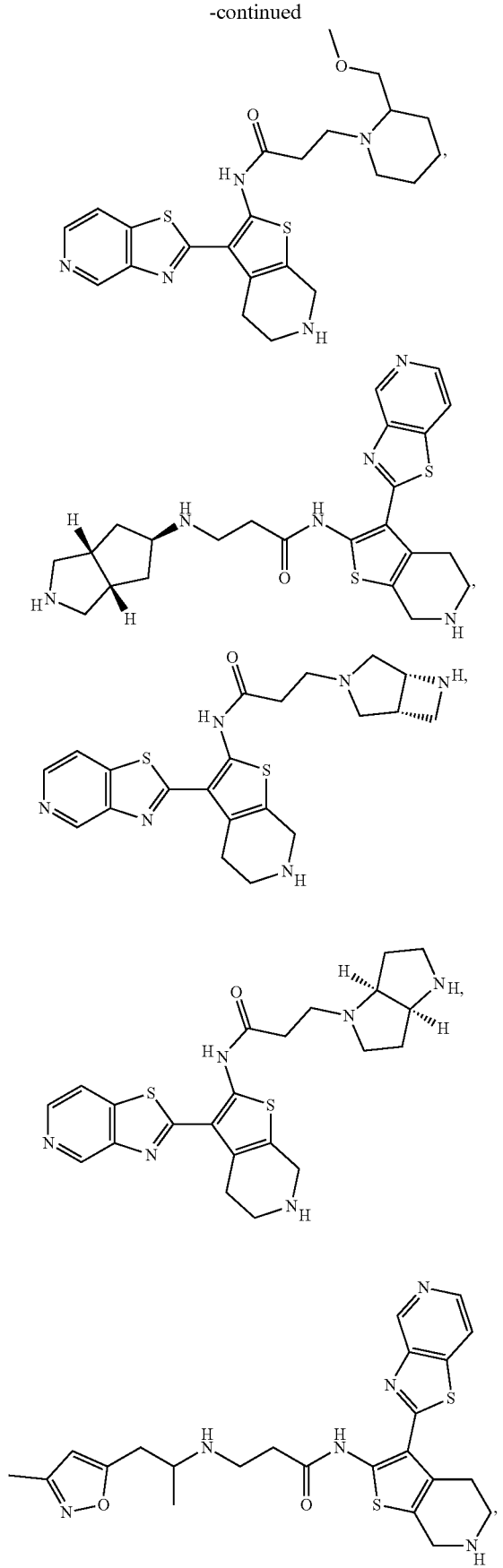
226
-continued
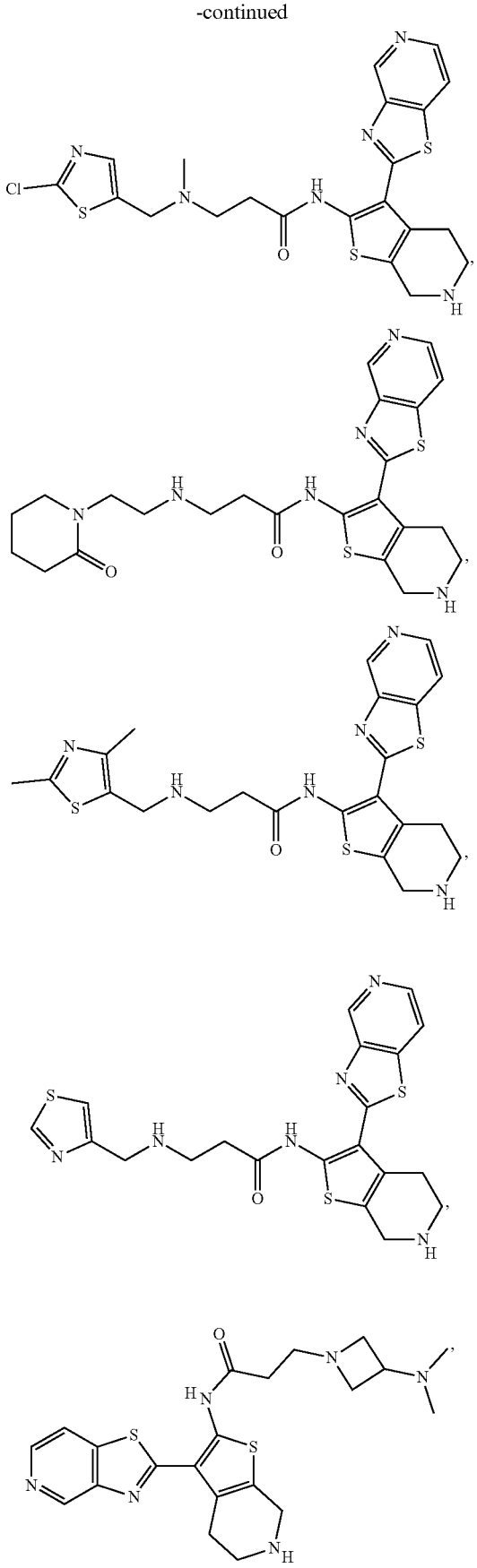

227
-continued
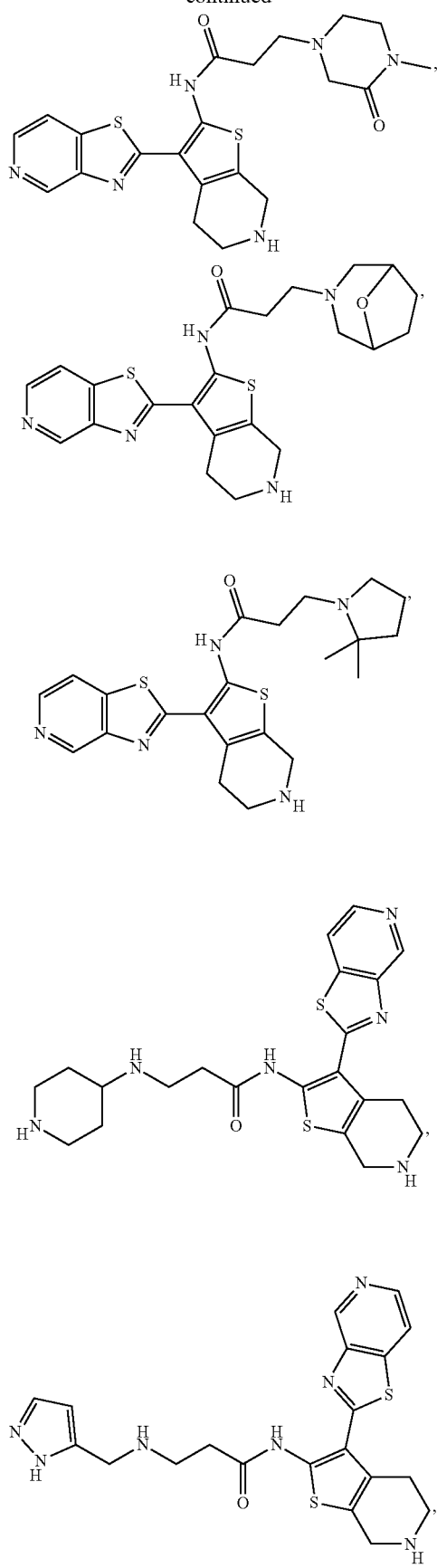
228
-continued
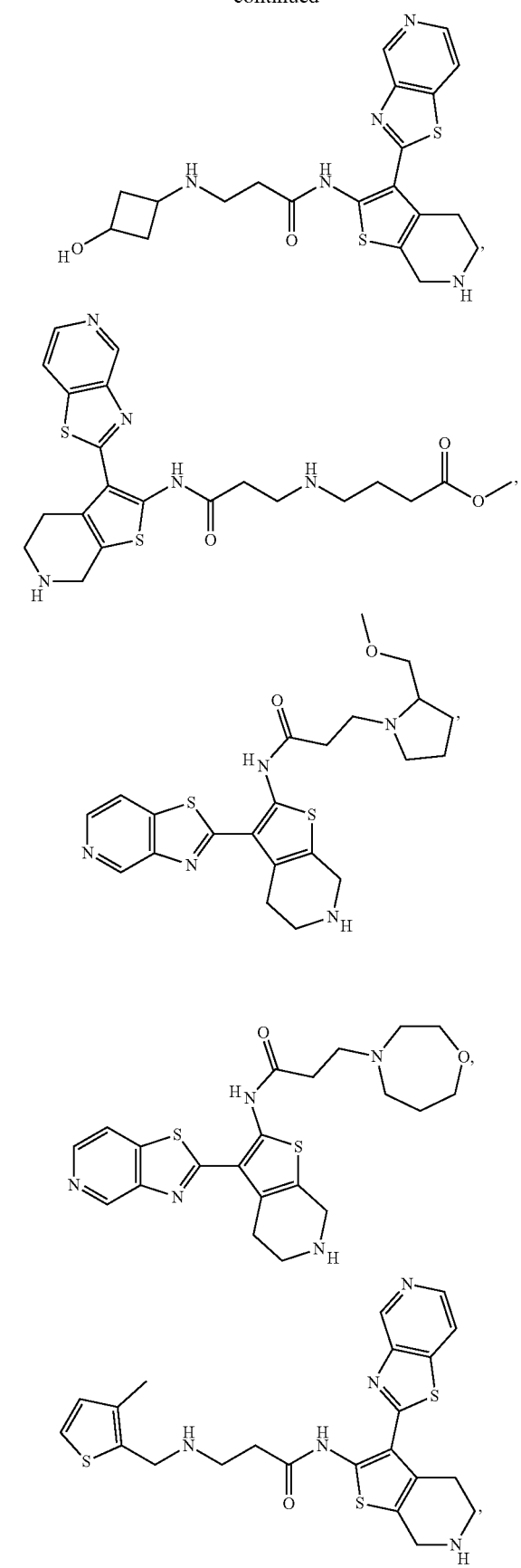

229
-continued
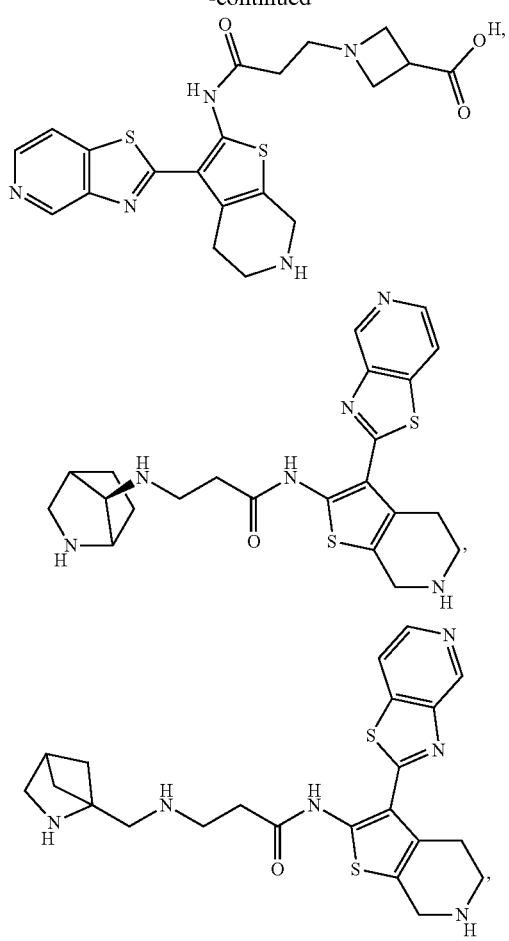
230
-continued
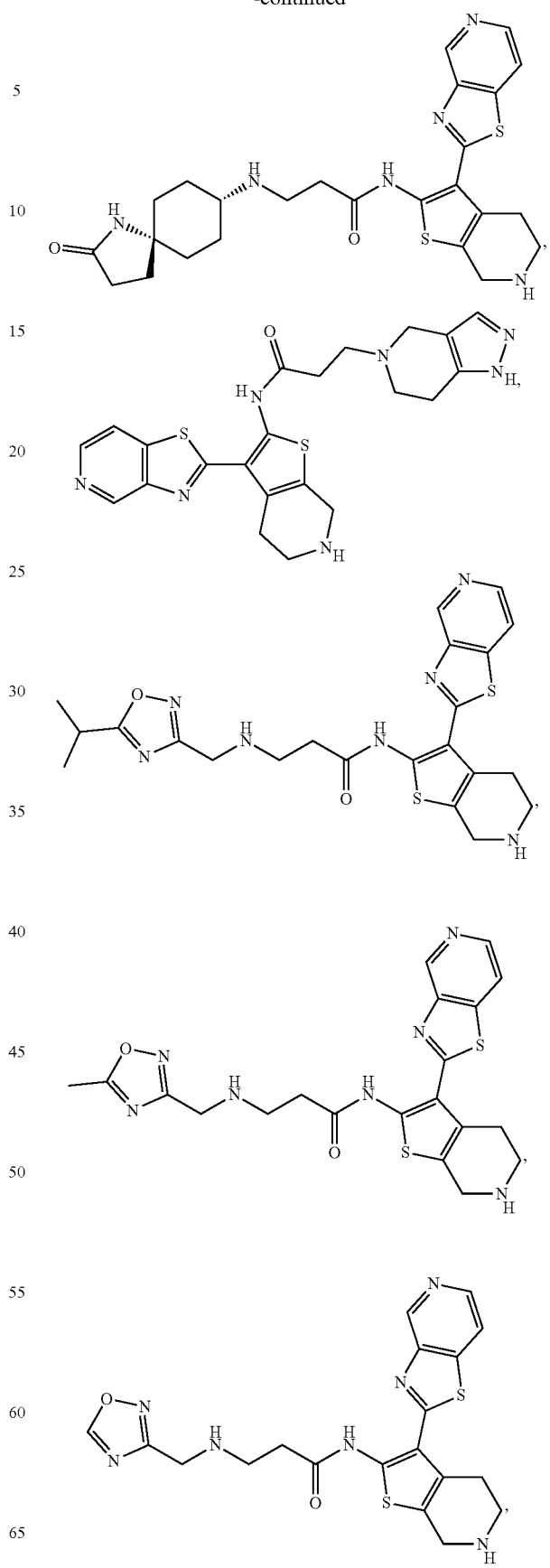

231
-continued
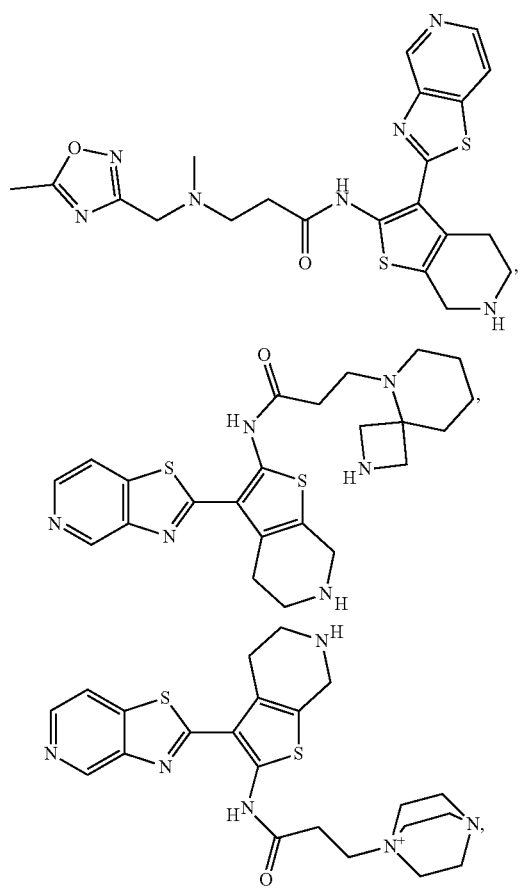
232
-continued
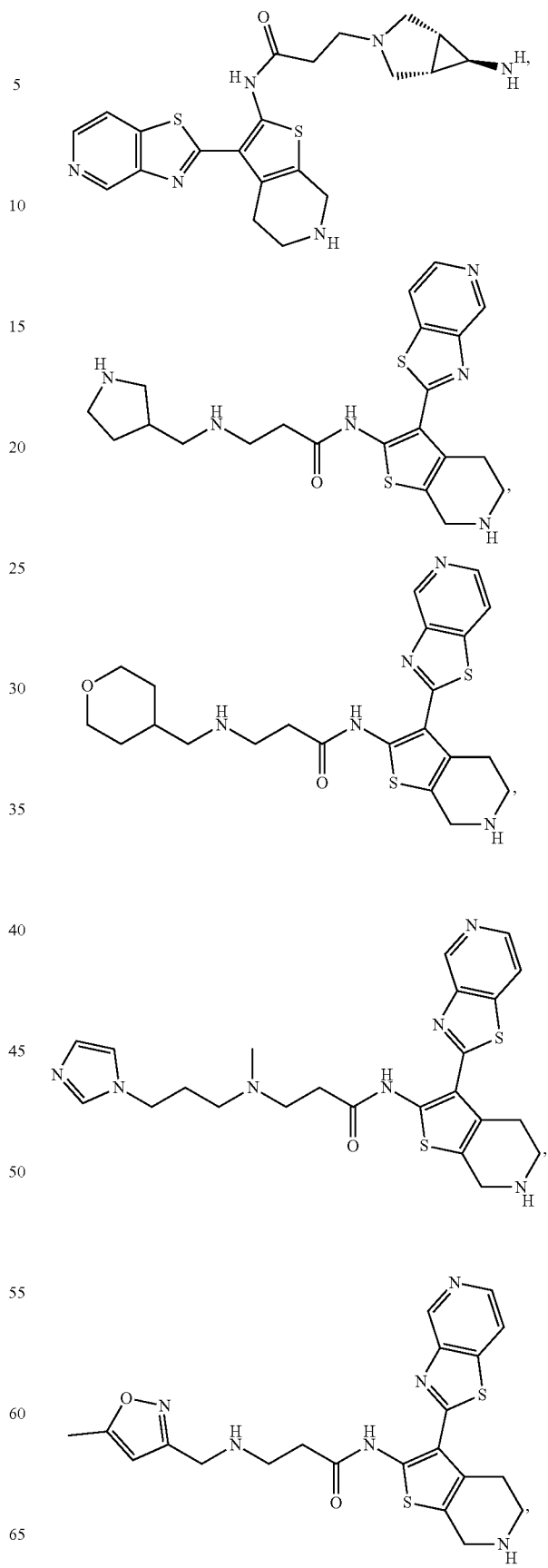

233
-continued
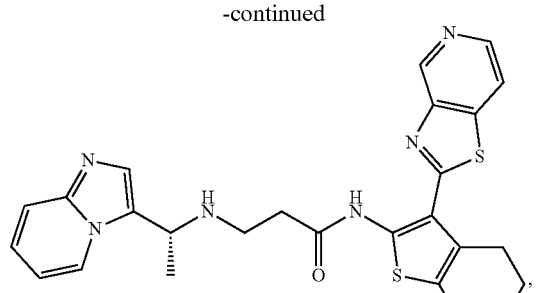
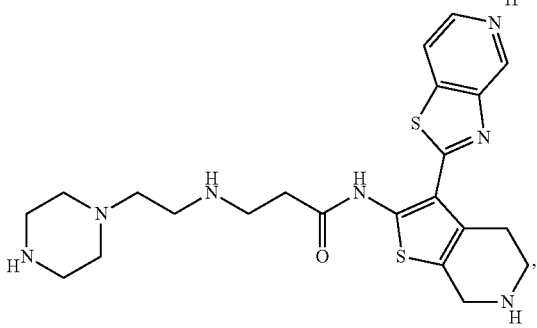
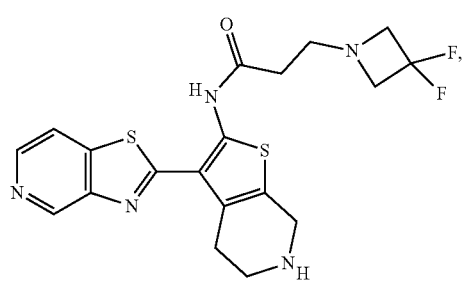
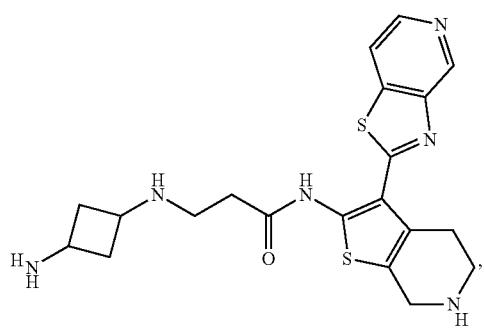
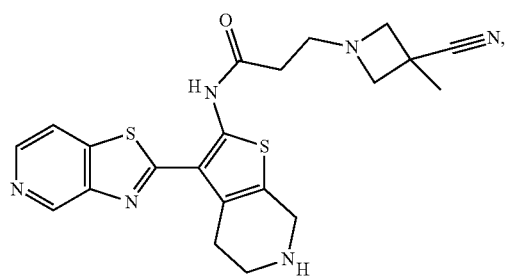
234
-continued
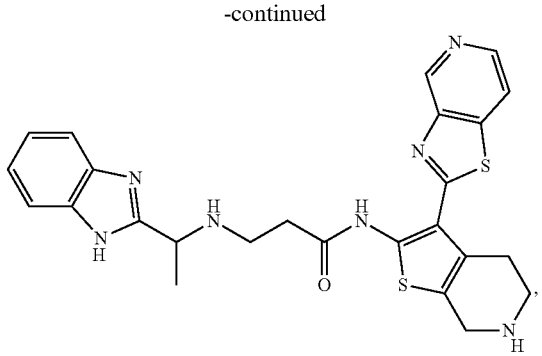
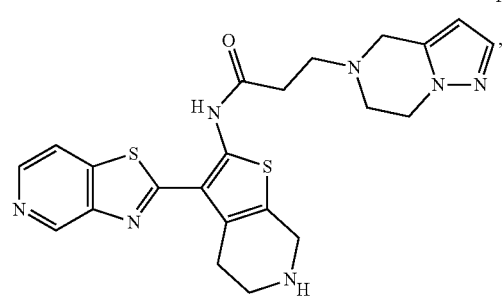
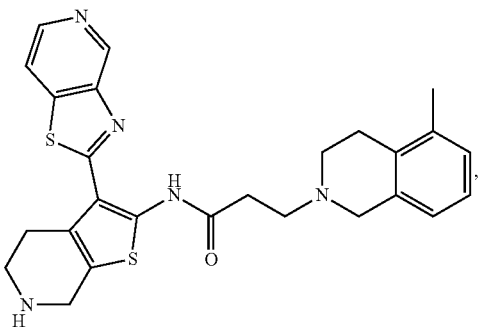
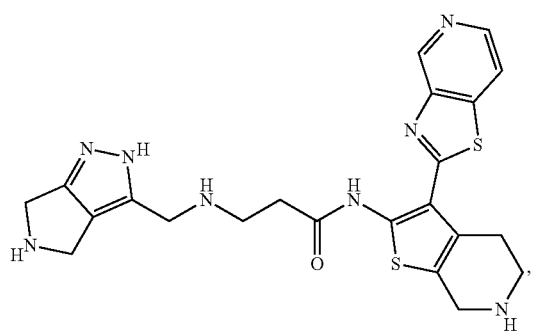
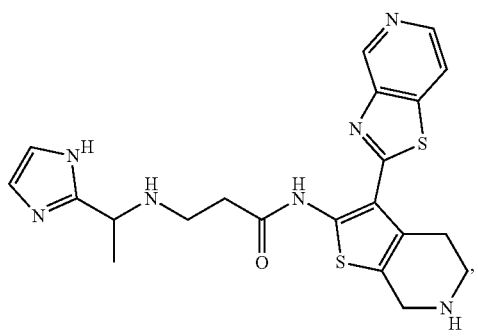

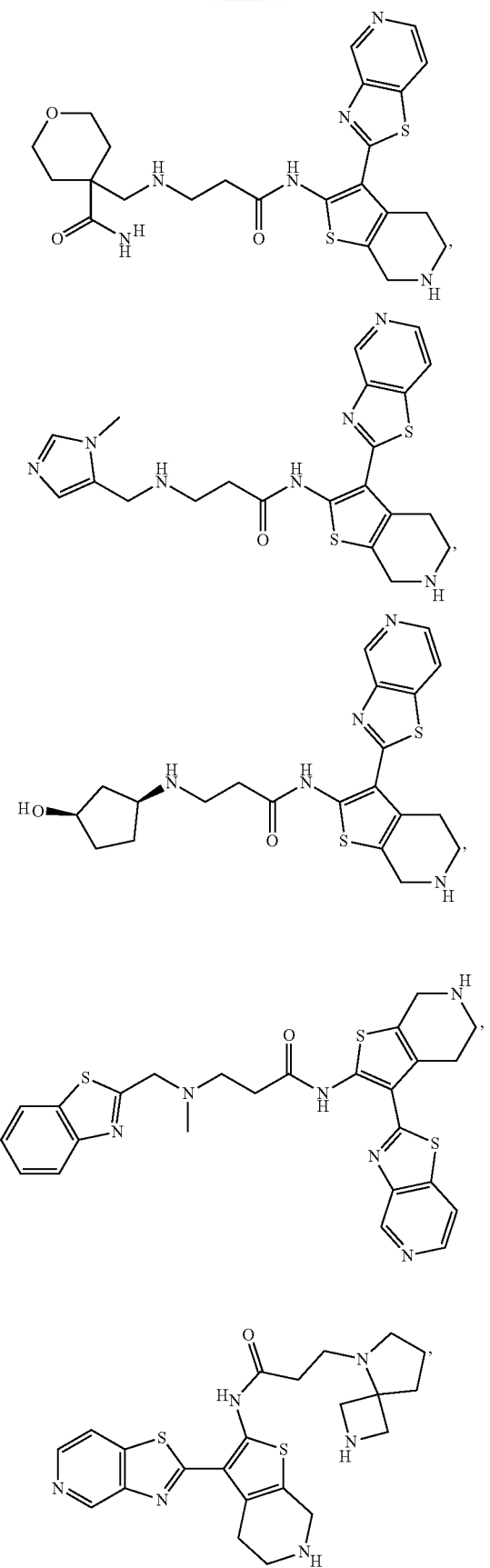
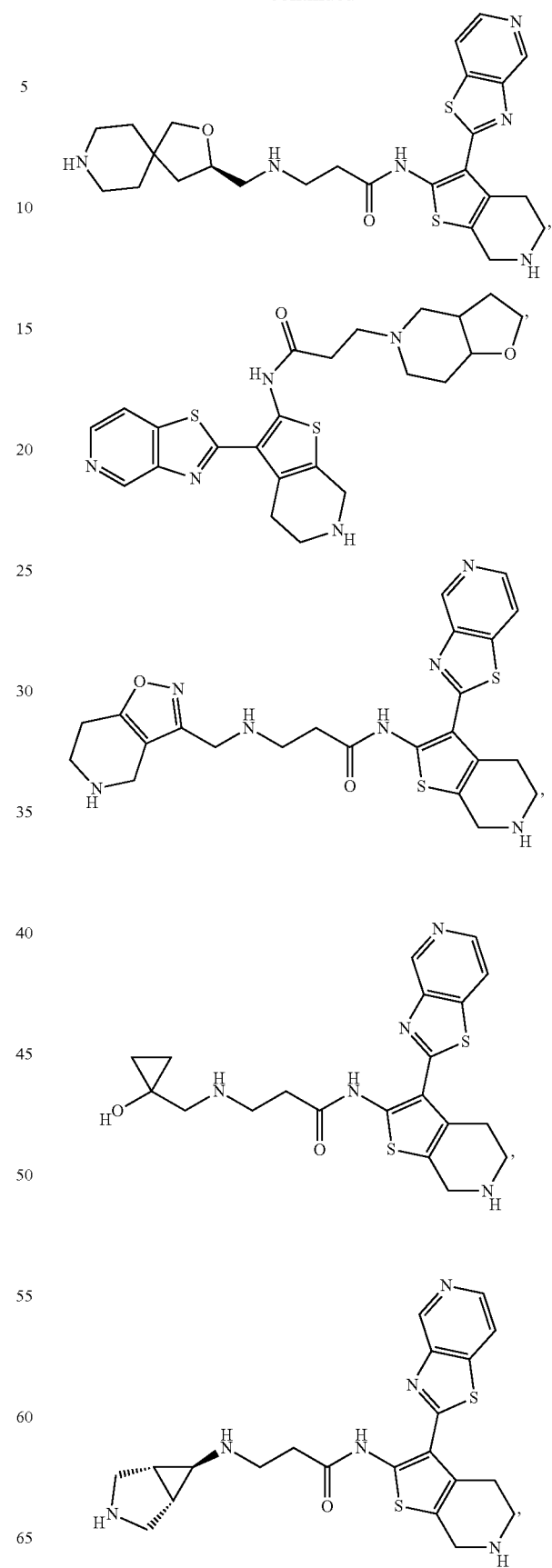

-continued
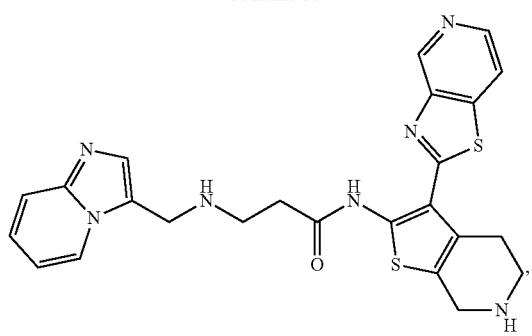
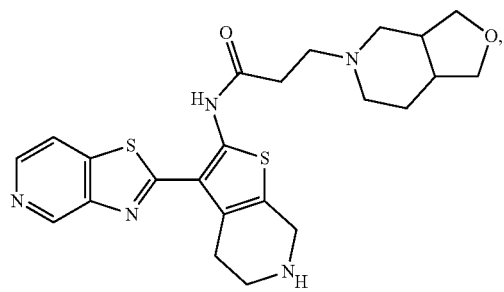
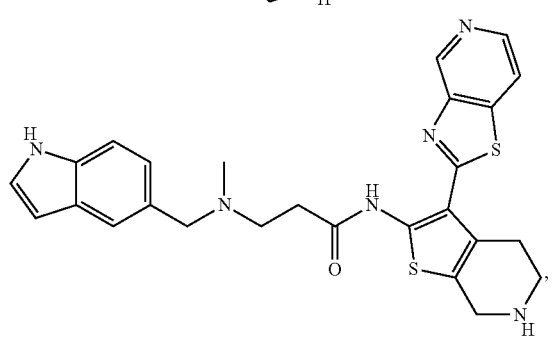
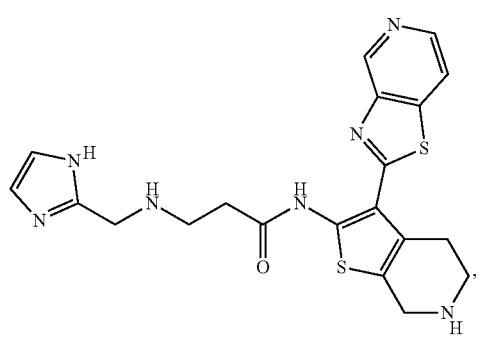
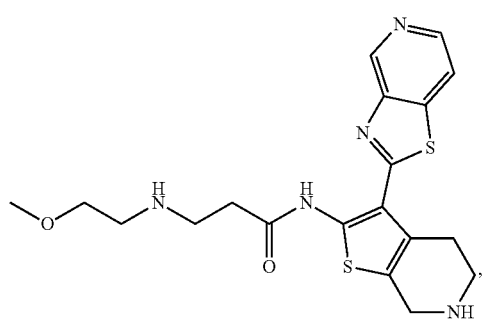
-continued
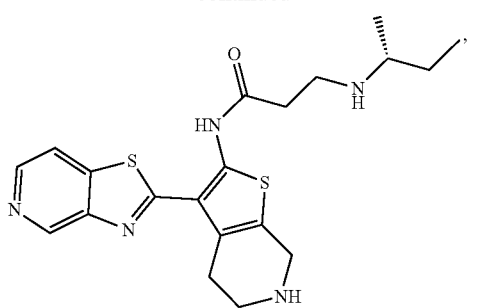
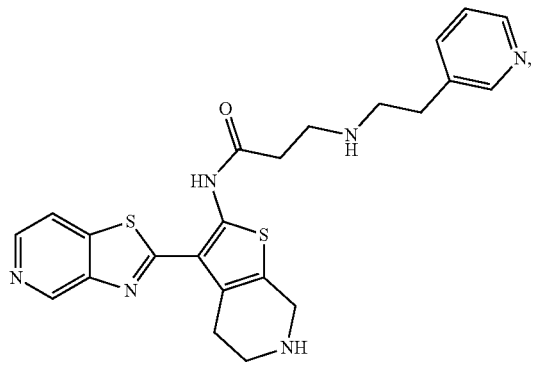
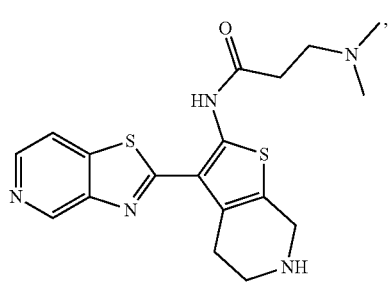
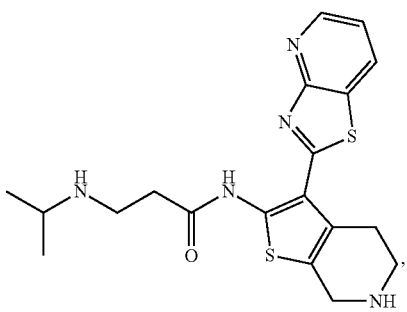
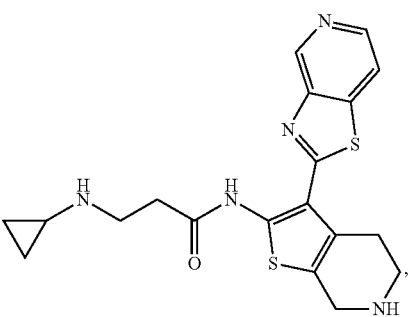

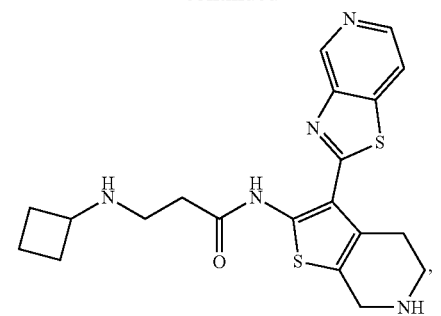
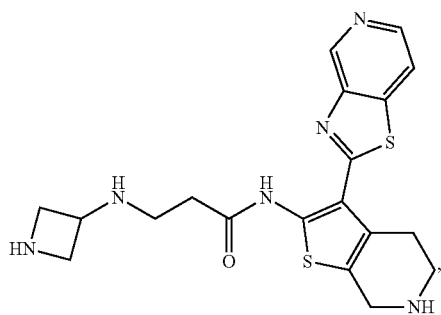
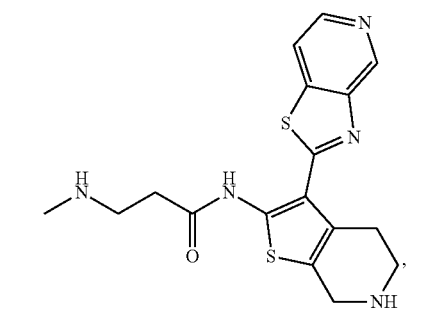
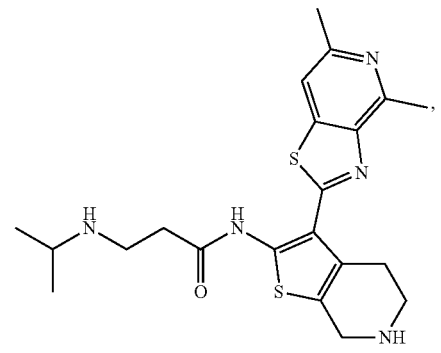
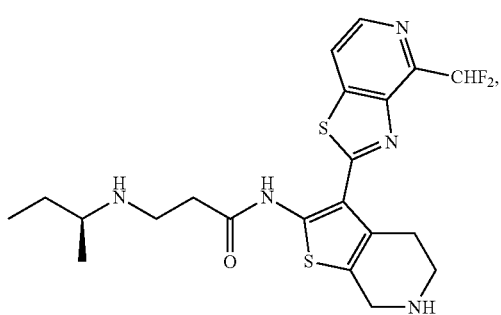
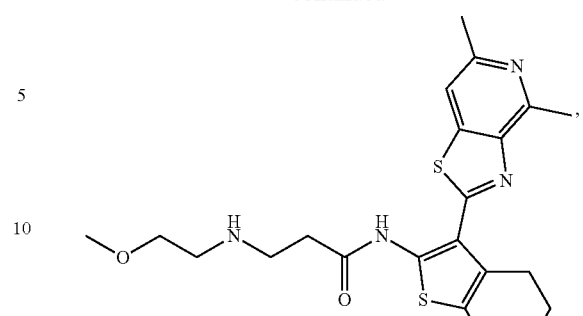
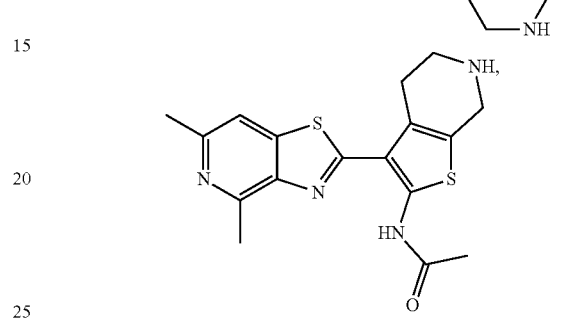
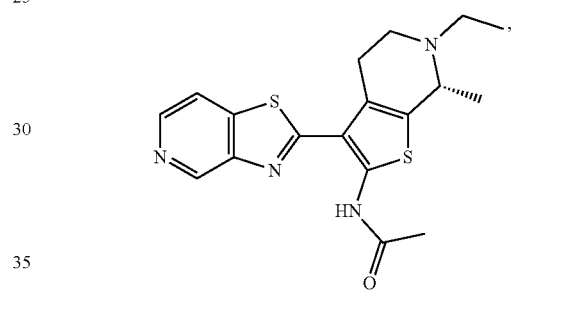
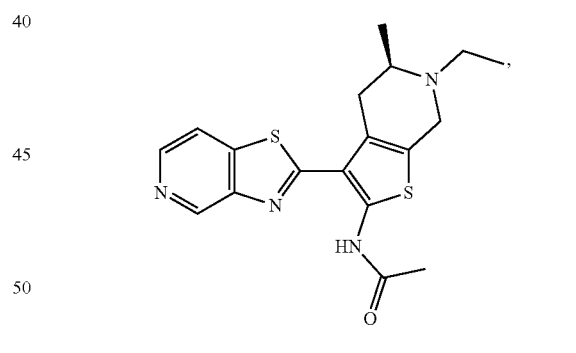
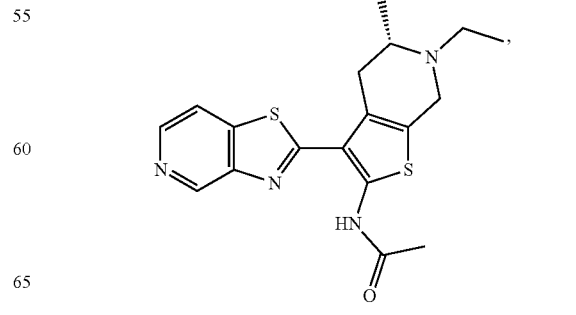

241
-continued
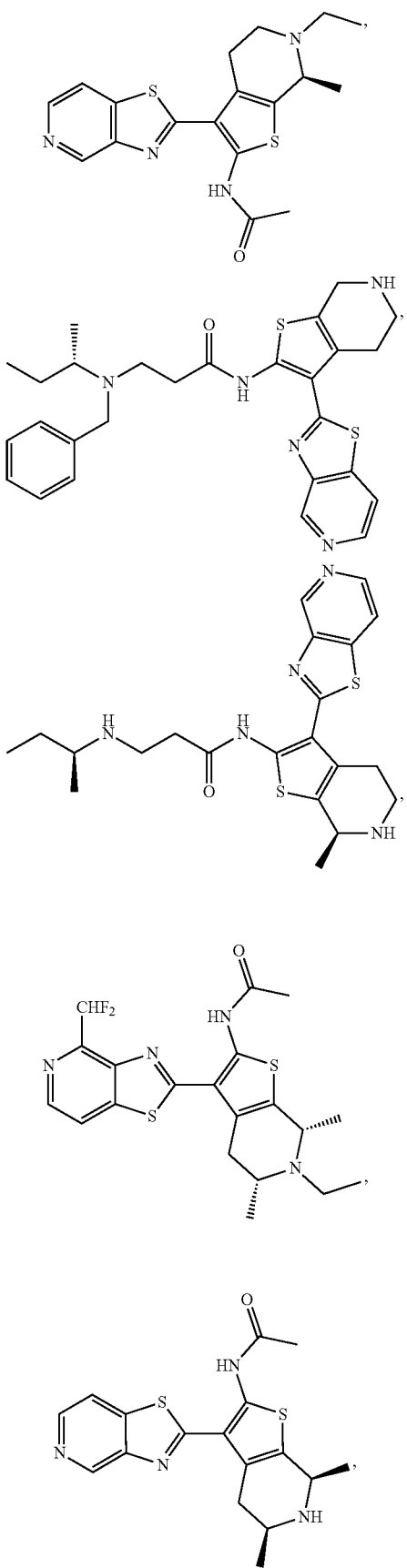
242
-continued
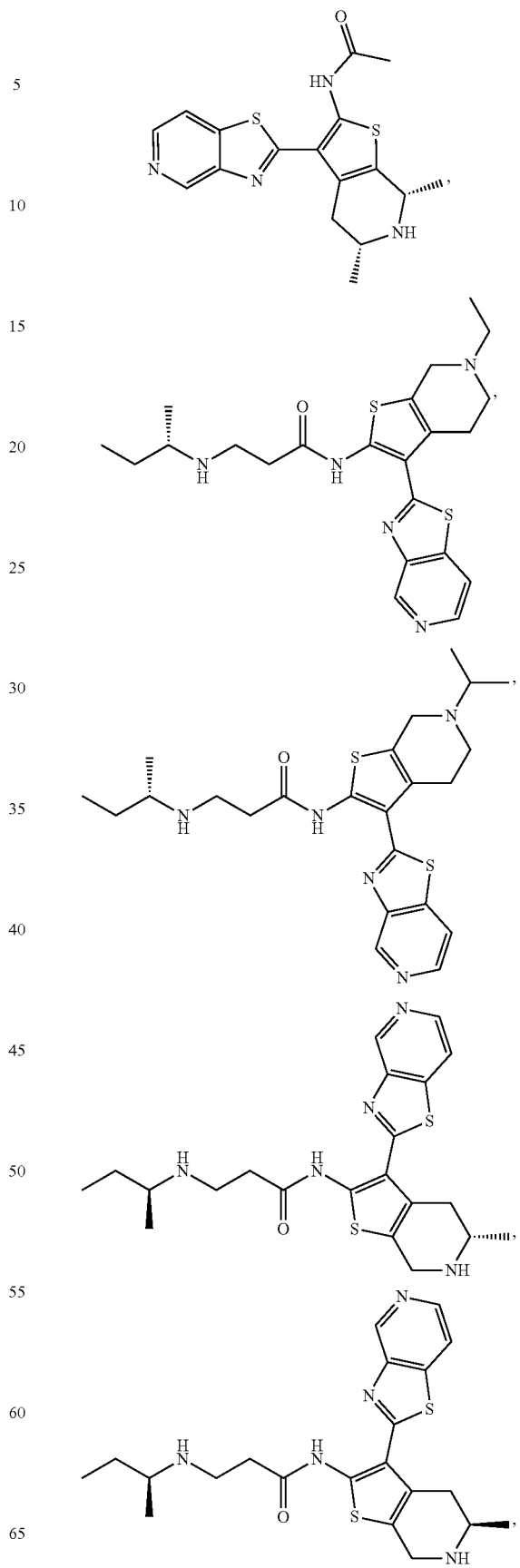

243
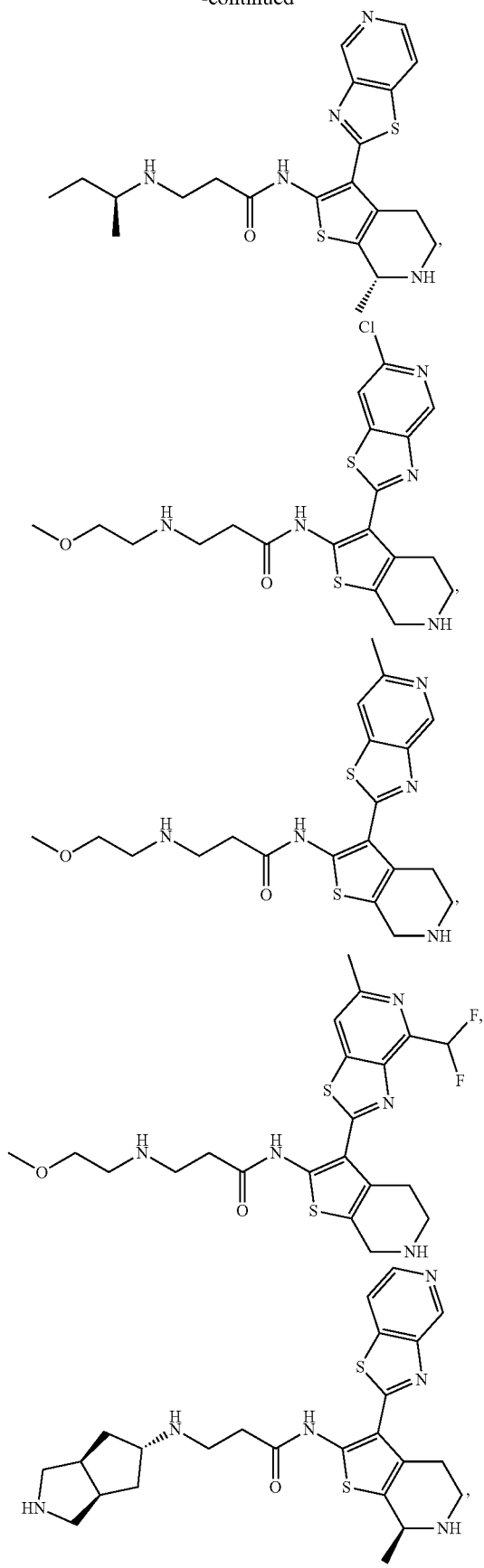
244
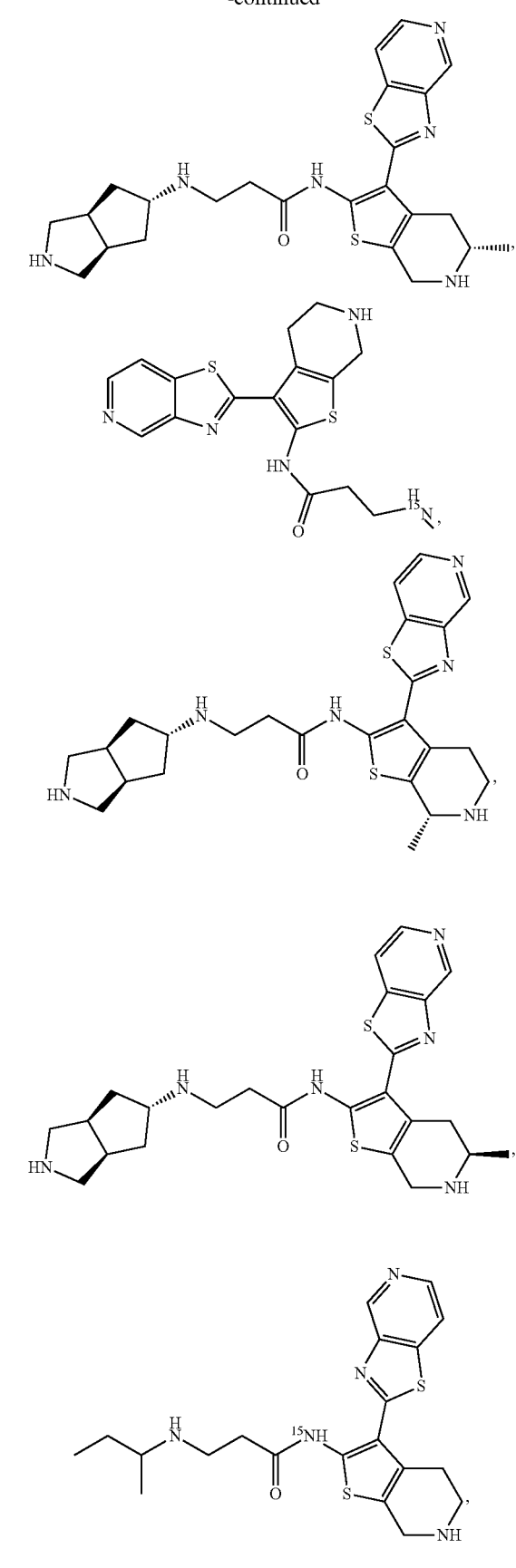

245
-continued

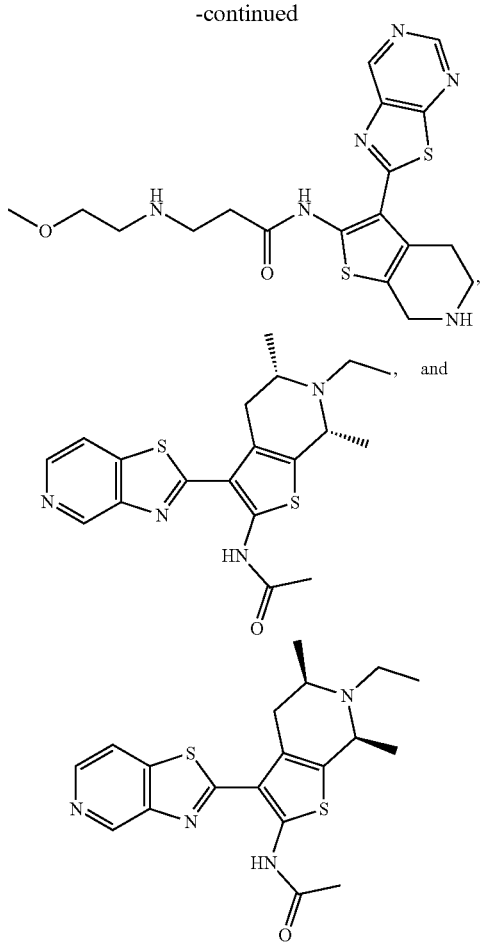

or a pharmaceutically acceptable salt, tautomer, or stereoisomer thereof.

27. A pharmaceutically acceptable composition comprising a compound of claim 1 and a pharmaceutically acceptable excipient.

28. A method of treating small cell lung cancer in a subject in need thereof, the method comprising administering to the subject a compound of claim 1 or a pharmaceutical composition comprising the compound of claim 1 and a pharmaceutically acceptable excipient.

29. The method of claim 28, wherein the subject has been determined to have deregulated c-Myc activity prior to administration of the compound or composition.

30. The method of claim 28, wherein the compound of claim 1 is selected from the group consisting of

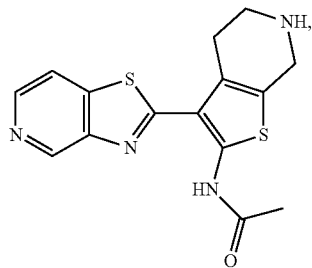

246
-continued

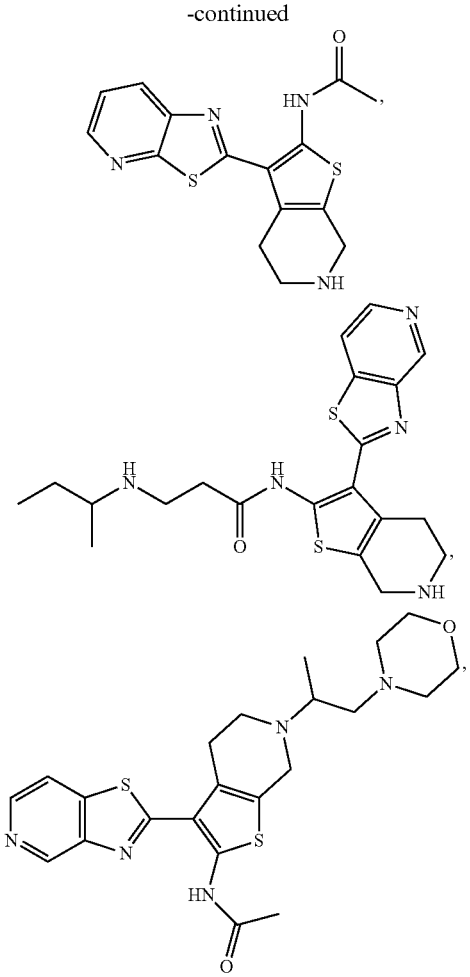

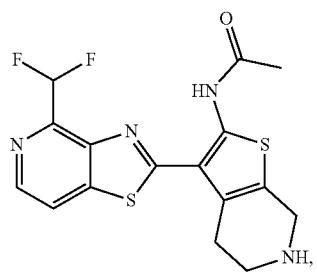

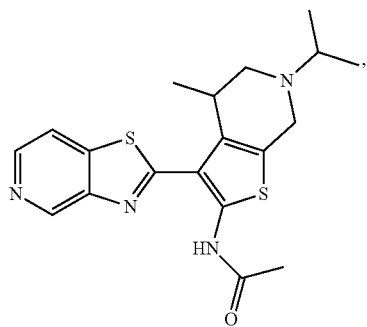

247
-continued
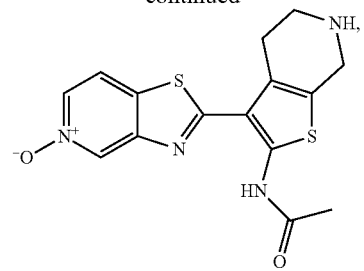
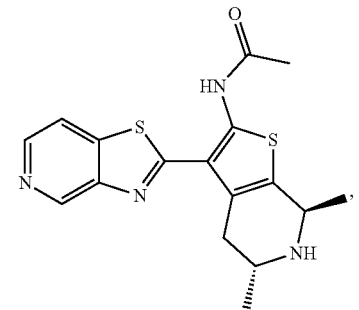
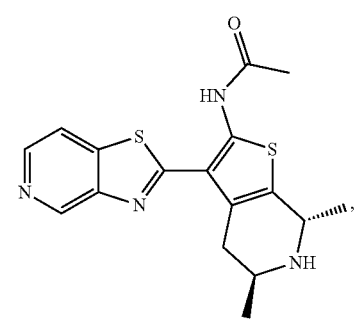
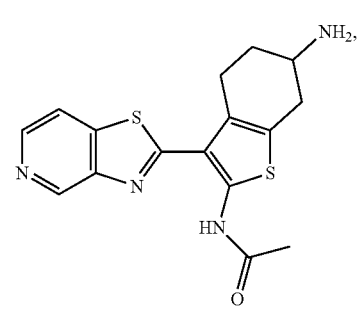
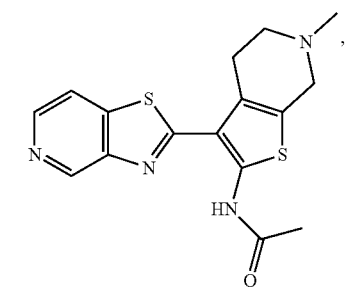
248
-continued
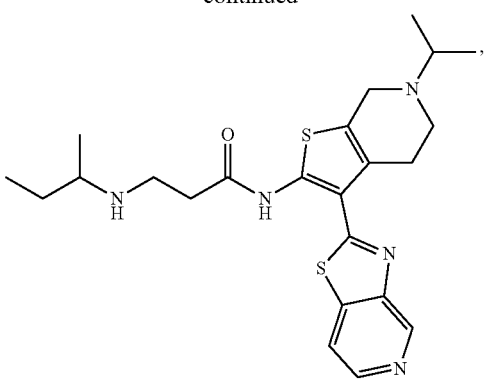
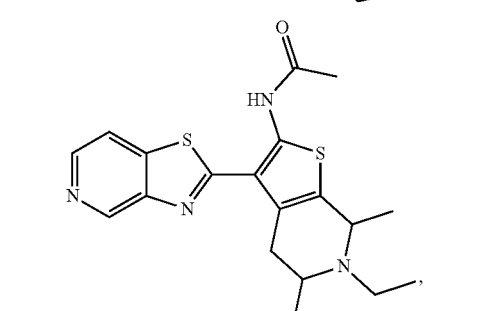
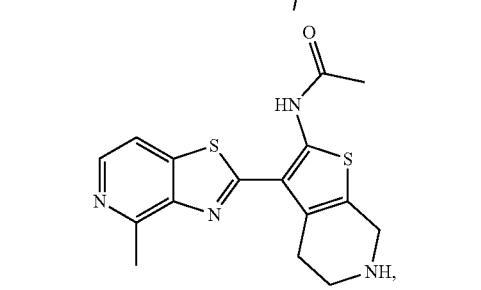
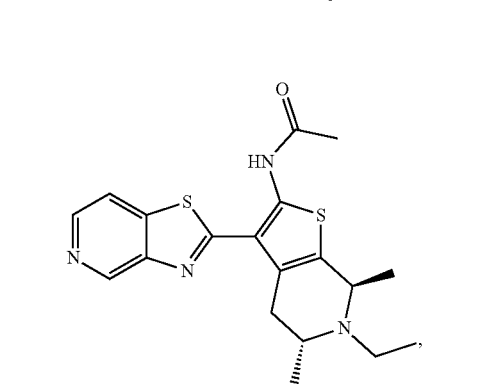
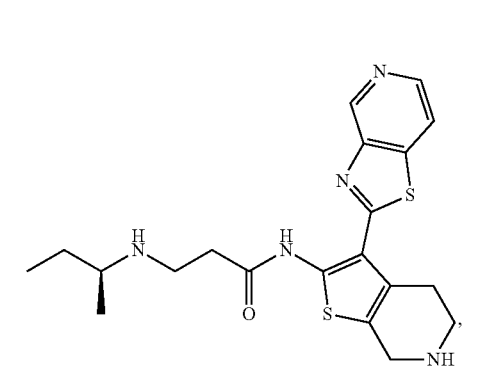

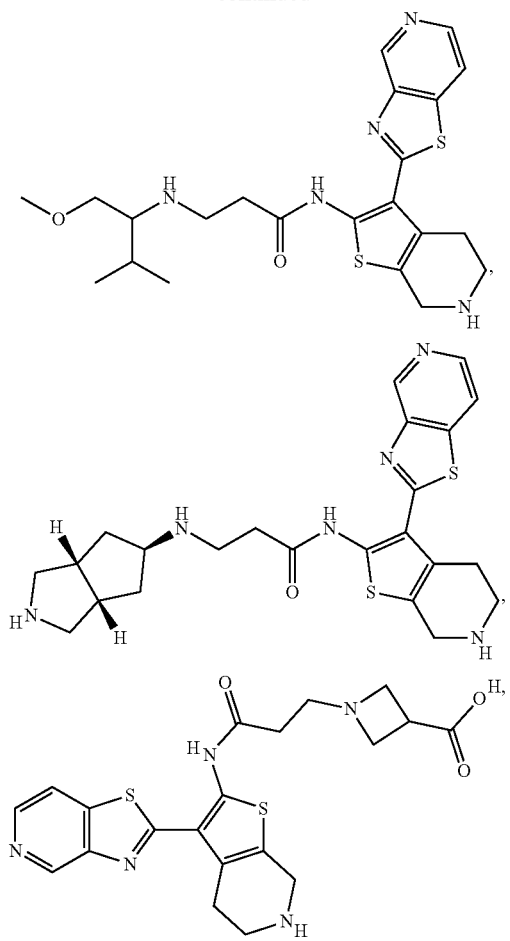
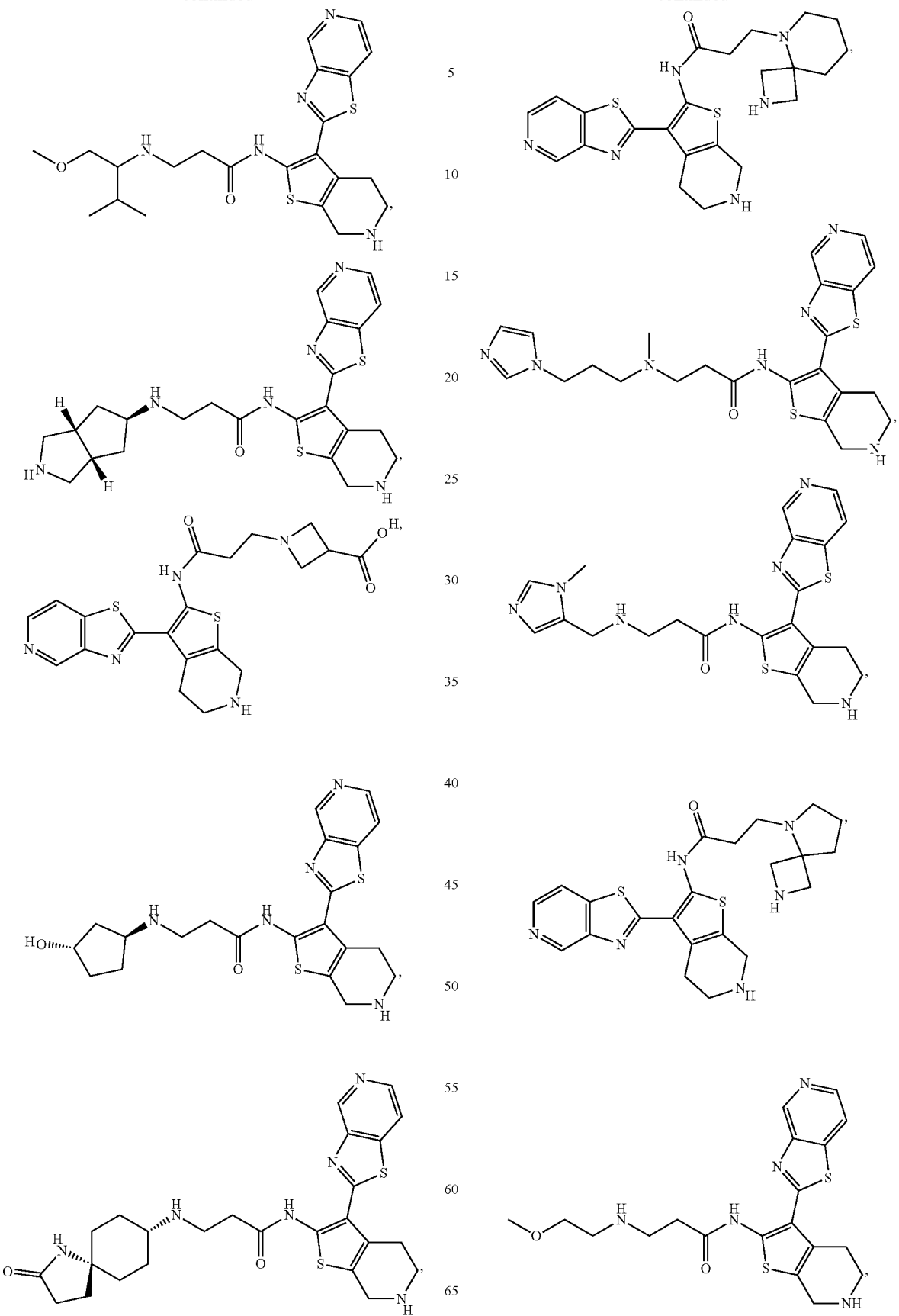

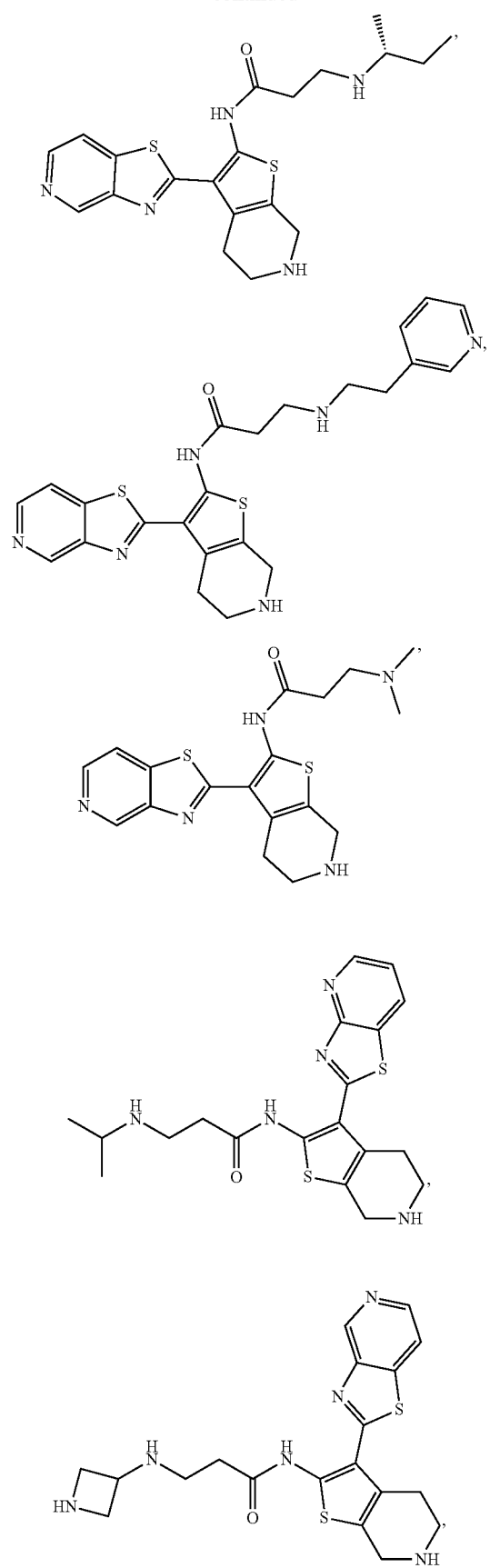
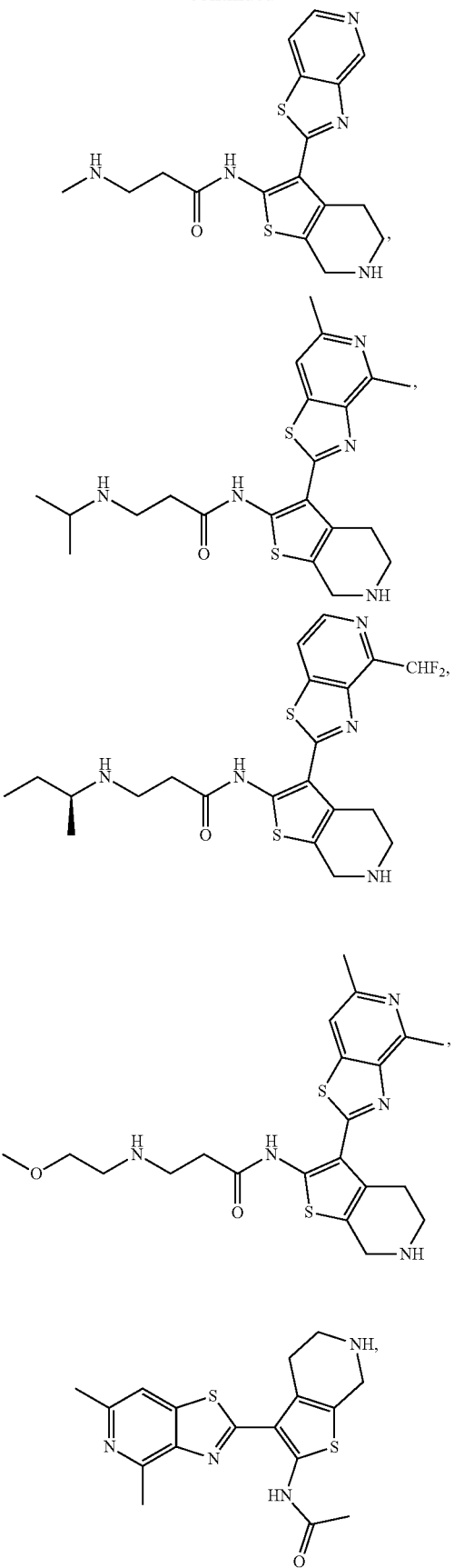

253
-continued
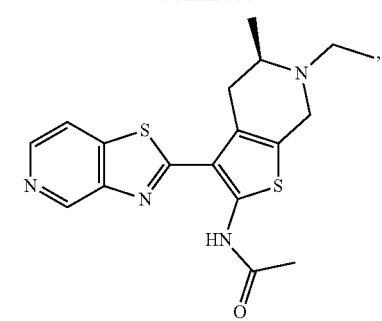
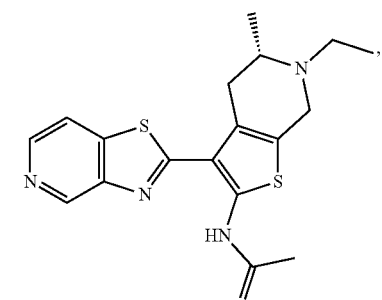
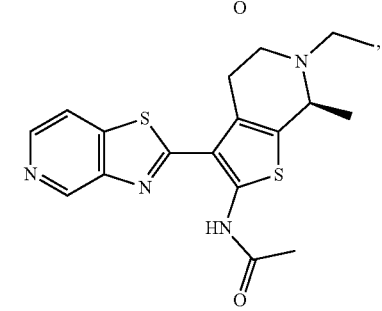
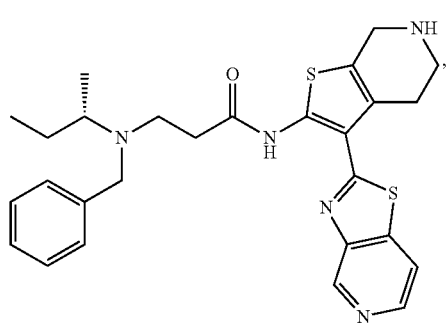
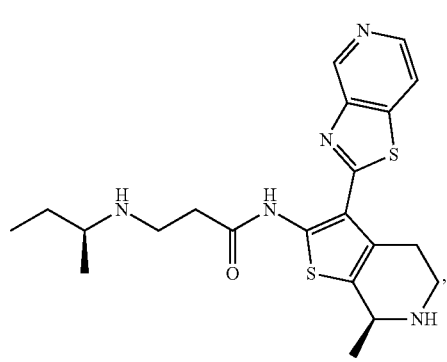
254
-continued
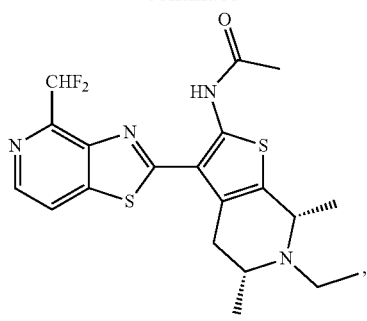
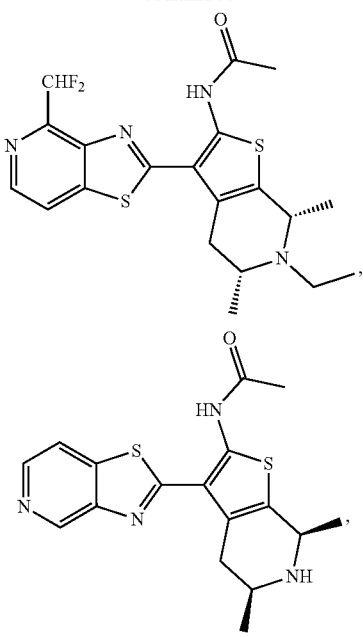
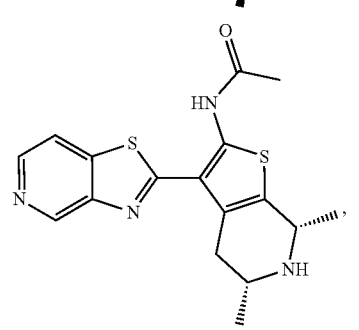
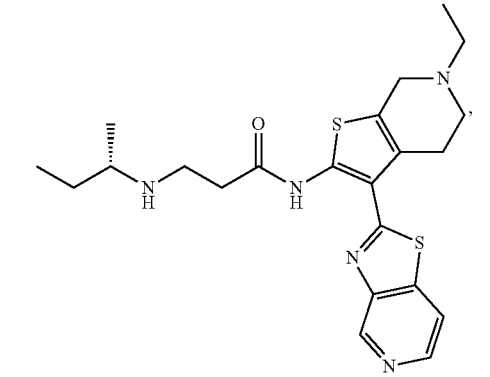
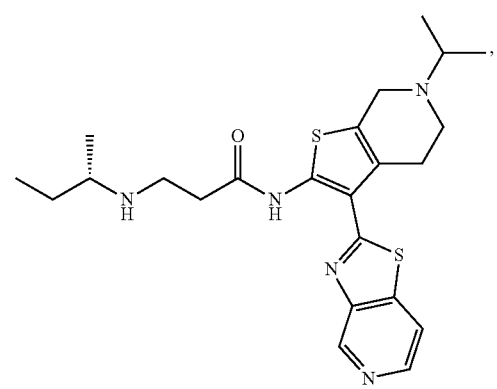

255
-continued
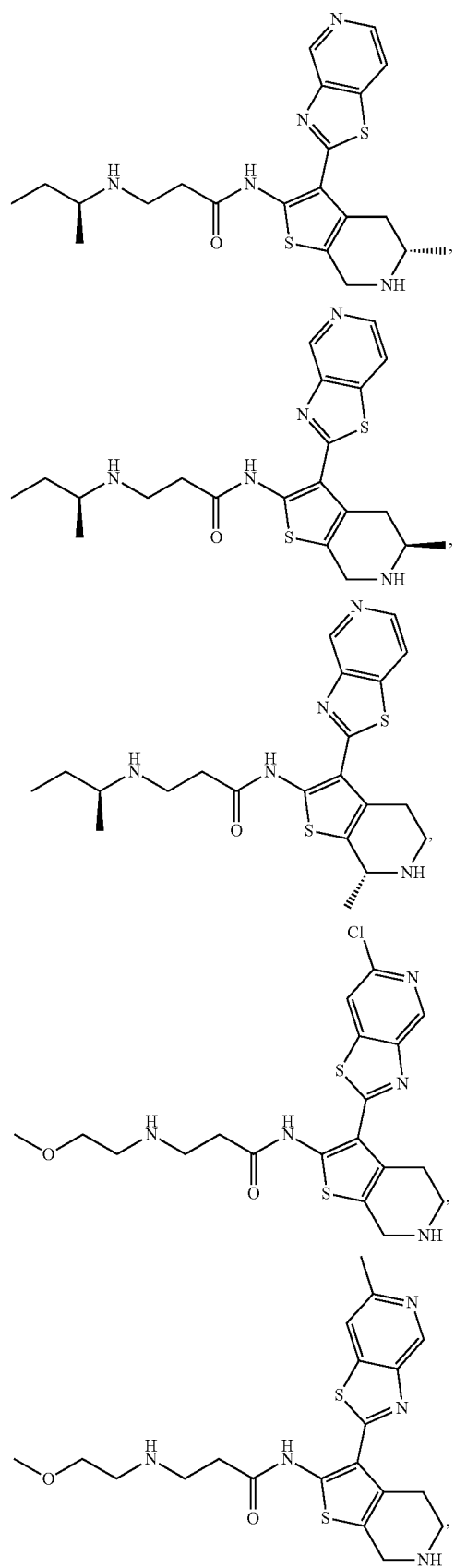
256
-continued
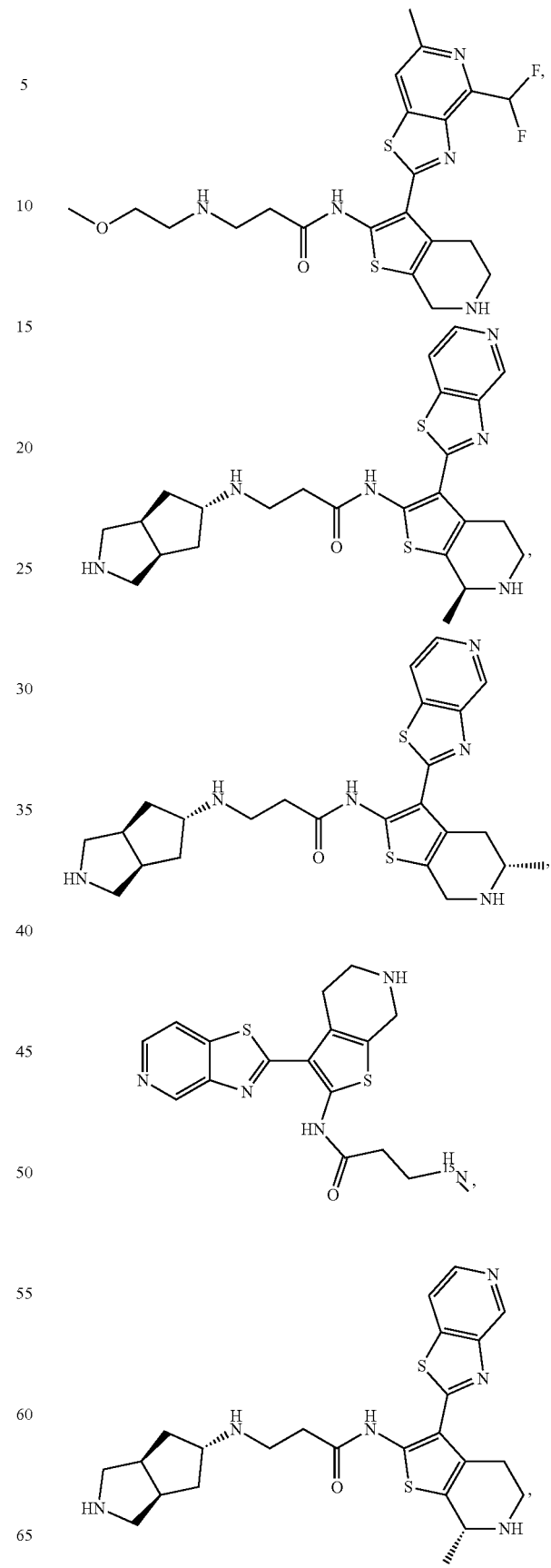

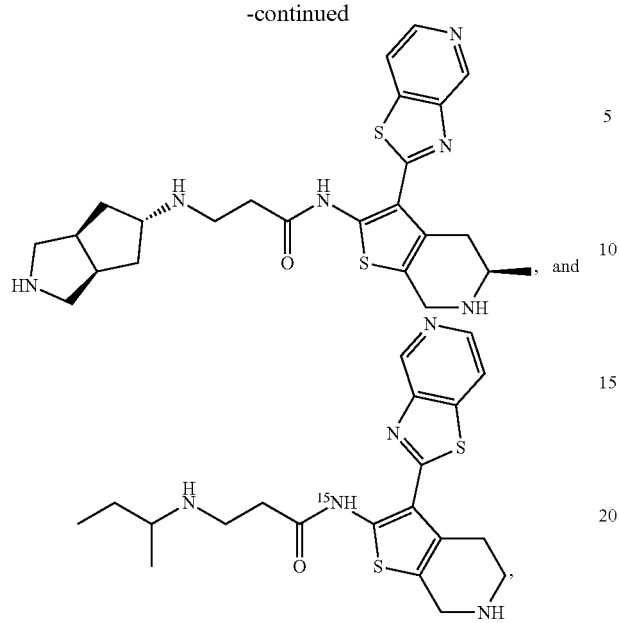
or a pharmaceutically acceptable salt, tautomer, or stereoisomer thereof.
* * * * *